(12) United States Patent
McKerrecher et al.

(10) Patent No.: US 7,642,263 B2
(45) Date of Patent: Jan. 5, 2010

(54) HETEROARYL BENZAMIDE DERIVATIVES FOR USE AS GLK ACTIVATORS IN THE TREATMENT OF DIABETES

(75) Inventors: Darren McKerrecher, Cheshire (GB); Kurt Gordon Pike, Cheshire (GB); Michael James Waring, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/202,800

(22) Filed: Sep. 2, 2008

(65) Prior Publication Data

US 2009/0029905 A1  Jan. 29, 2009

Related U.S. Application Data

(63) Continuation of application No. 11/995,077, filed as application No. PCT/GB2006/002471 on Jul. 3, 2006.

(30) Foreign Application Priority Data

| Jul. 9, 2005 | (GB) | .................. | 0514173.4 |
| Aug. 9, 2005 | (GB) | .................. | 0516297.9 |
| Nov. 24, 2005 | (GB) | .................. | 0523862.1 |
| Dec. 2, 2005 | (GB) | .................. | 0524589.9 |
| Apr. 22, 2006 | (GB) | .................. | 0607977.6 |

(51) Int. Cl.
*A61K 31/4965* (2006.01)

(52) U.S. Cl. ............... 514/255.05; 544/406; 548/375.1; 548/950

(58) Field of Classification Search ............ 514/255.05; 544/406; 548/375.1, 950
See application file for complete search history.

(56) References Cited

U.S. PATENT DOCUMENTS

| 2,750,393 A | 6/1956 | Elpern |
| 2,967,194 A | 1/1961 | Hauptschein |
| 3,917,625 A | 11/1975 | Lee et al. |
| 3,950,351 A | 4/1976 | Rossignol et al. |
| 4,009,174 A | 2/1977 | Cluzan et al. |
| 4,105,785 A | 8/1978 | Mauvernay et al. |
| 4,146,631 A | 3/1979 | Ford et al. |
| 4,434,170 A | 2/1984 | Dostert et al. |
| 4,474,792 A | 10/1984 | Erickson |
| 4,634,783 A | 1/1987 | Fujii et al. |
| 4,966,891 A | 10/1990 | Fujiu et al. |
| 5,258,407 A | 11/1993 | Washburn et al. |
| 5,273,986 A | 12/1993 | Holland et al. |
| 5,399,702 A | 3/1995 | Holland et al. |
| 5,466,715 A | 11/1995 | Washburn et al. |
| 5,510,478 A | 4/1996 | Sabb |
| 5,661,153 A | 8/1997 | Isobe et al. |
| 5,672,750 A | 9/1997 | Perry |
| 5,712,270 A | 1/1998 | Sabb |
| 5,849,735 A | 12/1998 | Albright et al. |
| 6,110,945 A | 8/2000 | Head et al. |
| 6,197,798 B1 | 3/2001 | Fink et al. |
| 6,200,995 B1 | 3/2001 | De la Brouse-Elwood et al. |
| 6,207,693 B1 | 3/2001 | Setoi et al. |
| 6,214,878 B1 | 4/2001 | Bernardon et al. |
| 6,242,474 B1 | 6/2001 | Yamasaki et al. |
| 6,255,335 B1 | 7/2001 | Himmler et al. |
| 6,316,482 B1 | 11/2001 | Setoi et al. |
| 6,320,050 B1 | 11/2001 | Bizzarro et al. |
| 6,348,474 B1 | 2/2002 | Kayakiri et al. |
| 6,369,229 B1 | 4/2002 | Head et al. |
| 6,376,515 B2 | 4/2002 | Zhu et al. |
| 6,388,071 B2 | 5/2002 | Mahaney |
| 6,448,399 B1 | 9/2002 | Corbett et al. |
| 6,486,349 B1 | 11/2002 | Flitter et al. |
| 6,528,543 B1 | 3/2003 | Bizzarro et al. |
| 6,545,155 B2 | 4/2003 | Corbett et al. |
| 6,610,846 B1 | 8/2003 | Bizzarro et al. |
| 6,613,942 B1 | 9/2003 | Ling et al. |
| 7,132,546 B2 | 11/2006 | Kato et al. |
| 7,199,140 B2 | 4/2007 | Hayter et al. |
| 7,230,108 B2 | 6/2007 | Hargreaves et al. |
| 2001/0027200 A1 | 10/2001 | De la Brouse-Elwood et al. |
| 2002/0002183 A1 | 1/2002 | Zhu et al. |

(Continued)

FOREIGN PATENT DOCUMENTS

CA  2605738  11/2006

(Continued)

OTHER PUBLICATIONS

Alvarez et al. "Evidence that glucokinase regulatory protein is expressed and interacts with glucokinase in rat brain" J. Neurochem. 80(1):45-53 (2002).

(Continued)

*Primary Examiner*—James O Wilson
*Assistant Examiner*—Douglas M Willis
(74) *Attorney, Agent, or Firm*—Morgan, Lewis & Bockius LLP

(57) ABSTRACT

Compounds of formula (I)

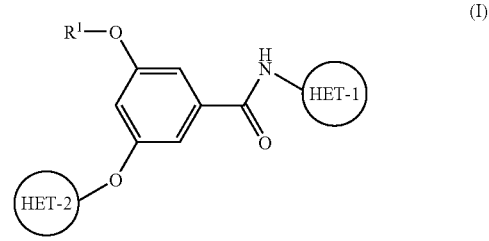

wherein $R^1$, HET-1 and HET-2 are as described in the specification, and their salts and prodrugs, are activators of glucokinase (GLK) and are thereby useful in the treatment of, for example, type 2 diabetes. Processes for preparing compounds of formula (I) are also described.

3 Claims, No Drawings

U.S. PATENT DOCUMENTS

| | | |
|---|---|---|
| 2002/0095044 A1 | 7/2002 | Jagtap et al. |
| 2003/0162690 A1 | 8/2003 | Zhu et al. |
| 2003/0228982 A1 | 12/2003 | Helmke et al. |
| 2004/0014968 A1 | 1/2004 | Bizzarro et al. |
| 2004/0077555 A1 | 4/2004 | Ishihara et al. |
| 2005/0080106 A1 | 4/2005 | Boyd et al. |
| 2005/0148605 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0261315 A1 | 11/2005 | Mehta et al. |
| 2006/0004010 A1 | 1/2006 | Habashita et al. |
| 2006/0167053 A1 | 7/2006 | Iino et al. |
| 2006/0258728 A1 | 11/2006 | Tani et al. |
| 2007/0078168 A1 | 4/2007 | Caulkett |
| 2008/0057074 A1 | 3/2008 | Takaoka et al. |

FOREIGN PATENT DOCUMENTS

| | | |
|---|---|---|
| CS | 173097 | 6/1978 |
| EP | 0316704 | 5/1989 |
| EP | 0353452 | 2/1990 |
| EP | 0219436 | 12/1993 |
| EP | 0619116 | 10/1994 |
| EP | 1048659 | 11/2000 |
| EP | 1132381 | 9/2001 |
| EP | 0620216 | 1/2003 |
| EP | 1336607 | 8/2003 |
| EP | 1357116 | 10/2003 |
| EP | 1400540 | 3/2004 |
| EP | 1496052 | 2/2005 |
| EP | 1790637 | 5/2005 |
| EP | 1541563 | 6/2005 |
| EP | 1600442 | 11/2005 |
| EP | 1604981 | 12/2005 |
| EP | 1702919 | 9/2006 |
| EP | 1995246 | 11/2008 |
| FR | 1526074 | 5/1968 |
| FR | 2088019 | 1/1972 |
| GB | 1352415 | 5/1974 |
| GB | 1561350 | 2/1980 |
| GB | 1588242 | 4/1981 |
| GB | 2216517 | 10/1989 |
| GB | 2331748 | 6/1999 |
| GB | 2385328 | 8/2003 |
| JP | 50105559 | 8/1975 |
| JP | 57021320 | 2/1982 |
| JP | 57075962 | 5/1982 |
| JP | 58069812 | 4/1983 |
| JP | 61205937 | 9/1986 |
| JP | 62158252 | 7/1987 |
| JP | 04300832 | 10/1992 |
| JP | 04300874 | 10/1992 |
| JP | 06027025 | 2/1994 |
| JP | 08143565 | 6/1996 |
| JP | 08173525 | 7/1996 |
| JP | 08301760 | 11/1996 |
| JP | 09040557 | 2/1997 |
| JP | 09202786 | 8/1997 |
| JP | 10101671 | 4/1998 |
| JP | 10101672 | 4/1998 |
| JP | 10212271 | 8/1998 |
| JP | 11029480 | 2/1999 |
| JP | 11171848 | 6/1999 |
| JP | 11222435 | 8/1999 |
| JP | 11292879 | 10/1999 |
| JP | 2000086657 | 3/2000 |
| WO | WO 91/09017 | 6/1991 |
| WO | WO 94/04525 | 3/1994 |
| WO | WO 94/12461 | 6/1994 |
| WO | WO 95/20578 | 8/1995 |
| WO | WO 95/35298 | 12/1995 |
| WO | WO 96/11902 | 4/1996 |
| WO | WO 96/19455 | 6/1996 |
| WO | WO 96/22282 | 7/1996 |
| WO | WO 96/22293 | 7/1996 |
| WO | WO 96/22294 | 7/1996 |
| WO | WO 96/22295 | 7/1996 |
| WO | WO 96/36619 | 11/1996 |
| WO | WO 96/41795 | 12/1996 |
| WO | WO 97/24355 | 7/1997 |
| WO | WO 97/36480 | 10/1997 |
| WO | WO 97/46560 | 12/1997 |
| WO | WO 97/49707 | 12/1997 |
| WO | WO 97/49708 | 12/1997 |
| WO | WO 98/24771 | 6/1998 |
| WO | WO 98/34632 | 8/1998 |
| WO | WO 98/45242 | 10/1998 |
| WO | WO 99/00359 | 1/1999 |
| WO | WO 99/00372 | 1/1999 |
| WO | WO 99/17777 | 4/1999 |
| WO | WO 99/20611 | 4/1999 |
| WO | WO 99/24415 | 5/1999 |
| WO | WO 99/26944 | 6/1999 |
| WO | WO 99/32477 | 7/1999 |
| WO | WO 99/38845 | 8/1999 |
| WO | WO 99/54301 | 10/1999 |
| WO | WO 99/62901 | 12/1999 |
| WO | WO 00/02850 | 1/2000 |
| WO | WO 00/26202 | 5/2000 |
| WO | WO 00/39118 | 7/2000 |
| WO | WO 00/46203 | 8/2000 |
| WO | WO 00/58293 | 10/2000 |
| WO | WO 01/00579 | 1/2001 |
| WO | WO 01/12621 | 2/2001 |
| WO | WO 01/16097 | 3/2001 |
| WO | WO 01/19788 | 3/2001 |
| WO | WO 01/20327 | 3/2001 |
| WO | WO 01/26652 | 4/2001 |
| WO | WO 01/32639 | 5/2001 |
| WO | WO 01/44216 | 6/2001 |
| WO | WO 01/64642 | 9/2001 |
| WO | WO 01/64643 | 9/2001 |
| WO | WO 01/74791 | 10/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/00633 | 1/2002 |
| WO | WO 02/08209 | 1/2002 |
| WO | WO 02/14312 | 2/2002 |
| WO | WO 02/24682 | 3/2002 |
| WO | WO 02/26718 | 4/2002 |
| WO | WO 02/26731 | 4/2002 |
| WO | WO 02/28835 | 4/2002 |
| WO | WO 02/42270 | 5/2002 |
| WO | WO 02/46173 | 6/2002 |
| WO | WO 02/48106 | 6/2002 |
| WO | WO 02/51831 | 7/2002 |
| WO | WO 02/64545 | 8/2002 |
| WO | WO 02/79145 | 10/2002 |
| WO | WO 03/000262 | 1/2003 |
| WO | WO 03/000267 | 1/2003 |
| WO | WO 03/015518 | 2/2003 |
| WO | WO 03/015774 | 2/2003 |
| WO | WO 03/022856 | 3/2003 |
| WO | WO 03/024222 | 3/2003 |
| WO | WO 03/026652 | 4/2003 |
| WO | WO 03/028641 | 4/2003 |
| WO | WO 03/047626 | 6/2003 |
| WO | WO 03/048152 | 6/2003 |
| WO | WO 03/051366 | 6/2003 |
| WO | WO 03/055482 | 7/2003 |
| WO | WO 03/066613 | 8/2003 |

| | | |
|---|---|---|
| WO | WO 03/080585 | 10/2003 |
| WO | WO 03/082838 | 10/2003 |
| WO | WO 03/095438 | 11/2003 |
| WO | WO 03/097824 | 11/2003 |
| WO | WO 2004/002481 | 1/2004 |
| WO | WO 2004/007472 | 1/2004 |
| WO | WO 2004/022536 | 3/2004 |
| WO | WO 2004/031179 | 4/2004 |
| WO | WO 2004/045614 | 6/2004 |
| WO | WO 2004/046139 | 6/2004 |
| WO | WO 2004/050645 | 6/2004 |
| WO | WO 2004/052869 | 6/2004 |
| WO | WO 2004/063179 | 7/2004 |
| WO | WO 2004/063194 | 7/2004 |
| WO | WO 2004/072031 | 8/2004 |
| WO | WO 2004/072066 | 8/2004 |
| WO | WO 2004/076420 | 9/2004 |
| WO | WO 2004/080966 | 9/2004 |
| WO | WO 2004/081001 | 9/2004 |
| WO | WO 2004/085385 | 10/2004 |
| WO | WO 2004/085406 | 10/2004 |
| WO | WO 2004/110350 | 12/2004 |
| WO | WO 2004/110375 | 12/2004 |
| WO | WO 2005/042513 | 5/2005 |
| WO | WO 2005/044801 | 5/2005 |
| WO | WO 2005/048953 | 6/2005 |
| WO | WO 2005/049019 | 6/2005 |
| WO | WO 2005/054200 | 6/2005 |
| WO | WO 2005/054233 | 6/2005 |
| WO | WO 2005/056530 | 6/2005 |
| WO | WO 2005/063738 | 7/2005 |
| WO | WO 2005/066145 | 7/2005 |
| WO | WO 2005/080359 | 9/2005 |
| WO | WO 2005/080360 | 9/2005 |
| WO | WO 2005/090332 | 9/2005 |
| WO | WO 2005/095417 | 10/2005 |
| WO | WO 2005/095418 | 10/2005 |
| WO | WO 2005/103021 | 11/2005 |
| WO | WO 2005/121110 | 12/2005 |
| WO | WO 2005/123132 | 12/2005 |
| WO | WO 2006/016174 | 2/2006 |
| WO | WO 2006/016178 | 2/2006 |
| WO | WO 2006/016194 | 2/2006 |
| WO | WO 2006/030925 | 3/2006 |
| WO | WO 2006/040527 | 4/2006 |
| WO | WO 2006/040528 | 4/2006 |
| WO | WO 2006/040529 | 4/2006 |
| WO | WO 2006/066613 | 6/2006 |
| WO | WO 2006/114180 | 11/2006 |
| WO | WO 2006/125958 | 11/2006 |
| WO | WO 2006/125972 | 11/2006 |
| WO | WO 2007/007040 | 1/2007 |
| WO | WO 2007/007042 | 1/2007 |
| WO | WO 2007/017649 | 2/2007 |
| WO | WO 2007/028135 | 3/2007 |
| WO | WO 2007/030567 | 3/2007 |
| WO | WO 2007/031739 | 3/2007 |
| WO | WO 2007/053657 | 5/2007 |
| WO | WO 2007/060448 | 5/2007 |
| WO | WO 2007/105637 | 9/2007 |
| WO | WO 2008/050101 | 5/2008 |
| WO | WO 2008/050117 | 5/2008 |
| WO | WO 2008/075073 | 6/2008 |

OTHER PUBLICATIONS

Alvarez et al. "Expression of the glucagon-like peptide-1 receptor gene in rat brain" J. Neurochem. 66(3):920-927 (1996).
Anderson et al "Pyridopyrimidines. 6. Nucleophilic substitutions in the pyrido[2,3-d]pyrimidine series" J. Org. Chem. 42(6):993-996 (1977).
Ando et al. "Fluoride salts on alumina as reagents for alkylation of phenols and alcohols" Bull. Chem. Soc. Jpn. 55(8):2504-2507 (1982).
Atwell et al. "Potential antitumor agents. VI. Bisquaternary salts" J. Med. Chem. 11(2):295-300 (1968).
Baker et al. "Structure and synthesis of Pallescansin E utilising a modified Wadsworth-Emmons reaction" J. Chem. Soc., Perkin Trans. 1, 12:3087-3091 (1981).
Baker et al. "Synthesis of Pallescensin-E: Use of crown ether in the Wadsworth procedure for olefin formation" Tetrahedron Letters 22:161-162 (1981).
Balant et al. "Metabolic considerations in prodrug desing" Chapter twenty-three, Burger's Medicinal Chemistry and Drug Discovery, 5th Edition, vol. 1, NY: John Wiley & Sons, Inc. 949-982 (1995).
Beilstein Registry No. 6511458 (Apr. 18, 1994) [XP002272206].
Bell et al. "Glucokinase mutations, insulin secretion, and diabetes mellitus" Annu. Rev. Physiol. 58:171-186 (1996).
Beller et al. "Photochemical synthesis of benzo[f]quinolines" J Org Chem. 42(22):3514-3518 (1977).
Berl et al. "Induced fit selection of a barbiturate receptor from a dynamic structural and conformational/ configurational library" European J. Org. Chem. (11):3089-3094 (1999).
Berl et al. "Template-induced and molecular recognition directed hierarchical generation of supramolecular assemblies from molecular strands" Chem. Eur. J. 6(11):1938-1946 (2000).
Bonina et al. "Synthesis and pharmacologic activity of 2-arylethenylthiazol-4-acetic and 4-carboxylic acids" II Farmaco 40(11):875-884 (1985).
Boucherle et al. "Recherches dans la serie des cetones polyphenoliques IV. Thiazoles" Chimica. Therapeutica. 3(5):360-363 (1968) (Translation enclosed).
Bowden et al. "Structure-activity relations. Part 10. Metal-ion-complexation studies of a series of substituted benzamidotetrazoles" J. Chem. Research (Synopses) 11:304 (1991).
Bowden et al. "Structure-activity relations. Part 13. Inhibitors of cyclic nucleotide phosphodiesterase and anaphylaxis. Inhibition by a series of substituted benzamidotetrazoles" J. Chem. Research (Synopses) 6:206 (1992).
Brenner et al. "Imino-bridged heterocycles. VII. (1) N-aminobenzocycloheptapyridinimines" J. Heterocyclic Chem. 23:1331-1332 (1986).
Brocklehurst et al. "Stimulation of hepatocyte glucose metabolism by novel small molecule glucokinase activators" Diabetes 53:535-541 (2004).
Caro et al. "Liver glucokinase: Decreased activity in patients with type II diabetes" Horm. Metab. Res. 27(1):19-22 (1995).
Carroll et al. "The in vitro characterisation of a novel Glucokinase activator" Stress, Signalling and Control, Biochemical Society Meeting 679, University of Essex, UK (Jul. 2-4, 2003).
Caulfield et al. "The first potent and selective inhibitors of the glycine transporter type 2" J. Med. Chem. 44(17):2679-2682 (2001).
Cavier et al. "Recherches sur les derives nitres d'interet biologique. XVI. Relations entre structures et activites protozoocides, anthelminthiques et molluscicides dans la serie du benzamido-2 nitro-5 thiazole" European Journal of Medicinal Chemistry, Chimica Therapeutica 13(6): 539-543 (1978) (Translation enclosed).
Chemical Abstracts Service, Columbus, Ohio, US: CAS Registry No. 438028-05-8 (Nov. 15, 2001); CAS Registry No. 438024-90-9 (Nov. 15, 2001), [XP002272448].
Chemical Abstracts Service, Columbus, Ohio, US: CAS Registry No. 445284-93-5 (Jul. 9, 2002); CAS Registry No. 445250-52-2 (Jul. 9, 2002); CAS Registry No. 445030-98-8 (Jul. 9, 2002); CAS Registry No. 445017-74-3 (Jul. 9, 2002); CAS Registry No. 444935-78-8 (Jul. 9, 2002); CAS Registry No. 444923-81-3 (Jul. 9, 2002); CAS Registry No. 438222-80-1 (Jul. 9, 2002); CAS Registry No. 438221-01-3 (Jul. 9, 2002); CAS Registry No. 354550-59-7 (Jul. 9, 2002); CAS Registry No. 438537-80-5 (Jul. 9, 2002); CAS Registry No. 353770-14-6 (Jul. 9, 2002); CAS Registry No. 352690-95-0 (Jul. 9, 2002); CAS Registry No. 353478-21-4 (Jul. 9, 2002); CAS Registry No. 353477-20-0 (Jul. 9, 2002); CAS Registry No. 353474-36-9 (Jul. 9, 2002); CAS Registry No. 362473-72-1 (Jul. 9, 2002); CAS Registry No. 303140-37-6 (Jul. 9, 2002); [XP002272449].

Chemical Abstracts Service, Columbus, Ohio, US: CAS Registry No. 354767-51-4 (Sep. 5, 2001).

Chemical Abstracts Service, Columbus, Ohio, US: CAS Registry No. 354767-66-1 (Sep. 5, 2001).

Christesen et al. "The second activating glucokinase mutation (A456V): Implications for glucose homeostasis and diabetes therapy" Diabetes 51(4):1240-1246 (2002).

Ciaceri et al. "Analgesic, antipyretic and anti-inflammatory action of some new acids of the phenylethylenethiazole series" Minerva Medica 63(42):2409-2413 (1972).

Coburn et al. "Mesoionic purinone analogs IV: Synthesis and in vitro antibacterial properties of mesoionic thiazolo(3,2-α)pyrimidin-5,7-diones and mesoionic 1,3,4-thiadizolo(3,2-α)pyrimidin-5,7-diones" J. Pharm. Sciences. 62(11):1785-1789 (1973).

Coghlan "Small molecule Glucokinase Activators (GKAs) as novel anti-diabetic agents" CIDEM seminar (May 2005).

Coghlan "Small molecule Glucokinase Activators (GKAs) as novel anti-diabetic agents" Society for Medicines Research Seminar (Jun. 2004).

Coghlan et al. "Glucokinase activators in diabetes management" Expert Opin. Investig. Drugs 17(2):145-167 (2008).

Coope et al. "Predictive blood glucose lowering efficacy by Glucokinase activators in high fat fed female Zucker rats" British Journal of Pharmacology 149(3):328-335 (2006).

Corbett "Glucokinase activators: Discovery of novel, orally active glucose lowering agents" Abstract, Cambridge Healthtech Institute's Eleventh Annual Molecular Medicine Tri-Conference, Moscone West Convention Center, San Francisco, CA (Mar. 24-26, 2004).

Corbett "Glucokinase activators: Discovery of novel, orally active glucose lowering agents" Presentation Slides, Cambridge Healthtech Institute's Eleventh Annual Molecular Medicine Tri-Conference, Moscone West Convention Center, San Francisco, CA (Mar. 24-26, 2004).

Cushman et al. "Synthesis and evaluation of new protein-tyrosine kinase inhibitors. Part 1. Pyridine-containing stilbenes and amides" Bioorganic & Medicinal Chemistry Letters 1(4):211-214 (1991).

De Paulis et al. "Potential antipsychotic agents. 6. Synthesis and antidopaminergic properties of substituted N-(1-benzyl-4-piperidinyl)salicylamides and related compounds. QSAR based design of more active members" Eur. J. Med. Chem. 25:507-517 (1990).

DeFronzo et al. "The triumvirate: β-cell, muscle, liver. A collusion responsible for NIDDM" Diabetes 37:667-687 (1988).

DeJohn et al. "Functionalization of Substituted 2(1H)- and 4(1H)-Pyridones. III. The preparation of substituted 6-vinyl-1,2-dihydro-2-oxo-- and 1,4-dihydro-4-oxo-3-pyridinecarboxylic acids through the chemistry of pyridone dianions" J. Heterocyclic Chem. 20(5):1295-1302 (1983).

Desai et al. "Phenotypic correction of diabetic mice by adenovirus-mediated glucokinase expression" Diabetes 50:2287-2295 (2001).

Edmont et al. "Synthesis and evaluation of quinoline carboxyguanidines as antidiabetic agents" Bioorg. Med. Chem. Lett. 10(16):1831-1834 (2000).

Elpern et al. "Iodinated Benzamidotetrazoles" J. Org. Chem. 22: 1686 (1957).

Ferre et al. "Correction of diabetic alterations by glucokinase" PNAS USA 93(14):7225-7230 (1996).

Ford et al. "Synthesis and quantitative structure-activity relationships of antiallergic 2-hydroxy-N-1H-tetrazol-5-ylbenzamides and N-(2-hydroxyphenyl)-1H-tetrazole-5-carboxamides" J. Med. Chem. 29(4):538-549 (1986).

Froguel et al. "Familial hyperglycemia due to mutations in glucokinase —Definition of a subtype of diabetes mellitus" New Engl. J. Med. 328:697-702 (1993).

Fujimoto et al. "Administration of D-glucosamine into the third cerebroventricle induced feeding accompanied by hyperglycemia in rats" Life Sciences 37(26):2475-2482 (1985).

Gill et al. "Stimulation of insulin release by a small molecule glucokinase activator" EASD Islet Study Group, Abstract (Nov. 2005).

Gill et al. "Stimulation of Insulin Release in MIN6 Cells and Isolated Rodent Islets by a Small Molecule Glucokinase Activator (GKA50)" Poster presented at 42nd EASD Meeting Copenhagen (2006) and Diabetologia vol. 49 (Supplement 1) 0501 (2006).

Gill et al. "Upregulation of key β-cell genes and improvement of function in rodent islets following chronic in vitro treatment with a glucokinase activator" Poster presented at 43rd EASD Meeting, Amsterdam (Sep. 17-21, 2007) and Diabetologia vol. 50 (Supplement 1) S218 (2007).

Glaser et al. "Familial hyperinsulinism caused by an activating glucokinase mutation" The New England Journal of Medicine 338(4):226-230 (1998).

Gorman et al. "Effect of high-fat diet on glucose homeostasis and gene expression in Glucokinase (GK) heterozygous knock-outs" Abstract Number: 0108-OR, 67th Annual Scientific Sessions, American Diabetes Association, Chicago, IL (Jun. 22-26, 2007).

Grimsby "Glucokinase activators: Potential treatment for type 2 diabetes" Roche, SMi Diabetes, London, UK (Oct. 28-29, 2002).

Grimsby et al. "Allosteric activators of glucokinase: Potential role in diabetes therapy" Science 301(5631):370-373 (2003).

Guertin et al. "Small molecule glucokinase activators as glucose lowering agents: A new paradigm for diabetes therapy" Current Medicinal Chemistry 13(15):1839-1843 (2006).

Hashimoto et al. "Evaluation of differentiation-inducing activity of retinoids on human leukemia cell lines HL-60 and NB4" Biol. Pharm. Bull. 19(10):1322-1328 (1996).

Hirst et al. "Molecular recognition of phosphate esters: A balance of hydrogen bonding and proton transfer interactions" Israel Journal of Chemistry 32:105-111(1992).

Horsak et al. "Method of evaluation of the phase diagram of a system with formation of a compound" Chem. Zvesti. 36(3):311-320 (1982).

Isomura et al. "Z-type deposition of a polymerizable amphiphile to fabricate an immobilized LB film showing strong second harmonic generation" Thin Solid Films 244:939-942 (1994).

Johnson et al. "Glucose-dependent modulation of insulin secretion and intracellular calcium ions by GKA50 — A glucokinase activator" Abstract No. 0592-P, 67th Annual Scientific Sessions, American Diabetes Association, Chicago, IL (Jun. 22-26, 2007).

Julia et al. "Synthesis of a 2,3,4,4a,5,6-hexahydrobenzo[f]quinoline system by "aryne substitution"" Bull Chem Soc France 11:4463-4467 (1968) (Translation enclosed).

Kamata et al. "Pyroelectricity of noncentrosymmetric Langmuir-Blodgett films of phenylpyrazine derivatives" Japan J. Appl. Phys. 33(2):1074-1078 (1994).

Kar "Cinchophen analogues as potential CNS agents" J Pharm Sci. 72(9):1082-1084 (1983).

Knoppova et al. "Synthesis and properties of 5-styryl-2-furancarboxlic acids" Collection Czechoslovak Chem. Commun. 46:2716-2728 (1981).

Konig et al. "Binding of heptanedioic acid to a threefold pyridine arylamide receptor. Enhancement of the stability of supramolecular solution structures by multiple binding sites" J. Org. Chem. 60(13):4291-4293 (1995).

Kunishima et al. "4-(4,6-Dimethoxy-1,3,5-triazin-2-yl)-4-methyl-morpholinium chloride: An efficient condensing agent leading to the formation of amides and esters" Tetrahedron 55:13159-13170 (1999).

Kurata et al. "D-Glucose suppression of eating after intra-third ventricle infusion in rat" Physiology & Behavior 37:615-620 (1986).

Kurata et al. "Structural evaluation of glucose analogues on feeding elicitation in rat" Metabolism 38(1):46-51 (1989).

Lai et al. "Formation of columnar arrangements in copper(ii) complexes of 2-phenylazomethinopyridine derivatives" J. Materials Chemistry 8(11):2379-2383 (1998).

Leighton et al. "Improved glycemic control after sub-acute administration of a Glucokinase activator to male zucker (fa/fa) rats" Abstract Number: 0377-OR, 67th Annual Scientific Sessions, American Diabetes Association, Chicago, IL (Jun. 22-26, 2007).

Leighton et al. "Small molecule glucokinase activators as novel anti-diabetic agents" Biochemical Society Transactions 33(Part 2):371-374 (2005).

Leighton, "Pre-clinical disease models —challenges and success stories"44th Drug Information Association Annual Meeting, Boston, MA, US (2008).

Levin "Glucosensing neurons do more than just sense glucose" International Journal of Obesity 25(Suppl 5): S68-S72 (2001).

Levin et al. "Brain glucose sensing and body energy homeostasis: role in obesity and diabetes" Am. J. Physiol. 276(5 Pt 2):R1223-R1231 (1999).

Levin et al. "Differential effects of diet and obesity on high and low affinity sulfonylurea binding sites in the rat brain" Brain Research 739(1-2):293-300 (1996).

Levin et al. "In vivo and in vitro regulation of [3H]glyburide binding to brain sulfonylurea receptors in obesity-prone and resistant rats by glucose" Brain Research 776(1-2):146-153 (1997).

Levin et al. "Reduced glucose-induced neuronal activation in the hypothalamus of diet-induced obese rats" Brain Research 808(2):317-319 (1998).

Levkoev et al. "Research on cyanide dyes 11. 7,7'-Dimethylthiacarbocyanines" Zhurnal Obshchei Khimii 27:3097-3107 (1957) (Translation enclosed).

Lith, "Evaluation of the effects on whole body glucose metabolism after single doses of X2000 —A glucose lowering agent" Poster presentation, Master thesis in Pharmaceutical Bioscience, Goteborgs University (2008).

Lynch et al. "Localization of glucokinase gene expression in the rat brain" Diabetes 49(5):693-700 (2000).

Mastafanova et al. "Features of the catalytic reduction of 4-(3-oxoquinuclidyl-2-methylene)-6-methoxyquinoline and its ethyleneketal" Khimiya Geterotsiklicheskikh Soedinenii (1):86-94 (1989) (Translation enclosed).

Mastafanova et al. "Synthesis and study of the antihypertensive activity of substituted N-acetylmercaptopropionyl-6-[2'-phenylethyl]pipecolinic acids" Khimiko Farmatsevticheskii Zhurnal 22(3):294-302 (1988).

Mastafanova et al. "Synthesis, Anti-Inflammatory and Analgesic Activity of 1,6-Disubstituted Pipecolic and 6-Substituted Picolinic Acids" Khimiko Farmatsevticheskii Zhurnal 22(4) 428-431 (1988).

Mazik et al. "Molecular recognition of carbohydrates by artificial receptors: systematic studies towards recognition motifs for carbohydrates" Chem. Eur. J. 7(3):664-670 (2001).

Mazik et al. "Molecular recognition of carbohydrates by artificial polypyridine and polypyrimidine receptors" Angewandte Chemie International Edition 39(3):551-554 (2000).

McKerrecher "Design and synthesis of novel glucokinase activators" 13th RSC-SCI Medicinal Chemistry Symposium, Churchill College, Cambridge (Sep. 4-7, 2005).

McKerrecher et al. "Design & synthesis of novel glucokinase activators as potential treatments for type 2 diabetes" 233rd ACS National Meeting, Chicago, IL (Mar. 25-29, 2007).

McKerrecher et al. "Design and synthesis of novel glucokinase activators as potential treatment for type 2 diabetes" Frontiers in Medicinal Chemistry, Frankfurt (Mar. 12-15, 2006).

McKerrecher et al. "Design of a potent, soluble glucokinase activator with excellent in vivo efficacy" Bioorg. Med. Chem. Lett. 16(10):2705-2709 (May 15, 2006) Epub 2006 Feb. 28.

McKerrecher et al. "Discovery, synthesis and biological evaluation of novel glucokinase activators" Bioorg Med Chem Lett. 15(8):2103-2106 (2005).

McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 28-Apr. 1, 2004 (paper 341).

McKerrecher et al. "Identification of orally bioavailable small molecule activators of glucokinase" Abstract, Anglo-Swedish Medicinal Chemistry Meeting (Mar. 2005).

Meijer et al "Chiral amplification in supramolecular stacks" Polymer Preprints 41(1):902-903 (2000).

Mobbs et al. "Brain glucose-sensing mechanisms: ubiquitous silencing by aglycemia vs. hypothalamic neuroendocrine responses" Am. J. Physiol. Endocrinol. Metab. 281(4):E649-E654 (2001).

Moore et al. "Acute fructose administration improves oral glucose tolerance in adults with type 2 diabetes" Diabetes Care 24(11):1882-1887 (2001).

Motesharei et al. "Molecular recognition in membrane mimics: A fluorescence probe" J. Am. Chem. Soc. 116(16):7413-7414 (1994).

Motesharei et al. "Molecular recognition on functionalized self-assembled monolayers of alkanethiols on gold" J. Am. Chem. Soc. 120(29): 7328 -7336 (1998).

Palmans "Extended-core discotic liquid crystals based on the intramolecular H-bonding in N-acylated 2,2'-bipyridine-3,3'-diamine moieties" Chem. Eur. J. 3(2):300-307 (1997).

Plieninger et al. "Synthesis of 7,8-dihydro-5,6-benzoquinoline-(3)-carboxylic acid" Chemische Berichte 87:882-887 (1954) (Translation enclosed).

Printz et al. "Mammalian glucokinase" Annu. Rev. Nutr. 13:463-496 (1993).

Prousek et al. "Preparation and electron transfer-induced cis-trans isomerization reactions of 1-(5-nitro-2-furyl)-, 1-(5-nitro-2-thienyl)-, and 1-(4-nitrophenyl)-2-R ethylenes" Collect. Czech. Chem. Commun. 54:1675-1682 (1989).

Qian-Cutrone et al. "Glucolipsin A and B, two new glucokinase activators produced by Streptomyces purpurogeniscleroticus and Nocardia vaccinii" Journal of Antibiotics (Tokyo), 52(3):245-255 (1999).

Ralph et al. "Glucose Modulation of Glucokinase Activation by Small Molecules" Biochemistry 47(17):5028-5036 (2008).

Rivalle et al. "2,3 Disubstituted furans and pyrroles —XVIII: Synthesis annd rearrangement of 4H-dihydro-9,10 benzo[4,5]cyclohepta[1,2-b]furannones-4" Tetrahedron 32(7):829-834 (1976).

Rogers et al. "Mesoionic purinone analogues as inhibitors of cyclic-AMP phosphodiesterase: a comparison of several ring systems" J. Med. Chem. 24(11):1284-1287 (1981).

Roncero et al. "Functional glucokinase isoforms are expressed in rat brain" J. Neurochem. 74(5):1848-1857 (2000).

Rowe et al. "Potassium channel dysfunction in hypothalamic glucose-receptive neurones of obese Zucker rats" Journal of Physiology 497.2:365-377 (1996).

Sarabu et al., "Glucokinase activators as new type 2 diabetes therapeutic agents" Expert Opinion on Therapeutic Patents 18(7):759-768 (2008).

Schuit et al. "Glucose sensing in pancreatic β-Cells. A model for the study of other glucose-regulated cells in gut, pancreas, and hypothalamus" Diabetes 50:1-11(2001).

Sekera et al. "No. 69. —Recherches sur les anesthesiques locaux (XI memoire) Synthese de quelques nouveaux β-alcoxyethoxycarbanilates et β-alcoxyethoxycinchonamides amines" Soc. Chim., 5th Series, Memoires 401-404 (1959) (Translation enclosed).

Seoane et al. "Glucokinase overexpression restores glucose utilization and storage in cultured hepatocytes from male Zucker diabetic fatty rats" J Biol Chem. 274(45):31833-31838 (1999).

Shiota et al. "Glucokinase gene locus transgenic mice are resistant to the development of obesity-induced type 2 diabetes" Diabetes 50(3):622-629 (2001).

Shorvon, "Pyrrolidone derivatives" Lancet 358(9296):1885-1892 (2001).

Spanswick et al. "Insulin activates ATP-sensitive K+ channels in hypothalamic neurons of lean, but not obese rats" Nature Neuroscience 3(8):757-758 (2000).

Spanswick et al. "Leptin inhibits hypothalamic neurons by activation of ATP-sensitive potassium channels" Nature 390(6659):521-525 (1997).

Stout et al. "Synthesis and antiarrhythmic and parasympatholytic properties of substituted phenols. 3. Modifications to the linkage region (region 3)" J. Med. Chem. 28(3):295-298 (1985).

Suhua et al. "Synthesis and biological activity of tyrosine protein kinase inhibitors" Acta Pharmaceutica Sinica 32(7): 515-523 (1997).

Tecilla et al. "Hydrogen-bonding self-assembly of multichromophore structures" J. Am. Chem. Soc. 112:9408-9410 (1990).

Tecilla et al. "Synthetic hydrogen bonding receptors as models of transacylase enzymes" Tetrahedron 51(2):435-448 (1995).

Tecilla et al. "Transition-state stabilization and molecular recognition: acceleration of phosphoryl-transfer reactions by an artificial receptor" J. Am. Chem. Soc. 112:9586-9590 (1990).

Tornetta et al. "Arylvinylthiazole derivatives with anti-inflammatory, analgesic and anti-pyretic activity" Bollettino Delle Sedute Accad. Giovenia Sci. Nat. Catanica. Series 6, 11(9-10):89-95 (1973) (Translation enclosed).

Tucker et al. "Novel Inhibitors of prolyl 4-hydroxylase. 2. 5-amide substituted pyridine-2-carboxylic acids" J. Med. Chem. 3(5)5:804-807 (1992).

Van Gorp et al. "C3-symmetrical supramolecular architectures: fibers and organic gels from discotic trisamides and trisureas" .J Am. Chem. Soc. 124(49):14759-14769 (2002).

Vanderstelt et al. "Synthesis and pharmacological properties of some derivatives of 5H-benzo[4,5] cyclohepta[1,2-b] pyridine and of 11H-benzo[5,6] cyclohepta[1,2-c] pyridine III" Arzneim. Forsch. 22(1):133-137 (1972).

Velho et al. "Impaired hepatic glycogen synthesis in glucokinase-deficient (MODY-2) subjects" J. Clin. Invest. 98(8):1755-1761 (1996).

Vertigan et al. "Impact of cell glycogen content on modulation of hepatocyte glucose metabolism by pharmacological agents" Diabetologia, 47 Supp 1, A 214, 589 (2004).

Williams et al. "Meeting the needs of type 2 diabetes patients" Highlights from the society for medicines research symposium type II diabetes: Mechanisms and emerging therapeutic targets, held Jun. 17, 2004, in London, United Kingdom, Drug News and Perspectives, 17(8) 1-4 (Oct. 2004).

Winzell et al. "Glucokinase Activation Reduces Glycemia and Improves Glucose Tolerance in Mice with High-fat Diet-induced Insulin Resistance" Abstract No. 1482-P, 67th Annual Scientific Sessions, American Diabetes Association, Chicago, IL (Jun. 22-26, 2007) and Diabetes vol. 56 (Supplement 1) 1482-P (2007).

Yakushijin et al. "Intramolecular ring formation of phenyl azide and furan" Heterocycles 12(8):1021-1026 (1979).

Yakushijin et al. "Intramolecular ring formation of phenyl azide and furan moieties" Chem. Pharm. Bull. 30(1):140-151 (1982).

Yang et al. "Hypothalamic glucose sensor: similarities to and differences from pancreatic beta-cell mechanisms" Diabetes 48(9):1763-1772 (1999).

Yoshina et al. "Studies of heterocyclic compounds. II. Synthesis of 2-furylvinyl-benzenes and studies of polarography" Yakugaku Zasshi 88(4):398-404 (1968).

Yoshina et al. "Studies of heterocyclic compounds. III. Synthesis of methyl 5-(2-phenylvinyl)2-furoate" Yakugaku Zasshi 88(4):405-409 (1968).

Yoshina et al. "Studies of heterocyclic compounds. IV. Ultraviolet spectra of 2-(2-furyl)vinylbenzenes and 2-(2-furyl)vinylfurans" Yakugaku Zasshi 88(4):410-416 (1968).

Yoshina et al. "Studies of heterocyclic compounds. VI. 2-(Carbomethoxy-2-furyl)vinyl benzenes and their ultraviolet spectra" Yakugaku Zasshi 88(4):977-983 (1968).

Youssefyeh et al. "Development of high-affinity 5-HT3 receptor antagonists. 1. Initial structure-activity relationship of novel benzamides" J. Med. Chem. 35(5): 895-903 (1992).

Zhang et al. "Synthesis based on affinity separation (SAS): separation of products having barbituric acid tag from untagged compounds by using hydrogen bond interaction" Synlett 5:590-596 (2001).

Eycken et al., Synthesis of (E)-5-(2-arylvinyl)-2-(hetero)arylpyridines, (E)-2-(2-arylvinyl)-5-methoxycarbonylpyridines and (E,E)-2,5-bis(2-arylvinyl)pyridines as polarity and pH probes, 2002, J. Chem. Soc., Perkin. Trans. 2, p. 929.

Robertson et al. "Structure-activity relationships of arylimidazopyridine cardiotonics: discovery and inotropic activity of 2-[2-methoxy-4-(methylsulfinyl)phenyl]-1H-imidazo[4,5-c]pyridine" Journal of Medicinal Chemistry 28:717-727 (1985).

West, Anthony R., "Solid State Chemistry and its Applications" Wiley, New York, pp. 358 and 365 (1988).

Wolff, Manfred E. "Burger's Medicinal Chemistry", 5th Edition, Part I, John Wiley & Sons, pp. 975-977 (1995).

Takagi et al. "Studies on metabolic fate of 3,4,5-trimethoxy-N-(3-piperidyl)benzamide(KU-54). (2). Metabolism in rats" Accession No. 1984:503556 HCAPLUS, Abstract of Oyo Yakuri 27(6):1167-1174 (1984).

HETEROARYL BENZAMIDE DERIVATIVES FOR USE AS GLK ACTIVATORS IN THE TREATMENT OF DIABETES

This application is a Continuation Application of copending U.S. patent application Ser. No. 11/995,077, filed Jul. 11, 2008, which is a U.S. National Phase Application of International Application No. PCT/GB2006/002471 (filed Jul. 3, 2006) which claims the benefit of Great Britain Patent Application No. 0514173.4 (filed Jul. 9, 2005), Great Britain Patent Application No. 0516297.9 (filed Aug. 9, 2005), Great Britain Patent Application No. 0523862.1 (filed Nov. 24, 2005), Great Britain Patent Application No. 0524589.9 (filed Dec. 2, 2005) and Great Britain Patent Application No. 0607977.6 (filed Apr. 22, 2006), all of which are hereby incorporated by reference in their entirety.

The present invention relates to a group of benzoyl amino heterocyclyl compounds which are useful in the treatment or prevention of a disease or medical condition mediated through glucokinase (GLK or GK), leading to a decreased glucose threshold for insulin secretion. In addition the compounds are predicted to lower blood glucose by increasing hepatic glucose uptake. Such compounds may have utility in the treatment of Type 2 diabetes and obesity. The invention also relates to pharmaceutical compositions comprising said compounds and to methods of treatment of diseases mediated by GLK using said compounds.

In the pancreatic β-cell and liver parenchymal cells the main plasma membrane glucose transporter is GLUT2. Under physiological glucose concentrations the rate at which GLUT2 transports glucose across the membrane is not rate limiting to the overall rate of glucose uptake in these cells. The rate of glucose uptake is limited by the rate of phosphorylation of glucose to glucose-6-phosphate (G-6-P) which is catalysed by glucokinase (GLK) [1]. GLK has a high (6-10 mM) Km for glucose and is not inhibited by physiological concentrations of G-6-P [1]. GLK expression is limited to a few tissues and cell types, most notably pancreatic β-cells and liver cells (hepatocytes) [1]. In these cells GLK activity is rate limiting for glucose utilisation and therefore regulates the extent of glucose induced insulin secretion and hepatic glycogen synthesis. These processes are critical in the maintenance of whole body glucose homeostasis and both are dysfunctional in diabetes [2].

In one sub-type of diabetes, Maturity-Onset Diabetes of the Young Type 2 (MODY-2), the diabetes is caused by GLK loss of function mutations [3,4]. Hyperglycaemia in MODY-2 patients results from defective glucose utilisation in both the pancreas and liver [5]. Defective glucose utilisation in the pancreas of MODY-2 patients results in a raised threshold for glucose stimulated, insulin secretion. Conversely, rare activating mutations of GLK reduce this threshold resulting in familial hyperinsulinism [6, 6a, 7]. In addition to the reduced GLK activity observed in MODY-2 diabetics, hepatic glucokinase activity is also decreased in type 2 diabetics [8]. Importantly, global or liver selective overexpression of GLK prevents or reverses the development of the diabetic phenotype in both dietary and genetic models of the disease [9-12]. Moreover, acute treatment of type 2 diabetics with fructose improves glucose tolerance through stimulation of hepatic glucose utilisation [13]. This effect is believed to be mediated through a fructose induced increase in cytosolic GLK activity in the hepatocyte by the mechanism described below [13].

Hepatic GLK activity is inhibited through association with GLK regulatory protein (GLKRP). The GLK/GLKRP complex is stabilised by fructose-6-phosphate (F6P) binding to the GLKRP and destabilised by displacement of this sugar phosphate by fructose-1-phosphate (F1P). F1P is generated by fructokinase mediated phosphorylation of dietary fructose. Consequently, GLK/GLKRP complex integrity and hepatic GLK activity is regulated in a nutritionally dependent manner as F6P is dominant in the post-absorptive state whereas F1P predominates in the post-prandial state. In contrast to the hepatocyte, the pancreatic β-cell expresses GLK in the absence of GLKRP. Therefore, β-cell GLK activity is regulated extensively by the availability of its substrate, glucose. Small molecules may activate GLK either directly or through destabilising the GLK/GLKRP complex. The former class of compounds are predicted to stimulate glucose utilisation in both the liver and the pancreas whereas the latter are predicted to act selectively in the liver. However, compounds with either profile are predicted to be of therapeutic benefit in treating Type 2 diabetes as this disease is characterised by defective glucose utilisation in both tissues.

GLK, GLKRP and the $K_{ATP}$ channel are expressed in neurones of the hypothalamus, a region of the brain that is important in the regulation of energy balance and the control of food intake [14-18]. These neurones have been shown to express orectic and anorectic neuropeptides [15, 19, 20] and have been assumed to be the glucose-sensing neurones within the hypothalamus that are either inhibited or excited by changes in ambient glucose concentrations [17, 19, 21, 22]. The ability of these neurones to sense changes in glucose levels is defective in a variety of genetic and experimentally induced models of obesity [23-28]. Intracerebroventricular (icv) infusion of glucose analogues, that are competitive inhibitors of glucokinase, stimulate food intake in lean rats [29, 30]. In contrast, icv infusion of glucose suppresses feeding [31]. Thus, small molecule activators of GLK may decrease food intake and weight gain through central effects on GLK. Therefore, GLK activators may be of therapeutic use in treating eating disorders, including obesity, in addition to diabetes. The hypothalamic effects will be additive or synergistic to the effects of the same compounds acting in the liver and/or pancreas in normalising glucose homeostasis, for the treatment of Type 2 diabetes. Thus the GLK/GLKRP system can be described as a potential "Diabesity" target (of benefit in both Diabetes and Obesity).

GLK is also expressed in specific entero-endocrine cells where it is believed to control the glucose sensitive secretion of the incretin peptides GIP (glucose-dependent insulinotropic polypeptide) and GLP-1 (Glucagon-Like Peptide-1) from gut K-cells and L-cells respectively (32, 33, 34). Therefore, small molecule activators of GLK may have additional beneficial effects on insulin secretion, b-cell function and survival and body weight as a consequence of stimulating GIP and GLP-1 secretion from these entero-endocrine cells.

In WO00/58293 and WO01/44216 (Roche), a series of benzylcarbamoyl compounds are described as glucokinase activators. The mechanism by which such compounds activate GLK is assessed by measuring the direct effect of such compounds in an assay in which GLK activity is linked to NADH production, which in turn is measured optically—see details of the in vitro assay described hereinafter. Compounds of the present invention may activate GLK directly or may activate GLK by inhibiting the interaction of GLKRP with GLK.

Further GLK activators have been described in WO03/095438 (substituted phenylacetamides, Roche), WO03/055482 (carboxamide and sulphonamide derivatives, Novo Nordisk), WO2004/002481 (arylcarbonyl derivatives, Novo Nordisk), and in WO03/080585 (amino-substituted benzoylaminoheterocycles, Banyu).

Our International application Number: WO03/000267 describes a group of benzoyl amino pyridyl carboxylic acids which are activators of the enzyme glucokinase (GLK).

Our International application Number: WO03/015774 describes compounds of the Formula (A):

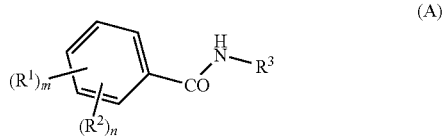

wherein $R^3$ is a substituted heterocycle other than a carboxylic acid substituted pyridyl.

International application WO2004/076420 (Banyu) describes compounds which are generally a subset of those described in WO03/015774, wherein for example $R^1$ is an (substituted) alkyl ether and $R^2$ is (substituted) phenoxy.

We have surprisingly found a small group of compounds, generally a selected subgroup of those described in WO 03/015774, which have generally superior potency for the GLK enzyme, and more advantageous physical properties, including, for example, higher aqueous solubility, higher permeability, and/or lower plasma protein binding. Consequently, such compounds having a balance of these properties would be expected to display higher plasma free drug levels and superior in vivo efficacy after oral dosing as determined, for example, by activity in Oral Glucose Tolerance Tests (OGTTs). Therefore this group of compounds would be expected to provide superior oral exposure at a lower dose and thereby be particularly suitable for use in the treatment or prevention of a disease or medical condition mediated through GLK. The compounds of the invention may also have superior potency and/or advantageous physical properties (as described above) and/or favourable toxicity profiles and/or favourable metabolic profiles in comparison with other GLK activators known in the art, as well as those described in WO 03/015774.

Thus, according to the first aspect of the invention there is provided a compound of Formula (I):

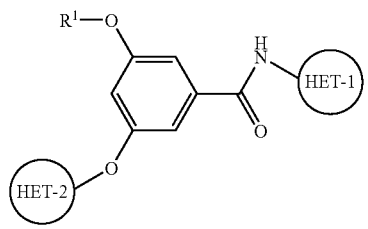

wherein:

$R^1$ is selected from isopropyl, but-2-yl, cyclopentyl, 1,1,1-trifluoroprop-2-yl, 1,3-difluoroprop-2-yl, but-1-yn-3-yl, 1-hydroxyprop-2-yl, 2-hydroxybut-3-yl, 1-hydroxybut-2-yl, tetrahydrofuryl, tetrahydropyranyl, 1-methoxyprop-2-yl, 1-methoxybut-2-yl, 2-hydroxyprop-1-yl, 2-methoxyprop-1-yl, 2-hydroxybut-1-yl, 2-methoxybut-1-yl, 1-fluoromethoxyprop-2-yl, 1,1-difluoromethoxyprop-2-yl and 1-trifluoromethoxyprop-2-yl;

HET-1 is a 5- or 6-membered, C-linked heteroaryl ring containing a nitrogen atom in the 2-position and optionally 1 or 2 further ring heteroatoms independently selected from O, N and S; which ring is optionally substituted on any nitrogen atom (provided it is not thereby quaternised) by a substituent selected from $R^7$ and/or on 1 or 2 available carbon atoms by a substituent independently selected from $R^6$;

HET-2 is a 5- or 6-membered heteroaryl ring, containing 1, 2 or 3 ring hetereoatoms independently selected from O, S and N; which ring is substituted on an available carbon atom by a substituent selected from $R^2$, and is optionally further substituted on 1 or 2 available carbon atoms by a substituent independently selected from $R^3$ and/or on an available nitrogen atom (provided it is not thereby quaternised) by a substituent selected from $R^{10}$;

$R^2$ is selected from —C(O)NR$^4$R$^5$ and —SO$_2$NR$^4$R$^5$;

$R^3$ is selected from methyl, trifluoromethyl and halo;

$R^4$ and $R^5$ together with the nitrogen atom to which they are attached form a 4 to 7 membered saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to a S(O) or S(O)$_2$ group; which ring is optionally substituted on an available carbon atom by 1 or 2 substituents independently selected from $R^8$ and/or on an available nitrogen atom by a substituent selected from $R^9$; or $R^4$ and $R^5$ together with the nitrogen atom to which they are attached form a 6-10 membered bicyclic saturated or partially unsaturated heterocyclyl ring, optionally containing 1 further nitrogen atom (in addition to the linking N atom), wherein a —CH$_2$— group can optionally be replaced by a —C(O)—; which ring is optionally substituted on an available carbon by 1 substituent selected from hydroxy and $R^3$ or on an available nitrogen atom by methyl;

$R^6$ is independently selected from (1-4C)alkyl, halo, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl;

$R^7$ is independently selected from (1-4C)alkyl, halo(1-4C)alkyl, dihalo(1-4C)alkyl, trihalo(1-4C)alkyl, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl;

$R^8$ is selected from hydroxy, (1-4C)alkoxy, (1-4C)alkyl, aminocarbonyl, (1-4C)alkylaminocarbonyl, di(1-4C)alkylaminocarbonyl, (1-4C)alkylamino, di(1-4C)alkylamino, (1-4C)alkoxy(1-4C)alkyl, hydroxy(1-4C)alkyl and —S(O)p(1-4C)alkyl;

$R^9$ is selected from (1-4C)alkyl, —C(O)(1-4C)alkyl, aminocarbonyl, (1-4C)alkylaminocarbonyl, di(1-4C)alkylaminocarbonyl, (1-4C)alkoxy(1-4C)alkyl, hydroxy(1-4C)alkyl and —S(O)p(1-4C)alkyl;

$R^{10}$ is selected from (1-4C)alkyl, (3-6C)cycloalkyl, hydroxy(1-4C)alkyl, (1-4C)alkoxy(1-4C)alkyl, —C(O)(1-4C)alkyl, benzyl, and (1-4C)alkylsulfonyl;

p is (independently at each occurrence) 0, 1 or 2;

or a salt thereof.

In another aspect of the invention there is provided a compound of formula (I) as hereinbefore defined wherein $R^1$ is selected from isopropyl, but-2-yl, 1,1,1-trifluoroprop-2-yl, 1,3-difluoroprop-2-yl, but-1-yn-3-yl, 1-hydroxyprop-2-yl, 2-hydroxybut-3-yl, 1-hydroxybut-2-yl, tetrahydrofuryl, tetrahydropyranyl, 1-methoxyprop-2-yl, 1-methoxybut-2-yl, 1-fluoromethoxyprop-2-yl, 1,1-difluoromethoxyprop-2-yl and 1-trifluoromethoxyprop-2-yl;

or a salt thereof.

In another aspect of the invention there is provided a compound of formula (I) as hereinbefore defined wherein $R^1$ is selected from isopropyl, but-2-yl, 1,1,1-trifluoroprop-2-yl, 1,3-difluoroprop-2-yl, but-1-yn-3-yl, 1-hydroxyprop-2-yl, 2-hydroxybut-3-yl, 1-hydroxybut-2-yl, tetrahydrofuryl, tetrahydropyranyl, 1-methoxyprop-2-yl, 1-methoxybut-2-yl, 2-hydroxyprop-1-yl, 2-methoxyprop-1-yl, 2-hydroxybut-1-yl, 2-methoxybut-1-yl, 1-fluoromethoxyprop-2-yl, 1,1-difluoromethoxyprop-2-yl and 1-trifluoromethoxyprop-2-yl; or a salt thereof.

In another aspect of the invention there is provided a compound of formula (I) as hereinbefore defined wherein $R^3$ is halo; or a salt thereof.

In another aspect of the invention there is provided a compound of formula (I) as hereinbefore defined wherein $R^7$ is independently selected from (1-4C)alkyl, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl and di(1-4C)alkylamino(1-4C)alkyl; or a salt thereof.

It will be appreciated that, where definitions of heterocylyl groups HET-1 and HET-2 encompass heteroaryl rings which may be substituted on nitrogen, such substitution may not result in charged quaternary nitrogen atoms, removal of aromaticity of the ring or unstable structures. It will be appreciated that the definitions of HET-1 and HET-2 are not intended to include any O—O, O—S or S—S bonds. It will be appreciated that the definitions of HET-1 and HET-2 are not intended to include unstable structures.

It will be understood that any single carbon atom in HET-1 may only be substituted by one group $R^6$ in order to maintain aromaticity of the ring. Up to two different carbon atoms in a HET-1 ring may be substituted by an $R^6$ group, each of which may be the same or different, provided the structure thereby formed is stable and aromatic.

It will be understood that any single carbon atom in HET-2 may only be substituted by one group $R^3$ in order to maintain aromaticity of the ring. Up to two different carbon atoms in a HET-2 ring may be substituted by an $R^3$ group, each of which may be the same or different, provided the structure thereby formed is stable and aromatic.

It will be understood that $R^8$ can be present on any or all available carbon atoms in the heterocyclic ring formed by $NR^4R^5$; each carbon atom can be substituted with 1 or 2 $R^8$ groups which may be the same or different, provided the structure thereby formed is stable (so, for example, it is not intended to cover gem-dihydroxy substitution).

It will be understood that where a compound of the formula (I) contains more than one group $R^5$, they may be the same or different.

It will be understood that where a compound of the formula (I) contains more than one group $R^3$, they may be the same or different.

A similar convention applies for all other groups and substituents on a compound of formula (I) as hereinbefore defined.

Compounds of Formula (I) may form salts which are within the ambit of the invention. Pharmaceutically acceptable salts are preferred although other salts may be useful in, for example, isolating or purifying compounds.

In another aspect, the invention relates to compounds of formula (I) as hereinabove defined or to a pharmaceutically acceptable salt.

In this specification the generic term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "(1-4C)alkyl" includes methyl, ethyl, propyl, isopropyl and t-butyl. An analogous convention applies to other generic terms.

For the avoidance of doubt, reference to the group HET-1 containing a nitrogen in the 2-position, is intended to refer to the 2-position relative to the amide nitrogen atom to which the group is attached. For example, HET-1 encompasses but is not limited to the following structures:

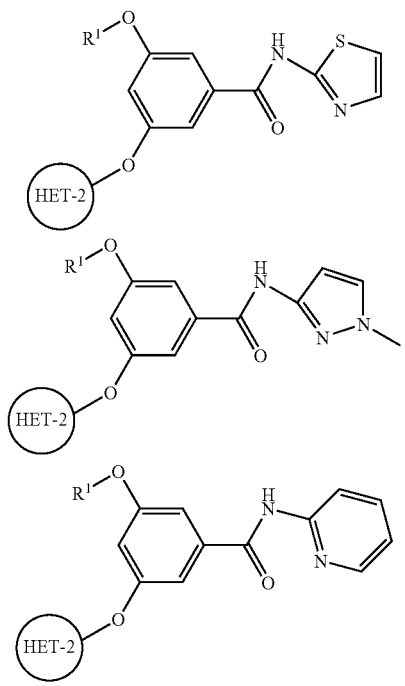

Suitable examples of HET-1 as a 5- or 6-membered, C-linked heteroaryl ring as hereinbefore defined, include thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl and triazolyl.

Suitable examples of HET-2 include thienyl, furyl, thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl and triazolyl. Further suitable examples of HET-2 include aromatic heterocycles where a ring nitrogen or sulfur atom has been oxidised but aromaticity has been preserved, for example a pyridine N-oxide. Further suitable examples of HET-2 include thiazolyl, pyridyl, pyrazinyl, pyridazinyl and pyrimidinyl.

Suitable examples for a 4-7 membered ring formed by $R^4$ and $R^5$ together with the nitrogen to which they are attached, as hereinbefore defined, include morpholino, piperidinyl, piperazinyl, pyrrolidinyl, azetidinyl, homopiperazinyl, homo-morpholino, homo-thiomorpholino (and versions thereof wherein the sulfur is oxidised to an SO or $S(O)_2$ group) and homo-piperidinyl. A further suitable example is thiomorpholino (and versions thereof wherein the sulfur is oxidised to an SO or S(O)₂ group).

Suitable examples for a 6-10 membered bicyclic heterocyclic ring formed by R⁴ and R⁵ together with the nitrogen to which they are attached, as hereinbefore defined, are bicyclic saturated or partially unsaturated heterocyclyl ring such as those illustrated by the structures shown below (wherein the dotted line indicates the point of attachment to the rest of the molecule and wherein R represents the optional substituents for carbon or nitrogen defined hereinbefore):

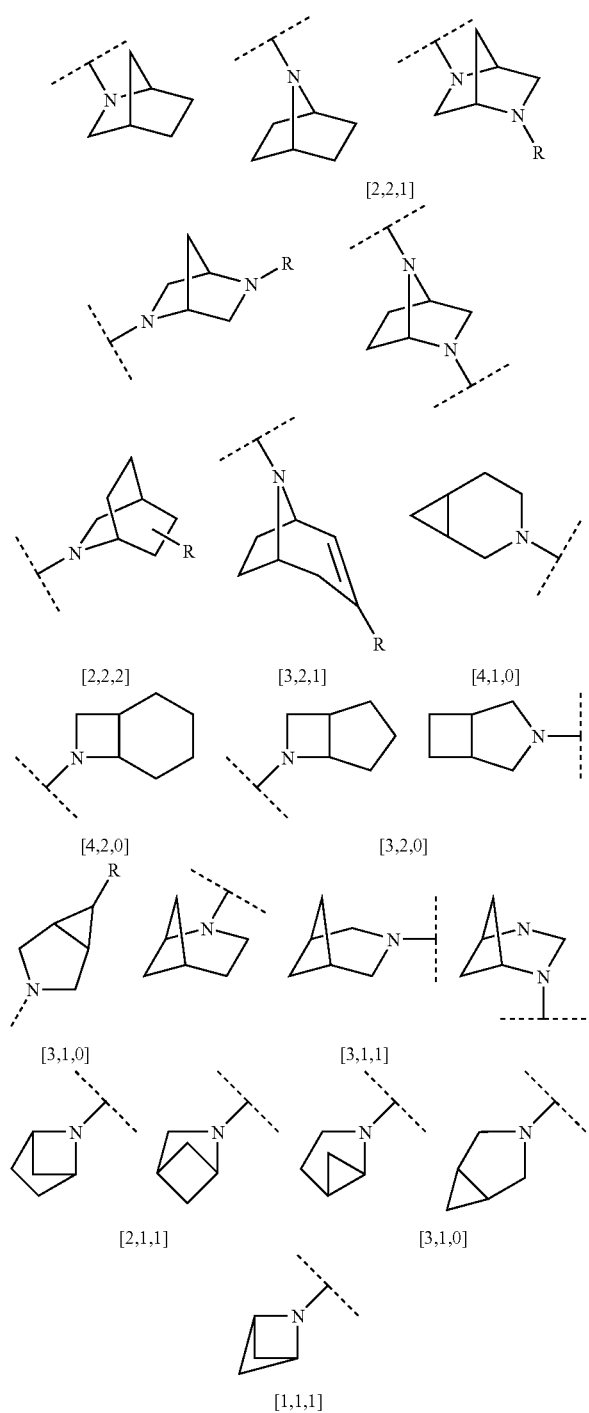

In particular such a ring system is a [2,2,1] system such as

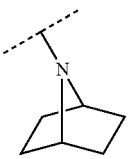

(7-azabicyclo[2.2.1]hept-7-yl).

In another embodiment, such a ring system is a [2.1.1] system such as

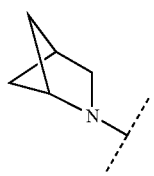

(2-azabicyclo[2.1.1]hex-2-yl).

Examples of (1-4C)alkyl include methyl, ethyl, propyl, isopropyl, butyl and tert-butyl; examples of (3-6C)cycloalkyl include cyclopropyl, cyclobutyl, cyclopentyl and cyclohexyl; examples of halo include fluoro, chloro, bromo and iodo; examples of halo(1-4C)alkyl include fluoromethyl, chloromethyl, fluoroethyl, chloroethyl, fluoropropyl and fluorobutyl; examples of dihalo(1-4C)alkyl include difluoromethyl, 1,1-difluoroeth-2-yl, 1,2-difluoroeth-2-yl, 1,1-dichloroeth-2-yl, 1,2-dichloroeth-2-yl, and 1,1-difluoroprop-3-yl; examples of trihalo(1-4C)alkyl include trifluoromethyl and 1,1,1-trifluoroeth-2-yl; examples of hydroxy(1-4C)alkyl include hydroxymethyl, 1-hydroxyethyl, 2-hydroxyethyl, 2-hydroxypropyl, 3-hydroxypropyl, 1-hydroxyisopropyl and 4-hydroxybutyl; examples of (1-4C)alkoxy(1-4C)alkyl include methoxymethyl, ethoxymethyl, tert-butoxymethyl, 2-methoxyethyl, 2-ethoxyethyl, methoxypropyl, 2-methoxypropyl and methoxybutyl; example of (1-4C)alkoxy include methoxy, ethoxy, propoxy, isopropoxy, butoxy and tert-butoxy; examples of (1-4C)alkylS(O)p(1-4C)alkyl (where p is 0, 1 or 2) include methylsulfinylmethyl, ethylsulfinylmethyl, ethylsulfinylethyl, methylsulfinylpropyl, methylsulfinylbutyl, methylsulfonylmethyl, ethylsulfonylmethyl, ethylsulfonylethyl, methylsulfonylpropyl, methylsulfonylbutyl, methylthiomethyl, ethylthiomethyl, ethylthioethyl, methylthiopropyl, and methylthiobutyl; examples of (1-4C) alkylsulfonyl include methylsulfonyl, ethylsulfonyl, propylsulfonyl, isopropylsulfonyl and tert-butylsulfonyl; examples of —S(O)p(1-4C)alkyl include (1-4C)alkylsulfonyl, methylsulfinyl, ethylsulfinyl, propylsulfinyl, isopropylsulfinyl, tert-butylsulfinyl, methylthio, ethylthio, propylthio, isopropylthio and tert-butylthio; examples of amino(1-4C) alkyl include aminomethyl, aminoethyl, 2-aminopropyl, 3-aminopropyl, 1-aminoisopropyl and 4-aminobutyl; examples of (1-4C)alkylamino(1-4C)alkyl include (N-methyl)aminomethyl, (N-ethyl)aminomethyl, 1-((N-methyl)amino)ethyl, 2-((N-methyl)amino)ethyl, (N-ethyl)aminoethyl, (N-methyl)aminopropyl, and 4-((N-methyl)amino) butyl; examples of di(1-4C)alkylamino(1-4C)alkyl include dimethylaminomethyl, methyl(ethyl)aminomethyl, methyl (ethyl)aminoethyl, (N,N-diethyl)aminoethyl, (N,N-dimethyl)aminopropyl and (N,N-dimethyl)aminobutyl; examples of —C(O)(1-4C)alkyl and (1-4C)alkylcarbonyl include methylcarbonyl, ethylcarbonyl, propylcarbonyl and tert-butyl carbonyl; examples of (1-4C)alkylamino include methylamino, ethylamino, propylamino, isopropylamino, butylamino and tert-butylamino; examples of di(1-4C)alkylamino include dimethylamino, diethylamino, N-methyl-N-ethylamino, dipropylamino, N-isopropyl-N-methylamino and dibutylamino; examples of (1-4C)alkylaminocarbonyl include methylaminocarbonyl, ethylaminocarbonyl, propylaminocarbonyl, isopropylaminocarbonyl, butylaminocarbonyl and tert-butylaminocarbonyl; examples of di(1-4C)alkylaminocarbonyl include dimethylaminocarbonyl, diethylaminocarbonyl, N-methyl-N-ethylaminocarbonyl, dipropylaminocarbonyl, N-isopropyl-N-methylaminocarbonyl and dibutylaminocarbonyl.

It is to be understood that, insofar as certain of the compounds of Formula (I) defined above may exist in optically active or racemic forms by virtue of one or more asymmetric carbon atoms, the invention includes in its definition any such optically active or racemic form which possesses the property of stimulating GLK directly or inhibiting the GLK/GLKRP interaction. The synthesis of optically active forms may be carried out by standard techniques of organic chemistry well known in the art, for example by synthesis from optically active starting materials or by resolution of a racemic form. It is also to be understood that certain compounds may exist in tautomeric forms and that the invention also relates to any and all tautomeric forms of the compounds of the invention which activate GLK.

It is also to be understood that certain compounds of the formula (I) and salts thereof can exist in solvated as well as unsolvated forms such as, for example, hydrated forms. It is to be understood that the invention encompasses all such solvated forms which activate GLK.

In another aspect, the invention relates to compounds of formula (I) as hereinabove defined or to a pro-drug thereof. Suitable examples of pro-drugs of compounds of formula (I) are in-vivo hydrolysable esters of compounds of formula (I). Therefore in another aspect, the invention relates to compounds of formula (I) as hereinabove defined or to an in-vivo hydrolysable ester thereof.

In one embodiment of the invention are provided compounds of formula (I), in an alternative embodiment are provided pharmaceutically-acceptable salts of compounds of formula (I), in a further alternative embodiment are provided in-vivo hydrolysable esters of compounds of formula (I), and in a further alternative embodiment are provided pharmaceutically-acceptable salts of in-vivo hydrolysable esters of compounds of formula (I).

The compounds of the invention may be administered in the form of a pro-drug. A pro-drug is a bioprecursor or pharmaceutically acceptable compound being degradable in the body to produce a compound of the invention (such as an ester or amide of a compound of the invention, particularly an in-vivo hydrolysable ester). Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen;
c) H. Bundgaard, Chapter 5 "Design and Application of Prodrugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988); and
f) N. Kakeya, et al., Chem Pharm Bull, 32, 692 (1984).

The contents of the above cited documents are incorporated herein by reference.

Examples of pro-drugs are as follows. An in-vivo hydrolysable ester of a compound of the invention containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$ to $C_6$alkoxymethyl esters for example methoxymethyl, $C_1$ to $C_6$alkanoyloxymethyl esters for example pivaloyloxymethyl, phthalidyl esters, $C_3$ to $C_8$cycloalkoxycarbonyloxy$C_1$ to $C_6$alkyl esters for example 1-cyclohexylcarbonyloxyethyl; 1,3-dioxolen-2-onylmethyl esters, for example 5-methyl-1,3-dioxolen-2-onylmethyl; and (1-6C)alkoxycarbonyloxyethyl esters.

An in-vivo hydrolysable ester of a compound of the invention containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a benzoxazinone derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl) amine.

In a further aspect of the invention there is provided a compound of formula (I) which is a compound of formula (IA), or a salt thereof:

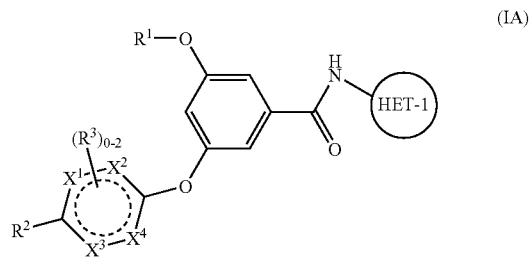

(IA)

wherein each of $X^1$, $X^2$ and $X^3$ is independently selected from CH, N, S and O;

$X^4$ is absent (to make a 5-membered ring) or is selected from CH, N, O and S;

provided that at least one of $X^1$, $X^2$, $X^3$ and $X^4$ is CH and provided that there are no O—O, O—S or S—S bonds within the ring;

$R^3$, if present, is selected from methyl, trifluoromethyl and halo;

$R^1$, $R^2$ and HET-1 are as defined for a compound of formula (I).

It will be understood that the dotted circle inside the ring containing $X^1$ to $X^4$ (that is, the HET-2 ring) is intended to indicate that the ring is aromatic, although the precise number and position of the double bonds will be dependent on the nature of $X^1$ to $X^4$.

References herein to a compound of formula (I) should generally be understood to apply equally to a compound of formula (IA), whether explicitly stated or not, unless the context indicates otherwise.

Particular examples of compounds of formula (I) and (IA) include compounds of formulae (IB), (IC) and/or (ID):

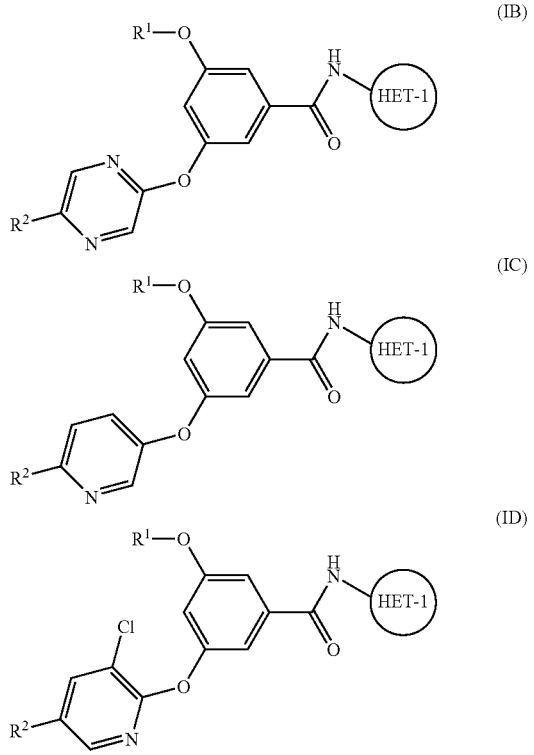

wherein $R^1$, $R^2$ and HET-1 are as defined for a compound of formula (I).

Preferred values of each variable group are as follows. Such values may be used where appropriate with any of the values, definitions, claims, aspects or embodiments defined hereinbefore or hereinafter. In particular, each may be used as an individual limitation on the broadest definition of formula (I) or (IA). Further, each of the following values may be used in combination with one or more of the other following values to limit the broadest definition of formula (I) or (IA) or to limit any narrower definitions of formula (I) or (IA) in any of the aspects hereinbefore or hereinafter. Where appropriate each of the following values may also be used to limit any definition within formulae (IB), (IC) and/or (ID).

(1) $R^1$ is of sub-formula X:

wherein $R^x$ is selected from methyl, ethyl, trifluoromethyl, ethynyl, hydroxymethyl, hydroxyethyl, methoxymethyl, fluoromethoxymethyl, difluoromethoxymethyl and trifluoromethoxymethyl; preferably $R^x$ is selected from methyl, ethyl, trifluoromethyl, ethynyl, hydroxymethyl, hydroxyethyl, methoxymethyl, fluoromethoxymethyl and difluoromethoxymethyl (2) $R^1$ is of sub-formula Y:

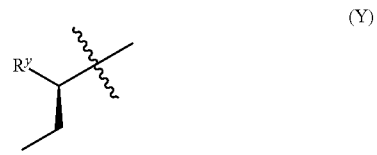

wherein $R^y$ is selected from hydroxymethyl and methoxymethyl (3) $R^1$ is 1-hydroxyprop-2-yl and the configuration is preferably (S), that is $R^1$—O— is:

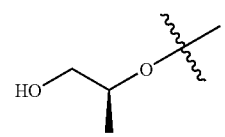

(4) $R^1$ is 1-methoxyprop-2-yl and the configuration is preferably (S), that is $R^1$—O— is:

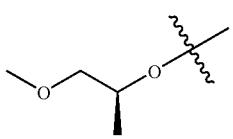

(5) $R^1$ is selected from isopropyl, 1,3-difluoroprop-2-yl, but-1-yn-3-yl, 1-hydroxyprop-2-yl, hydroxybut-3-yl and 1-methoxyprop-2-yl (6) $R^1$ is 1,1,1-trifluoroprop-2-yl, 1-fluoromethoxyprop-2-yl, 1,1-difluoromethoxyprop-2-yl or 1-trifluoromethoxyprop-2-yl (7) $R^1$ is 1-fluoromethoxyprop-2-yl, 1,1-difluoromethoxyprop-2-yl or 1-trifluoromethoxyprop-2-yl, particularly 1-fluoromethoxyprop-2-yl or 1,1-difluoromethoxyprop-2-yl (8) $R^1$ is 1,1-difluoromethoxyprop-2-yl, particularly with the stereochemistry:

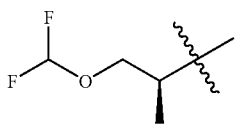

(9) $R^1$ is tetrahydrofuryl or tetrahydropyranyl

(10) $R^1$ is tetrahydrofuryl in the (S) configuration, that is:

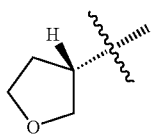

(11) $R^1$ is tetrahydrofuryl in the (R) configuration, that is:

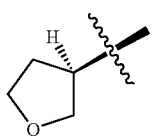

(12) $R^1$ is 4-tetrahydropyranyl:

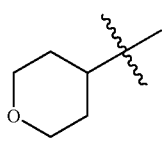

(13) $R^1$ is 2-hydroxy-but-3-yl and the configuration is preferably such that $R^1$—O— is:

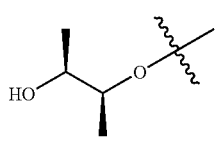

(14) $R^1$ is 1-hydroxybut-2-yl or 1-methoxybut-2-yl

(15) $R^1$ is selected from isopropyl, but-2-yl, 1,1,1-trifluoroprop-2-yl, 1,3-difluoroprop-2-yl, but-1-yn-3-yl, 1-hydroxyprop-2-yl, 2-hydroxybut-3-yl, tetrahydrofuryl, tetrahydropyranyl, 1-methoxyprop-2-yl, 1-fluoromethoxyprop-2-yl, 1,1-difluoromethoxyprop-2-yl and 1-trifluoromethoxyprop-2-yl

(16) $R^1$ is selected from 2-hydroxyprop-1-yl, 2-methoxyprop-1-yl, 2-hydroxybut-1-yl and 2-methoxybut-1-yl

(17) $R^1$ is selected from isopropyl, 1,3-difluoroprop-2-yl, but-2-yl, 1-hydroxyprop-2-yl, 2-hydroxybut-3-yl, 1,1-difluoromethoxyprop-2-yl, tetrahydrofuryl, 1-hydroxybut-2-yl and 1-methoxyprop-2-yl

(18) $R^1$ is selected from isopropyl, cyclopentyl, 1,3-difluoroprop-2-yl, but-2-yl, 1-hydroxyprop-2-yl, 2-hydroxybut-3-yl, 1,1-difluoromethoxyprop-2-yl, tetrahydrofuryl, tetrahydropyranyl, 1-hydroxybut-2-yl and 1-methoxyprop-2-yl

(19) $R^1$ is selected from tetrahydrofuryl, 1-difluoromethoxyprop-2-yl, 1,3-difluoroprop-2-yl, and 2-hydroxybut-3-yl

(20) $R^1$ is selected from isopropyl, tetrahydrofuryl, 1-hydroxyprop-2-yl and 1-methoxyprop-2-yl

(21) $R^1$ is selected from 1-hydroxyprop-2-yl and 1-methoxyprop-2-yl, for example (2S)-1-hydroxyprop-2-yl and (2S)-1-methoxyprop-2-yl

(22) $R^1$ is selected from isopropyl, but-2-yl, cyclopentyl, 1,1,1-trifluoroprop-2-yl, 1,3-difluoroprop-2-yl, but-1-yn-3-yl, 1-hydroxyprop-2-yl, 2-hydroxybut-3-yl, 1-hydroxybut-2-yl, tetrahydrofuryl, tetrahydropyranyl, 1-methoxyprop-2-yl, 1-methoxybut-2-yl, 2-hydroxyprop-1-yl, 2-methoxyprop-1-yl, 2-hydroxybut-1-yl, 2-methoxybut-1-yl, 1-fluoromethoxyprop-2-yl and 1,1-difluoromethoxyprop-2-yl

(23) $R^1$ is selected from isopropyl, but-2-yl, cyclopentyl, 1,1,1-trifluoroprop-2-yl, 1,3-difluoroprop-2-yl, but-1-yn-3-yl, 1-hydroxyprop-2-yl, 2-hydroxybut-3-yl, 1-hydroxybut-2-yl, tetrahydrofuryl, tetrahydropyranyl, 1-methoxyprop-2-yl, 1-methoxybut-2-yl, 2-hydroxyprop-1-yl, 2-methoxyprop-1-yl, 2-hydroxybut-1-yl, 2-methoxybut-1-yl and 1,1-difluoromethoxyprop-2-yl

(24) HET-1 is a 5-membered heteroaryl ring

(25) HET-1 is a 6-membered heteroaryl ring

(26) HET-1 is substituted with 1 or 2 substituents independently selected from $R^6$

(27) HET-1 is substituted with 1 substituent selected from $R^6$

(28) HET-1 is substituted with 1 substituent selected from $R^7$

(29) HET-1 is unsubstituted

(30) HET-1 is selected from thiazolyl, isothiazolyl, thiadiazolyl, pyridyl, pyrazinyl, pyridazinyl, pyrazolyl, imidazolyl, pyrimidinyl, oxazolyl, isoxazolyl, oxadiazolyl, and triazolyl

(31) HET-1 is selected from thiazolyl, isothiazolyl, thiadiazolyl, pyrazolyl, imidazolyl, oxazolyl, isoxazolyl and oxadiazolyl

(32) HET-1 is selected from pyridyl, pyrazinyl, pyridazinyl and pyrimidinyl

(33) HET-1 is selected from thiazolyl, pyrazolyl and oxazolyl

(34) HET-1 is selected from thiadiazolyl and oxadiazolyl

(35) HET-1 is selected from 1,3,4-thiadiazolyl and 1,3,4-oxadiazolyl

(36) HET-1 is selected from 1,2,4-oxadiazolyl and 1,2,4-oxadiazolyl

(37) HET-1 is pyrazolyl, particularly N-methylpyrazolyl

(38) HET-1 is pyrazinyl

(39) HET-1 is selected from thiazolyl, pyrazolyl, thiadiazolyl and pyrazinyl

(40) HET-1 is selected from thiazolyl, pyrazolyl, and thiadiazolyl, optionally substituted with (1-4C)alkyl

(41) HET-1 is pyrazolyl, particularly N-methylpyrazolyl

(42) HET-1 is pyrazolyl (optionally substituted with ethyl, isopropyl or 1 or 2 methyl), thiazolyl (optionally substituted with methyl), pyrazinyl (optionally substituted with methyl),

(43) HET-1 is pyrazolyl (optionally substituted with ethyl, isopropyl, difluoromethyl, or 1 or 2 methyl), thiazolyl (optionally substituted with methyl), pyrazinyl (optionally substituted with methyl), pyridyl (optionally substituted by fluoro), isoxazolyl (optionally substituted with methyl) and thiadiazolyl (optionally substituted with methyl)

(44) HET-1 is selected from pyrazinyl (optionally substituted with methyl), pyrazolyl (optionally substituted on carbon by methyl), methylthiadiazolyl (particularly 1,2,4-thiadiazol-5-yl, more particularly 3-methyl-1,2,4-thiadiazol-5-yl), thiazolyl (optionally substituted with methyl), pyridyl (optionally substituted by fluoro) and isoxazolyl

(45) HET-1 is N-difluoromethylpyrazolyl

(46) HET-1 is 5-methylpyrazin-2-yl

(47) HET-1 is pyrazolyl (optionally substituted with ethyl, isopropyl, difluoromethyl, or 1 or 2 methyl), thiazolyl (optionally substituted with methyl), pyrazinyl (optionally substituted with methyl), pyridyl (optionally substituted by fluoro), isoxazolyl (optionally substituted with methyl) and thiadiazolyl (optionally substituted with methyl); and $R^1$ is selected from isopropyl, cyclopentyl, 1,3-difluoroprop-2-yl, but-2-yl, 1-hydroxyprop-2-yl, 2-hydroxybut-3-yl, 1,1-difluoromethoxyprop-2-yl, tetrahydrofuryl, tetrahydropyranyl, 1-hydroxybut-2-yl and 1-methoxyprop-2-yl; when HET-1 is pyrazolyl unsubstituted on nitrogen (ie NH-pyrazolyl), particularly $R^1$ is selected from 1-methoxyprop-2-yl, isopropyl, and tetrahydrofuryl

(48) HET-1 is pyrazolyl (optionally substituted on carbon with methyl), thiazolyl (optionally substituted with methyl), pyrazinyl (optionally substituted with methyl), pyridyl (optionally substituted by fluoro), isoxazolyl and methylthiadiazolyl (particularly 3-methyl-1,2,4-thiadiazol-5-yl);

$R^1$ is selected from isopropyl, cyclopentyl, 1,3-difluoroprop-2-yl, but-2-yl, 1-hydroxyprop-2-yl, 2-hydroxybut-3-yl, 1,1-difluoromethoxyprop-2-yl, tetrahydrofuryl, tetrahydropyranyl, 1-hydroxybut-2-yl and 1-methoxyprop-2-yl; when HET-1 is pyrazolyl, particularly $R^1$ is selected from 1-methoxyprop-2-yl, isopropyl, and tetrahydrofuryl

(49) HET-1 is methylpyrazinyl and $R^1$ is selected from 1-hydroxyprop-2-yl and 1-methoxyprop-2-yl, for example (2S)-1-hydroxyprop-2-yl and (2S)-1-methoxyprop-2-yl

(50) HET-1 is pyrazolyl and $R^1$ is selected from isopropyl, tetrahydrofuryl and 1-methoxyprop-2-yl, for example (2S)-1-methoxyprop-2-yl

(51) $R^6$ is selected from (1-4C)alkyl, halo, hydroxy(1-4C)alkyl and di(1-4C)alkylamino(1-4C)alkyl

(52) $R^6$ is selected from methyl, ethyl, bromo, chloro, fluoro, hydroxymethyl, methoxymethyl, aminomethyl, N-methylaminomethyl, dimethylaminomethyl

(53) $R^6$ is selected from (1-4C)alkyl, halo, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl, and di(1-4C)alkylamino(1-4C)alkyl

(54) $R^6$ is selected from methyl, ethyl, bromo, chloro, fluoro, hydroxymethyl and methoxymethyl

(55) $R^6$ is selected from methyl, ethyl, chloro and fluoro

(56) $R^6$ is methyl or fluoro, preferably methyl

(57) $R^6$ is selected from methyl, ethyl, bromo, chloro, fluoro, aminomethyl, N-methylaminomethyl, dimethylaminomethyl, hydroxymethyl and methoxymethyl

(58) $R^6$ is selected from methyl, ethyl, aminomethyl, N-methylaminomethyl, dimethylaminomethyl, hydroxymethyl and methoxymethyl

(59) $R^6$ is selected from methyl, ethyl, isopropyl and methoxymethyl

(60) when 2 substituents $R^6$ are present, both are selected from methyl, ethyl, bromo, chloro and fluoro; preferably both are methyl

(61) $R^6$ is selected from (1-4C)alkylS(O)p(1-4C)alkyl, (1-4C)alkylamino(1-4C)alkyl and di(1-4C)alkylamino(1-4C)alkyl

(62) $R^7$ is selected from (1-4C)alkyl, hydroxy(1-4C)alkyl and di(1-4C)alkylamino(1-4C)alkyl

(63) $R^7$ is selected from methyl, ethyl, hydroxymethyl, methoxymethyl, aminomethyl, N-methylaminomethyl, dimethylaminomethyl

(64) $R^7$ is selected from (1-4C)alkyl, hydroxy(1-4C)alkyl, (1-4C)alkoxy(1-4C)alkyl, (1-4C)alkylS(O)p(1-4C)alkyl, amino(1-4C)alkyl, (1-4C)alkylamino(1-4C)alkyl, and di(1-4C)alkylamino(1-4C)alkyl

(65) $R^7$ is selected from methyl, ethyl, aminomethyl, N-methylaminomethyl, and dimethylaminomethyl

(66) $R^7$ is selected from methyl, ethyl, hydroxymethyl and methoxymethyl

(67) $R^7$ is selected from methyl, isopropyl and ethyl

(68) $R^7$ is selected from methyl, isopropyl, difluoromethyl and ethyl

(69) $R^7$ is selected from isopropyl and difluoromethyl, particularly difluoromethyl

(70) $R^7$ is selected from methyl and ethyl

(71) $R^7$ is methyl

(72) $R^7$ is selected from methyl, ethyl, aminomethyl, N-methylaminomethyl, dimethylaminomethyl, hydroxymethyl and methoxymethyl

(73) $R^7$ is selected from methyl, ethyl, isopropyl and methoxymethyl

(74) when $R^7$ is selected from halo(1-4C)alkyl, dihalo(1-4C)alkyl and trihalo(1-4C)alkyl, each halo is selected from chloro and fluoro, and is in particular fluoro.

(75) when $R^7$ is selected from halo(1-4C)alkyl, dihalo(1-4C)alkyl and trihalo(1-4C)alkyl, $R^7$ is particularly selected from fluoromethyl, difluoroethyl, difluoromethyl and trifluoromethyl

(76) HET-2 is a 5-membered ring

(77) HET-2 is a 6-membered ring

(78) HET-2 is selected from thienyl, furyl, thiazolyl, isothiazolyl, thiadiazolyl, pyridyl, pyrazinyl, pyridazinyl, pyrazolyl, imidazolyl, pyrimidinyl, oxazolyl, isoxazolyl and oxadiazolyl

(79) HET-2 is selected from thienyl, furyl, thiadiazolyl, pyridyl, pyrazinyl, pyridazinyl, pyrazolyl, imidazolyl, pyrimidinyl and oxadiazolyl

(80) HET-2 is selected from pyridyl, pyrazinyl, thiazolyl and thienyl

(81) HET-2 is selected from pyridyl, pyrazinyl and thiazolyl

(82) HET-2 is selected from pyridyl, pyrazinyl, pyridazinyl and thiazolyl

(83) HET-2 is selected from pyridyl and pyrazinyl

(84) HET-2 is pyrazinyl

(85) HET-2 is substituted with a substituent selected from $R^3$

(86) HET-2 has one nitrogen substituent selected from $R^{10}$

(87) $R^3$ is chloro or fluoro

(88) $R^3$ is chloro

(89) $R^3$ is fluoro

(90) $R^3$ is chloro or methyl

(91) $R^3$ is fluoro, chloro or methyl

(92) $R^2$ is —C(O)NR$^4$R$^5$

(93) $R^2$ is —SO$_2$NR$^4$R$^5$

(94) $R^4$ and $R^5$ together with the nitrogen atom to which they are attached form a 4 membered ring

(95) $R^4$ and $R^5$ together with the nitrogen atom to which they are attached form a 5 membered ring

(96) $R^4$ and $R^5$ together with the nitrogen atom to which they are attached form a 6 membered ring

(97) $R^4$ and $R^5$ together with the nitrogen atom to which they are attached form a 7 membered ring

(98) $R^4$ and $R^5$ together with the nitrogen atom to which they are attached form a fully saturated ring

(99) $R^4$ and $R^5$ together with the nitrogen atom to which they are attached form a ring selected from morpholino, piperidinyl, piperazinyl, pyrrolidinyl and azetidinyl (100) $R^4$ and $R^5$ together with the nitrogen atom to which they are attached form a ring selected from pyrrolidinyl, morpholino and azetidinyl (101) $R^4$ and $R^5$ together with the nitrogen atom to which they are attached form a ring selected from 7-azabicyclo[2.2.1]hept-7-yl, pyrrolidinyl, morpholino and azetidinyl (102) $R^4$ and $R^5$ together with the nitrogen atom to which they are attached form an azetidinyl ring (103) $R^4$ and $R^5$ together with the nitrogen atom to which they are attached form an azetidinyl or pyrrolidinyl ring (104) $R^4$ and $R^5$ together with the nitrogen atom to which they are attached form an unsubstituted ring (105) $R^4$ and $R^5$ together with the nitrogen atom to which they are attached form an ring mono-substituted either with a substituent $R^8$ or with a substituent $R^9$ (106) $R^4$ and $R^5$ together with the nitrogen atom to which they are attached form a 6-10 membered bicyclic saturated or partially unsaturated ring (107) $R^8$ is selected from hydroxy, (1-4C)alkoxy, (1-4C)alkyl (108) $R^8$ is selected from hydroxy, methoxy and methyl (109) $R^9$ is selected from (1-4C)alkyl and —C(O)(1-4C)alkyl (110) $R^2$ is azetidinylcarbonyl or pyrrolidinylcarbonyl, preferably azetidinylcarbonyl (109) $R^{10}$ is (1-4C)alkyl (111) $R^{10}$ is (3-6C)cycloalkyl (112) $R^{10}$ is hydroxy(1-4C)alkyl or (1-4C)alkoxy(1-4C)alkyl (113) $R^{10}$ is —C(O)(1-4C)alkyl (114) $R^{10}$ is benzyl (115) $R^{10}$ is (1-4C)alkylsulfonyl (116) $R^{10}$ is (1-4C)alkyl or benzyl According to a further feature of the invention there is provided the following preferred groups of compounds of the invention:

In one aspect of the invention there is provided a compound of formula (I) or (IA) as hereinbefore defined, or a salt thereof, wherein:

$R^1$ is selected from isopropyl, but-2-yl, 1,1,1-trifluoroprop-2-yl, 1,3-difluoroprop-2-yl, but-1-yn-3-yl, 1-hydroxyprop-2-yl, 2-hydroxybut-3-yl, tetrahydrofuryl, tetrahydropyranyl, 1-methoxyprop-2-yl, 1-fluoromethoxyprop-2-yl and 1,1-difluoromethoxyprop-2-yl;

HET-1 is a 5- or 6-membered, C-linked heteroaryl ring containing a nitrogen atom in the 2-position and optionally 1 or 2 further ring heteroatoms independently selected from O, N and S; which ring is optionally substituted on any nitrogen atom (provided it is not thereby quaternised) by a methyl or ethyl group and/or on 1 or 2 available carbon atoms by a methyl or ethyl group;

HET-2 is a 5- or 6-membered heteroaryl ring, containing 1, 2 or 3 ring heteroatoms independently selected from O, S and N; which ring is substituted on an available carbon atom by a substituent selected from $R^2$, and is optionally further substituted on 1 or 2 available carbon atoms by a substituent independently selected from $R^3$ and/or on an available nitrogen atom (provided it is not thereby quaternised) by a substituent selected from $R^{10}$;

$R^2$ is selected from —C(O)NR$^4$R$^5$ and —SO$_2$NR$^4$R$^5$;

$R^3$ is selected from halo;

$R^4$ and $R^5$ together with the nitrogen atom to which they are attached form a 4 to 7 membered saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to a S(O) or S(O)$_2$ group; which ring is optionally substituted on an available carbon atom by 1 or 2 substituents independently selected from $R^8$ and/or on an available nitrogen atom by a substituent selected from $R^9$;

$R^8$ is selected from hydroxy, (1-4C)alkoxy and (1-4C)alkyl;

$R^9$ is selected from (1-4C)alkyl, —C(O)(1-4C)alkyl, and —S(O)p(1-4C)alkyl;

$R^{10}$ is selected from (1-4C)alkyl, —C(O)(1-4C)alkyl, benzyl, and (1-4C)alkylsulfonyl;

p is (independently at each occurrence) 0, 1 or 2.

In one aspect of the invention there is provided a compound of formula (I) or (IA) as hereinbefore defined, or a salt thereof, wherein:

$R^1$ is selected from isopropyl, but-2-yl, 1,1,1-trifluoroprop-2-yl, 1,3-difluoroprop-2-yl, but-1-yn-3-yl, 1-hydroxyprop-2-yl, 2-hydroxybut-3-yl, tetrahydrofuryl, tetrahydropyranyl, 1-methoxyprop-2-yl, 2-hydroxyprop-1-yl, 2-methoxyprop-1-yl, 2-hydroxybut-1-yl, 2-methoxybut-1-yl, 1-fluoromethoxyprop-2-yl and 1,1-difluoromethoxyprop-2-yl;

HET-1 is a 5- or 6-membered, C-linked heteroaryl ring containing a nitrogen atom in the 2-position and optionally 1 or 2 further ring heteroatoms independently selected from O, N and S; which ring is optionally substituted on any nitrogen atom (provided it is not thereby quaternised) by a methyl or ethyl group and/or on 1 or 2 available carbon atoms by a methyl or ethyl group;

HET-2 is a 5- or 6-membered heteroaryl ring, containing 1, 2 or 3 ring hetereoatoms independently selected from O, S and N; which ring is substituted on an available carbon atom by a substituent selected from $R^2$, and is optionally further substituted on 1 or 2 available carbon atoms by a substituent independently selected from $R^3$ and/or on an available nitrogen atom (provided it is not thereby quaternised) by a substituent selected from $R^{10}$;

$R^2$ is selected from —C(O)NR$^4$R$^5$ and —SO$_2$NR$^4$R$^5$;

$R^3$ is selected from halo;

$R^4$ and $R^5$ together with the nitrogen atom to which they are attached form a 4 to 7 membered saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to a S(O) or S(O)$_2$ group; which ring is optionally substituted on an available carbon atom by 1 or 2 substituents independently selected from $R^8$ and/or on an available nitrogen atom by a substituent selected from $R^9$;

$R^8$ is selected from hydroxy, (1-4C)alkoxy and (1-4C)alkyl;

$R^9$ is selected from (1-4C)alkyl, —C(O)(1-4C)alkyl, and —S(O)p(1-4C)alkyl;

$R^{10}$ is selected from (1-4C)alkyl, —C(O)(1-4C)alkyl, benzyl, and (1-4C)alkylsulfonyl;

p is (independently at each occurrence) 0, 1 or 2.

In another aspect of the invention there is provided a compound of formula (I) or (IA) as hereinbefore defined, or a salt thereof, wherein:

$R^1$ is selected from isopropyl, but-2-yl, cyclopentyl, 1,1,1-trifluoroprop-2-yl, 1,3-difluoroprop-2-yl, but-1-yn-3-yl, 1-hydroxyprop-2-yl, 2-hydroxybut-3-yl, tetrahydrofuryl, tetrahydropyranyl, 1-methoxyprop-2-yl, 2-hydroxyprop-1-yl, 2-methoxyprop-1-yl, 2-hydroxybut-1-yl, 2-methoxybut-1-yl, 1-fluoromethoxyprop-2-yl and 1,1-difluoromethoxyprop-2-yl;

HET-1 is a 5- or 6-membered, C-linked heteroaryl ring containing a nitrogen atom in the 2-position and optionally 1 or 2 further ring heteroatoms independently selected from O, N and S; which ring is optionally substituted on any nitrogen atom (provided it is not thereby quaternised) by a methyl, ethyl or isopropyl group and/or on 1 or 2 available carbon atoms by a methyl, ethyl or fluoro group;

HET-2 is a 5- or 6-membered heteroaryl ring, containing 1, 2 or 3 ring hetereoatoms independently selected from O, S and N; which ring is substituted on an available carbon atom by a substituent selected from $R^2$, and is optionally further substituted on 1 or 2 available carbon atoms by a substituent independently selected from $R^3$ and/or on an available nitrogen atom (provided it is not thereby quaternised) by a substituent selected from $R^{10}$;

$R^2$ is selected from —C(O)NR$^4$R$^5$ and —SO$_2$NR$^4$R$^5$;

$R^3$ is selected from halo;

$R^4$ and $R^5$ together with the nitrogen atom to which they are attached form a 4 to 7 membered saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to a S(O) or S(O)$_2$ group; which ring is optionally substituted on an available carbon atom by 1 or 2 substituents independently selected from $R^8$ and/or on an available nitrogen atom by a substituent selected from $R^9$;

$R^8$ is selected from hydroxy, (1-4C)alkoxy and (1-4C)alkyl;

$R^9$ is selected from (1-4C)alkyl, —C(O)(1-4C)alkyl, and —S(O)p(1-4C)alkyl;

$R^{10}$ is selected from (1-4C)alkyl, —C(O)(1-4C)alkyl, benzyl, and (1-4C)alkylsulfonyl;

p is (independently at each occurrence) 0, 1 or 2.

In another aspect of the invention there is provided a compound of formula (I) or (IA) as hereinbefore defined, or a salt thereof, wherein:

$R^1$ is selected from isopropyl, but-2-yl, cyclopentyl, 1,1,1-trifluoroprop-2-yl, 1,3-difluoroprop-2-yl, but-1-yn-3-yl, 1-hydroxyprop-2-yl, 2-hydroxybut-3-yl, tetrahydrofuryl, tetrahydropyranyl, 1-methoxyprop-2-yl, 2-hydroxyprop-1-yl, 2-methoxyprop-1-yl, 2-hydroxybut-1-yl, 2-methoxybut-1-yl, 1-fluoromethoxyprop-2-yl and 1,1-difluoromethoxyprop-2-yl;

HET-1 is a 5- or 6-membered, C-linked heteroaryl ring containing a nitrogen atom in the 2-position and optionally 1 or 2 further ring heteroatoms independently selected from O, N and S; which ring is optionally substituted on any nitrogen atom (provided it is not thereby quaternised) by a methyl, ethyl or isopropyl group and/or on 1 or 2 available carbon atoms by a methyl, ethyl or fluoro group;

HET-2 is a 5- or 6-membered heteroaryl ring, containing 1, 2 or 3 ring hetereoatoms independently selected from O, S and N; which ring is substituted on an available carbon atom by a substituent selected from $R^2$, and is optionally further substituted on 1 or 2 available carbon atoms by a substituent independently selected from $R^3$ and/or on an available nitrogen atom (provided it is not thereby quaternised) by a substituent selected from $R^{10}$;

$R^2$ is selected from —C(O)NR$^4$R$^5$ and —SO$_2$NR$^4$R$^5$;

$R^3$ is selected from methyl and halo;

$R^4$ and $R^5$ together with the nitrogen atom to which they are attached form a 4 to 7 membered saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to a S(O) or S(O)$_2$ group; which ring is optionally substituted on an available carbon atom by 1 or 2 substituents independently selected from $R^8$ and/or on an available nitrogen atom by a substituent selected from $R^9$;

$R^8$ is selected from hydroxy, (1-4C)alkoxy and (1-4C)alkyl;

$R^9$ is selected from (1-4C)alkyl, —C(O)(1-4C)alkyl, and —S(O)p(1-4C)alkyl;

$R^{10}$ is selected from (1-4C)alkyl, —C(O)(1-4C)alkyl, benzyl, and (1-4C)alkylsulfonyl;

p is (independently at each occurrence) 0, 1 or 2.

In another aspect of the invention there is provided a compound of formula (I) or (IA) as hereinbefore defined, or a salt thereof, wherein:

$R^1$ is selected from isopropyl, but-2-yl, cyclopentyl, 1,1,1-trifluoroprop-2-yl, 1,3-difluoroprop-2-yl, but-1-yn-3-yl, 1-hydroxyprop-2-yl, 2-hydroxybut-3-yl, tetrahydrofuryl, tetrahydropyranyl, 1-methoxyprop-2-yl, 2-hydroxyprop-1-yl, 2-methoxyprop-1-yl, 2-hydroxybut-1-yl, 2-methoxybut-1-yl, 1-fluoromethoxyprop-2-yl and 1,1-difluoromethoxyprop-2-yl;

HET-1 is a 5- or 6-membered, C-linked heteroaryl ring containing a nitrogen atom in the 2-position and optionally 1 or 2 further ring heteroatoms independently selected from O, N and S; which ring is optionally substituted on any nitrogen atom (provided it is not thereby quaternised) by a methyl, ethyl or isopropyl group and/or on 1 or 2 available carbon atoms by a methyl, ethyl or fluoro group;

HET-2 is a 5- or 6-membered heteroaryl ring, containing 1, 2 or 3 ring hetereoatoms independently selected from O, S and N; which ring is substituted on an available carbon atom by a substituent selected from $R^2$, and is optionally further substituted on 1 or 2 available carbon atoms by a substituent independently selected from $R^3$;

$R^2$ is selected from —C(O)NR$^4$R$^5$ and —SO$_2$NR$^4$R$^5$;

$R^3$ is selected from methyl and halo;

$R^4$ and $R^5$ together with the nitrogen atom to which they are attached form a 4 to 7 membered saturated or partially unsaturated heterocyclyl ring, optionally containing 1 or 2 further heteroatoms (in addition to the linking N atom) independently selected from O, N and S, wherein a —CH$_2$— group can optionally be replaced by a —C(O)— and wherein a sulphur atom in the ring may optionally be oxidised to a S(O) or S(O)$_2$ group; or $R^4$ and $R^5$ together with the nitrogen atom to which they are attached form a 6-10 membered bicyclic saturated or partially unsaturated heterocyclyl ring, optionally containing 1 further nitrogen atom (in addition to the linking N atom), wherein a —CH$_2$— group can optionally be replaced by a —C(O)—.

In another aspect of the invention there is provided a compound of formula (I) or (IA) as hereinbefore defined, or a salt thereof, wherein:

$R^1$ is selected from isopropyl, but-2-yl, 1,3-difluoroprop-2-yl, 1-hydroxyprop-2-yl and 1-methoxyprop-2-yl and tetrahydrofuryl;

HET-1 is an optionally substituted 5- or 6-membered heteroaryl ring as hereinbefore defined;

HET-2 is a substituted 5- or 6-membered heteroaryl ring as hereinbefore defined;

$R^2$ is —CONR$^4$R$^5$;

$R^4$ and $R^5$ together form an azetidinyl, pyrrolidinyl or morpholino ring.

In another aspect of the invention there is provided a compound of formula (I) or (IA) as hereinbefore defined, or a salt thereof, wherein:

$R^1$ is selected from isopropyl, 1,3-difluoroprop-2-yl, but-2-yl, 1-hydroxyprop-2-yl, 2-hydroxybut-3-yl, 1-difluoromethoxyprop-2-yl, tetrahydrofuryl, 1-hydroxybut-2-yl and 1-methoxyprop-2-yl;

HET-1 is an optionally substituted 5- or 6-membered heteroaryl ring as hereinbefore defined;

HET-2 is a substituted 5- or 6-membered heteroaryl ring as hereinbefore defined;

$R^2$ is —CONR$^4$R$^5$;

$R^4$ and $R^5$ together form an azetidinyl, pyrrolidinyl or morpholino ring.

In another aspect of the invention there is provided a compound of formula (I) or (IA) as hereinbefore defined, or a salt thereof, wherein:

$R^1$ is selected from isopropyl, cyclopentyl, 1,3-difluoroprop-2-yl, but-2-yl, 1-hydroxyprop-2-yl, 2-hydroxybut-3-yl, 1-difluoromethoxyprop-2-yl, tetrahydrofuryl, tetrahydropyranyl, 1-hydroxybut-2-yl and 1-methoxyprop-2-yl;

HET-1 is an optionally substituted 5- or 6-membered heteroaryl ring as hereinbefore defined;

HET-2 is a substituted 5- or 6-membered heteroaryl ring as hereinbefore defined;

$R^2$ is —CONR$^4$R$^5$;

$R^4$ and $R^5$ together form an azetidinyl or pyrrolidinyl ring.

In another aspect of the invention there is provided a compound of formula (I) or (IA) as hereinbefore defined, or a salt thereof, wherein:

$R^1$ is selected from isopropyl, 1,3-difluoroprop-2-yl, 1-hydroxyprop-2-yl and 1-methoxyprop-2-yl, HET-1 is selected from thiazolyl, pyrazolyl, thiadiazolyl and pyrazinyl, wherein $R^1$ is optionally substituted on carbon or nitrogen with a methyl or ethyl group;

HET-2 is selected from pyridyl, pyrazinyl, thiazolyl and thienyl, substituted by $R^2$ and optionally substituted by $R^3$;

$R^3$ is fluoro or chloro;

$R^2$ is —CONR$^4$R$^5$;

$R^4$ and $R^5$ together form an azetidinyl, pyrrolidinyl or morpholino ring.

In another aspect of the invention there is provided a compound of formula (I) or (IA) as hereinbefore defined, or a salt thereof, wherein:

$R^1$ is selected from isopropyl, 1,3-difluoroprop-2-yl, but-2-yl, 1-hydroxyprop-2-yl, 2-hydroxybut-3-yl, 1-difluoromethoxyprop-2-yl, tetrahydrofuryl, 1-hydroxybut-2-yl and 1-methoxyprop-2-yl;

HET-1 is selected from thiazolyl, pyrazolyl, thiadiazolyl and pyrazinyl, wherein $R^1$ is optionally substituted with a methyl, isopropyl or ethyl group;

HET-2 is selected from pyridyl, pyrazinyl, thiazolyl and pyrimidinyl, substituted by $R^2$ and optionally substituted by $R^3$;

$R^3$ is fluoro or chloro;

$R^2$ is —CONR$^4$R$^5$;

$R^4$ and $R^5$ together form an azetidinyl, pyrrolidinyl or morpholino ring.

In another aspect of the invention there is provided a compound of formula (I) or (IA) as hereinbefore defined, or a salt thereof, wherein:

$R^1$ is selected from isopropyl, cyclopentyl, 1,3-difluoroprop-2-yl, but-2-yl, 1-hydroxyprop-2-yl, 2-hydroxybut-3-yl, 1-difluoromethoxyprop-2-yl, tetrahydrofuryl, tetrahydropyranyl, 1-hydroxybut-2-yl and 1-methoxyprop-2-yl;

HET-1 is selected from thiazolyl, pyrazolyl, thiadiazolyl, pyridyl, isoxazolyl and pyrazinyl, wherein $R^1$ is optionally substituted with a methyl, isopropyl or ethyl group and/or (on a carbon atom) by fluoro;

HET-2 is selected from pyridyl, pyrazinyl, pyridazinyl, thiazolyl and pyrimidinyl, substituted by $R^2$ and optionally substituted by $R^3$;

$R^3$ is fluoro or chloro;

$R^2$ is —CONR$^4$R$^5$;

$R^4$ and $R^5$ together form an azetidinyl or pyrrolidinyl ring.

In another aspect of the invention there is provided a compound of formula (I) or (IA) as hereinbefore defined, or a salt thereof, wherein:

$R^1$ is selected from isopropyl, cyclopentyl, 1,3-difluoroprop-2-yl, but-2-yl, 1-hydroxyprop-2-yl, 2-hydroxybut-3-yl, 1-difluoromethoxyprop-2-yl, tetrahydrofuryl, tetrahydropyranyl, 1-hydroxybut-2-yl and 1-methoxyprop-2-yl;

HET-1 is selected from thiazolyl, pyrazolyl, thiadiazolyl, pyridyl, isoxazolyl and pyrazinyl, wherein $R^1$ is optionally substituted with a methyl, isopropyl or ethyl group and/or (on a carbon atom) by fluoro;

HET-2 is selected from pyridyl, pyrazinyl, pyridazinyl, thiazolyl and pyrimidinyl, substituted by $R^2$ and optionally substituted by $R^3$;

$R^3$ is methyl, fluoro or chloro;

$R^2$ is —CONR$^4$R$^5$;

$R^4$ and $R^5$ together form an azetidinyl, 7-azabicyclo[2.2.1]hept-7-yl, morpholino, or pyrrolidinyl ring.

In another aspect of the invention there is provided a compound of formula (I) or (IA) as hereinbefore defined, or a salt thereof, wherein:

$R^1$ is selected from isopropyl, cyclopentyl, 1,3-difluoroprop-2-yl, but-2-yl, 1-hydroxyprop-2-yl, 2-hydroxybut-3-yl, 1-difluoromethoxyprop-2-yl, tetrahydrofuryl, tetrahydropyranyl, 1-hydroxybut-2-yl and 1-methoxyprop-2-yl;

HET-1 is selected from thiazolyl, pyrazolyl, thiadiazolyl, pyridyl, isoxazolyl and pyrazinyl, wherein $R^1$ is optionally substituted with a methyl, isopropyl or ethyl group and/or (on a carbon atom) by fluoro;

HET-2 is selected from pyridyl, pyrazinyl, pyridazinyl, thiazolyl and pyrimidinyl, substituted by $R^2$ and optionally substituted by $R^3$;

$R^3$ is methyl, fluoro or chloro;

$R^2$ is —CONR$^4$R$^5$;

$R^4$ and $R^5$ together form an azetidinyl or pyrrolidinyl ring.

In another aspect of the invention there is provided a compound of formula (I) or (IA) as hereinbefore defined, or a salt thereof, wherein:

$R^1$ is selected from isopropyl, cyclopentyl, 1,3-difluoroprop-2-yl, but-2-yl, 1-hydroxyprop-2-yl, 2-hydroxybut-3-yl, 1-difluoromethoxyprop-2-yl, tetrahydrofuryl, tetrahydropyranyl, 1-hydroxybut-2-yl and 1-methoxyprop-2-yl;

HET-1 is selected from thiazolyl, pyrazolyl, thiadiazolyl, pyridyl, isoxazolyl and pyrazinyl, wherein $R^1$ is optionally substituted on a nitrogen atom with methyl, difluoromethyl, isopropyl or ethyl and/or on a carbon atom by fluoro or methyl; provided that when HET-1 is pyrazolyl, $R^1$ is selected from 1-methoxyprop-2-yl, isopropyl, and tetrahydrofuryl;

HET-2 is selected from pyridyl, pyrazinyl, pyridazinyl, thiazolyl and pyrimidinyl, substituted by $R^2$ and optionally substituted by $R^3$;

$R^3$ is methyl, fluoro or chloro;

$R^2$ is —CONR$^4$R$^5$ or —SO$_2$NR$^4$R$^5$, particularly —CONR$^4$R$^5$;

$R^4$ and $R^5$ together form an azetidinyl, 7-azabicyclo[2.2.1]hept-7-yl, morpholino, or pyrrolidinyl ring.

In another aspect, Aspect A, of the invention there is provided a compound of formula (I) or (IA) as hereinbefore defined, or a salt thereof, wherein:

$R^1$ is selected from isopropyl, cyclopentyl, 1,3-difluoroprop-2-yl, but-2-yl, 1-hydroxyprop-2-yl, 2-hydroxybut-3-yl, 1-difluoromethoxyprop-2-yl, tetrahydrofuryl, tetrahydropyranyl, 1-hydroxybut-2-yl and 1-methoxyprop-2-yl;

HET-1 is selected from pyrazinyl (optionally substituted with methyl), pyrazolyl (optionally substituted on carbon by methyl), methylthiadiazolyl (particularly 3-methyl-1,2,4-thiadiazol-5-yl), thiazolyl (optionally substituted with methyl), pyridyl (optionally substituted by fluoro) and isoxazolyl; provided that when HET-1 is pyrazolyl, particularly $R^1$ is selected from 1-methoxyprop-2-yl, isopropyl, and tetrahydrofuryl;

HET-2 is selected from pyridyl, pyrazinyl, pyridazinyl, thiazolyl and pyrimidinyl, substituted by $R^2$ and optionally substituted by $R^3$;

$R^3$ is methyl, fluoro or chloro;

$R^2$ is —CONR$^4$R$^5$ or —SO$_2$NR$^4$R$^5$, particularly —CONR$^4$R$^5$;

$R^4$ and $R^5$ together form an azetidinyl, 7-azabicyclo[2.2.1]hept-7-yl, morpholino, or pyrrolidinyl ring.

In another aspect, Aspect B, of the invention there is provided a compound of formula (I) or (IA) as hereinbefore defined, or a salt thereof, wherein:

$R^1$ is selected from isopropyl, cyclopentyl, 1,3-difluoroprop-2-yl, but-2-yl, 1-hydroxyprop-2-yl, 2-hydroxybut-3-yl, 1-difluoromethoxyprop-2-yl, tetrahydrofuryl, tetrahydropyranyl, 1-hydroxybut-2-yl and 1-methoxyprop-2-yl;

HET-1 is selected from pyrazinyl (optionally substituted with methyl), pyrazolyl (optionally substituted on carbon by methyl), methylthiadiazolyl (particularly 3-methyl-1,2,4-thiadiazol-5-yl), thiazolyl (optionally substituted with methyl), pyridyl (optionally substituted by fluoro) and isoxazolyl; provided that when HET-1 is pyrazolyl, particularly $R^1$ is selected from 1-methoxyprop-2-yl, isopropyl, and tetrahydrofuryl;

HET-2 is selected from pyridyl and pyrazinyl, substituted by $R^2$ and optionally substituted by $R^3$;

$R^3$ is methyl, fluoro or chloro;

R² is —CONR⁴R⁵ or —SO₂NR⁴R⁵, particularly —CONR⁴R⁵;

R⁴ and R⁵ together form an azetidinyl or pyrrolidinyl ring, particularly azetidinyl. Particular compounds of Aspect B are those of formulae (IB), (IC) and/or (ID).

In another aspect, Aspect C, of the invention there is provided a compound of formula (IB), (IC) or (ID) as hereinbefore defined, or a salt thereof, wherein:

R¹ is selected from isopropyl, 1-hydroxyprop-2-yl, tetrahydrofuryl and 1-methoxyprop-2-yl; (particularly R¹ is selected from isopropyl, (2S)-1-hydroxyprop-2-yl, tetrahydrofuryl and (2S)-1-methoxyprop-2-yl);

HET-1 is methylpyrazinyl;

R² is —CONR⁴R⁵;

R⁴ and R⁵ together form an azetidinyl ring.

In another aspect, Aspect D, of the invention there is provided a compound of formula (IB) as hereinbefore defined, or a salt thereof, wherein:

R¹ is selected from isopropyl, 1-hydroxyprop-2-yl, tetrahydrofuryl and 1-methoxyprop-2-yl; (particularly R¹ is selected from isopropyl, (2S)-1-hydroxyprop-2-yl, tetrahydrofuryl and (2S)-1-methoxyprop-2-yl);

HET-1 is methylpyrazinyl;

R² is —CONR⁴R⁵;

R⁴ and R⁵ together form an azetidinyl ring.

In another aspect, Aspect E, of the invention there is provided a compound of formula (IB), (IC) or (ID) as hereinbefore defined, or a salt thereof, wherein:

R¹ is selected from isopropyl, tetrahydrofuryl and 1-methoxyprop-2-yl (particularly (2S)-1-methoxyprop-2-yl);

HET-1 is pyrazolyl;

R² is —CONR⁴R⁵;

R⁴ and R⁵ together form an azetidinyl ring.

In another aspect, Aspect F, of the invention there is provided a compound of formula (IB) as hereinbefore defined, or a salt thereof, wherein:

R¹ is selected from isopropyl, tetrahydrofuryl and 1-methoxyprop-2-yl (particularly (2S)-1-methoxyprop-2-yl);

HET-1 is pyrazolyl;

R² is —CONR⁴R⁵;

R⁴ and R⁵ together form an azetidinyl ring.

In another aspect of the invention there is provided a compound of formula (I) (or IA) as hereinbefore defined, or a salt thereof, wherein:

R¹ is selected from isopropyl, but-2-yl, 1,3-difluoroprop-2-yl, 1-hydroxyprop-2-yl and 1-methoxyprop-2-yl and tetrahydrofuryl;

HET-1 is an optionally substituted 5- or 6-membered heteroaryl ring as hereinbefore defined;

HET-2 is an optionally substituted 5- or 6-membered heteroaryl ring as hereinbefore defined;

R² is —SO₂NR⁴R⁵;

R⁴ and R⁵ together form an azetidinyl, pyrrolidinyl or morpholino ring.

In another aspect of the invention there is provided a compound of formula (I) (or IA) as hereinbefore defined, or a salt thereof, wherein:

R¹ is selected from isopropyl, 1,3-difluoroprop-2-yl, 1-hydroxyprop-2-yl and 1-methoxyprop-2-yl, HET-1 is selected from thiazolyl, pyrazolyl, thiadiazolyl and pyrazinyl, wherein R¹ is optionally substituted on carbon or nitrogen with a methyl or ethyl group;

HET-2 is selected from pyridyl, pyrazinyl, thiazolyl and thienyl, substituted by R² and optionally substituted by R³;

R³ is fluoro or chloro,

R² is —SO₂NR⁴R⁵;

R⁴ and R⁵ together form an azetidinyl, pyrrolidinyl or morpholino ring.

In another aspect of the invention there is provided a compound of formula (I) (or IA) as hereinbefore defined, or a salt thereof, wherein:

R¹ is selected from isopropyl, 1,3-difluoroprop-2-yl, but-2-yl, 1-hydroxyprop-2-yl, 2-hydroxybut-3-yl, 1-difluoromethoxyprop-2-yl, tetrahydrofuryl, 1-hydroxybut-2-yl and 1-methoxyprop-2-yl;

HET-1 is an optionally substituted 5- or 6-membered heteroaryl ring as hereinbefore defined;

HET-2 is an optionally substituted 5- or 6-membered heteroaryl ring as hereinbefore defined;

R² is —SO₂NR⁴R⁵;

R⁴ and R⁵ together form an azetidinyl, pyrrolidinyl or morpholino ring.

In another aspect of the invention there is provided a compound of formula (I) (or IA) as hereinbefore defined, or a salt thereof, wherein:

R¹ is selected from isopropyl, 1,3-difluoroprop-2-yl, but-2-yl, 1-hydroxyprop-2-yl, 2-hydroxybut-3-yl, 1-difluoromethoxyprop-2-yl, tetrahydrofuryl, 1-hydroxybut-2-yl and 1-methoxyprop-2-yl;

HET-1 is selected from thiazolyl, pyrazolyl, thiadiazolyl and pyrazinyl, wherein R¹ is optionally substituted with a methyl, isopropyl or ethyl group;

HET-2 is selected from pyridyl, pyrazinyl, thiazolyl and pyrimidinyl, substituted by R² and optionally substituted by R³;

R³ is fluoro or chloro;

R² is —SO₂NR⁴R⁵;

R⁴ and R⁵ together form an azetidinyl, pyrrolidinyl or morpholino ring.

In another aspect of the invention there is provided a compound of formula (I) (or IA) as hereinbefore defined, or a salt thereof, wherein:

R¹ is selected from isopropyl, 1,3-difluoroprop-2-yl, but-2-yl, 1-hydroxyprop-2-yl, 2-hydroxybut-3-yl, 1-difluoromethoxyprop-2-yl, tetrahydrofuryl, 1-hydroxybut-2-yl and 1-methoxyprop-2-yl;

HET-1 is selected from thiazolyl, pyrazolyl, thiadiazolyl and pyrazinyl, wherein R¹ is optionally substituted with a methyl, isopropyl or ethyl group;

HET-2 is selected from pyridyl, pyrazinyl, thiazolyl and pyrimidinyl, substituted by R² and optionally substituted by R³;

$R^3$ is fluoro or chloro;

$R^2$ is —CONR$^4$R$^5$ or —SO$_2$NR$^4$R$^5$;

$R^4$ and $R^5$ together form an azetidinyl, pyrrolidinyl or morpholino ring.

In one aspect of the invention there is provided a compound of formula (I) (or IA) as hereinbefore defined, or a salt thereof, wherein:

$R^1$ is selected from 1-fluoromethoxyprop-2-yl and 1,1-difluoromethoxyprop-2-yl;

HET-1 is an optionally substituted 5- or 6-membered heteroaryl ring as hereinbefore defined;

HET-2 is an optionally substituted 5- or 6-membered heteroaryl ring as hereinbefore defined;

$R^2$ is —CONR$^4$R$^5$;

$R^4$ and $R^5$ together form an azetidinyl, pyrrolidinyl or morpholino ring.

In another aspect of the invention there is provided a compound of formula (I) (or IA) as hereinbefore defined, or a salt thereof, wherein:

$R^1$ is selected from 1-fluoromethoxyprop-2-yl and 1,1-difluoromethoxyprop-2-yl;

HET-1 is selected from thiazolyl, pyrazolyl, thiadiazolyl and pyrazinyl, wherein $R^1$ is optionally substituted on carbon or nitrogen with a methyl or ethyl group;

HET-2 is selected from pyridyl, pyrazinyl, thiazolyl and thienyl, substituted by $R^2$ and optionally substituted by $R^3$;

$R^3$ is fluoro or chloro;

$R^2$ is —CONR$^4$R$^5$;

$R^4$ and $R^5$ together form an azetidinyl, pyrrolidinyl or morpholino ring.

In one aspect of the invention there is provided a compound of formula (I) (or IA) as hereinbefore defined, or a salt thereof, wherein:

$R^1$ is selected from 1-fluoromethoxyprop-2-yl and 1,1-difluoromethoxyprop-2-yl;

HET-1 is an optionally substituted 5- or 6-membered heteroaryl ring as hereinbefore defined;

HET-2 is an optionally substituted 5- or 6-membered heteroaryl ring as hereinbefore defined;

$R^2$ is —SO$_2$NR$^4$R$^5$;

$R^4$ and $R^5$ together form an azetidinyl, pyrrolidinyl or morpholino ring.

In another aspect of the invention there is provided a compound of formula (I) (or IA) as hereinbefore defined, or a salt thereof, wherein:

$R^1$ is selected from 1-fluoromethoxyprop-2-yl and 1,1-difluoromethoxyprop-2-yl;

HET-1 is selected from thiazolyl, pyrazolyl, thiadiazolyl and pyrazinyl, wherein $R^1$ is optionally substituted on carbon or nitrogen with a methyl or ethyl group;

HET-2 is selected from pyridyl, pyrazinyl, thiazolyl and thienyl, substituted by $R^2$ and optionally substituted by $R^3$;

$R^3$ is fluoro or chloro;

$R^2$ is —SO$_2$NR$^4$R$^5$;

$R^4$ and $R^5$ together form an azetidinyl, pyrrolidinyl or morpholino ring.

Further preferred compounds of the invention are each of the Examples (and salts thereof), each of which provides a further independent aspect of the invention. In further aspects, the present invention also comprises any two or more compounds of the Examples (and salts thereof).

Particular compounds of the invention include any one or more of:

3-{[5-(azetidin-1-ylcarbonyl)pyridin-2-yl]oxy}-5-{[(1S)-2-hydroxy-1-methylethyl]oxy}-N-1,3-thiazol-2-ylbenzamide;

3-{[5-(azetidin-1-ylcarbonyl)-3-chloropyridin-2-yl]oxy}-5-{[(1S)-2-hydroxy-1-methylethyl]oxy}-N-1,3-thiazol-2-ylbenzamide;

3-{[6-(azetidin-1-ylcarbonyl)pyridin-3-yl]oxy}-5-{[(1S)-2-hydroxy-1-methylethyl]oxy}-N-1,3-thiazol-2-ylbenzamide;

3-{[5-(azetidin-1-ylcarbonyl)pyridin-3-yl]oxy}-5-{[(1S)-2-hydroxy-1-methylethyl]oxy}-N-(1-methyl-1H-pyrazol-3-yl)benzamide;

3-{[6-(azetidin-1-ylcarbonyl)pyridin-3-yl]oxy}-5-{[(1S)-2-hydroxy-1-methylethyl]oxy}-N-(1-methyl-1H-pyrazol-3-yl)benzamide;

3-{[5-(azetidin-1-ylcarbonyl)pyridin-2-yl]oxy}-5-{[(1S)-1-methyl-2-(methyloxy)ethyl]oxy}-N-(1-methyl-1H-pyrazol-3-yl)benzamide;

3-{[5-(azetidin-1-ylcarbonyl)-3-chloropyridin-2-yl]oxy}-5-{[(1S)-1-methyl-2-(methyloxy)ethyl]oxy}-N-(1-methyl-1H-pyrazol-3-yl)benzamide;

3-{[5-(azetidin-1-ylcarbonyl)pyridin-2-yl]oxy}-5-[(1-methylethyl)oxy]-N-1,3-thiazol-2-ylbenzamide;

3-{[5-(azetidin-1-ylcarbonyl)-3-chloropyridin-2-yl]oxy}-5-[(1-methylethyl)oxy]-N-1,3-thiazol-2-ylbenzamide;

3-{[5-(azetidin-1-ylcarbonyl)pyridin-2-yl]oxy}-5-[(1-methylethyl)oxy]-N-(1-methyl-1H-pyrazol-3-yl)benzamide;

3-{[5-(azetidin-1-ylcarbonyl)-3-chloropyridin-2-yl]oxy}-5-[(1-methylethyl)oxy]-N-(1-methyl-1H-pyrazol-3-yl)benzamide;

3-{[5-(azetidin-1-ylcarbonyl)pyridin-2-yl]oxy}-5-{[(1S)-1-methyl-2-(methyloxy)ethyl]oxy}-N-(3-methyl-1,2,4-thiadiazol-5-yl)benzamide;

3-{[5-(azetidin-1-ylcarbonyl)-3-chloropyridin-2-yl]oxy}-5-{[(1S)-1-methyl-2-(methyloxy)ethyl]oxy}-N-(3-methyl-1,2,4-thiadiazol-5-yl)benzamide;

3-{[6-(azetidin-1-ylcarbonyl)pyridin-3-yl]oxy}-5-{[(1S)-1-methyl-2-(methyloxy)ethyl]oxy}-N-(1-methyl-1H-pyrazol-3-yl)benzamide;

3-{[5-(azetidin-1-ylcarbonyl)pyridin-3-yl]oxy}-5-{[(1S)-1-methyl-2-(methyloxy)ethyl]oxy}-N-(1-methyl-1H-pyrazol-3-yl)benzamide;

3-{[5-(azetidin-1-ylcarbonyl)pyridin-3-yl]oxy}-5-[(1-methylethyl)oxy]-N-(1-methyl-1H-pyrazol-3-yl)benzamide;

3-{[6-(azetidin-1-ylcarbonyl)pyridin-3-yl]oxy}-5-[(1-methylethyl)oxy]-N-1,3-thiazol-2-ylbenzamide;

3-{[6-(azetidin-1-ylcarbonyl)pyridin-3-yl]oxy}-5-[(1-methylethyl)oxy]-N-(1-methyl-1H-pyrazol-3-yl)benzamide;

3-{[6-(azetidin-1-ylcarbonyl)pyridin-3-yl]oxy}-5-{[(1S)-1-methyl-2-(methyloxy)ethyl]oxy}-N-1,3-thiazol-2-ylbenzamide;

3-{[6-(azetidin-1-ylcarbonyl)pyridin-3-yl]oxy}-5-{[(1S)-1-methyl-2-(methyloxy)ethyl]oxy}-N-(3-methyl-1,2,4-thiadiazol-5-yl)benzamide;

3-{[6-(azetidin-1-ylcarbonyl)pyridin-3-yl]oxy}-5-[(1-methylethyl)oxy]-N-(3-methyl-1,2,4-thiadiazol-5-yl)benzamide;

3-{[5-(azetidin-1-ylsulfonyl)pyridin-2-yl]oxy}-5-{[(1S)-1-methyl-2-(methyloxy)ethyl]oxy}-N-(1-methyl-1H-pyrazol-3-yl)benzamide;

3-{[5-(azetidin-1-ylcarbonyl)pyrazin-2-yl]oxy}-5-{[(1S)-1-methyl-2-(methyloxy)ethyl]oxy}-N-(1-methyl-1H-pyrazol-3-yl)benzamide;

3-{[5-(azetidin-1-ylcarbonyl)-1,3-thiazol-2-yl]oxy}-5-[(1-methylethyl)oxy]-N-(1-methyl-1H-pyrazol-3-yl)benzamide;

3-{[5-(azetidin-1-ylcarbonyl)pyridin-2-yl]oxy}-5-{[(1S)-2-hydroxy-1-methylethyl]oxy}-N-(1-methyl-1H-pyrazol-3-yl)benzamide;

3-{[3-chloro-5-(morpholin-4-ylcarbonyl)pyridin-2-yl]oxy}-5-{[(1S)-2-hydroxy-1-methylethyl]oxy}-N-(1-methyl-1H-pyrazol-3-yl)benzamide; and 3-{[5-(azetidin-1-ylcarbonyl)-3-chloropyridin-2-yl]oxy}-5-{[2-fluoro-1-(fluoromethyl)ethyl]oxy}-N-(1-methyl-1H-pyrazol-3-yl)benzamide; and/or 3-{[5-(azetidin-1-ylcarbonyl)-1,3-thiazol-2-yl]oxy}-5-{[(1S)-1-methyl-2-(methyloxy)ethyl]oxy}-N-(1-methyl-1H-pyrazol-3-yl)benzamide;

3-{[5-(azetidin-1-ylcarbonyl)-3-chloropyridin-2-yl]oxy}-5-{[(1S)-1-methylpropyl]oxy}-N-(1-methyl-1H-pyrazol-3-yl)benzamide;

3-{[5-(azetidin-1-ylcarbonyl)pyrazin-2-yl]oxy}-5-{[(1S)-1-methylpropyl]oxy}-N-(1-methyl-1H-pyrazol-3-yl)benzamide;

3-{[6-(azetidin-1-ylcarbonyl)pyridin-3-yl]oxy}-5-{[(1S)-1-methylpropyl]oxy}-N-(1-methyl-1H-pyrazol-3-yl)benzamide;

3-{[2-(azetidin-1-ylcarbonyl)pyrimidin-5-yl]oxy}-5-[(1-methylethyl)oxy]-N-(1-methyl-1H-pyrazol-3-yl)benzamide;

3-{[2-(azetidin-1-ylcarbonyl)pyrimidin-5-yl]oxy}-5-{[(1S)-1-methyl-2-(methyloxy)ethyl]oxy}-N-(1-methyl-1H-pyrazol-3-yl)benzamide;

3-{[6-(azetidin-1-ylcarbonyl)pyridin-3-yl]oxy}-5-{[2-fluoro-1-(fluoromethyl)ethyl]oxy}-N-(1-methyl-1H-pyrazol-3-yl)benzamide;

3-{[5-(azetidin-1-ylcarbonyl)pyrazin-2-yl]oxy}-5-{[2-fluoro-1-(fluoromethyl)ethyl]oxy}-N-(1-methyl-1H-pyrazol-3-yl)benzamide;

3-{[5-(azetidin-1-ylcarbonyl)pyrazin-2-yl]oxy}-5-[(1-methylethyl)oxy]-N-(1-methyl-1H-pyrazol-3-yl)benzamide;

3-{[5-(azetidin-1-ylcarbonyl)-3-chloropyridin-2-yl]oxy}-5-({(1S)-2-[(difluoromethyl)oxy]-1-methylethyl}oxy)-N-(1-methyl-1H-pyrazol-3-yl)benzamide;

3-{[5-(azetidin-1-ylcarbonyl)pyridin-2-yl]oxy}-5-({(1S)-2-[(difluoromethyl)oxy]-1-methylethyl}oxy)-N-(1-methyl-1H-pyrazol-3-yl)benzamide;

3-{[6-(azetidin-1-ylcarbonyl)pyridin-3-yl]oxy}-5-({(1S)-2-[(difluoromethyl)oxy]-1-methylethyl}oxy)-N-(1-methyl-1H-pyrazol-3-yl)benzamide;

3-{[5-(azetidin-1-ylcarbonyl)pyrazin-2-yl]oxy}-5-({(1S)-2-[(difluoromethyl)oxy]-1-methylethyl}oxy)-N-(1-methyl-1H-pyrazol-3-yl)benzamide;

3-{[5-(azetidin-1-ylcarbonyl)-3-chloropyridin-2-yl]oxy}-5-{[(1R,2R)-2-hydroxy-1-methylpropyl]oxy}-N-(1-methyl-1H-pyrazol-3-yl)benzamide;

3-{[5-(azetidin-1-ylcarbonyl)-3-chloropyridin-2-yl]oxy}-5-{[(1S,2S)-2-hydroxy-1-methylpropyl]oxy}-N-(1-methyl-1H-pyrazol-3-yl)benzamide;

3-{[5-(azetidin-1-ylcarbonyl)-3-chloropyridin-2-yl]oxy}-N-(1-ethyl-1H-pyrazol-3-yl)-5-{[(1S)-1-methyl-2-(methyloxy)ethyl]oxy}benzamide;

3-{[6-(azetidin-1-ylcarbonyl)pyridin-3-yl]oxy}-N-(1-ethyl-1H-pyrazol-3-yl)-5-{[(1S)-1-methyl-2-(methyloxy)ethyl]oxy}benzamide;

3-{[5-(azetidin-1-ylcarbonyl)pyrazin-2-yl]oxy}-N-(1-ethyl-1H-pyrazol-3-yl)-5-{[(1S)-1-methyl-2-(methyloxy)ethyl]oxy}benzamide;

3-{[5-(azetidin-1-ylcarbonyl)-3-chloropyridin-2-yl]oxy}-5-{[(1S)-2-hydroxy-1-methylethyl]oxy}-N-[1-(1-methylethyl)-1H-pyrazol-3-yl]benzamide;

3-{[5-(azetidin-1-ylcarbonyl)pyridin-2-yl]oxy}-5-{[(1S)-1-methyl-2-(methyloxy)ethyl]oxy}-N-1H-pyrazol-3-ylbenzamide;

3-{[5-(azetidin-1-ylcarbonyl)-3-chloropyridin-2-yl]oxy}-N-(1-methyl-1H-pyrazol-3-yl)-5-[(3S)-tetrahydrofuran-3-yloxy]benzamide;

3-{[6-(azetidin-1-ylcarbonyl)pyridin-3-yl]oxy}-N-(1-methyl-1H-pyrazol-3-yl)-5-[(3S)-tetrahydrofuran-3-yloxy]benzamide;

3-{[5-(azetidin-1-ylcarbonyl)pyrazin-2-yl]oxy}-N-(1-methyl-1H-pyrazol-3-yl)-5-[(3S)-tetrahydrofuran-3-yloxy]benzamide;

3-{[4-(azetidin-1-ylcarbonyl)-1,3-thiazol-2-yl]oxy}-5-{[(1S)-1-methyl-2-(methyloxy)ethyl]oxy}-N-(1-methyl-1H-pyrazol-3-yl)benzamide;

3-{[4-(azetidin-1-ylcarbonyl)-1,3-thiazol-2-yl]oxy}-5-[(1-methylethyl)oxy]-N-(1-methyl-1H-pyrazol-3-yl)benzamide;

3-{[5-(azetidin-1-ylcarbonyl)pyrazin-2-yl]oxy}-5-{[(1S)-1-(hydroxymethyl)propyl]oxy}-N-(1-methyl-1H-pyrazol-3-yl)benzamide; and/or 3-{[2-(azetidin-1-ylcarbonyl)pyrimidin-5-yl]oxy}-5-{[(1S)-1-methyl-2-(methyloxy)ethyl]oxy}-N-1,3-thiazol-2-ylbenzamide;

3-{[5-(azetidin-1-ylcarbonyl)pyrazin-2-yl]oxy}-5-(cyclopentyloxy)-N-(1-methyl-1H-pyrazol-3-yl)benzamide;

3-{[5-(azetidin-1-ylcarbonyl)-3-chloropyridin-2-yl]oxy}-5-(cyclopentyloxy)-N-(1-methyl-1H-pyrazol-3-yl)benzamide;

3-{[6-(azetidin-1-ylcarbonyl)pyridin-3-yl]oxy}-5-(cyclopentyloxy)-N-(1-methyl-1H-pyrazol-3-yl)benzamide;

3-{[5-(azetidin-1-ylcarbonyl)pyrazin-2-yl]oxy}-5-{[(1R,2R)-2-hydroxy-1-methylpropyl]oxy}-N-(1-methyl-1H-pyrazol-3-yl)benzamide;

3-{[5-(azetidin-1-ylcarbonyl)pyrazin-2-yl]oxy}-5-{[(1S,2S)-2-hydroxy-1-methylpropyl]oxy}-N-(1-methyl-1H-pyrazol-3-yl)benzamide;

3-{[5-(azetidin-1-ylcarbonyl)-1,3-thiazol-2-yl]oxy}-5-{[(1S)-1-methyl-2-(methyloxy)ethyl]oxy}-N-(5-methylpyrazin-2-yl)benzamide;

3-{[5-(azetidin-1-ylcarbonyl)-3-chloropyridin-2-yl]oxy}-5-{[(1S)-1-methyl-2-(methyloxy)ethyl]oxy}-N-(5-methylpyrazin-2-yl)benzamide;

3-{[5-(azetidin-1-ylcarbonyl)pyrazin-2-yl]oxy}-5-{[(1S)-1-methyl-2-(methyloxy)ethyl]oxy}-N-(5-methylpyrazin-2-yl)benzamide;

3-{[5-(azetidin-1-ylcarbonyl)pyridin-2-yl]oxy}-5-{[(1S)-1-methyl-2-(methyloxy)ethyl]oxy}-N-(5-methylpyrazin-2-yl)benzamide;

3-{[4-(azetidin-1-ylcarbonyl)-1,3-thiazol-2-yl]oxy}-5-{[(1S)-1-methyl-2-(methyloxy)ethyl]oxy}-N-(5-methylpyrazin-2-yl)benzamide;

3-{[5-(azetidin-1-ylcarbonyl)-4-methyl-1,3-thiazol-2-yl]oxy}-5-{[(1S)-1-methyl-2-(methyloxy)ethyl]oxy}-N-(5-methylpyrazin-2-yl)benzamide;

3-{[5-(azetidin-1-ylcarbonyl)-4-methyl-1,3-thiazol-2-yl]oxy}-5-{[(1S)-1-methyl-2-(methyloxy)ethyl]oxy}-N-(1-methyl-1H-pyrazol-3-yl)benzamide;

3-{[5-(azetidin-1-ylcarbonyl)-3-chloropyridin-2-yl]oxy}-5-[(1-methylethyl)oxy]-N-(5-methylpyrazin-2-yl)benzamide;

3-{[5-(azetidin-1-ylcarbonyl)pyrazin-2-yl]oxy}-5-[(1-methylethyl)oxy]-N-(5-methylpyrazin-2-yl)benzamide;

3-{[5-(azetidin-1-ylcarbonyl)pyridin-2-yl]oxy}-5-[(1-methylethyl)oxy]-N-(5-methylpyrazin-2-yl)benzamide;

3-{[5-(azetidin-1-ylcarbonyl)-4-methyl-1,3-thiazol-2-yl]oxy}-5-[(1-methylethyl)oxy]-N-(5-methylpyrazin-2-yl)benzamide;

3-{[6-(azetidin-1-ylcarbonyl)pyridin-3-yl]oxy}-5-{[(1S)-1-methyl-2-(methyloxy)ethyl]oxy}-N-(5-methylpyrazin-2-yl)benzamide;

3-{[6-(azetidin-1-ylcarbonyl)pyridin-3-yl]oxy}-5-[(1-methylethyl)oxy]-N-(5-methylpyrazin-2-yl)benzamide;

3-{[5-(azetidin-1-ylcarbonyl)-3-chloropyridin-2-yl]oxy}-5-{[(1S)-1-methyl-2-(methyloxy)ethyl]oxy}-N-1H-pyrazol-3-ylbenzamide;

3-{[5-(azetidin-1-ylcarbonyl)-3-chloropyridin-2-yl]oxy}-5-{[(1S)-1-methyl-2-(methyloxy)ethyl]oxy}-N-1,3-thiazol-2-ylbenzamide;

3-{[5-(azetidin-1-ylcarbonyl)-3-chloropyridin-2-yl]oxy}-5-{[(1S)-1-methyl-2-(methyloxy)ethyl]oxy}-N-pyridin-2-ylbenzamide;

3-{[5-(azetidin-1-ylcarbonyl)-3-chloropyridin-2-yl]oxy}-N-(1-ethyl-1H-pyrazol-3-yl)-5-[(1-methylethyl)oxy]benzamide;

3-{[5-(azetidin-1-ylcarbonyl)pyrazin-2-yl]oxy}-N-(1-ethyl-1H-pyrazol-3-yl)-5-[(1-methylethyl)oxy]benzamide;

3-{[5-(azetidin-1-ylcarbonyl)pyrazin-2-yl]oxy}-N-[1-(1-methylethyl)-1H-pyrazol-3-yl]-5-{[(1S)-1-methyl-2-(methyloxy)ethyl]oxy}benzamide;

3-{[6-(azetidin-1-ylcarbonyl)pyridin-3-yl]oxy}-N-(1-ethyl-1H-pyrazol-3-yl)-5-[(1-methylethyl)oxy]benzamide;

3-{[6-(azetidin-1-ylcarbonyl)pyridin-3-yl]oxy}-5-{[(1S)-1-methyl-2-(methyloxy)ethyl]oxy}-N-pyridin-2-ylbenzamide;

3-{[6-(azetidin-1-ylcarbonyl)pyridin-3-yl]oxy}-N-isoxazol-3-yl-5-{[(1S)-1-methyl-2-(methyloxy)ethyl]oxy}benzamide;

3-{[5-(azetidin-1-ylcarbonyl)-3-chloropyridin-2-yl]oxy}-5-[(1-methylethyl)oxy]-N-(3-methyl-1,2,4-thiadiazol-5-yl)benzamide;

3-{[6-(azetidin-1-ylcarbonyl)pyridin-3-yl]oxy}-5-[(1-methylethyl)oxy]-N-1H-pyrazol-3-ylbenzamide;

3-{[6-(azetidin-1-ylcarbonyl)pyridin-3-yl]oxy}-5-{[(1S)-1-methyl-2-(methyloxy)ethyl]oxy}-N-1H-pyrazol-3-ylbenzamide;

3-{[5-(azetidin-1-ylcarbonyl)pyrazin-2-yl]oxy}-5-[(1-methylethyl)oxy]-N-1H-pyrazol-3-ylbenzamide;

3-{[5-(azetidin-1-ylcarbonyl)pyrazin-2-yl]oxy}-5-{[(1S)-1-methyl-2-(methyloxy)ethyl]oxy}-N-1H-pyrazol-3-ylbenzamide;

3-{[5-(azetidin-1-ylcarbonyl)-3-chloropyridin-2-yl]oxy}-5-[(1-methylethyl)oxy]-N-1H-pyrazol-3-ylbenzamide;

3-{[5-(azetidin-1-ylcarbonyl)-3-chloropyridin-2-yl]oxy}-N-(1,5-dimethyl-1H-pyrazol-3-yl)-5-{[(1S)-1-methyl-2-(methyloxy)ethyl]oxy}benzamide;

3-{[5-(azetidin-1-ylcarbonyl)-3-chloropyridin-2-yl]oxy}-N-(1,5-dimethyl-1H-pyrazol-3-yl)-5-{[2-fluoro-1-(fluoromethyl)ethyl]oxy}benzamide;

3-{[6-(azetidin-1-ylcarbonyl)pyridazin-3-yl]oxy}-5-{[(1S)-1-methyl-2-(methyloxy)ethyl]oxy}-N-(1-methyl-1H-pyrazol-3-yl)benzamide;

3-{[5-(azetidin-1-ylcarbonyl)pyrazin-2-yl]oxy}-N-(4-methyl-1,3-thiazol-2-yl)-5-[(3S)-tetrahydrofuran-3-yloxy]benzamide;

3-{[5-(azetidin-1-ylcarbonyl)pyrazin-2-yl]oxy}-N-(5-methyl-1,3-thiazol-2-yl)-5-[(3S)-tetrahydrofuran-3-yloxy]benzamide;

3-{[5-(azetidin-1-ylcarbonyl)pyrazin-2-yl]oxy}-N-(1-ethyl-1H-pyrazol-3-yl)-5-[(3S)-tetrahydrofuran-3-yloxy]benzamide;

3-{[5-(azetidin-1-ylcarbonyl)pyrazin-2-yl]oxy}-N-[1-(1-methylethyl)-1H-pyrazol-3-yl]-5-[(3S)-tetrahydrofuran-3-yloxy]benzamide;

3-{[5-(azetidin-1-ylcarbonyl)pyrazin-2-yl]oxy}-N-1H-pyrazol-3-yl-5-[(3S)-tetrahydrofuran-3-yloxy]benzamide;

3-{[5-(azetidin-1-ylcarbonyl)pyrazin-2-yl]oxy}-N-(1,5-dimethyl-1H-pyrazol-3-yl)-5-[(3S)-tetrahydrofuran-3-yloxy]benzamide;

3-{[5-(azetidin-1-ylcarbonyl)-3-chloropyridin-2-yl]oxy}-N-(4-methyl-1,3-thiazol-2-yl)-5-[(3S)-tetrahydrofuran-3-yloxy]benzamide;

3-{[5-(azetidin-1-ylcarbonyl)-3-chloropyridin-2-yl]oxy}-N-(5-methyl-1,3-thiazol-2-yl)-5-[(3S)-tetrahydrofuran-3-yloxy]benzamide;

3-{[5-(azetidin-1-ylcarbonyl)-3-chloropyridin-2-yl]oxy}-N-(5-methylpyrazin-2-yl)-5-[(3S)-tetrahydrofuran-3-yloxy]benzamide;

3-{[5-(azetidin-1-ylcarbonyl)-3-chloropyridin-2-yl]oxy}-N-(1-ethyl-1H-pyrazol-3-yl)-5-[(3S)-tetrahydrofuran-3-yloxy]benzamide;

3-{[5-(azetidin-1-ylcarbonyl)-3-chloropyridin-2-yl]oxy}-N-[1-(1-methylethyl)-1H-pyrazol-3-yl]-5-[(3S)-tetrahydrofuran-3-yloxy]benzamide;

3-{[5-(azetidin-1-ylcarbonyl)-3-chloropyridin-2-yl]oxy}-N-1H-pyrazol-3-yl-5-[(3S)-tetrahydrofuran-3-yloxy]benzamide;

3-{[6-(azetidin-1-ylcarbonyl)pyridin-3-yl]oxy}-N-(5-methylpyrazin-2-yl)-5-[(3S)-tetrahydrofuran-3-yloxy]benzamide;

3-{[5-(azetidin-1-ylcarbonyl)pyrazin-2-yl]oxy}-N-(5-methylpyrazin-2-yl)-5-[(3S)-tetrahydrofuran-3-yloxy]benzamide;

3-{[6-(azetidin-1-ylcarbonyl)pyridin-3-yl]oxy}-N-(5-fluoropyridin-2-yl)-5-[(3S)-tetrahydrofuran-3-yloxy]benzamide;

3-{[3-chloro-5-(pyrrolidin-1-ylcarbonyl)pyridin-2-yl]oxy}-5-[(1-methylethyl)oxy]-N-(5-methylpyrazin-2-yl)benzamide;

3-{[3-chloro-5-(pyrrolidin-1-ylcarbonyl)pyridin-2-yl]oxy}-5-{[(1S)-1-methyl-2-(methyloxy)ethyl]oxy}-N-(5-methylpyrazin-2-yl)benzamide;

3-{[3-chloro-5-(pyrrolidin-1-ylcarbonyl)pyridin-2-yl]oxy}-N-(1-methyl-1H-pyrazol-3-yl)-5-[(3S)-tetrahydrofuran-3-yloxy]benzamide;

3-{[5-(azetidin-1-ylcarbonyl)pyrazin-2-yl]oxy}-N-(1-methyl-1H-pyrazol-3-yl)-5-(tetrahydro-2H-pyran-4-yloxy)benzamide;

3-{[5-(azetidin-1-ylcarbonyl)-3-chloropyridin-2-yl]oxy}-N-(1-methyl-1H-pyrazol-3-yl)-5-(tetrahydro-2H-pyran-4-yloxy)benzamide;

3-{[5-(azetidin-1-ylcarbonyl)pyrazin-2-yl]oxy}-N-(5-methylpyrazin-2-yl)-5-(tetrahydro-2H-pyran-4-yloxy)benzamide;

3-{[5-(azetidin-1-ylcarbonyl)-3-chloropyridin-2-yl]oxy}-N-(5-methylpyrazin-2-yl)-5-(tetrahydro-2H-pyran-4-yloxy)benzamide;

3-{[6-(azetidin-1-ylcarbonyl)pyridin-3-yl]oxy}-N-(1-methyl-1H-pyrazol-3-yl)-5-(tetrahydro-2H-pyran-4-yloxy)benzamide;

3-{[6-(azetidin-1-ylcarbonyl)pyridin-3-yl]oxy}-N-(5-methylpyrazin-2-yl)-5-(tetrahydro-2H-pyran-4-yloxy)benzamide; and
3-{[6-(azetidin-1-ylcarbonyl)pyridin-3-yl]oxy}-N-(1-methyl-1H-pyrazol-3-yl)-5-[(3R)-tetrahydrofuran-3-yloxy]benzamide; and/or
3-{[6-(azetidin-1-ylcarbonyl)pyridin-3-yl]oxy}-N-isoxazol-3-yl-5-[(3S)-tetrahydrofuran-3-yloxy]benzamide;
3-{[5-(azetidin-1-ylcarbonyl)pyrazin-2-yl]oxy}-N-pyrazin-2-yl-5-[(3S)-tetrahydrofuran-3-yloxy]benzamide;
3-{[5-(azetidin-1-ylcarbonyl)pyrazin-2-yl]oxy}-N-(5-fluoropyridin-2-yl)-5-[(3S)-tetrahydrofuran-3-yloxy]benzamide;
3-{[5-(azetidin-1-ylcarbonyl)pyrazin-2-yl]oxy}-5-{[(1S)-1-methyl-2-(methyloxy)ethyl]oxy}-N-pyridin-2-ylbenzamide;
3-{[5-(azetidin-1-ylcarbonyl)pyrazin-2-yl]oxy}-N-isoxazol-3-yl-5-{[(1S)-1-methyl-2-(methyloxy)ethyl]oxy}benzamide;
3-{[5-(azetidin-1-ylcarbonyl)pyrazin-2-yl]oxy}-5-{[(1S)-1-methyl-2-(methyloxy)ethyl]oxy}-N-(4-methyl-1,3-thiazol-2-yl)benzamide;
3-{[5-(azetidin-1-ylcarbonyl)pyrazin-2-yl]oxy}-5-{[(1S)-1-methyl-2-(methyloxy)ethyl]oxy}-N-(5-methyl-1,3-thiazol-2-yl)benzamide;
3-{[5-(azetidin-1-ylcarbonyl)pyrazin-2-yl]oxy}-5-{[(1S)-1-methyl-2-(methyloxy)ethyl]oxy}-N-pyrazin-2-ylbenzamide;
3-{[5-(azetidin-1-ylcarbonyl)pyrazin-2-yl]oxy}-5-[(1-methylethyl)oxy]-N-pyrazin-2-ylbenzamide;
3-{[6-(azetidin-1-ylcarbonyl)pyridin-3-yl]oxy}-5-{[(1S)-1-methyl-2-(methyloxy)ethyl]oxy}-N-pyrazin-2-ylbenzamide;
3-{[5-(azetidin-1-ylcarbonyl)-3-chloropyridin-2-yl]oxy}-5-[(1-methylethyl)oxy]-N-pyrazin-2-ylbenzamide;
3-{[5-(azetidin-1-ylcarbonyl)-3-chloropyridin-2-yl]oxy}-5-{[(1S)-1-methyl-2-(methyloxy)ethyl]oxy}-N-pyrazin-2-ylbenzamide;
3-{[3-chloro-5-(morpholin-4-ylcarbonyl)pyridin-2-yl]oxy}-N-(1-methyl-1H-pyrazol-3-yl)-5-[(3S)-tetrahydrofuran-3-yloxy]benzamide;
3-{[5-(7-azabicyclo[2.2.1]hept-7-ylcarbonyl)-3-chloropyridin-2-yl]oxy}-N-(1-methyl-1H-pyrazol-3-yl)-5-[(3S)-tetrahydrofuran-3-yloxy]benzamide; and
3-{[5-(azetidin-1-ylcarbonyl)-4-methyl-1,3-thiazol-2-yl]oxy}-N-(1-methyl-1H-pyrazol-3-yl)-5-[(3S)-tetrahydrofuran-3-yloxy]benzamide; and/or
3-{[6-(azetidin-1-ylcarbonyl)pyridin-3-yl]oxy}-5-{[(1S)-2-hydroxy-1-methylethyl]oxy}-N-(5-methylpyrazin-2-yl)benzamide;
3-{[6-(azetidin-1-ylcarbonyl)pyridin-3-yl]oxy}-5-{[(1S)-2-hydroxy-1-methylethyl]oxy}-N-(3-methyl-1,2,4-thiadiazol-5-yl)benzamide;
3-{[5-(azetidin-1-ylcarbonyl)-3-chloropyridin-2-yl]oxy}-5-{[(1S)-2-hydroxy-1-methylethyl]oxy}-N-(5-methylpyrazin-2-yl)benzamide;
3-{[5-(azetidin-1-ylcarbonyl)-3-chloropyridin-2-yl]oxy}-5-{[(1S)-2-hydroxy-1-methylethyl]oxy}-N-(3-methyl-1,2,4-thiadiazol-5-yl)benzamide;
3-{[5-(azetidin-1-ylcarbonyl)-3-chloropyridin-2-yl]oxy}-5-{[(1S)-2-hydroxy-1-methylethyl]oxy}-N-pyrazin-2-ylbenzamide;
3-{[5-(azetidin-1-ylcarbonyl)-3-chloropyridin-2-yl]oxy}-5-{[(1S)-2-hydroxy-1-methylethyl]oxy}-N-pyridin-2-ylbenzamide;
3-{[5-(azetidin-1-ylcarbonyl)pyridin-2-yl]oxy}-5-{[(1S)-2-hydroxy-1-methylethyl]oxy}-N-(3-methyl-1,2,4-thiadiazol-5-yl)benzamide;
N-(1-methyl-1H-pyrazol-3-yl)-3-{[6-(pyrrolidin-1-ylcarbonyl)pyridin-3-yl]oxy}-5-[(3S)-tetrahydrofuran-3-yloxy]benzamide;
3-{[6-(azetidin-1-ylcarbonyl)pyridin-3-yl]oxy}-N-pyrazin-2-yl-5-[(3S)-tetrahydrofuran-3-yloxy]benzamide;
3-{[6-(azetidin-1-ylcarbonyl)pyridin-3-yl]oxy}-N-(5-methyl-1H-pyrazol-3-yl)-5-[(3S)-tetrahydrofuran-3-yloxy]benzamide;
3-{[6-(azetidin-1-ylcarbonyl)pyridin-3-yl]oxy}-N-1H-pyrazol-3-yl-5-[(3S)-tetrahydrofuran-3-yloxy]benzamide;
3-{[5-(azetidin-1-ylcarbonyl)-3-chloropyridin-2-yl]oxy}-5-{[2-fluoro-1-(fluoromethyl)ethyl]oxy}-N-(5-methylpyrazin-2-yl)benzamide;
3-{[5-(azetidin-1-ylcarbonyl)-3-chloropyridin-2-yl]oxy}-5-{[2-fluoro-1-(fluoromethyl)ethyl]oxy}-N-1H-pyrazol-3-ylbenzamide;
3-{[5-(azetidin-1-ylcarbonyl)-3-chloropyridin-2-yl]oxy}-5-{[2-fluoro-1-(fluoromethyl)ethyl]oxy}-N-(5-methyl-1H-pyrazol-3-yl)benzamide;
3-{[5-(azetidin-1-ylcarbonyl)pyrazin-2-yl]oxy}-5-{[2-fluoro-1-(fluoromethyl)ethyl]oxy}-N-1H-pyrazol-3-ylbenzamide;
3-{[5-(azetidin-1-ylcarbonyl)pyrazin-2-yl]oxy}-5-{[2-fluoro-1-(fluoromethyl)ethyl]oxy}-N-(5-methylpyrazin-2-yl)benzamide;
3-{[5-(azetidin-1-ylcarbonyl)pyrazin-2-yl]oxy}-5-{[(1S)-2-hydroxy-1-methylethyl]oxy}-N-(5-methylpyrazin-2-yl)benzamide;
3-{[5-(azetidin-1-ylcarbonyl)pyrazin-2-yl]oxy}-5-({(1S)-2-[(difluoromethyl)oxy]-1-methylethyl}oxy)-N-1H-pyrazol-3-ylbenzamide;
3-{[5-(azetidin-1-ylsulfonyl)-4-methyl-1,3-thiazol-2-yl]oxy}-5-{[(1S)-1-methyl-2-(methyloxy)ethyl]oxy}-N-(5-methylpyrazin-2-yl)benzamide;
3-{[6-(azetidin-1-ylcarbonyl)pyridin-3-yl]oxy}-N-[1-(difluoromethyl)-1H-pyrazol-3-yl]-5-[(3S)-tetrahydrofuran-3-yloxy]benzamide;
3-{[5-(azetidin-1-ylcarbonyl)pyrazin-2-yl]oxy}-N-[1-(difluoromethyl)-1H-pyrazol-3-yl]-5-{[(1S)-1-methyl-2-(methyloxy)ethyl]oxy}benzamide;
3-{[6-(azetidin-1-ylcarbonyl)pyridin-3-yl]oxy}-N-[1-(difluoromethyl)-1H-pyrazol-3-yl]-5-{[(1S)-1-methyl-2-(methyloxy)ethyl]oxy}benzamide; and/or
3-{[5-(azetidin-1-ylcarbonyl)pyrazin-2-yl]oxy}-5-{[(1R)-1-methyl-2-(methyloxy)ethyl]oxy}-N-(5-methylpyrazin-2-yl)benzamide;
3-{[6-(azetidin-1-ylcarbonyl)pyridin-3-yl]oxy}-5-{[(1R)-1-methyl-2-(methyloxy)ethyl]oxy}-N-(5-methylpyrazin-2-yl)benzamide;

or a salt thereof.

A further feature of the invention is a pharmaceutical composition comprising a compound of Formula (I), (IA), (IB), (IC) or (ID) as defined above, or a pharmaceutically-acceptable salt thereof, together with a pharmaceutically-acceptable diluent or carrier.

According to another aspect of the invention there is provided the compound of Formula (I), (IA), (IB), (IC) or (ID) or a pharmaceutically-acceptable salt thereof as defined above for use as a medicament.

According to another aspect of the invention there is provided the compound of Formula (I), (IA), (IB), (IC) or (ID) or a pharmaceutically-acceptable salt thereof as defined above for use as a medicament for treatment of a disease mediated through GLK, in particular type 2 diabetes.

Further according to the invention there is provided the use a compound of Formula (I), (IA), (IB), (IC) or (ID) or a pharmaceutically-acceptable salt thereof in the preparation of a medicament for treatment of a disease mediated through GLK, in particular type 2 diabetes.

The compound is suitably formulated as a pharmaceutical composition for use in this way.

According to another aspect of the present invention there is provided a method of treating GLK mediated diseases, especially diabetes, by administering an effective amount of a compound of Formula (I), (IA), (IB), (IC) or (ID) or a pharmaceutically-acceptable salt thereof, to a mammal in need of such treatment.

Specific diseases which may be treated by a compound or composition of the invention include: blood glucose lowering in Type 2 Diabetes Mellitus without a serious risk of hypoglycaemia (and potential to treat type 1), dyslipidemia, obesity, insulin resistance, metabolic syndrome X, impaired glucose tolerance.

As discussed above, thus the GLK/GLKRP system can be described as a potential "Diabesity" target (of benefit in both Diabetes and Obesity). Thus, according to another aspect of the invention there is provided the use of a compound of Formula (I), (IA), (IB), (IC) or (ID) or a pharmaceutically-acceptable salt thereof, in the preparation of a medicament for use in the combined treatment or prevention, particularly treatment of diabetes and obesity.

According to another aspect of the invention there is provided the use of a compound of Formula (I), (IA), (IB), (IC) or (ID) or a pharmaceutically-acceptable salt thereof, in the preparation of a medicament for use in the treatment or prevention, particularly treatment of obesity.

According to another aspect of the invention there is provided the a compound of Formula (I), (IA), (IB), (IC) or (ID) or a pharmaceutically-acceptable salt thereof as defined above for use as a medicament for treatment or prevention, particularly treatment of obesity.

According to a further aspect of the invention there is provided a method for the combined treatment of obesity and diabetes by administering an effective amount of a compound of Formula (I), (IA), (IB), (IC) or (ID) or a pharmaceutically-acceptable salt thereof, to a mammal in need of such treatment.

According to a further aspect of the invention there is provided a method for the treatment of obesity by administering an effective amount of a compound of Formula (I), (IA), (IB), (IC) or (ID) or a pharmaceutically-acceptable salt thereof, to a mammal in need of such treatment.

Compounds of the invention may be particularly suitable for use as pharmaceuticals because of advantageous physical and/or pharmacokinetic properties, and/or favourable toxicity profile and/or favourable metabolic profile.

Favourable toxicity profile may be demonstrated, for example, by use of an Ames test assay, and/or by testing against the hERG ion channel. A favourable metabolic profile may mean, for example, reduced rate of metabolism, leading to reduction in clearance of the compound from the body and hence increased exposure to the compound, or a favourable metabolic profile may mean, for example, not forming active metabolites (which might be considered undesirable in some circumstances).

For example, compounds of Aspects A to F may have favourable toxicological profiles.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing). Dosage forms suitable for oral use are preferred.

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I), (IA), (IB), (IC) or (ID) will naturally vary according to the nature and severity of the conditions, the age and sex of the animal or patient and the route of administration, according to well known principles of medicine.

In using a compound of the Formula (I), (IA), (IB), (IC) or (ID) for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

The elevation of GLK activity described herein may be applied as a sole therapy or in combination with one or more other substances and/or treatments for the indication being treated. Such conjoint treatment may be achieved by way of the simultaneous, sequential or separate administration of the individual components of the treatment. Simultaneous treatment may be in a single tablet or in separate tablets. For example in the treatment of diabetes mellitus, chemotherapy may include the following main categories of treatment:

1) Insulin and insulin analogues;

2) Insulin secretagogues including sulphonylureas (for example glibenclamide, glipizide), prandial glucose regulators (for example repaglinide, nateglinide);

3) Agents that improve incretin action (for example dipeptidyl peptidase IV inhibitors, and GLP-1 agonists);

4) Insulin sensitising agents including PPARgamma agonists (for example pioglitazone and rosiglitazone), and agents with combined PPARalpha and gamma activity;

5) Agents that modulate hepatic glucose balance (for example metformin, fructose 1, 6 bisphosphatase inhibitors, glycogen phopsphorylase inhibitors, glycogen synthase kinase inhibitors);

6) Agents designed to reduce the absorption of glucose from the intestine (for example acarbose);

7) Agents that prevent the reabsorption of glucose by the kidney (SGLT inhibitors);

8) Agents designed to treat the complications of prolonged hyperglycaemia (for example aldose reductase inhibitors);

9) Anti-obesity agents (for example sibutramine and orlistat);

10) Anti-dyslipidaemia agents such as, HMG-CoA reductase inhibitors (eg statins); PPARα agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);

11) Antihypertensive agents such as, β blockers (eg atenolol, inderal); ACE inhibitors (eg lisinopril); Calcium antagonists (eg. nifedipine); Angiotensin receptor antagonists (eg candesartan), a antagonists and diuretic agents (eg. furosemide, benzthiazide);

12) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin;

13) Agents which antagonise the actions of glucagon; and

14) Anti-inflammatory agents, such as non-steroidal anti-inflammatory drugs (eg. aspirin) and steroidal anti-inflammatory agents (eg. cortisone).

According to another aspect of the present invention there is provided individual compounds produced as end products in the Examples set out below and salts thereof.

A compound of the invention, or a salt thereof, may be prepared by any process known to be applicable to the preparation of such compounds or structurally related compounds. Functional groups may be protected and deprotected using conventional methods. For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991.

Processes for the synthesis of compounds of Formula (I), (IA), (IB), (IC) or (ID) are provided as a further feature of the invention. Thus, according to a further aspect of the invention there is provided a process for the preparation of a compound of Formula (I), (IA), (IB), (IC) or (ID), which comprises a process a) to e) (wherein the variables are as defined hereinbefore for compounds of Formula (I), (IA), (IB), (IC) or (ID) unless otherwise defined):

(a) reaction of an acid of Formula (III) or activated derivative thereof with a compound of Formula (IV), wherein $R^1$ is as hereinbefore defined or a protected version thereof;

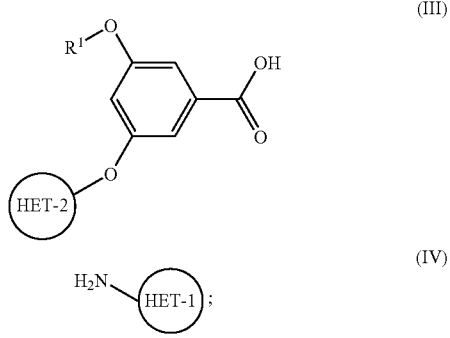

(III)

(IV)

or (b) reaction of a compound of Formula (V) with a compound of Formula (VI),

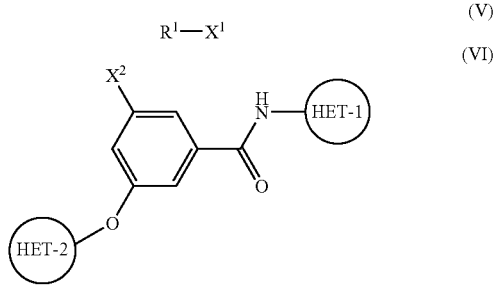

(V)

(VI)

wherein $X^1$ is a leaving group and $X^2$ is a hydroxyl group or $X^1$ is a hydroxyl group and $X^2$ is a leaving group, and wherein $R^1$ is as hereinbefore defined or a protected version thereof;

process (b) could also be accomplished using the intermediate ester Formula (VII), wherein $P^1$ is a protecting group as hereinafter described, followed by ester hydrolysis and amide formation by procedures described elsewhere and well known to those skilled in the art;

(V)

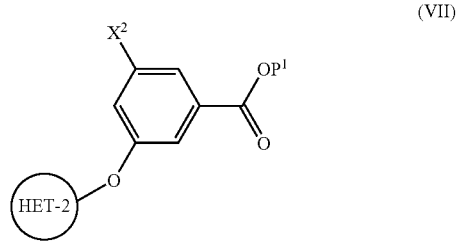

(VII)

or (c) reaction of a compound of Formula (VIII) with a compound of Formula (IX)

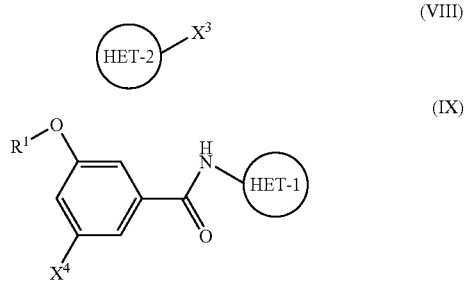

(VIII)

(IX)

wherein $X^3$ is a leaving group or an organometallic reagent and $X^4$ is a hydroxyl group or $X^3$ is a hydroxyl group and $X^4$ is a leaving group or an organometallic reagent, and wherein $R^1$ is as hereinbefore defined or a protected version thereof;

process (c) could also be accomplished using the intermediate ester Formula (X), followed by ester hydrolysis and amide formation by procedures described elsewhere and well known to those skilled in the art;

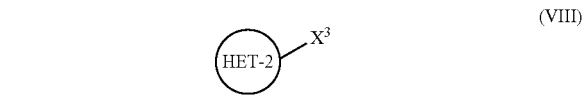

(VIII)

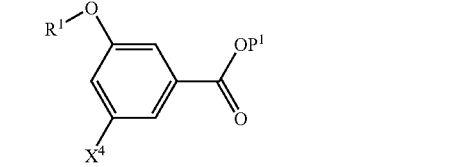

(X)

(d) reaction of a compound of Formula (XI) with a compound of Formula (XII),

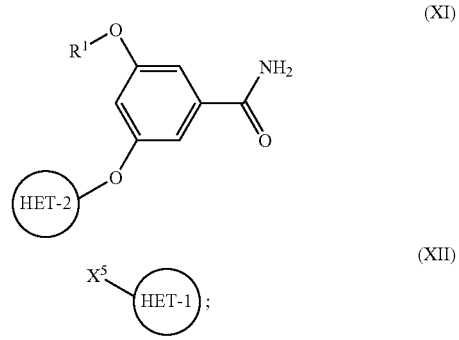

(XI)

(XII)

wherein $X^5$ is a leaving group; and wherein $R^1$ is as hereinbefore defined or a protected version thereof; or e) reaction of a compound of formula (XIII)

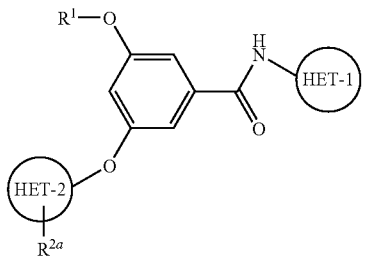

(XIII)

wherein $R^{2a}$ is a precursor to $R^1$, such as a carboxylic acid, ester or anhydride (for $R^2$=—$CONR^4R^5$) or the sulfonic acid equivalents (for $R^2$ is —$SO^2NR^4R^5$); with an amine of formula —$NR^4R^5$;

and thereafter, if necessary:

i) converting a compound of Formula (I) into another compound of Formula (I);

ii) removing any protecting groups; and/or iii) forming a salt thereof.

Suitable leaving groups $X^1$ to $X^5$ for processes b) to d) are any leaving group known in the art for these types of reactions, for example halo, alkoxy, trifluoromethanesulfonyloxy, methanesulfonyloxy, or p-toluenesulfonyloxy; or a group (such as a hydroxy group) that may be converted into a leaving group (such as an oxytriphenylphosphonium group) in situ.

Suitable values for $R^1$ containing a protected hydroxy group are any suitable protected hydroxy group known in the art, for example simple ethers such as a methyl ether, tert-butyl ether or silylethers such as —OSi[(1-4C)alkyl]$_3$ (wherein each (1-4C)alkyl group is independently selected from methyl, ethyl, propyl, isopropyl, and tertbutyl). Examples of such trialkylsilyl groups are trimethylsilyl, triethylsilyl, triisopropylsilyl and tert-butyldimethylsilyl. Further suitable silyl ethers are those containing phenyl and substituted phenyl groups, such as —Si(PhMe$_2$) and —Si(TolMe$_2$) (wherein Tol=methylbenzene). Further suitable values for hydroxy protecting groups are given hereinafter.

Compounds of Formulae (III) to (XII) are commercially available, or are known in the art, or may be made by processes known in the art, for example as shown in the accompanying Examples, or as described below. For further information on processes for making such compounds, we refer to our PCT publications WO 03/000267, WO 03/015774 and WO 03/000262 and references therein. In general it will be appreciated that any aryl-O or alkyl-O bond may be formed by nucleophilic substitution or metal catalysed processes, optionally in the presence of a suitable base.

Compounds of Formula (XIII) may be made by processes such as those shown in processes a) to d) and/or by those processes mentioned above for compounds of formulae (III) to (XII).

The group $R^1$ in the compounds of formulae (III), (IX), (X), (XI) and (XIII) may be made by reaction of suitable precursors with compounds of formula (V) or derivatives thereof, depending on the nature of the $R^1$ group, for example, by nucleophilic displacement of a leaving group $X^1$ in a compound of formula (V). Compounds of formula (V) are generally commercially available or maybe made by simple functional group interconversions from commercially available compounds, or by literature methods. Further information is available in WO2004/076420, WO2005/054200, WO2005/054233, WO 2005/044801 and WO 2005/056530. Some illustrative examples using various $R^1$ groups are given in the Schemes below, and/or in the accompanying examples, and may generally be applied analogously to $R^1$ groups not shown below by methods known in the art, see for example Bull. Chem. Soc. Japan, 73 (2000), 471-484, International Patent Application WO 2002/050003 and Bioorganic and Medicinal Chemistry Letters, (2001), 11, 407.

Scheme 1

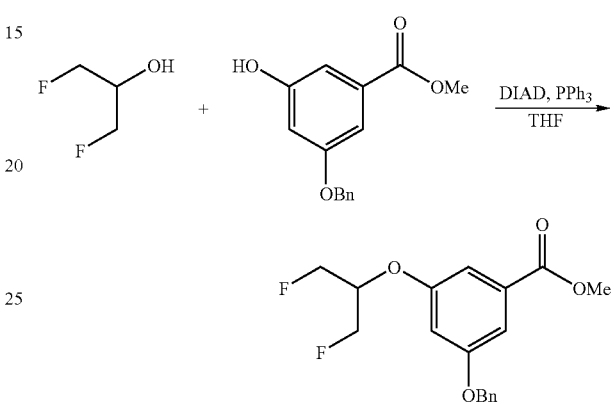

Scheme 2

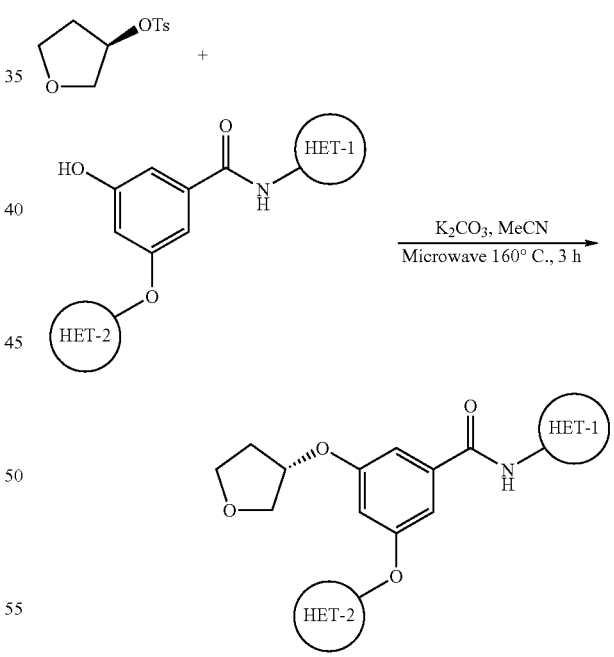

Scheme 3

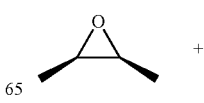

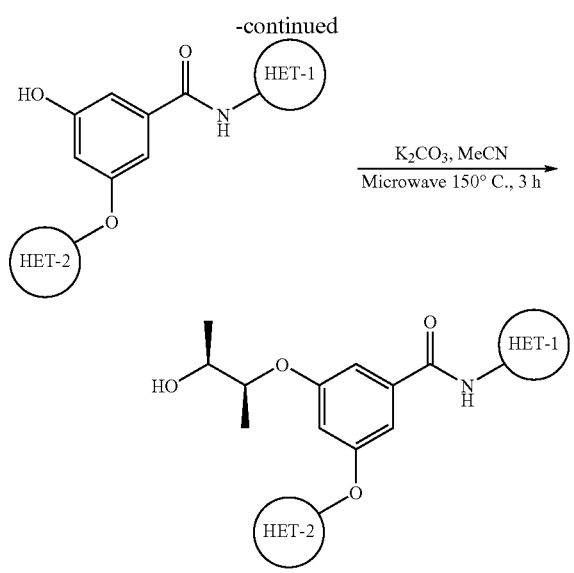

It will be understood that substituents $R^3$, $R^6$ and/or $R^7$ may be introduced into the molecule at any convenient point in the synthetic sequence or may be present in the starting materials. A precursor to one of these substituents may be present in the molecule during the process steps a) to e) above, and then be transformed into the desired substituent as a final step to form the compound of formula (I); followed where necessary by i) converting a compound of Formula (I) into another compound of Formula (I);

ii) removing any protecting groups; and/or iii) forming a salt thereof.

Specific reaction conditions for the above reactions are as follows, wherein when $P^1$ is a protecting group $P^1$ is preferably (1-4C)alkyl, for example methyl or ethyl:

Process a)—coupling reactions of amino groups with carboxylic acids to form an amide are well known in the art. For example, (i) using an appropriate coupling reaction, such as a carbodiimide coupling reaction performed with EDAC (1-(3-dimethylaminopropyl)-3-ethylcarbodiimide hydrochloride) in the presence of dimethylaminopyridine (DMAP) in a suitable

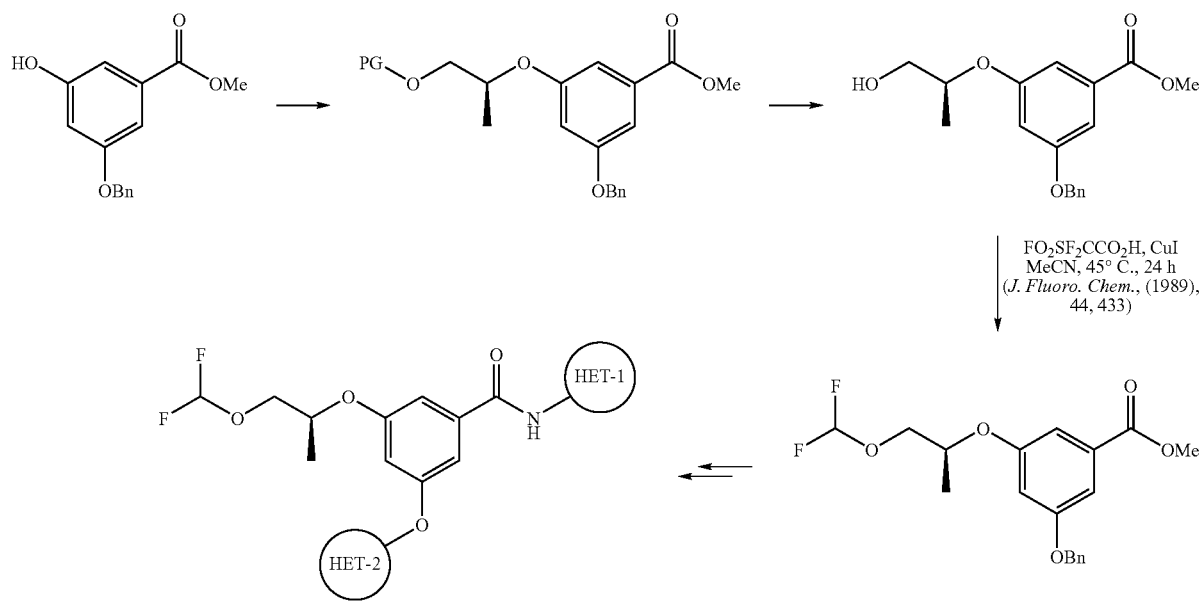

Scheme 4

[PG is protecting group, Ts is p-toluenesulfonyl].

Examples of conversions of a compound of Formula (I) into another compound of Formula (I), well known to those skilled in the art, include functional group interconversions such as hydrolysis, hydrogenation, hydrogenolysis, oxidation or reduction, and/or further functionalisation by standard reactions such as amide or metal-catalysed coupling, or nucleophilic displacement reactions. Further examples of a conversion of a compound of Formula (I) into another compound of Formula (I) is methylation of a hydroxy group in $R^1$ to give a methoxy group, and conversion of, for example, a hydroxymethyl group in $R^1$ (such as when $R^1$ is hydroxyprop-2-yl) into a difluoromethoxy group, using reactions such as those as illustrated in Scheme 4.

solvent such as dichloromethane (DCM), chloroform or dimethylformamide (DMF) at room temperature; or (ii) reaction in which the carboxylic group is activated to an acid chloride by reaction with oxalyl chloride in the presence of a suitable solvent such as DCM. The acid chloride can then be reacted with a compound of Formula (IV) in the presence of a base, such as triethylamine or pyridine, in a suitable solvent such as chloroform or DCM at a temperature between 0° C. and 80° C.

Process b)—compounds of Formula (V) and (VI) can be reacted together in a suitable solvent, such as DMF or tetrahydrofuran (THF), with a base such as sodium hydride or potassium tert-butoxide, at a temperature in the range 0 to 200° C., optionally using microwave heating or metal catalysis such as palladium(II) acetate, palladium on carbon, copper (II) acetate or copper(I) iodide; alternatively, compounds of Formula (V) and (VI) can be reacted together in a suitable solvent, such as THF or DCM, with a suitable phosphine such as triphenylphosphine, and azodicarboxylate such as diethylazodicarboxylate; process b) could also be carried out using a precursor to the ester of formula (VII) such as an aryl-nitrile or trifluoromethyl derivative, followed by conversion to a carboxylic acid and amide formation as previously described;

Process c)—compounds of Formula (VIII) and (IX) can be reacted together in a suitable solvent, such as DMF or THF, with a base such as sodium hydride or potassium tert-butoxide, at a temperature in the range 0 to 200° C., optionally using microwave heating or metal catalysis such as palladium(II) acetate, palladium on carbon, copper(II) acetate or copper(I) iodide; process c) could also be carried out using a precursor to the ester of formula (X) such as an aryl-nitrile or trifluoromethyl derivative, followed by conversion to a carboxylic acid and amide formation as previously described;

compounds of the formula (VIII) are commercially available or can be prepared from commercially available materials by processes well known to those skilled in the art, for example functional group interconversions (such as hydrolysis, hydrogenation, hydrogenolysis, oxidation or reduction), and/or further functionalisation and/or cyclisation by standard reactions (such as amide or sulphonamide or metal-catalysed coupling, or nucleophilic displacement or electrophilic substitution reactions);

Process d)—reaction of a compound of Formula (XI) with a compound of Formula (XII) can be performed in a polar solvent, such as DMF or a non-polar solvent such as THF with a strong base, such as sodium hydride or potassium tert-butoxide at a temperature between 0 and 200° C., optionally using microwave heating or metal catalysis, such as palladium(II) acetate, palladium on carbon, copper(II) acetate or copper(I) iodide;

Process e)—coupling reactions of amino groups with carboxylic or sulfonic acids or acid derivatives to form an amide are well known in the art and are described above for Process a).

Certain intermediates of formula (III), (VI), (VII), (IX) and/or (XI) are believed to be novel and comprise an independent aspect of the invention.

Certain intermediates of formula (III), (IX) and/or (XI) wherein $R^1$ is as defined herein for a compound of formula (I) are believed to be novel and comprise an independent aspect of the invention.

Certain intermediates of formula (XIII) are believed to be novel and comprise an independent aspect of the invention.

During the preparation process, it may be advantageous to use a protecting group for a functional group within the molecule. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1-20 carbon atoms). Examples of carboxy protecting groups include straight or branched chain (1-12C)alkyl groups (e.g. isopropyl, t-butyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl) silyl groups (e.g. trimethylsilyl and t-butyldimethylsilyl); tri (lower alkyl)silyl lower alkyl groups (e.g. trimethylsilylethyl); and (2-6C)alkenyl groups (e.g. allyl and vinylethyl).

Methods particularly appropriate for the removal of carboxyl protecting groups include for example acid-, metal- or enzymically-catalysed hydrolysis. Hydrogenation may also be used.

Examples of hydroxy protecting groups include methyl, t-butyl, lower alkenyl groups (e.g. allyl); lower alkanoyl groups (e.g. acetyl); lower alkoxycarbonyl groups (e.g. t-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); tetrahydropyran-2-yl; aryl lower alkyl groups (e.g. benzyl) groups; and triaryl lower alkyl groups (e.g. triphenylmethyl). Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, hydrogenation, nucleophilic displacement, acid-, base, metal- or enzymically-catalysed hydrolysis, catalytic hydrogenolysis or photolytically for groups such as o-nitrobenzyloxycarbonyl, or with fluoride ions for silyl groups. For example, methylether protecting groups for hydroxy groups may be removed by trimethylsilyliodide. A tert-butyl ether protecting group for a hydroxy group may be removed by hydrolysis, for example by use of hydrochloric acid in methanol.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl (e.g. t-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

In the above other pharmaceutical composition, process, method, use and medicament manufacture features, the alternative and preferred aspects and embodiments of the compounds of the invention described herein also apply.

The following examples are for illustration purposes and are not intended to limit the scope of this application. Each exemplified compound represents a particular and independent aspect of the invention. In the following non-limiting Examples, unless otherwise stated:

(i) evaporations were carried out by rotary evaporation in vacuo and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) with a field strength (for proton) of 300 MHz (generally using a Varian Gemini 2000) or 400 MHz (generally using a Bruker Avance DPX400), unless otherwise stated, and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (1R) or NMR analysis;

(vi) Purification by chromatography generally refers to flash column chromatography, on silica unless otherwise stated. Column chromatography was generally carried out using prepacked silica cartridges (from 4 g up to 400 g) such as Redisep™ (available, for example, from Presearch Ltd, Hitchin, Herts, UK) or Biotage (Biotage UK Ltd, Hertford, Herts, UK), eluted using a pump and fraction collector system. Purification by Solid Phase Extraction (SPE) methods generally refers to the use of chromatography cartridges packed with SPE materials such as ISOLUTE® SCX-2 columns (available, for example, From International Sorbent Technology Ltd, Dryffryn Business Park, Hengoed, Mid Glamorgan, UK);

(vii) Mass spectra (MS) data was generated on an LCMS system where the HPLC component comprised generally either a Agilent 1100 or Waters Alliance HT (2790 & 2795) equipment and was run on a Phemonenex Gemini C18 5 µm, 50×2 mm column (or similar) eluting with either acidic eluent (for example, using a gradient between 0-95% water/acetonitrile with 5% of a 1% formic acid in 50:50 water:acetonitrile (v/v) mixture; or using an equivalent solvent system with methanol instead of acetonitrile), or basic eluent (for example, using a gradient between 0-95% water/acetonitrile with 5% of a 0.1% 880 Ammonia in acetonitrile mixture); and the MS component comprised generally a Waters ZQ spectrometer. Chromatograms for Electrospray (ESI) positive and negative Base Peak Intensity, and UV Total Absorption Chromatogram from 220-300 nm, are generated and values for m/z are given; generally, only ions which indicate the parent mass are reported and unless otherwise stated the value quoted is $(M-H)^-$;

(viii) Suitable microwave reactors include "Smith Creator", "CEM Explorer", "Biotage Initiator sixty" and "Biotage Initiator eight".

(ix) Melting points were generally carried out by Differential Scanning Calorimetry (DSC); analysis was generally conducted using equipment such as a Mettler DSC822e or a Mettler DSC820. Samples of typically less than 5 mg of material, contained in a 40 µL aluminum pan fitted with a pierced lid, were heated over the temperature range 25° C. to 325° C. at a constant heating rate of 10° C. per minute. A purge gas using nitrogen was used at a flow rate of 100 mL per minute. It will be understood that the onset and/or peak temperature values of the DSC may vary slightly from one machine to another, one method to another or from one sample to another, and so the values quoted are not to be construed as absolute. It will be appreciated that some samples may be solvates and that this may also affect melting points.

Abbreviations

DCM dichloromethane

DEAD diethylazodicarboxylate

DIAD diisopropylazodicarboxylate

DIPEA N,N-Diisopropylethylamine

DMA dimethylacetamide

DMSO dimethyl sulphoxide

DMF dimethylformamide

EDAC 1-(3-dimethylaminopropyl)-3-ethylcarbodiimide hydrochloride

HATU O-(7-Azabenzotriazol-1-yl)-N,N,N',N'-tetramethyluronium hexafluorophosphate HPLC high pressure liquid chromatography HPMC Hydroxypropylmethylcellulose LCMS liquid chromatography/mass spectroscopy NMP N-methyl-2-pyrrolidone NMR nuclear magnetic resonance spectroscopy RT room temperature THF tetrahydrofuran TFA trifluoroacetic acid $CDCl_3$ deuterochloroform $MgSO_4$ magnesium sulfate NaHMDS sodium hexamethyldisilazide All compound names were derived using ACD NAME computer package.

EXAMPLE 1

3-{[5-(Azetidin-1-ylcarbonyl)pyridin-2-yl]oxy}-5-{[(1S)-2-hydroxy-1-methylethyl]oxy}-N-1,3-thiazol-2-ylbenzamide

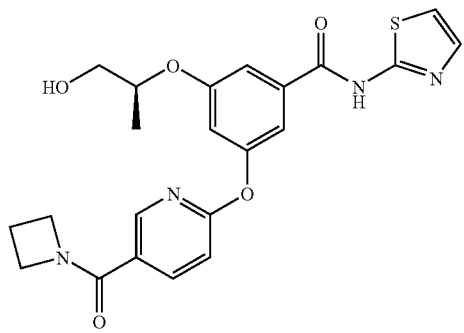

A mixture of 3-{[5-(azetidin-1-ylcarbonyl)pyridin-2-yl]oxy}-5-[(1S)-2-{[(1,1-dimethylethyl)(dimethyl)silyl]oxy}-1-methylethyl)oxy]-N-1,3-thiazol-2-ylbenzamide (0.15 g, 0.33 mmol) in methanol (10 mL) and 1M hydrochloric acid (10 mL) was stirred for 90 mins at RT. The volatiles were removed in vacuo and the residue taken to pH6 with saturated aqueous sodium bicarbonate solution then extracted into ethyl acetate (3×30 mL) and the combined organic layers washed with water (30 mL), brine (30 mL), dried (MgSO$_4$), filtered and the solvents removed in vacuo to a residue which was chromatographed on silica eluting with a gradient of 0-10% methanol in ethyl acetate to give the desired compound (65 mg).

$^1$H NMR δ (CDCl$_3$): 1.32 (d, 3H), 2.30 (s, 1H), 2.39 (quin, 2H), 3.79 (m, 2H), 4.20-4.40 (brm, 4H), 4.58 (m, 1H), 6.98 (m, 2H), 7.27 (m, 1H), 7.35 (m, 1H), 7.39 (s, 1H), 7.41 (s, 1H), 8.11 (d, 1H), 8.41 (s, 1H), 11.50 (s, 1H). m/z 455 (M+H)$^+$ The following compounds were synthesised in an analogous fashion from the appropriate silyl ether.

| Example | Structure | m/z | NMR |
|---|---|---|---|
| 1a | 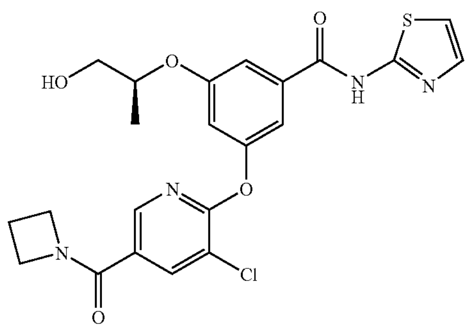 | 489, 491 (M + H)$^+$ | $^1$NMR δ (CDCl$_3$): 1.35 (d, 3H), 2.25 (s, 1H), 2.43 (quin, 2H), 3.77 (m, 2H), 4.20-4.40 (brm, 4H), 4.59 (m, 1H), 6.95 (d, 1H), 7.03 (s, 1H), 7.31 (d, 1H), 7.39 (s, 1H), 7.47 (s, 1H), 8.17 (s, 1H), 8.27 (s, 1H), 11.60 (brs, 1H). |
| 1b | 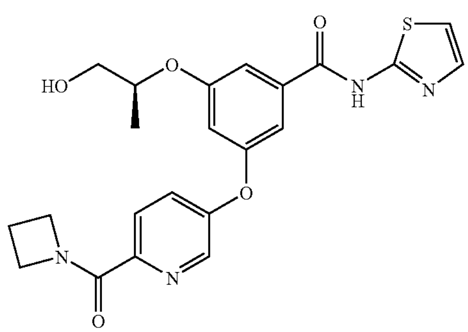 | 455 (M + H)$^+$ | $^1$NMR δ (CDCl$_3$): 1.22 (d, 3H), 2.38 (m, 3H), 3.68 (m, 2H), 4.19 (t, 2H), 4.48 (m, 1H), 4.63 (t, 2H), 6.75 (m, 1H), 6.91 (d, 1H), 7.13 (s, 1H), 7.19 (m, 1H), 7.28 (m, 2H), 8.03 (d, 1H), 8.22 (s, 1H), 11.40 (brs, 1H). |
| 1c | 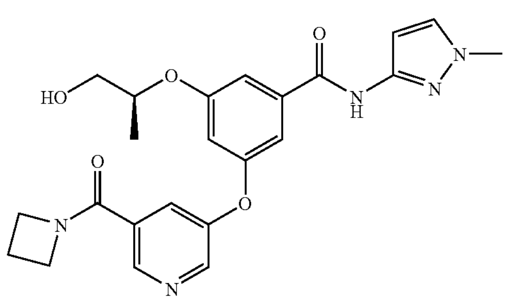 | 452 (M + H)$^+$ | $^1$H NMR δ (CDCl$_3$): 1.33 (d, 3H), 2.40 (quin, 2H), 3.78 (m, 2H), 3.82 (s, 3H), 4.25 (t, 2H), 4.37 (t, 2H), 4.57 (sextet, 1H), 6.80 (d, 2H), 7.11 (s, 1H), 7.28 (m, 2H), 7.63 (s, 1H), 8.52 (s, 1H), 8.61 (s, 2H) |

| Example | Structure | m/z | NMR |
|---|---|---|---|
| 1d | 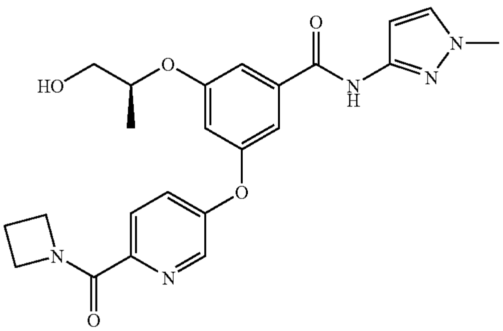 | 452 (M + H)+ | ¹H NMR δ (CDCl₃): 1.28 (d, 3H), 2.26 (quin, 2H), 2.48 (t, 1H), 3.67 (m, 2H), 3.69 (s, 3H), 4.18 (t, 2H), 4.45 (sextet, 1H), 4.63 (t, 2H), 6.70 9m, 2H), 7.05 (m, 1H), 7.20 (m, 2H), 7.28 (m, 1H), 8.02 (d, 1H), 8.21 (d, 1H), 8.73 (s, 1H) |

The preparation of 3-{[5-(azetidin-1-ylcarbonyl)pyridin-2-yl]oxy}-5-[(1S)-2-{[(1,1-dimethylethyl)(dimethyl)silyl]oxy}-1-methylethyl)oxy]-N-1,3-thiazol-2-ylbenzamide used in Example 1 is described below:

3-{[5-(Azetidin-1-ylcarbonyl)pyridin-2-yl]oxy}-5-[(1S)-2-{[(1,1-dimethylethyl)(dimethyl)silyl]oxy}-1-methylethyl)oxy]-N-1,3-thiazol-2-ylbenzamide

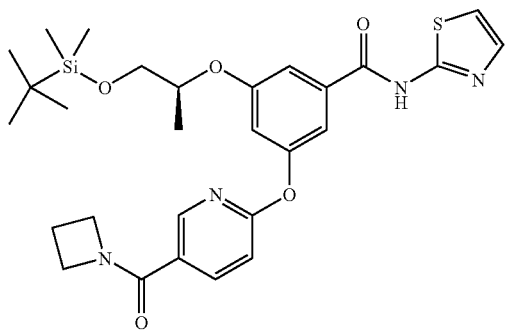

Potassium carbonate (0.14 g, 0.98 mmol) was added to a mixture of 3-[((1S)-2-{[(1,1-dimethylethyl)(dimethyl)silyl]oxy}-1-methylethyl)oxy]-5-hydroxy-N-1,3-thiazol-2-ylbenzamide (200 mg, 0.49 mmol) and 5-(azetidin-1-ylcarbonyl)-2-chloropyridine (96 mg, 0.49 mmol) in acetonitrile (5.0 mL) and the stirred mixture heated at 160° C. in a 'Biotage initiator Microwave' for 4 hours. The mixture was allowed to reach RT and pressure and was partitioned between ethyl acetate (50 mL) and water (50 mL). The ethyl acetate layer was separated, washed with water (5×50 mL), brine (50 mL), dried (MgSO₄) and evaporated to a residue which was chromatographed on silica, eluting with a gradient of 60-100% ethyl acetate in isohexane, to give the desired compound. (0.15 g). m/z 569 (M+H)+

The precursor for Example 1a was prepared in a similar fashion from 3-[((1S)-2-{[(1,1-dimethylethyl)(dimethyl)silyl]oxy}-1-methylethyl)oxy]-5-hydroxy-N-1,3-thiazol-2-ylbenzamide using 5-(azetidin-1-ylcarbonyl)-2,3-dichloropyridine:

| Structure | m/z | NMR |
|---|---|---|
| 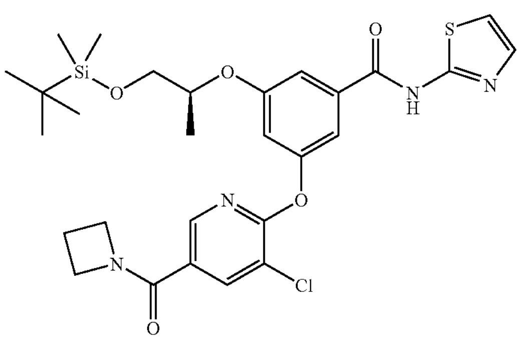 | 603, 605 (M + H)+ | ¹NMR δ (CDCl₃): 0.00 (s, 3H), 0.03 (s, 3H), 0.81 (s, 9H), 1.27 (d, 3H), 2.32 (quin, 2H), 3.60-3.80 (m, 2H), 4.15-4.35 (brm, 4H), 4.45 (m, 1H), 6.83 (d, 1H), 6.95 (m, 1H), 7.19 (d, 1H), 7.25 (s, 1H), 7.30 (s, 1H), 8.08 (d, 1H), 8.17 (d, 1H), 11.95 (brs, 1H). |

The precursor for Example 1b was prepared as described below:

3-{[6-(Azetidin-1-ylcarbonyl)pyridin-3-yl]oxy}-5-[((1S)-2-{[(1,1-dimethylethyl)(dimethyl)silyl]oxy}-1-methylethyl)oxy]-N-1,3-thiazol-2-ylbenzamide

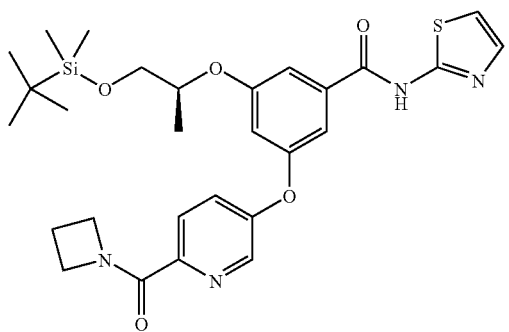

Cesium carbonate (0.478 g, 1.47 mmol) was added to a mixture of 3-[((1S)-2-{[(1,1-dimethylethyl)(dimethyl)silyl]oxy}-1-methylethyl)oxy]-5-hydroxy-N-1,3-thiazol-2-ylbenzamide (200 mg, 0.49 mmol), bromotris(triphenylphosphine)copper (46 mg, 0.049 mmol) and 2-(azetidin-1-ylcarbonyl)-5-bromopyridine (130 mg, 5.39 mmol) in DMA (5.0 mL) and the stirred mixture heated at 160° C. in a 'Biotage initiator Microwave' for 3 hours. The mixture was allowed to reach RT and pressure and was partitioned between ethyl acetate (50 mL) and water (50 mL). The ethyl acetate layer was separated, washed with water (5×50 mL), brine (50 mL), dried (MgSO$_4$) and evaporated to a residue which was chromatographed on silica, eluting with a gradient of 0-100% ethyl acetate in isohexane, to give the desired compound. (47 mg).

$^1$H NMR δ (CDCl$_3$): 0.00 (s, 3H), 0.03 (s, 3H), 0.83 (s, 9H), 1.29 (d, 3H), 2.32 (quin, 2H), 3.65-3.80 (m, 2H), 4.21 (t, 2H), 4.46 (m, 1H), 4.68 (t, 2H), 6.81 (s, 1H), 6.92 (m, 1H), 7.25 (m, 1H), 7.30-7.50 (m, 2H), 7.65 (m, 1H), 8.08 (d, 1H), 8.28 (s, 1H), 11.50 (brs, 1H). m/z 569 (M+H)$^+$ The precursors for examples 1c-1d were prepared in a similar fashion from 3-hydroxy-N-(1-methyl-1H-pyrazol-3-yl)-5-[((1S)-1-methyl-2-{[tris(1-methylethyl)silyl]oxy}ethyl)oxy]benzamide using the appropriate bromopyridine:

| Structure | m/z | NMR |
|---|---|---|
| | 608 (M + H)$^+$ | |
| | 608 (M + H)$^+$ | |

Bromotris(triphenylphosphine)copper may be prepared according to Synthetic Communications, 31(18), 2865-2879 (2001). The preparation of bromotris(triphenylphosphine) copper is described below.

Bromotris(triphenylphosphine)copper

Copper (II) bromide (111.7 g, 0.5 mol) was added in portions to a stirred solution of triphenylphosphine (557.4 g, 2.13 mol) in methanol (1.85 L) at RT (an exotherm to 32° C. was observed). The reaction was stirred for 10 minutes then heated to 65° C. and cooled overnight. The solid was collected by filtration, washed with ethanol (5 vol), diethyl ether (3×5 vol), dried on sinter under vacuum for 2 hours, then in a vacuum oven at 30° C. overnight to give product as crystalline solid (460 g).

The preparation of 5-(azetidin-1-ylcarbonyl)-2-chloropyridine used in the preparation of 3-{[5-(azetidin-1-ylcarbonyl)pyridin-2-yl]oxy}-5-[((1S)-2-{[(1,1-dimethylethyl)(dimethyl)silyl]oxy}-1-methylethyl)oxy]-N-1,3-thiazol-2-ylbenzamide, a precursor to Example 1, is described below:

DMF (2 drops) was added to a solution of 6-chloronicotinic acid (1.00 g, 6.35 mmol) and oxalyl chloride (0.67 mL, 7.62 mmol) in DCM (20 mL) and 2M hydrogen chloride in ether (3.15 mL, 6.35 mmol). The mixture was stirred at RT for 4 hours and the DCM and excess oxalyl chloride evaporated in vacuo. The residual acid chloride was dissolved in DCM (10 mL) and added to a mixture of azetidine hydrochloride (0.66 g, 6.99 mmol) and triethylamine (2.14 mL, 13.97 mmol) in DCM (10 mL) then stirred at RT for 24 hours. The DCM was evaporated in vacuo, and the residue partitioned between ethyl acetate (100 mL) and 1M citric acid (50 mL). The ethyl acetate layer was washed sequentially with saturated aqueous sodium hydrogen carbonate (50 mL) and brine (50 mL), dried (MgSO$_4$), and the solvent removed in vacuo to give a residue which was chromatographed on silica, eluting with a gradient of 50-100% ethyl acetate in isohexane, to give the desired compound (0.73 g). $^1$H NMR δ (CDCl$_3$) 2.43 (quin, 2H), 4.2-4.4 (brm, 4H), 7.42 (d, 1H), 7.97 (d, 1H), 8.63 (s, 1H). m/z 197 (M+H)$^+$ The halopyridines used in the preparation of precursors for Examples 1a-1d were prepared in a similar fashion from the appropriate nicotinic acid:

| Structure | m/z | NMR |
|---|---|---|
| | | $^1$H NMR δ (CDCl$_3$): 2.43 (quin, 2H), 4.21-4.44 (m, 4H), 8.11 (d, 1H), 8.53 (d, 1H) |
| | 241, 243 (M + H)$^+$ | $^1$H NMR δ (CDCl$_3$): 2.35 (quin, 2H), 4.25 (t, 2H), 4.70 (t, 2H), 7.93 (d, 1H), 8.03 (d, 1H), 8.63 (s, 1H). |
| | 241, 243 (M + H)$^+$ | $^1$H NMR δ (CDCl$_3$): 2.42 (quin, 2H), 4.20-4.45 (m, 4H), 8.16 (t, 1H), 8.76 (t, 2H) |

5-(Azetidin-1-ylcarbonyl)-2-chloropyridine

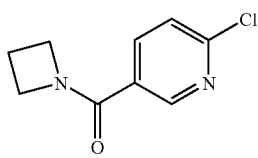

The nicotinic acids were either commercially available compounds or compounds known in the literature. Reference for 2-(azetidin-1-ylcarbonyl)-5-bromopyridine (Heterocycles, 15(1) 1981, 213-23).

The preparation of 3-[((1S)-2-{[(1,1-dimethylethyl)(dimethyl)silyl]oxy}-1-methylethyl)oxy]-5-hydroxy-N-1,3-thiazol-2-ylbenzamide used in the synthesis of Example 1, 1a and 1b is described below:

3-[((1S)-2-{[(1,1-Dimethylethyl)(dimethyl)silyl]oxy}-1-methylethyl)oxy]-5-hydroxy-N-1,3-thiazol-2-ylbenzamide

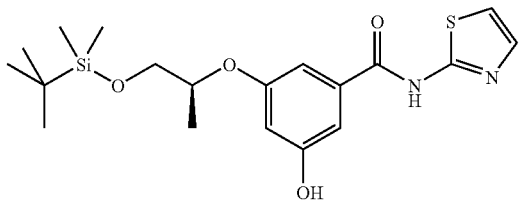

An aqueous solution of lithium hydroxide monohydrate (0.304 g, 7.25 mmol) was added to a solution of 3-{[(1,1-dimethylethyl)(dimethyl)silyl]oxy}-5-[((1S)-2-{[(1,1-dimethylethyl)(dimethyl)silyl]oxy}-1-methylethyl)oxy]-N-1,3-thiazol-2-ylbenzamide (1.552 g, 2.90 mmol) in THF (40 mL) and stirred at RT overnight. The THF was removed in vacuo and the residual solution adjusted to pH 7 by addition of 1N hydrochloric acid (7.25 mL). A gum formed, and the solution was filtered and the gum dissolved in methanol. The filtrate was partitioned with ethyl acetate (75 mL) and the organics washed with brine, dried (MgSO$_4$), combined with the methanol solution and evaporated to a residue which was chromatographed on silica, eluting with 40% ethyl acetate in isohexane, to give the required product (0.865 g)

$^1$H NMR δ (CDCl$_3$): −0.02 (d, 6H), 0.81 (s, 9H), 1.24 (d, 3H), 3.67 (m, 2H), 4.43 (sextet, 1H), 6.65 (t, 1H), 7.00 (d, 1H), 7.13 (t, 1H), 7.15 (t, 1H), 7.40 (d, 1H). m/z 409 (M+H)$^+$

3-{[(1,1-Dimethylethyl)(dimethyl)silyl]oxy}-5-[((1S)-2-{[(1,1-dimethylethyl)(dimethyl)silyl]oxy}-1-methylethyl)oxy]-N-1,3-thiazol-2-ylbenzamide

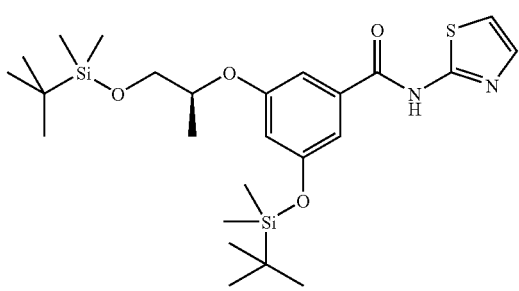

tert-Butyldimethylsilyl chloride (1.66 g, 11.0 mmol) and imidazole (1.78 g, 26.0 mmol) were a to a solution of 3-hydroxy-5-{[(1S)-2-hydroxy-1-methylethyl]oxy}-N-1,3-thiazol-2-ylbenzamide (1.541 g, 5.24 mmol) in DMF (10 mL) and the reaction stirred at RT under a silica drying tube overnight. Water (30 mL) was added and the solution partitioned with ethyl acetate (100 mL). The organic phase was washed with brine, dried (MgSO$_4$) and evaporated to a residue which was chromatographed on silica, eluting with 15% ethyl acetate in isohexane, to give the required product (1.525 g). $^1$H NMR δ (CDCl$_3$): −0.17 (d, 6H), 0.00 (s, 6H), 0.65 (s, 9H), 0.76 (s, 9H), 1.08 (d, 3H), 3.50 (m, 2H), 4.25 (sextet, 1H), 6.43 (t, 1H), 6.77 (d, 1H), 6.83 (t, 1H), 6.96 (t, 1H), 7.06 (d, 1H). m/z 423 (M−H)$^-$

3-Hydroxy-5-{[(1S)-2-hydroxy-1-methylethyl]oxy}-N-1,3-thiazol-2-ylbenzamide

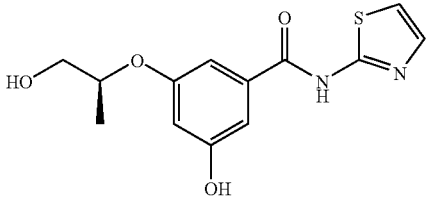

Iodo(trimethyl)silane (7.19 mL, 50.5 mmol) was added dropwise to a solution of 3-hydroxy-5-{[(1S)-2-methoxy-(1-methylethyl)oxy}-N-1,3-thiazol-2-ylbenzamide (3.116 g, 10.1 mmol) in acetonitrile (60 mL) under an inert atmosphere and the reaction stirred at RT overnight. Methanol (5 mL) was added and the reaction stirred a further 10 minutes. Saturated sodium thiosulphate solution (5 mL) and saturated potassium carbonate solution (5 mL) were added and the reaction stirred a further 10 minutes. The organic solvents were removed in vacuo and the resulting solution partitioned extracted with ethyl acetate (100 mL). The Aqueous layer was adjusted to pH 5 with the addition of 1M hydrochloric acid and extracted with ethyl acetate. The combined organic layers were washed with brine (20 mL), dried (MgSO$_4$), and evaporated to a residue which was chromatographed on silica, eluting with ethyl acetate, to give the desired compound (1.541 g).

$^1$H NMR δ (d$_6$-DMSO): 1.23 (d, 3H), 3.52 (m, 2H), 4.50 (sextet, 1H), 6.55 (t, 1H), 7.04 (t, 1H), 7.18 (t, 1H), 7.27 (d, 1H), 7.55 (d, 1H), 12.47 (s, 1H). m/z 295 (M+H)$^+$

3-Hydroxy-5-{[(1S)-2-methoxy-(1-methylethyl)oxy}-N-1,3-thiazol-2-ylbenzamide

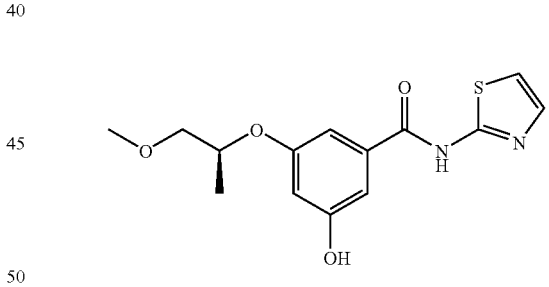

A solution of 3-{[(1S)-2-methoxy-(1-methylethyl)oxy}-5-{[(2-methylphenyl)methyl]oxy}-N-1,3-thiazol-2-ylbenzamide (6.9 g) and thioanisole (10 mL) in trifluoroacetic acid (65 mL) was stirred at ambient temperature for 16 hours. The trifluoroacetic acid was removed in vacuo and the residual oil partitioned between ethyl acetate (75 mL) and aqueous sodium hydrogen carbonate solution (200 mL). The aqueous layer was separated, extracted with ethyl acetate (2×75 mL), and the combined organic extracts washed with brine, dried (MgSO$_4$), and evaporated to a residue which was chromatographed on silica with 50% ethyl acetate in isohexane as eluant to give the desired compound (4.6 g).

$^1$H NMR δ (CDCl$_3$): 1.3 (d, 3H), 3.4 (s, 3H), 3.5-3.6 (m, 2H), 4.5-4.6 (m, 1H), 6.65 (s, 1H), 6.95 (d, 1H), 7.05 (s, 1H), 7.1 (s, 1H), 7.25 (d, 1H). m/z 309 (M+H)$^+$

3-{[(1S)-2-Methoxy-(1-methylethyl)oxy}-5-{[(2-methylphenyl)methyl]oxy}-N-1,3-thiazol-2-ylbenzamide

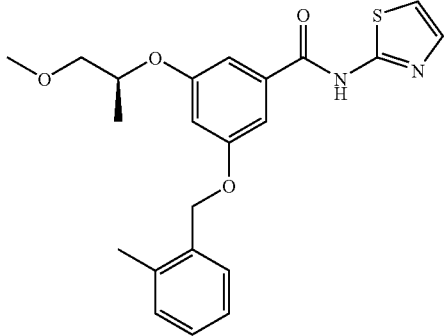

To a solution of 3-[(1S)-2-methoxy-(1-methylethyl)oxy]-5-{[(2-methylphenyl)methyl]oxy}benzoic acid (9.55 g) in DCM (140 mL) was added oxalyl chloride (2.83 mL), followed by DMF (1 drop), and the mixture stirred at ambient temperature for 16 hours. The DCM and excess oxalyl chloride were removed in vacuo, the residual oil dissolved in DCM (25 mL) and added to a solution of 2-aminothiazole (2.84 g) and triethylamine (7.88 mL) in DCM (75 mL) at 0-5° C., and the mixture stirred at ambient temperature for 4 hours. The DCM and excess triethylamine were removed in vacuo, the residual oil partitioned between ethyl acetate (100 mL) and 1M hydrochloric acid (100 mL). The ethyl acetate layer was separated, washed sequentially with 1M hydrochloric acid, aqueous sodium hydrogen carbonate solution, and brine, dried (MgSO$_4$), and evaporated to a residue which was chromatographed on alumina with ethyl acetate as eluant to give the desired compound (11.0 g). $^1$H NMR δ (CDCl$_3$): 1.3 (d, 3H), 2.35 (s, 3H), 3.4 (s, 3H), 3.5-3.6 (m, 2H), 4.55-4.6 (m, 1H), 5.0 (s, 2H), 6.8 (s, 1H), 6.95 (d, 1H), 7.15 (s, 1H), 7.25 (m, 5H), 7.4 (d, 1H). m/z 413 (M+H)$^+$

3-[(1S)-2-Methoxy-(1-methylethyl)oxy]-5-{[(2-methylphenyl)methyl]oxy}benzoic acid

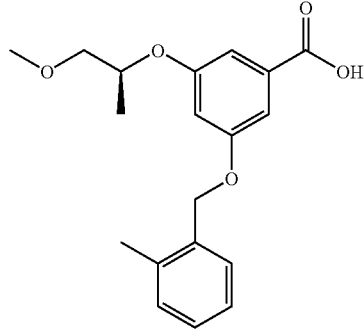

A solution of methyl 3-[{(1S)-2-methoxy-(1-methylethyl)oxy]-5-{[(2-methylphenyl)methyl]oxy}benzoate (10.65 g) in THF (200 mL) and methanol (50 mL) was added to a solution of lithium hydroxide monohydrate (6.0 g) in water (100 mL). The mixture was stirred at ambient temperature for 16 hours and the THF and methanol removed in vacuo. The aqueous layer was acidified to pH1 with hydrochloric acid, and extracted with ethyl acetate (3×50 mL). The combined organic extracts were washed with brine, dried (MgSO$_4$), and evaporated to give the desired compound (9.55 g). m/z 329 (M–H)$^-$

Methyl 3-[{(1S)-2-methoxy-(1-methylethyl)oxy]-5-{[(2-methylphenyl)methyl]oxy}benzoate

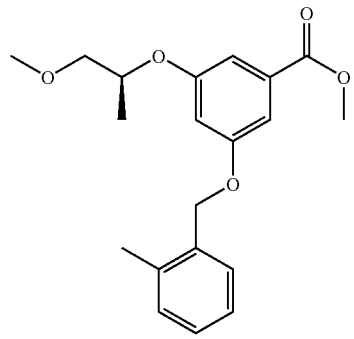

A stirred suspension of methyl 3-hydroxy-5-{[(2-methylphenyl)methyl]oxy}benzoate (15.3 g) and polymer-supported triphenyl phosphine (39.2 g) in dry DCM (900 mL) was cooled in an ice-bath and diisopropyl azodicarboxylate (11.88 mL) was added drop wise. The reaction mixture was stirred at 0-5° C. for 30 minutes and (R)-1-methoxy-propan-2-ol was added dropwise. The reaction mixture was stirred at ambient temperature for 16 hours, filtered through diatomaceous earth and the DCM evaporated to a residue which was chromatographed on silica with 10% ethyl acetate in isohexane as eluant to give the desired compound (10.7 g). $^1$H NMR δ (CDCl$_3$): 1.3 (d, 3H), 2.4 (s, 3H), 3.4 (s, 3H), 3.5-3.6 (m, 2H), 3.9 (s, 3H), 4.55-4.6 (m, 1H), 5.0 (s, 2H), 6.8 (s, 1H), 7.25 (m, 5H), 7.4 (d, 1H)

Methyl 3-hydroxy-5-5{[(2-methylphenyl)methyl]oxy}benzoate

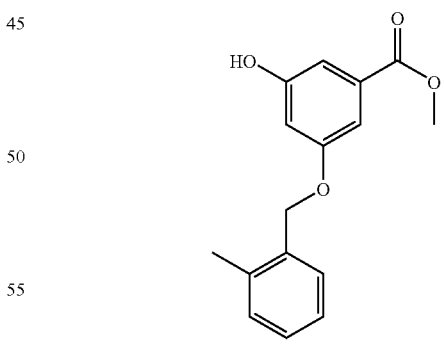

To a solution of methyl 3,5-dihydroxybenzoate (50 g, 0.30 mol) in DMF (500 mL) at 0° C. was added sodium hydride (10.8 g, 0.27 mol) portionwise, maintaining the reaction temperature below 10° C. The reaction was allowed to warm to 15° C., and was stirred for 20 minutes. The mixture was cooled to 0° C. and a solution of 2-methylbenzyl bromide (36 mL, 0.27 mol) in DMF (50 mL) was added over 30 minutes. The reaction was warmed to ambient temperature and concentrated in vacuo, the residual oil partitioned between ethyl acetate (500 mL) and water (250 mL), the ethyl acetate layer separated, washed sequentially with water and brine, dried (MgSO₄) and evaporated to a residue which was chromatographed on silica eluting with a gradient of 0-100% ethyl acetate in isohexane to give the desired compound (21.9 g). ¹H NMR δ (CDCl₃) 2.39 (s, 3H), 3.90 (s, 3H), 5.02 (s, 2H), 5.61 (s, 1H), 6.69 (t, 1H), 7.15-7.42 (m, 6H).

The preparation of 3-hydroxy-N-(1-methyl-1H-pyrazol-3-yl)-5-[((1S)-1-methyl-2-{[tris(1-methylethyl)silyl]oxy}ethyl)oxy]benzamide used in the synthesis of Example 1c-1d is described below:

3-Hydroxy-N-(1-methyl-1H-pyrazol-3-yl)-5-[((1S)-1-methyl-2-{[tris(1-methylethyl)silyl]oxy}ethyl)oxy]benzamide

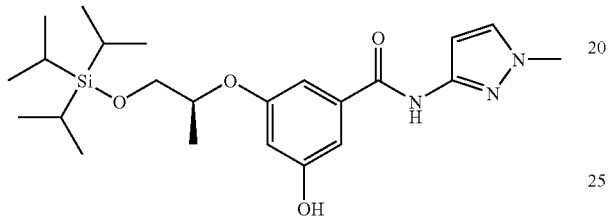

10% Palladium on carbon was added to 3-(benzyloxy)-N-(1-methyl-1H-pyrazol-3-yl)-5-{(1S)-1-methyl-2-[(triisopropylsilyl)oxy]ethoxy}benzamide (21.7 g, 40.4 mmol) in dry THF (480 mL) under argon. The reaction mixture was degassed and placed under a hydrogen balloon and stirred for 16 hours. The atmosphere was replaced with argon and mixture was filtered through diatomaceous earth then the filtrate evaporated and dried under high vacuum for 1 hour to give the title compound (18.2 g). ¹H NMR δ (CDCl₃): 1.05 (s, 18H), 1.05-1.1 (m, 3H), 1.3 (d, 3H), 3.7 (m, 1H), 3.8 (s, 3H), 3.9 (m, 1H), 4.5 (m, 1H), 6.6 (s, 1H), 6.8 (s, 1H), 7.0 (m, 2H), 7.20 (s, 1H), 7.3 (s, 1H), 8.7 (s, 1H). m/z 448 (M+H)⁺, 446 (M−H)⁻

3-(Benzyloxy)-N-(1-methyl-1H-pyrazol-3-yl)-5-{(1S)-1-methyl-2-[(triisopropylsilyl)oxy]ethoxy}benzamide

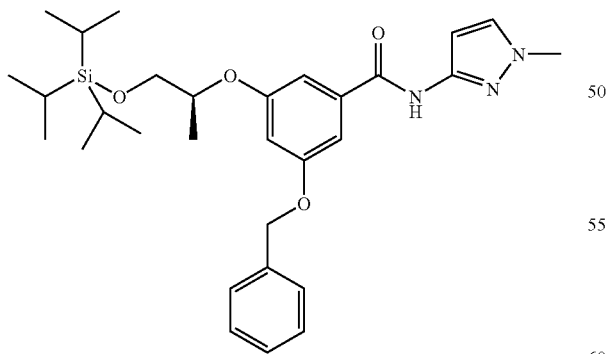

HATU (23.5 g, 61.8 mmol) was added to 3-(benzyloxy)-5-{(1S)-1-methyl-2-[(triisopropylsilyl)oxy]ethoxy}benzoic acid (23.6 g, 51.5 mmol), followed by addition of DMF (140 mL), and cooled to 0° C. 3-Amino-1-methylpyrazole (6.00 g. 61.8 mmol) was added followed by DIPEA (21.3 mL) and the reaction was stirred under argon at 0° C. for 3 hours. The solvent was evaporated and the residue was dissolved in ethyl acetate (500 mL) and washed with citric acid solution (200 mL), sodium hydrogen carbonate solution (150 mL), and saturated brine solution (2×150 mL). The organic layer was separated and dried (MgSO₄), filtered and evaporated. Purification by column chromatography, eluting with 1:4 to 1:1 ethyl acetate:hexanes, afforded the title compound as a colourless oil (21.7 g).

¹H NMR δ (CDCl₃): 1.05 (s, 18H), 1.05-1.1 (m, 3H), 1.3 (d, 3H), 3.7 (m, 1H), 3.8 (s, 3H), 3.9 (m, 1H), 4.5 (m, 1H), 5.1 (s, 2H), 6.7 (s, 1H), 6.8 (s, 1H), 7.0 (m, 2H), 7.1 (s, 1H), 7.3 (s, 1H), 7.35-7.5 (m, 5H), 8.5 (s, 1H). m/z 538 (M+H)⁺

3-(Benzyloxy)-5-{(1S)-1-methyl-2-[(triisopropylsilyl)oxy]ethoxy}benzoic acid

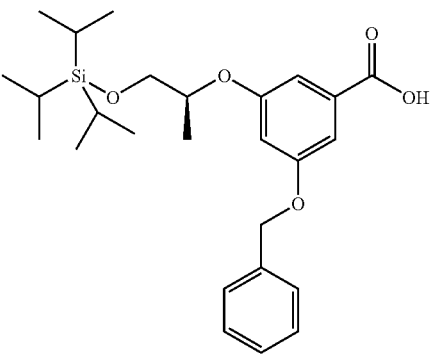

Lithium hydroxide monohydrate (12.14 g, 0.289 mol) in water (100 mL) was added to a solution of methyl 3-(benzyloxy)-5-{(1S)-1-methyl-2-[(triisopropylsilyl)oxy]ethoxy}benzoate (62 g, 0.131 mol) in THF (300 mL) and warmed to 43° C. The reaction was stirred for 16 hours, the THF removed in vacuo and the resultant mixture acidified to pH 5 with 10% w/v citric acid. This was extracted with ethyl acetate (2×300 mL) and the combined organic layers were dried (MgSO₄), filtered and evaporated to afford the title compound (60.2 g).

¹H NMR δ (CDCl₃): 1.05 (s, 18H), 1.05-1.1 (m, 3H), 1.35 (d, 3H), 3.7 (m, 1H), 3.9 (m, 1H), 4.5 (m, 1H), 5.1 (s, 2H), 6.8 (s, 1H), 7.3-7.5 (m, 7H). m/z 457 (M−H)⁻

Methyl 3-(benzyloxy)-5-{(1S)-1-methyl-2-[(triisopropylsilyl)oxy]ethoxy}benzoate

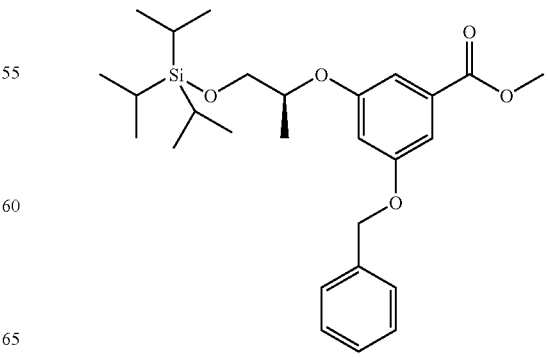

(2R)-1-[(Triisopropylsilyl)oxy]propan-2-ol (56.1 g, 242 mmol) was added to a solution of methyl 3-hydroxy-5-{[phenylmethyl]oxy}benzoate (50 g, 194 mmol) and triphenylphosphine (63.5 g, 242 mmol) in dry THF (500 mL), at to 0° C., followed by addition of DIAD (47.6 mL, 242 mmol) over 45 minutes under an argon atmosphere. The reaction was stirred at 0° C. for 1 hour and allowed to warm up to RT over an hour then stirred at RT for 1 hour. The THF was evaporated and a mixture of ethyl acetate (80 mL) and hexane (120 mL) was added. This mixture stirred for 2 hours and filtered. The precipitate was washed with a mixture of ethyl acetate (20 mL) and hexane (180 mL) and the filtrate evaporated. The residue was purified by column chromatography, eluting with 1:20 to 1:10 ethyl acetate:hexanes, to afford the title compound (65.5 g).

¹H NMR δ (CDCl₃): 1.05 (s, 18H), 1.05-1.1 (m, 3H), 1.35 (d, 3H), 3.7 (m, 1H), 3.9 (m, 1H), 3.9 (s, 3H), 4.5 (m, 1H), 5.05 (s, 2H), 6.75 (s, 1H), 7.2 (s, 1H). 7.3-7.5 (m, 6H). m/z 471 (M−H)⁻

(2R)-1-[(Triisopropylsilyl)oxy]propan-2-ol

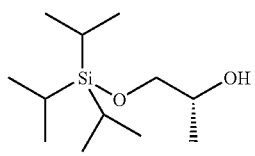

Triisopropylsilyl chloride (83.8 mL, 390 mmol) was added slowly over 15 minutes to a solution of (2R)-propane-1,2-diol (29.7 g, 390 mmol) in DMF at 0° C. (100 mL) keeping the internal temperature below 15° C. This was followed by addition of imidazole (66.4 g, 975 mmol) and the reaction mixture was allowed to warm to RT and stirred under argon for 20 hours. The reaction was quenched with 1M hydrochloric acid/diethyl ether (300 mL/800 mL). The organic layer was separated and washed with 1M hydrochloric acid followed by saturated brine solution. The organic layer was dried (MgSO₄), filtered and evaporated. Purification by distillation at 10 mmHg, 90-104° C., afforded the title compound as colourless oil (69.5 g). ¹H NMR δ (CDCl₃): 1.05 (s, 18H), 1.05-1.1 (m, 3H), 1.05 (d, 3H), 2.55 (s, 1H), 3.45 (dd, 1H), 3.7 (dd, 1H), 3.85 (m, 1H).

Methyl 3-hydroxy-5-{[phenylmethyl]oxy}benzoate

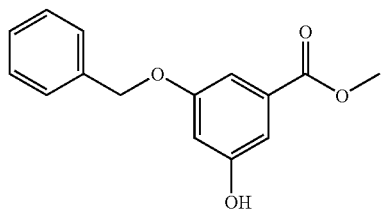

To a stirred solution of methyl 3,5-dihydroxybenzoate (5.95 mol) in DMF (6 L) was added potassium carbonate (9 mol), and the suspension stirred at ambient temperature under argon. To this was added benzyl bromide (8.42 mol) slowly over 1 hour, with a slight exotherm, and the reaction mixture stirred overnight at ambient temperature. The reaction was quenched cautiously with ammonium chloride solution (5 L) followed by water (35 L). The aqueous suspension was extracted with DCM (1×3 L and 2×5 L). The combined extracts were washed with water (10 L) and dried overnight (MgSO₄). The solution was evaporated in vacuo, and the crude product chromatographed in 3 batches (flash column, 3×2 kg silica, eluting with a gradient consisting of hexane containing 10% DCM, to neat DCM, to DCM containing 50% ethyl acetate) to eliminate starting material. The crude eluant was further chromatographed in 175 g batches (Amicon HPLC, 5 kg normal-phase silica, eluting with isohexane containing 20% v/v of ethyl acetate) to give the desired compound (21% yield). ¹H NMR δ (d₆-DMSO): 3.8 (s, 3H), 5.1 (s, 2H), 6.65 (m, 1H), 7.0 (m, 1H), 7.05 (m, 1H), 7.3-7.5 (m, 5H), 9.85 (br s, 1H).

EXAMPLE 2

3-{[5-(Azetidin-1-ylcarbonyl)pyridin-2-yl]oxy}-5-{[(1S)-1-methyl-2-(methyloxy)ethyl]oxy}-N-(1-methyl-1H-pyrazol-3-yl)benzamide

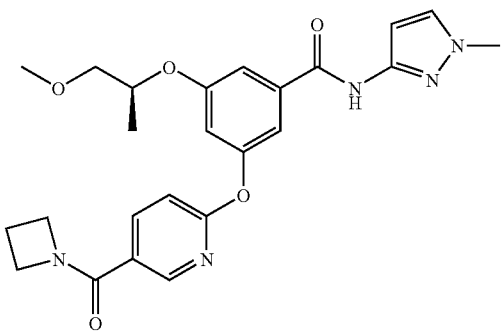

Potassium carbonate (0.181 g, 1.31 mmol) was added to a mixture of 3-hydroxy-5-[(1S)-2-methoxy-(1-methylethyl)oxy]-N-(1-methyl-1H-pyrazol-3-yl)benzamide (0.2 g, 0.66 mmol) and 5-(azetidin-1-ylcarbonyl)-2-chloropyridine (129 mg, 0.66 mmol) in acetonitrile (5.0 mL) and the stirred mixture heated at 160° C. in a 'Biotage initiator Microwave' for 6 hours. The mixture was allowed to reach RT and pressure and was partitioned between ethyl acetate (50 mL) and water (50 mL). The ethyl acetate layer was separated, washed with water (5×50 mL) brine (50 mL), dried (MgSO₄) and evaporated to a residue which was chromatographed on silica, eluting with a gradient of 0-5% methanol in ethyl acetate, to give the desired compound (202 mg). ¹H NMR δ (CDCl₃): 1.33 (d, 3H), 2.38 (quin, 2H), 3.40 (s, 3H), 3.61-3.47 (m, 2H), 3.74 (s, 3H), 4.42-4.18 (m, 4H), 4.58 (sextet, 1H), 6.80 (d, 1H), 6.91 (t, 1H), 6.97 (d, 1H), 7.21 (t, 1H), 7.26 (d, 1H), 7.33 (t, 1H), 8.09-8.05 (m, 1H), 8.42 (d, 1H), 8.92 (s, 1H); m/z 466 (M+H)⁺

In a similar manner, Examples 2a-2g were prepared using the appropriate phenol and halopyridine:

| Example | Structure | m/z | NMR |
|---------|-----------|-----|-----|
| 2a | 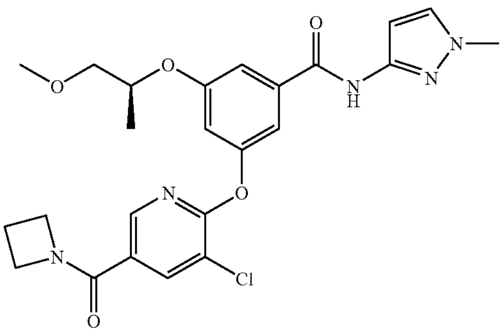 | 500 (M + H)+ | ¹H NMR δ (CDCl₃): 1.31 (d, 3H), 2.36 (quintet, 2H), 3.38 (s, 3H), 3.59-3.45 (m, 2H), 3.67 (s, 3H), 4.39-4.15 (m, 4H), 4.55 (sextet, 1H), 6.79 (d, 1H), 6.92 (t, 1H), 7.20 (t, 1H), 7.25 (d, 1H), 7.35 (t, 1H), 8.14 (d, 1H), 8.20 (d, 1H), 9.42 (s, 1H) |
| 2b | 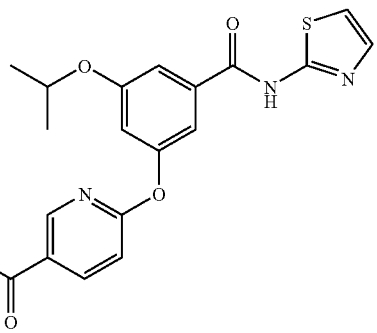 | 439 (M + H)+ | ¹H NMR δ (CDCl₃): 1.36 (d, 6H), 2.39 (m, 2H), 4.42-4.19 (m, 4H), 4.58 (septet, 1H), 6.90 (d, 1H), 6.93 (t, 1H), 6.98 (d, 1H), 7.22 (d, 1H), 7.34 (t, 1H), 7.40 (m, 1H), 8.08 (m, 1H), 8.41 (d, 1H), 12.21 (s, 1H) |
| 2c | 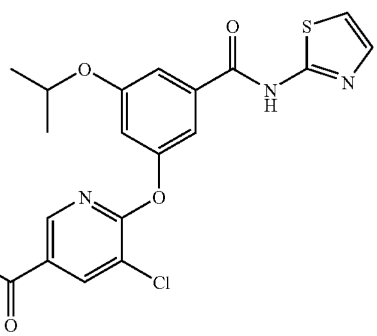 | 473 (M + H)+ | ¹NMR δ (CDCl₃): 1.37 (d, 6H), 2.39 (quintet, 2H), 4.39-4.20 (m, 4H), 4.59 (septet, 1H), 6.92 (d, 1H), 6.96 (t, 1H), 7.23 (d, 1H), 7.36 (t, 1H), 7.44 (t, 1H), 8.16 (d, 1H), 8.23 (d, 1H), 12.37 (s, 1H) |
| 2d | 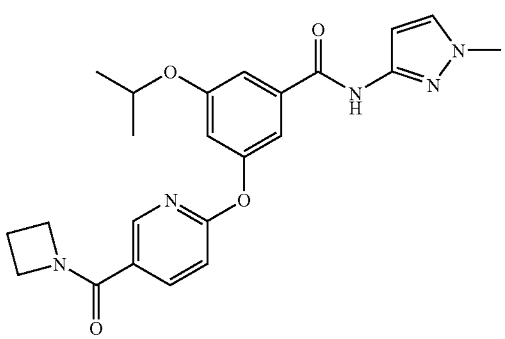 | 436 (M + H)+ | ¹H NMR δ (CDCl₃): 1.32 (d, 6H), 2.34 (quintet, 2H), 3.71 (s, 3H), 4.37-4.17 (m, 4H), 4.54 (septet, 1H), 6.77 (d, 1H), 6.82 (t, 1H), 6.94 (d, 1H), 7.15 (t, 1H), 7.23 (d, 1H), 7.25 (m, 1H), 8.04 (m, 1H), 8.38 (d, 1H), 8.85 (s, 1H) |

| Example | Structure | m/z | NMR |
|---|---|---|---|
| 2e | 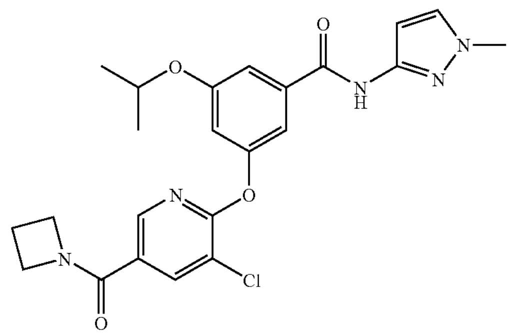 | 470 (M + H)⁺ | ¹H NMR δ (CDCl₃): 1.37 (d, 6H), 2.40 (quintet, 2H), 3.78 (s, 3H), 4.41-4.20 (m, 4H), 4.61 (septet, 1H), 6.81 (d, 1H), 6.89 (t, 1H), 7.20 (t, 1H), 7.29 (m, 1H), 7.32 (t, 1H), 8.17 (d, 1H), 8.25 (d, 1H), 8.72 (s, 1H) |
| 2f | 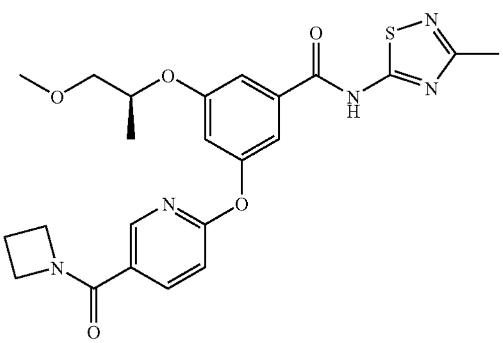 | 484 (M + H)⁺ | ¹H NMR δ (CDCl₃): 1.34 (d, 3H), 2.39 (quintet, 2H), 2.47 (s, 3H), 3.41 (s, 3H), 3.63-3.49 (m, 2H), 4.43-4.20 (m, 4H), 4.61 (sextet, 1H), 7.00 (m, 2H), 7.37 (t, 1H), 7.44 (t, 1H), 8.40 (d, 1H), 11.08 (s, 1H) |
| 2g | 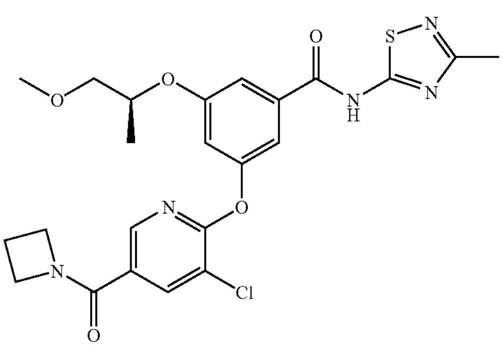 | 518 (M + H)⁺ | ¹H NMR δ (CDCl₃): 1.34 (d, 3H), 2.40 (quintet, 2H), 2.44 (s, 3H), 3.41 (s, 3H), 3.64-3.49 (m, 2H), 4.45-4.20 (m, 4H), 4.61 (sextet, 1H), 7.04 (t, 1H), 7.40 (t, 1H), 7.42 (s, 1H), 8.17 (d, 1H), 8.21 (d, 1H), 11.32 (s, 1H) |

The preparation of the halopyridines is described in Example 1.

The preparation of 3-hydroxy-5-[(1S)-2-methoxy-(1-methylethyl)oxy]-N-(1-methyl-1H-pyrazol-3-yl)benzamide used in the synthesis of Examples 2 and 2a is described below:

3-Hydroxy-5-[(1S)-2-methoxy-(1-methylethyl)oxy]-N-(1-methyl-1H-pyrazol-3-yl)benzamide

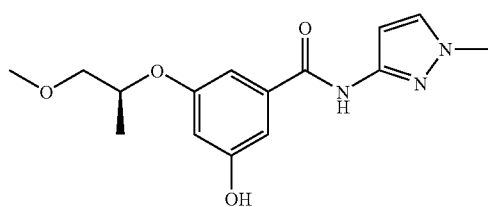

To a solution of 3-[(1S)-2-methoxy-(1-methylethyl)oxy]-N-(1-methyl-1H-pyrazol-3-yl)-5-[(phenylmethyl)oxy]benzamide (7.07 g) in THF (50 mL) and methanol (50 mL) was added 10% palladium on carbon (727 mg) as a slurry in THF (1 mL) and methanol (1 mL). The mixture was placed under vacuum and stirred under an atmosphere of hydrogen for 70 hours. The mixture was filtered through diatomaceous earth, and the diatomaceous earth washed with methanol (2×100 mL), followed by evaporation in vacuo. The residues were dissolved in ethyl acetate (10 mL), treated with isohexane (40 mL), the solid filtered off and washed with isohexane (50 mL) to afford the desired compound (5.17 g) which was used without further purification.

¹H NMR δ (d₆-DMSO): 1.22 (d, 3H), 3.28 (s, 3H, obscured by water), 3.38-3.53 (m, 2H), 3.76 (s, 3H), 4.65 (m, 1H), 6.44 (m, 1H), 6.54 (m, 1H), 6.93 (s, 1H), 7.04 (s, 1H), 7.57 (m, 1H), 9.63 (br s, 1H), 10.60 (s, 1H). m/z 306 (M+H)⁺, 304 (M−H)⁻

3-[(1S)-2-Methoxy-(1-methylethyl)oxy]-N-(1-methyl-1H-pyrazol-3-yl)-5-[(phenylmethyl)oxy]benzamide

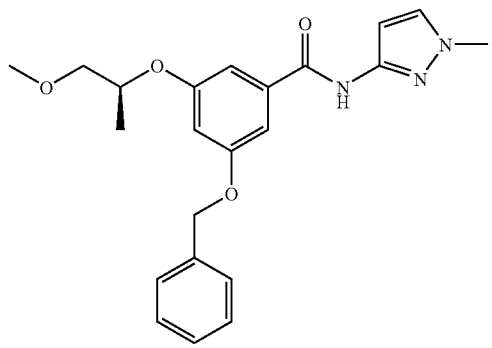

A solution of 3-[(1S)-2-methoxy-(1-methylethyl)oxy]-5-{[phenylmethyl]oxy}benzoic acid (8.73 g) in DCM (150 mL) was cooled to 0° C. Oxalyl chloride (4.81 mL) and DMF (0.15 mL) were slowly added with stirring. The mixture was allowed to warm to ambient temperature and stirred for 16 hours, following which the organics were removed in vacuo, and the residues azeotroped with toluene (75 mL). The crude material was dissolved in DCM (75 mL) and slowly added to a stirred suspension of 3-amino-1-methylpyrazole (3.35 g) and DIPEA (14.4 mL) in DCM (75 mL). The mixture was stirred at ambient temperature for 18 hours, before the organics were evaporated in vacuo and the residue dissolved in ethyl acetate (150 mL). The organics were washed with 1M aqueous hydrochloric acid (100 mL) and brine (50 mL), and dried (MgSO$_4$), before evaporation in vacuo to give crude material. This was chromatographed on a 200 g Biotage Flash 75 SiO$_2$ column (eluting with 30 to 90% ethyl acetate in isohexane), and evaporated in vacuo to afford the desired compound (7.07 g).

$^1$H NMR δ (d$_6$-DMSO): 1.23 (d, 3H), 3.28 (s, 3H, obscured by water), 3.40-3.52 (m, 2H), 3.77 (s, 3H), 4.70 (m, 1H), 5.03 (s, 2H), 6.56 (m, 1H), 6.71 (m, 1H), 7.18 (s, 1H), 7.24 (s, 1H), 7.32-7.47 (br m, 5H), 7.58 (m, 1H), 10.73 (s, 1H). m/z 396 (M+H)$^+$.

3-[(1S)-2-Methoxy-(1-methylethyl)oxy]-5-{[phenylmethyl]oxy}benzoic acid

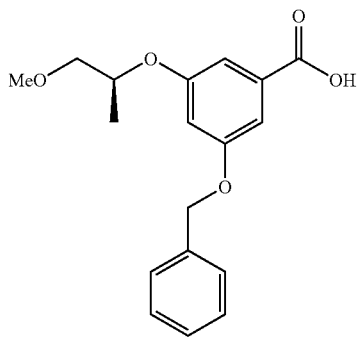

A solution of methyl 3-[(1S)-2-methoxy-(1-methylethyl)oxy]-5-{[phenylmethyl]oxy}benzoate (77.4 mmol) in a mixture of THF (232 mL) and methanol (232 mL) was treated with a solution of 2M sodium hydroxide (232 mmol), and the reaction mixture stirred for 4 hours at ambient temperature. The resulting solution was diluted with water (250 mL) and most of the organic solvent removed in vacuo. The resulting suspension was washed with diethyl ether (3×200 mL) and the organic washings discarded. The resulting aqueous solution was acidified to pH4 with 2M hydrochloric acid solution and extracted with ethyl acetate (2×200 mL). The extracts were combined, washed with brine, dried (MgSO$_4$), and evaporated to give the desired compound (99% yield).

$^1$H NMR δ (d$_6$-DMSO): 1.20 (d, 3H), 3.46 (m, 2H), 4.64 (m, 1H), 5.15 (s, 2H), 6.83 (app t, 1H), 7.06 (s, 1H), 7.13 (s, 1H), 7.30-7.49 (m, 5H), 12.67 (br s, 1H)

Methyl 3-[(1S)-2-methoxy-(1-methylethyl)oxy]-5-{[phenylmethyl]oxy}benzoate

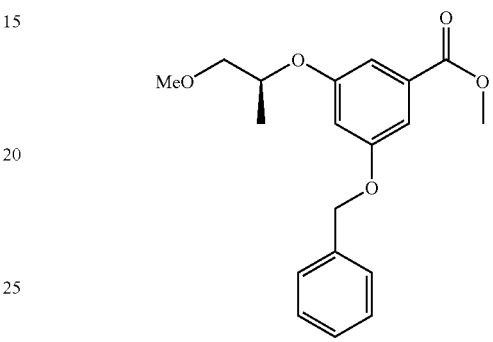

To a solution of methyl 3-hydroxy-5-{[phenylmethyl]oxy}benzoate (77.4 mmol) in THF was added polymer-supported triphenylphosphine (51.7 g of 3 mmol/g loading, 155 mmol) and (R)-(−)-1-methoxy-2-propanol (102 mmol). The stirred solution was blanketed with argon and cooled in an ice bath. A solution of DIAD (116 mmol) was added dropwise by syringe over 10 minutes. The solution was stirred for 20 minutes and filtered, washing the residue with THF (500 mL). The filtrate and washings were combined, and evaporated to give the desired compound which was used without further purification.

$^1$H NMR δ (d$_6$-DMSO): 3.26 (s, 3H), 3.44 (m, 2H), 3.82 (s, 3H), 4.63 (m, 1H), 5.14 (s, 2H), 6.85 (s, 1H), 7.05 (s, 1H), 7.11 (s, 1H), 7.30-7.47 (m, 5H)

The $^1$H NMR spectrum also contained signals consistent with a small amount of bis(1-methylethyl)hydrazine-1,2-dicarboxylate.

The preparation of methyl 3-hydroxy-5-{[phenylmethyl]oxy}benzoate is described in Example 1c.

The preparation of 3-hydroxy-5-[(1-methylethyl)oxy]-N-1,3-thiazol-2-ylbenzamide used in the preparation of Examples 2b and 2c is described below:

3-Hydroxy-5-[(1-methylethyl)oxy]-N-1,3-thiazol-2-ylbenzamide

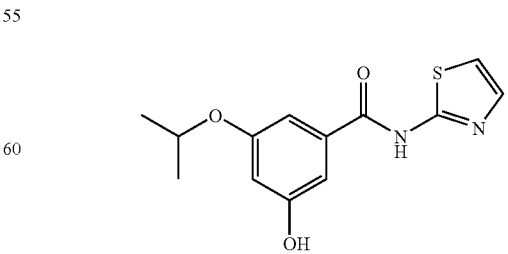

3-[(1-Methylethyl)oxy]-5-[(phenylmethyl)oxy]-N-1,3-thiazol-2-ylbenzamide (11.2 g) was dissolved in trifluoroacetic acid (60 mL) and treated with thioanisole (17.8 mL). The mixture was left to stir at ambient temperature for 18 hours before the trifluoroacetic acid was removed in vacuo. The residues were treated with isohexane (100 mL) and the solid filtered off, before being washed with further isohexane (2×20 mL). The solid was dissolved in ethyl acetate (200 mL) and washed with aqueous saturated sodium hydrogen carbonate solution (100 mL). The organics were washed with water (100 mL) and brine (100 mL), and dried (MgSO$_4$) before evaporation in vacuo to afford a solid which was washed with isohexane (200 mL) and dried in vacuo to give the desired compound (7.18 g). $^1$H NMR δ (d$_6$-DMSO): 1.27 (d, 6H), 4.55 (m, 1H), 6.49 (m, 1H), 7.02 (s, 1H), 7.14 (s, 1H), 7.25 (d, 1H), 7.54 (d, 1H), 9.73 (s, 1H), 12.44 (s, 1H). m/z 279 (M+H)$^+$, 277 (M−H)$^−$ 3-[(1-Methylethyl)oxy]-5-[(phenylmethyl)oxy]-N-1,3-thiazol-2-ylbenzamide

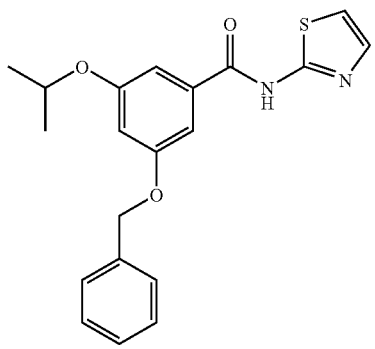

To a solution of 3-[(1-methylethyl)oxy]-5-[(phenylmethyl)oxy]benzoic acid (20 g) in DCM (400 mL), cooled to 0° C. was slowly added oxalyl chloride (12.2 mL) and DMF (0.4 mL), with stirring. The mixture was allowed to warm to ambient temperature and stirred for a further 16 hours, following which the organics were removed in vacuo, and the residues azeotroped with toluene (100 mL). The crude material was dissolved in DCM (200 mL) and slowly added to a stirred suspension of 2-aminothiazole (10.5 g) and diisopropylethylamine (24.3 mL), in DCM (200 mL). The mixture was stirred at ambient temperature for 70 hours, before the organics were removed in vacuo. The residues were dissolved in ethyl acetate (300 mL) and washed with 1M aqueous hydrochloric acid (300 mL). The aqueous layer was extracted with further ethyl acetate (300 mL), and the combined organics washed with brine (75 mL), and dried (MgSO$_4$), before evaporation in vacuo to give the desired compound (28 g) which was used without further purification.

$^1$H NMR δ (d$_6$-DMSO): 1.27 (d, 6H), 4.70 (m, 1H), 5.15 (s, 2H), 6.77 (m, 1H), 7.27 (m, 2H), 7.33-7.47 (brm, 6H), 7.55 (d, 1H). m/z 369 (M+H)$^+$, 367 (M−H)$^−$;

The $^1$H NMR spectrum also contained signals consistent with a small amount of ethyl acetate.

3-[(1-Methylethyl)oxy]-5-[(phenylmethyl)oxy]benzoic acid

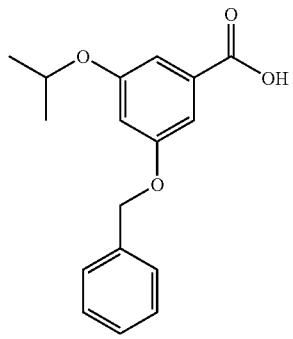

To a solution of methyl 3-[(1-methylethyl)oxy]-5-[(phenylmethyl)oxy]benzoate (37 g) in a 1:1 mixture of THF:methanol (300 mL) was added 4M sodium hydroxide solution (150 mL). The mixture was refluxed for 45 minutes, following which the organics were removed in vacuo. The aqueous was acidified to pH4 with hydrochloric acid (2M), and extracted with ethyl acetate. The organics were combined, washed with water and brine, dried (MgSO$_4$) and concentrated in vacuo to give the desired compound (33.5 g), which was used without further purification.

$^1$H NMR δ (d$_6$-DMSO): 1.26 (d, 6H), 4.59-4.69 (m, 1H), 5.15 (s, 2H), 6.80 (app t, 1H), 7.04 (m, 1H), 7.12 (m, 1H), 7.33 (app t, 1H), 7.40 (t, 2H), 7.46 (d, 2H), 12.95 (s, 1H)

Methyl 3-[(1-methylethyl)oxy]-5-[(phenylmethyl)oxy]benzoate

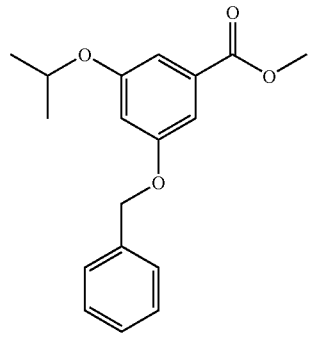

To a solution of methyl 3-hydroxy-5-[(1-methylethyl)oxy]benzoate (25 g) in DMF (250 mL) was added anhydrous potassium carbonate (297 mmol), and benzyl bromide (143 mmol). The mixture was stirred at 60° C. for 5 hours, then cooled to room temperature. The solvent was removed in vacuo and the residue partitioned between ethyl acetate and water. The organics were combined and washed with further water, brine, dried (MgSO$_4$) and concentrated in vacuo to give the desired compound (37 g) which was used without further purification.

$^1$H NMR δ (d$_6$-DMSO): 1.26 (d, 6H), 3.84 (s, 3H), 4.61-4.70 (m, 1H), 5.12 (s, 2H), 6.84 (t, 1H), 7.05 (app t, 1H), 7.12-7.15 (m, 1H), 7.31-7.37 (m, 1H), 7.40 (t, 2H), 7.46 (d, 2H)

Methyl 3-hydroxy-5-[(1-methylethyl)oxy]benzoate

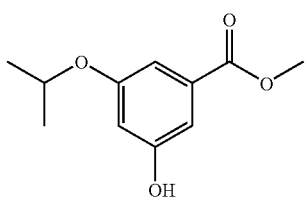

To a stirred solution of methyl 3,5-dihydroxybenzoate (0.1 mol) in DMF (180 mL) was added powdered potassium carbonate (0.2 mol) and 2-iodopropane (0.1 mol), and the resulting mixture stirred at ambient temperature for 16 hours. The reaction mixture was poured into water (1000 mL) and the mixture extracted with ether. The extracts were combined and washed sequentially with water (twice) and brine; the solution was dried (MgSO$_4$), filtered and evaporated in vacuo to give the crude product as a pale yellow oil (12.6 g). This was treated with toluene (40 mL) and allowed to stand overnight. The insoluble material (starting phenol) was removed by filtration, and the filtrate evaporated in vacuo. The resulting oil was chromatographed (2×90 g Biotage silica cartridges), eluting with hexane containing ethyl acetate (10% increasing to 15% v/v). The title compound was obtained as an oil (25% yield), which was identical by tlc to a sample prepared by a similar procedure. $^1$H NMR δ (d$_6$-DMSO): 1.2 (d, 6H), 3.8 (s, 3H), 4.5-4.6 (hept, 1H), 6.55 (m, 1H), 7.85 (m, 1H), 7.95 (m, 1H), 9.8 (s, 1H)

The preparation of 3-hydroxy-5-[(1-methylethyl)oxy]-N-(1-methyl-1H-pyrazol-3-yl)benzamide used in Example 2d and 2e is described below:

3-Hydroxy-5-[(1-methylethyl)oxy]-N-(1-methyl-1H-pyrazol-3-yl)benzamide

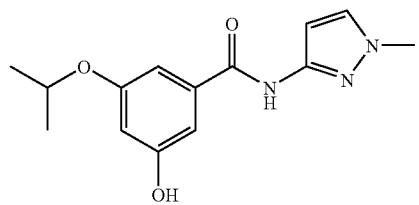

3-[(1-Methylethyl)oxy]-N-(1-methyl-1H-pyrazol-3-yl)-5-[(phenylmethyl)oxy]benzamide (51 g; 0.14 mol) was dissolved in methanol (500 mL) and THF (500 mL) and the flask evacuated and purged with argon (3 times). 10% Palladium on carbon (5.1 g) was added and the flask further evacuated and finally purged with hydrogen gas. The reaction mixture was stirred at ambient temperature for 20 hours. The reaction mixture was evacuated and purged with nitrogen (3 times). The catalyst was filtered off through celite, and the filtrate concentrated in vacuo. Ethyl acetate was added and filtered to give the desired compound. (30.5 g). A second crop of material was obtained in the same way (4.0 g).
$^1$H NMR δ (d$_6$-DMSO): 1.30 (d, 6H), 3.78 (s, 3H), 4.68 (sept, 1H), 6.47 (m, 1H), 6.60 (s, 1H), 6.94 (s, 1H), 7.05 (s, 1H), 7.60 (s, 1H), 10.63 (s, 1H). m/z 276 (M+H)$^+$ 3-[(1-Methylethyl)oxy]-N-(1-methyl-1H-pyrazol-3-yl)-5-[(phenylmethyl)oxy]benzamide

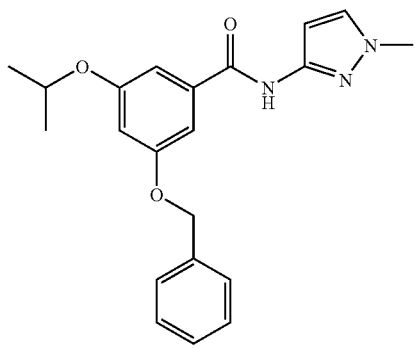

DMF (2 drops) was added to a solution of 3-[(1-methylethyl)oxy]-5-[(phenylmethyl)oxy]benzoic acid (40.0 g, 0.14 mol) and oxalyl chloride (14.6 mL, 0.17 mol) in DCM (700 mL) The mixture was stirred at ambient temperature for 4 hours and the DCM and excess oxalyl chloride evaporated in vacuo. The residual acid chloride was dissolved in DCM (300 mL) and added dropwise to 1-methyl-3-aminopyrazole (14.25 g, 0.147 mol) and triethylamine (41 mL, 0.29 mmol) in DCM (300 mL), at 0° C. Stirred at ambient temperature for 24 hours. The DCM was evaporated in vacuo, and the residue partitioned between ethyl acetate (400 mL) and 1N hydrochloric acid (200 mL). The ethyl acetate layer was washed sequentially with saturated aqueous sodium hydrogen carbonate (200 mL) and brine (100 mL), dried (MgSO$_4$) and evaporated in vacuo. The residue was chromatographed on silica, eluting with a gradient of 50% ethyl acetate in isohexane, to give the desired compound (51 g). $^1$H NMR δ (CDCl$_3$): 1.30 (d, 6H), 3.61 (s, 3H), 4.50 (sept, 1H), 5.01 (s, 2H), 6.66 (m, 1H), 6.88 (m, 1H), 7.00 (m, 1H), 7.06 (m, 1H), 7.24 (m, 1H), 7.39 (m, 5H), 9.50 (s, 1H). m/z 366 (M+H)$^+$ The preparation of 3-[(1-methylethyl)oxy]-5-[(phenylmethyl)oxy]benzoic acid was described above.

The preparation of 3-hydroxy-5-{[(1S)-2-methoxy-(1-methylethyl)oxy}-N-(3-methyl-1,2,4-thiadiazol-2-yl)benzamide used in Examples 2f and 2 g is described below:

3-Hydroxy-5-{[(1S)-2-methoxy-(1-methylethyl)oxy}-N-(3-methyl-1,2,4-thiadiazol-2-yl)benzamide

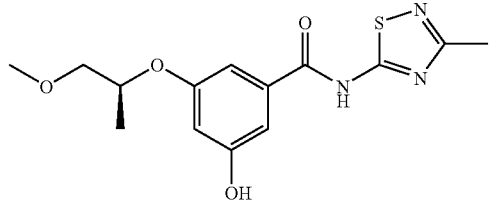

A solution of 3-{[(1S)-2-methoxy-(1-methylethyl)oxy}-5-{phenylmethyloxy}-N-(3-methyl-1,2,4-thiadiazol-2-yl) benzamide (9.53 g) and thioanisole (13.9 mL) in trifluoroacetic acid (45 mL) was stirred at ambient temperature for 16 hours. The trifluoroacetic acid was removed in vacuo and the residual oil partitioned between ethyl acetate (100 mL) and aqueous sodium hydrogen carbonate solution (300 mL). The aqueous layer was separated, extracted with ethyl acetate (2×100 mL), and the combined organic extracts washed with brine, dried (MgSO$_4$), and evaporated to a residue which was chromatographed on silica with 50% ethyl acetate in isohexane as eluant to give the desired compound (4.5 g).

$^1$H NMR δ (CDCl$_3$): 1.2 (d, 3H), 2.5 (s, 3H), 3.3 (s, 3H), 3.4-3.6 (m, 2H), 4.6-4.7 (m, 1H), 6.6 (s, 1H), 7.05 (s, 1H), 7.1 (s, 1H), 9.85 (s, 1H), 13.2 (s, 1H). m/z 324 (M+H)$^+$

3-{[(1S)-2-Methoxy-(1-methylethyl)oxy}5-{phenylmethyloxy}-N-(3-methyl-1,2,4-thiadiazol-2-ylbenzamide

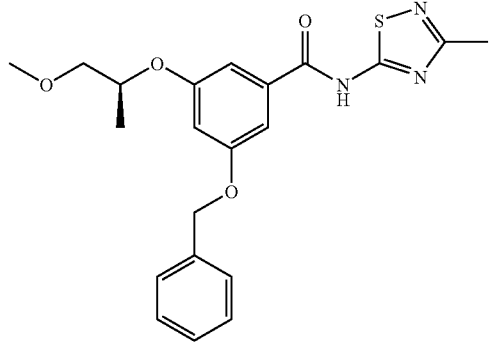

To a solution of 3-[(1S)-2-methoxy-(1-methylethyl)oxy]-5-{[phenylmethyl]oxy}benzoic acid (15.8 g) in DCM (260 mL) was added oxalyl chloride (5.24 mL), followed by DMF (1 drop), and the mixture stirred at ambient temperature for 16 hours. The DCM and excess oxalyl chloride were removed in vacuo, the residual oil dissolved in DCM (50 mL) and added to a solution of 5-amino-3-methyl-1,2,4 thiadiazole (6.05 g) and triethylamine (14.6 mL) in DCM (150 mL) at 0-5° C., and the mixture stirred at ambient temperature for 16 hours. The DCM and excess triethylamine were removed in vacuo, and the residual oil partitioned between ethyl acetate (250 mL) and 1M hydrochloric acid (150 mL). The ethyl acetate layer was separated, washed sequentially with 1M hydrochloric acid, aqueous sodium hydrogen carbonate solution, and brine, dried (MgSO$_4$), and evaporated to a residue which was chromatographed on alumina with ethyl acetate as eluant, then on silica with 30% ethyl acetate in isohexane as eluant to give the desired compound (9.6 g).

$^1$H NMR δ (CDCl$_3$): 1.3 (d, 3H), 2.45 (s, 3H), 3.4 (s, 3H), 3.5-3.6 (m, 2H), 4.55-4.6 (m, 1H), 5.05 (s, 2H), 6.8 (s, 1H), 7.1 (m, 2H), 7.25 (m, 5H), 10.7 (s, 1H). m/z 414 (M+H)$^+$

The synthesis of 3-[(1S)-2-methoxy-(1-methylethyl)oxy]-5-{[phenylmethyl]oxy}benzoic acid is described above.

EXAMPLE 3

3-{[6-(Azetidin-1-ylcarbonyl)pyridin-3-yl]oxy}-5-{[(1S)-1-methyl-2-(methyloxy)ethyl]oxy}-N-(1-methyl-1H-pyrazol-3-yl)benzamide

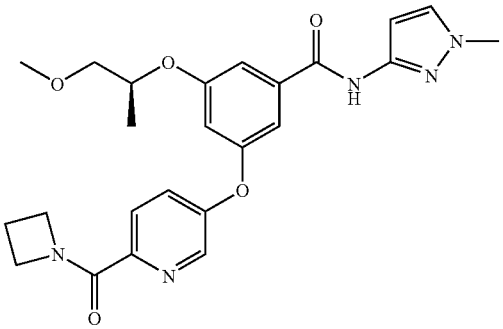

A mixture of 3-hydroxy-5-[(1S)-2-methoxy-(1-methylethyl)oxy]-N-(1-methyl-1H-pyrazol-3-yl)benzamide (0.2 g, 0.66 mmol), 5-(azetidin-1-ylcarbonyl)-2-chloropyridine (158 mg, 0.66 mmol), cesium carbonate (640 mg, 1.97 mmol) and bromotris(triphenylphosphine)copper(I) (62 mg, 0.07 mmol) in DMA (5 mL) was stirred in a 'Biotage initiator Microwave' for 3 hours. The mixture was allowed to reach RT and pressure and was partitioned between ethyl acetate (50 mL) and water (50 mL). The ethyl acetate layer was separated, washed with water (5×50 mL), brine (50 mL), dried (MgSO$_4$) and evaporated to a residue which was chromatographed on silica, eluting with a gradient of 0-5% methanol in ethyl acetate, to give the desired compound (113 mg). The compound was partially crystallised from methanol. The material was also partially crystallised from isopropyl alcohol/isohexane or ethyl acetate/isohexane. Mpt (melting onset) 132.7° C.

$^1$H NMR δ (CDCl$_3$): 1.32 (d, 3H), 2.36 (quin, 2H), 3.40 (s, 3H), 3.61-3.47 (m, 2H), 3.78 (s, 3H), 4.25 (t, 2H), 4.58 (sextet, 1H), 4.72 (t, 2H), 6.80 (t, 2H), 7.11 (s, 1H), 7.31-7.27 (m, 2H), 7.40-7.35 (m, 1H), 8.12 (d, 1H), 8.32 (s, 1H), 8.32 (s, 1H). m/z 466 (M+H)$^+$ The following compounds were synthesised in an analogous fashion from the appropriate phenol and bromopyridine:

| Example | Structure | m/z | NMR |
|---|---|---|---|
| 3a | 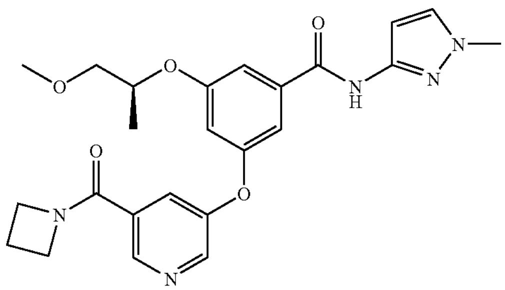 | 466 (M + H)+ | 1H NMR δ (CDCl3): 1.34 (d, 3H), 2.40 (quintet, 2H), 3.41 (s, 3H), 3.49-3.62 (m, 2H), 3.80 (s, 3H), 4.25 (t, 2H), 4.37 (t, 2H), 4.60 (sextet, 1H), 6.80 (m, 2H), 7.10 (t, 1H), 7.27 (t, 1H), 7.30 (d, 1H), 7.62 (t, 1H), 8.51 (d, 1H), 8.61 (s, 2H) |
| 3b | 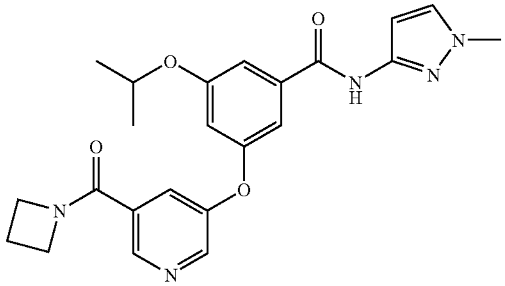 | 436 (M + H)+ | 1H NMR δ (CDCl3): 1.37 (d, 6H), 2.40 (quintet, 2H), 3.80 (s, 3H), 4.25 (t, 2H), 4.37 (t, 2H), 4.60 (septet, 1H), 6.74 (t, 1H), 6.80 (s, 1H), 7.07 (s, 1H), 7.07 (s, 1H), 7.30 (d, 1H), 7.62 (t, 1H), 8.51 (s, 1H), 8.61 (s, 2H) |
| 3c | 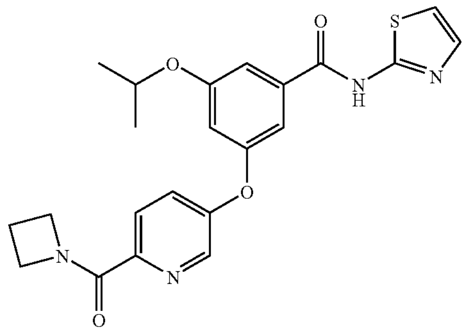 | 439 (M + H)+ | 1H NMR δ (CDCl3): 1.35 (d, 6H), 2.38 (quintet, 2H), 4.25 (t, 2H), 4.58 (septet, 1H), 4.73 (t, 2H), 6.80 (s, 1H), 6.98 (d, 1H), 7.20 (d, 1H), 7.25 (d, 1H), 7.35 (m, 2H), 8.13 (d, 1H), 8.31 (d, 1H), 12.15 (s, 1H) |
| 3d | 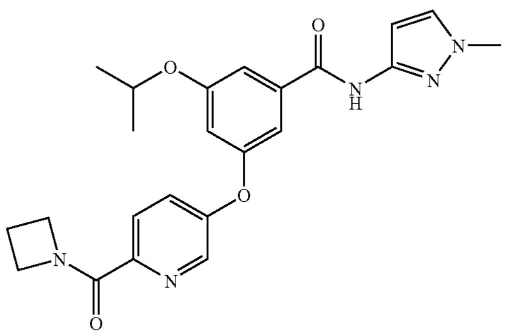 | 436 (M + H)+ | 1H NMR δ (CDCl3): 1.28 (d, 6H), 2.26 (quintet, 2H), 3.69 (s, 3H), 4.18 (t, 2H), 4.49 (septet, 1H), 4.63 (t, 2H), 6.65 (s, 1H), 6.72 (s, 1H), 7.00 (s, 1H), 7.15 (m, 1H), 7.20 (m, 2H), 7.28 (m, 1H), 8.02 (d, 1H), 8.21 (d, 1H), 8.63 (s, 1H) |
| 3e | 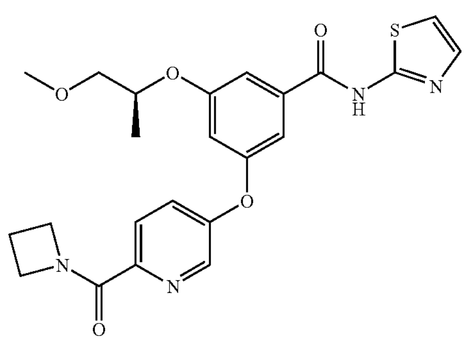 | 469 (M + H)+ | 1H NMR δ (CDCl3): 1.33 (d, 6H), 2.36 (quintet, 2H), 3.38 (s, 3H), 3.48-3.60 (m, 2H), 4.25 (t, 2H), 4.59 (sextet, 1H), 4.72 (t, 2H), 6.88 (m, 1H), 6.97 (d, 1H), 7.19 (d, 1H), 7.28 (m, 2H), 7.38 (m, 2H), 8.12 (d, 1H), 8.30 (d, 1H), 12.30 (s, 1H) |

| Example | Structure | m/z | NMR |
|---|---|---|---|
| 3f | 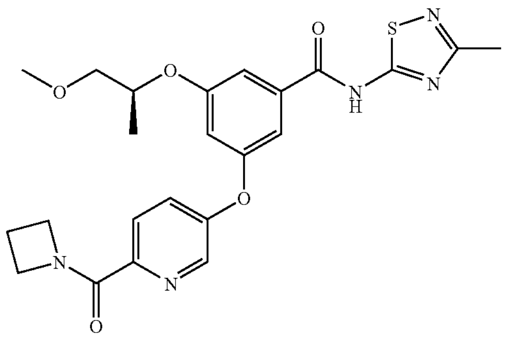 | 484 (M + H)+ | ¹H NMR δ (CDCl₃): 1.27 (d, 3H), 2.29 (quintet, 2H), 2.44 (s, 3H), 3.31 (s, 3H), 3.4-3.52 (m, 2H), 4.15 (m, 2H), 4.55 (sextet, 1H), 4.65 (t, 1H), 6.80 (m, 1H), 7.25 (m, 2H), 7.40 (m, 1H), 7.60 (m, 1H), 8.00 (d, 1H), 8.21 (s, 1H). |
| 3g | 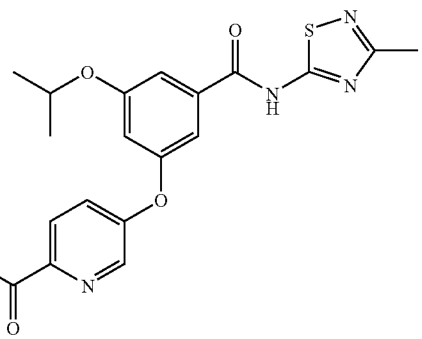 | 454 (M + H)+ | ¹H NMR δ (CDCl₃): 1.30 (d, 6H), 2.29 (quintet, 2H), 2.44 (s, 3H), 4.18 (m, 2H), 4.55 (septet, 1H), 4.65 (t, 1H), 6.74 (m, 1H), 7.18 (m, 1H), 7.30 (m, 1H), 7.40 (m, 1H), 8.00 (d, 1H), 8.23 (s, 1H), 10.05 (s, 1H) |

The preparation of the required bromopyridines is described earlier.

The preparation of 3-hydroxy-5-[(1S)-2-methoxy-(1-methylethyl)oxy]-N-(1-methyl-1H-pyrazol-3-yl)benzamide, 3-hydroxy-5-[(1-methylethyl)oxy]-N-(1-methyl-1H-pyrazol-3-yl)benzamide, 3-hydroxy-5-[(1-methylethyl)oxy]-N-1,3-thiazol-2-ylbenzamide, 3-hydroxy-5-{[(1S)-2-methoxy-(1-methylethyl)oxy}-N-1,3-thiazol-2-ylbenzamide and 3-hydroxy-5-{[(1S)-2-methoxy-(1-methylethyl)oxy}-N-(3-methyl-1,2,4-thiadiazol-2-yl)benzamide is described earlier.

The preparation of 3-hydroxy-5-[(1-methylethyl)oxy]-N-(3-methyl-1,2,4-thiadiazol-5-yl)benzamide used in Example 3g is described below:

3-Hydroxy-5-[(1-methylethyl)oxy]-N-(3-methyl-1,2,4-thiadiazol-5-yl)benzamide

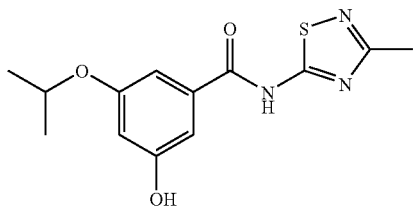

A solution of 3-[(1-methylethyl)oxy]-N-(3-methyl-1,2,4-thiadiazol-5-yl)-5-[(phenylmethyl)oxy]benzamide (33 g, 86 mmol), trifluoroacetic acid (160 mL) and thioanisole (50.5 mL) was stirred at ambient temperature for 48 hours. The TFA was removed in vacuo and the residue poured into saturated sodium bicarbonate solution (300 mL) and extracted into ethyl acetate (twice). The combined organic extracts were washed with brine, dried (MgSO₄), filtered and the solvent removed in vacuo. The residue was triturated with DCM and washed with 5% ethyl acetate in isohexane to give the desired compound (12.8 g). ¹H NMR δ (d₆-DMSO): 1.31 (d, 6H), 2.51 (s, 3H), 4.67 (sept, 1H), 6.58 (s, 1H), 7.08 (s, 1H), 7.24 (s, 1H), 9.88 (s, 1H), 13.25 (brs, 1H). m/z 294 (M+H)+

3-[(1-Methylethyl)oxy]-N-(3-methyl-1,2,4-thiadiazol-5-yl)-5-[(phenylmethyl)oxy]benzamide

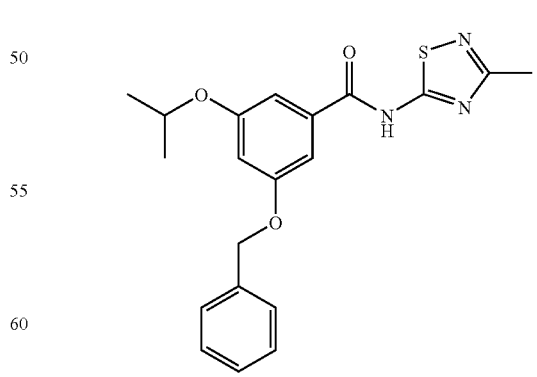

DMF (2 drops) was added to a solution of 3-[(1-methylethyl)oxy]-5-[(phenylmethyl)oxy]benzoic acid (29.6 g, 0.103 mol) and oxalyl chloride (10.78 mL, 0.12 mol) in DCM (500 mL) The mixture was stirred at ambient temperature for 4 hours and the DCM and excess oxalyl chloride removed in vacuo. The residual acid chloride was dissolved in DCM (220 mL) and added dropwise to 5-amino-3-methyl-1,2,4-thiadiazole (12.43 g, 0.108 mol) and triethylamine (30.34 mL, 0.216 mol) in DCM (220 mL), at 0° C. The reaction was allowed to warm and stirred at ambient temperature for 72 hours. The DCM was removed in vacuo, and the residue partitioned between ethyl acetate (400 mL) and 1N hydrochloric acid (200 mL). The ethyl acetate layer was washed sequentially with saturated aqueous sodium hydrogen carbonate (200 mL) and brine (100 mL), dried (MgSO$_4$) and concentrated in vacuo. The residue was chromatographed on silica, eluting with a gradient of 20% ethyl acetate in isohexane, to give the desired compound (33 g).

$^1$H NMR δ (CDCl$_3$): 1.32 (d, 6H), 2.31 (s, 3H), 4.51 (sept, 1H), 5.05 (s, 2H), 6.74 (m, 1H), 7.03 (m, 1H), 7.10 (m, 1H), 7.38 (m, 5H), 11.48 (brs, 1H). m/z 384 (M+H)$^+$ The preparation of 3-[(1-methylethyl)oxy]-5-[(phenylmethyl)oxy]benzoic acid is described above.

EXAMPLE 4

3-{[5-(Azetidin-1-ylsulfonyl)pyridin-2-yl]oxy}-5-{[(1S)-1-methyl-2-(methyloxy)ethyl]oxy}-N-(1-methyl-1H-pyrazol-3-yl)benzamide

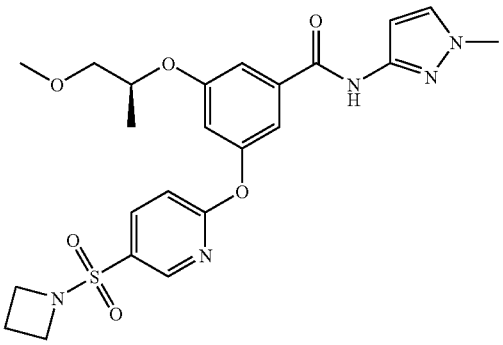

Triethylamine (0.025 mL, 0.18 mmol) then triethylsilane (0.96 mL, 6.03 mmol) were added to palladium (II) acetate (12 mg) in DCM (2 mL) and stirred under argon for 15 mins. 3-{[5-(Azetidin-1-ylsulfonyl)-3-bromopyridin-2-yl]oxy}-5-{[(1S)-1-methyl-2-(methyloxy)ethyl]oxy}-N-(1-methyl-1H-pyrazol-3-yl)benzamide (0.175 g, 0.3 mmol) in DCM (2 mL) was added dropwise and the reaction stirred at RT for 24 hours. Methanol was added, the reaction filtered through celite and the solvent removed in vacuo. Ethyl acetate (30 mL) was added and the mixture washed with water (30 mL), citric acid (30 mL), brine (30 mL), dried (MgSO4), filtered and the solvent removed in vacuo to give a white solid. This was chromatographed on silica, eluting with a gradient of 0-100% ethyl acetate in isohexane, to give the desired compound (69 mg).

$^1$H NMR δ (CDCl$_3$): 1.26 (d, 3H), 2.09 (quin, 2H), 3.33 (s, 3H), 3.41-3.55 (m, 2H), 3.69 (s, 3H), 3.76 (t, 4H), 4.52 (sextet, 1H), 6.73 (d, 1H), 6.87 (t, 1H), 7.02 (d, 1H), 7.17 (t, 1H), 7.20 (m, 1H), 7.28 (s, 1H), 8.04 (m, 1H), 8.54 (d, 1H), 8.65 (s, 1H). m/z 502 (M+H)$^+$ The preparation of 3-{[5-(azetidin-1-ylsulfonyl)-3-bromopyridin-2-yl]oxy}-5-{[(1S)-1-methyl-2-(methyloxy)ethyl]oxy}-N-(1-methyl-1H-pyrazol-3-yl)benzamide is described below:

3-{[5-(Azetidin-1-ylsulfonyl-3-bromopyridin-2-yl]oxy}-5-{[(1S)-1-methyl-2-(methyloxy)ethyl]oxy}-N-(1-methyl-1H-pyrazol-3-yl)benzamide

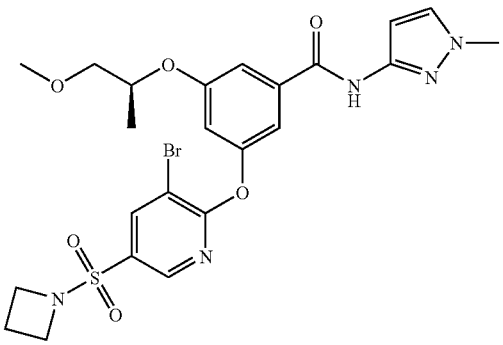

A mixture of 3-hydroxy-5-[(1S)-2-methoxy-(1-methylethyl)oxy]-N-(1-methyl-1H-pyrazol-3-yl)benzamide (0.2 g, 0.66 mmol), 5-(azetidin-1-ylsulfonyl)-3-bromo-2-chloropyridine (204 mg, 0.66 mmol) and potassium carbonate (181 mg, 1.31 mmol) in acetonitrile (5 mL) was stirred in a 'Biotage initiator Microwave' at 160° C. for 2 hours. The solvent was removed in vacuo and the residue dissolved in ethyl acetate and water, the organic layer washed with brine (50 mL), dried (MgSO4), filtered and the solvent removed in vacuo to give a brown oil which was chromatographed on silica, eluting with a gradient of 50-100% ethyl acetate in isohexane, to give the desired compound (175 mg).

$^1$H NMR δ (CDCl$_3$): 1.26 (d, 3H), 2.12 (quin, 2H), 3.33 (s, 3H), 3.54-3.40 (m, 2H), 3.68 (s, 3H), 3.79 (t, 4H), 4.52 (sextet, 1H), 6.73 (d, 1H), 6.89 (t, 1H), 7.18 (t, 1H), 7.21 (d, 1H), 7.30 (t, 1H), 8.27 (d, 1H), 8.38 (d, 1H), 8.77 (s, 1H). m/z 580, 582 (M+H)$^+$ 5-(Azetidin-1-ylsulfonyl)-3-bromo-2-chloropyridine

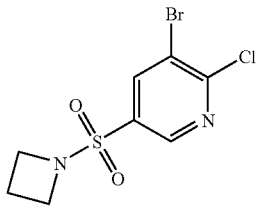

Azetidine hydrochloride (0.32 g, 3.44 mmol) was added to a solution of 3-bromo-2-chloropyridine-5-sulfonyl chloride (1 g, 3.44 mmol) in DCM (4 mL) and pyridine (10 mL) and stirred at RT for 22 hours. The solvent was removed in vacuo and ethyl acetate (30 mL) added. The organic phase was washed with 1M hydrochloric acid (20 mL), water (20 mL), brine (20 mL), dried (MgSO4), filtered and the solvent removed in vacuo to give the desired compound (0.4 g).

$^1$H NMR δ (CDCl$_3$): 2.18 (quin, 2H), 3.83 (t, 4H), 8.26 (s, 1H), 8.66 (s, 1H).

EXAMPLE 5

3-{[5-(Azetidin-1-ylcarbonyl)pyrazin-2-yl]oxy}-5-{[(1S)-1-methyl-2-(methyloxy)ethyl]oxy}-N-(1-methyl-1H-pyrazol-3-yl)benzamide

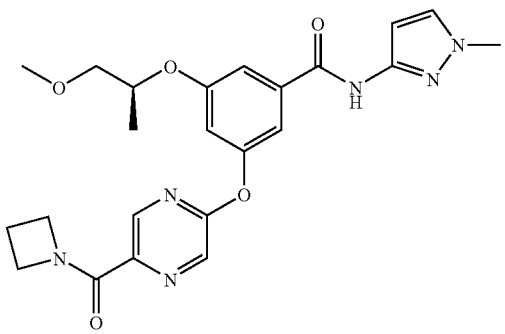

DIPEA (0.28 mL, 1.59 mmol) was added to a suspension of 5-[(3-{[(1S)-1-methyl-2-(methyloxy)ethyl]oxy}-5-{[(1-methyl-1H-pyrazol-3-yl)amino]carbonyl}phenyl)oxy]pyrazine-2-carboxylic acid (170 mg, 0.4 mmol), HATU (318 mg, 0.84 mmol) and azetidine hydrochloride (75 mg, 0.8 mmol) in DMF (5 mL) and the mixture stirred at RT for 72 hours. Ethyl acetate (40 mL) was added and washed with water (2×30 mL), brine (30 mL), dried (MgSO4), filtered and reduced in vacuo to give a yellow oil which was chromatographed on silica, eluting with 0-100% ethyl acetate in isohexane, to give the desired compound (48 mg).
$^1$H NMR δ (CDCl$_3$): 1.26 (d, 3H), 2.31 (quin, 2H), 3.32 (s, 3H), 3.41-3.55 (m, 2H), 3.71 (s, 3H), 4.19 (t, 2H), 4.52 (m, 1H), 4.60 (t, 2H), 6.72 (s, 1H), 6.86 (m, 1H), 7.16 (m, 1H), 7.20 (m, 1H), 7.28 (m, 1H), 8.25 (s, 1H), 8.52 (s, 1H), 8.52 (s, 1H). m/z 467 (M+H)$^+$ The preparation of 5-[(3-{[(1S)-1-methyl-2-(methyloxy)ethyl]oxy}-5-{[(1-methyl-1H-pyrazol-3-yl)amino]carbonyl}phenyl)oxy]pyrazine-2-carboxylic acid is described below:

5-[(3-{[(1S)-1-Methyl-2-(methyloxy)ethyl]oxy}-5-{[(1-methyl-1H-pyrazol-3-yl)amino]carbonyl}phenyl)oxy]pyrazine-2-carboxylic acid

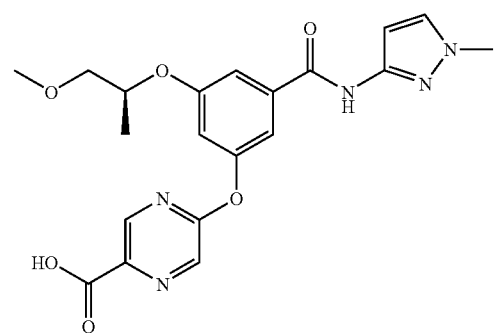

A mixture of 3-hydroxy-5-[(1S)-2-methoxy-(1-methylethyl)oxy]-N-(1-methyl-1H-pyrazol-3-yl)benzamide (0.226 g, 0.74 mmol), methyl 5-chloropyrazine-2-carboxylate (192 mg, 1.11 mmol) and potassium carbonate (205 mg, 1.48 mmol) in acetonitrile (5 mL) was stirred in a 'Biotage initiator Microwave' at 160° C. for 4 hours. The solvent was removed in vacuo and water (30 mL) added. The mixture was acidified and extracted into ethyl acetate (3×50 mL), the combined organics washed with brine (30 mL), dried (MgSO4), filtered and reduced in vacuo to give a brown oil which was a mixture of the acid and methyl ester. Lithium hydroxide monohydrate (78 mg, 1.85 mmol) in water (2 mL) was added to the mixture of acid and ester (326 mg, 0.74 mmol) in THF (4 mL) and the mixture stirred at RT for 20 hours. The THF was removed in vacuo and the aqueous residue washed with ethyl acetate (20 mL) to remove impurities then acidified with 1M citric acid. The product was extracted into ethyl acetate (2×100 mL) and the combined organics washed with brine (50 mL), dried (MgSO4), filtered and reduced in vacuo to give a yellow solid (0.17 g). m/z 428 (M+H)$^+$

EXAMPLE 6

3-{[5-(Azetidin-1-ylcarbonyl)-1,3-thiazol-2-yl]oxy}-5-[(1-methylethyl)oxy]-N-(1-methyl-1H-pyrazol-3-yl)benzamide

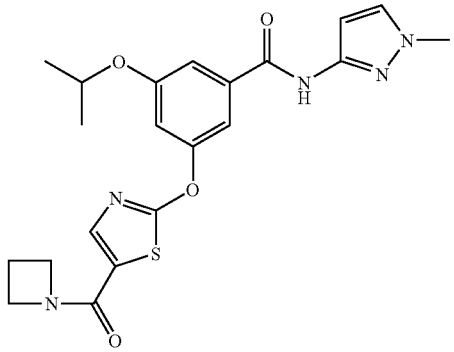

Cesium carbonate (488 mg, 1.5 mmol) was added to a solution of 3-hydroxy-5-[(1-methylethyl)oxy]-N-(1-methyl-1H-pyrazol-3-yl)benzamide (187 mg, 0.5 mmol) and 5-(azetidin-1-ylcarbonyl)-2-chloro-1,3-thiazole (152 mg, 0.75 mmol) in acetonitrile (5 mL) and the stirred mixture heated at 160° in a Biotage Initiator Microwave for 2 hours. The mixture was cooled to RT and pressure, poured onto water (75 mL) then extracted with ethyl acetate (3×25 mL). The combined organic layers were washed with brine, dried (MgSO$_4$) and evaporated to a residue which was chromatographed on silica eluting with ethyl acetate, to give the desired compound (142 mg). $^1$H NMR δ (CDCl$_3$): 1.3 (d, 6H), 2.4 (m, 2H), 3.7 (s, 3H), 4.1-4.4 (m, 4H), 4.5 (m, 1H), 6.75 (s, 1H), 6.9 (s, 1H), 7.2 (s, 1H), 7.25 (d, 1H), 7.4 (s, 1H) and 8.95 (s, 1H). m/z 442 (M+H)$^+$.

The following example was made in an analogous fashion from 5-(azetidin-1-ylcarbonyl)-2-chloro-1,3-thiazole and 3-hydroxy-5-[(1S)-2-methoxy-(1-methylethyl)oxy]-N-(1-methyl-1H-pyrazol-3-yl)benzamide.

| Example | Structure | m/z | NMR |
|---|---|---|---|
| 6a | 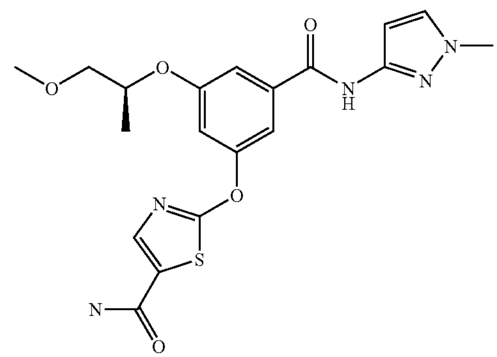 | 472 (M + H)⁺ | ¹H NMR δ (CDCl₃): 1.3 (d, 3H), 2.35 (m, 2H), 3.3 (s, 1H), 3.4-3.55 (m, 2H), 3.7 (s, 3H), 4.1-4.4 (m, 4H), 4.5 (m, 1H), 6.7 (s, 1H), 6.95 (s, 1H), 7.25 (s, 1H), 7.3 (d, 2H), 7.4 (s, 1H) and 8.9 (s, 1H). |

The preparation of 5-(azetidin-1-ylcarbonyl)-2-chloro-1,3-thiazole is described below:

5-(Azetidin-1-ylcarbonyl)-2-chloro-1,3-thiazole

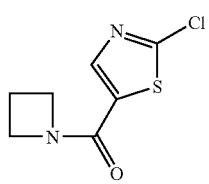

To a solution of 2-chlorothiazole-5-carboxylic acid (815 mg, 5 mmol) in dichloromethane (10 mL) was slowly added oxalyl chloride (0.53 mL, 6 mmol) and then N,N dimethylformamide (1 drop) with stirring. The mixture was stirred for 16 hours, following which the organics were removed in vacuo, and the residues azeotroped with toluene (100 ml). The crude material was dissolved in dichloromethane (10 mL) and slowly added to a stirred suspension of azetidine hydrochloride (560 mg, 6 mmol) and triethylamine (2.5 mL, 18 mmol) in dichloromethane (25 mL). The mixture was stirred at ambient temperature for 2 hours before the organics were removed in vacuo. The residue was dissolved in ethyl acetate (50 mL) and water (25 mL), the organic layer washed with brine (25 mL), dried (MgSO₄) and evaporated to a residue which was chromatographed on silica with 40% ethyl acetate in iso-hexane as eluant to give 5-(azetidin-1-ylcarbonyl)-2-chloro-1,3-thiazoline. ¹H NMR δ (CDCl₃): 2.4 (m, 2H), 4.1-4.4 (m, 4H), 4.55 (m, 1H), 7.2 (s, 1H) and 7.75 (s, 1H); m/z 203 (M+H)⁺.

The preparation of 3-hydroxy-5-[(1-methylethyl)oxy]-N-(1-methyl-1H-pyrazol-3-yl)benzamide and 3-hydroxy-5-[(1S)-2-methoxy-(1-methylethyl)oxy]-N-(1-methyl-1H-pyrazol-3-yl)benzamide are described earlier.

EXAMPLE 7

3-{[5-(Azetidin-1-ylcarbonyl)pyridin-2-yl]oxy}-5-{[(1S)-2-hydroxy-1-methylethyl]oxy}-N-(1-methyl-1H-pyrazol-3-yl)benzamide

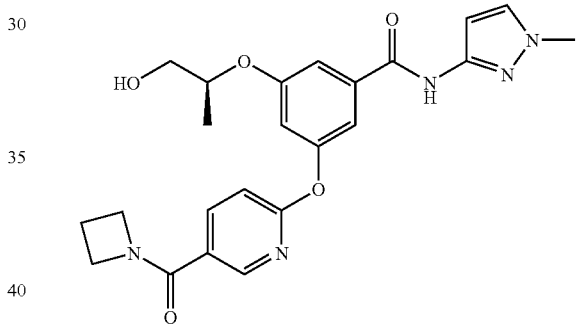

A solution of 6-[(3-[((1S)-2-{[(1,1-dimethylethyl)(dimethyl)silyl]oxy}-1-methylethyl)oxy]-5-{[(1-methyl-1H-pyrazol-3-yl)amino]carbonyl}phenyl)oxy]pyridine-3-carboxylic acid (0.20 g, 0.378 mmol), azetidine hydrochloride (0.106 g, 0.114 mmol), HATU (0.302 g, 0.794 mmol) and DIPEA (0.39 mL, 0564 mmol) in DMF (7 mL) was stirred at RT overnight. 3.5M Hydrochloric acid (0.5 mL) was added and the solution left to stir for 20 minutes. The solution was neutralised with saturated sodium bicarbonate solution. Water (20 mL) was added and the solution extracted with ethyl acetate (50 mL). The ethyl acetate layer was washed with brine, dried (MgSO₄), and evaporated to a residue which was chromatographed on silica, eluting with 50% ethyl acetate in isohexane, to give the desired product (27 mg). ¹H NMR δ (CDCl₃): 1.32 (d, 3H), 2.38 (quintet, 2H), 3.77 (m, 2H), 3.80 (s, 3H), 4.29 (d, 4H), 4.57 (sextet, 1H), 6.81 (d, 1H), 6.91 (t, 1H), 6.99 (d, 1H), 7.27 (m, 2H), 7.38 (m, 1H), 8.42 (d, 1H), 8.86 (s, 1H). m/z 452 (M+H)⁺

The preparation of 6-[(3-[((1S)-2-{[(1,1-dimethylethyl)(dimethyl)silyl]oxy}-1-methylethyl)oxy]-5-{[(1-methyl-1H-pyrazol-3-yl)amino]carbonyl}phenyl)oxy]pyridine-3-carboxylic acid is described below:

6-[(3-[((1S)-2-{[(1,1-Dimethylethyl)(dimethyl)silyl]oxy}-1-methylethyl)oxy]-5-{[(1-methyl-1H-pyrazol-3-yl)amino]carbonyl}phenyl)oxy]pyridine-3-carboxylic acid

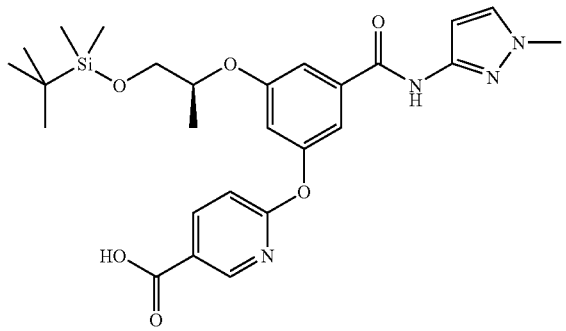

A solution of lithium hydroxide monohydrate (0.10 g, 4.17 mmol) in water (15 mL) was added to a solution of methyl 6-[(3-[((1S)-2-{[(1,1-dimethylethyl)(dimethyl)silyl]oxy}-1-methylethyl)oxy]-5-{[(1-methyl-1H-pyrazol-3-yl)amino]carbonyl}phenyl)oxy]pyridine-3-carboxylate (0.90 g, 1.67 mmol) in THF (30 mL). The mixture was allowed to stir at RT overnight. The THF was removed in vaccuo and the resulting solution was partitioned between water (50 mL) and ethyl acetate (75 mL), then the ethyl acetate layer separated, washed with brine and dried (MgSO$_4$). The aqueous layer was then taken to pH 7 by addition of 1N hydrochloric acid (5.2 mL) and extracted with ethyl acetate (75 mL). The ethyl acetate layer was separated, washed with brine and dried (MgSO$_4$). The ethyl acetate layers were combined and evaporated to give the required product (0.84 g).

$^1$H NMR δ (CDCl$_3$): 0.05 (d, 6H), 0.88 (s, 9H), 1.36 (d, 3H), 3.70-3.88 (m, 5H), 4.52-4.61 (sex, 1H), 6.98 (d, 2H), 7.01 (d, 1H), 6.28 (s, 1H), 7.44 (s, 1H), 7.57 (s, 1H), 8.04 (m, 1H), 8.72 (s, 1H), 10.62 (s, 1H). m/z 527 (M+H)$^+$

Methyl 6-[(3-[((1S)-2-{[(1,1-dimethylethyl)(dimethyl)silyl]oxy}-1-methylethyl)oxy]-5-{[(1-methyl-1H-pyrazol-3-yl)amino]carbonyl}phenyl)oxy]pyridine-3-carboxylate

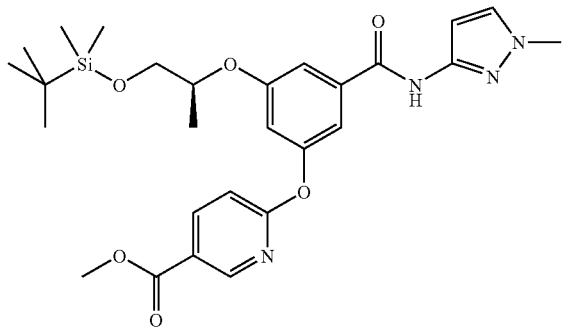

A solution of 3-[((1S)-2-{[(1,1-dimethylethyl)(dimethyl)silyl]oxy}-1-methylethyl)oxy]-5-hydroxy-N-(1-methyl-1H-pyrazol-3-yl)benzamide (1.00 g, 2.47 mmol), methyl 6-chloronicotinate (0.450 g, 2.60 mmol), and cesium carbonate (1.204 g, 3.71 mmol) in acetonitrile (15 mL) was heated at 160° C. using microwave heating for 90 minutes. The acetonitrile was removed in vaccuo and the residual oil partitioned between water (50 mL) and ethyl acetate (75 mL). The ethyl acetate layer was separated, washed with brine, dried (MgSO$_4$), and evaporated to a residue which was chromatographed on silica, eluting with 50% ethyl acetate in isohexane, to give the desired compound (0.977 g).

$^1$H NMR δ (CDCl$_3$): 0.05 (d, 6H), 0.87 (s, 9H), 1.34 (d, 3H), 3.54 (m, 3H), 3.79 (s, 3H), 3.93 (s, 3H), 4.59 (sextet, 1H), 6.79 (d, 1H), 6.92 (t, 1H), 6.96 (s, 1H), 6.99 (s, 1H), 7.20 (t, 1H), 7.27 (d, 1H), 7.33 (t, 1H), 8.28 (d, 1H), 8.31 (d, 1H), 8.39 (s, 1H), 8.82 (d, 1H). m/z (M+H)$^+$

3-[((1S)-2-{[(1,1-Dimethylethyl)(dimethyl)silyl]oxy}-1-methylethyl)oxy]-5-hydroxy-N-(1-methyl-1H-pyrazol-3-yl)benzamide

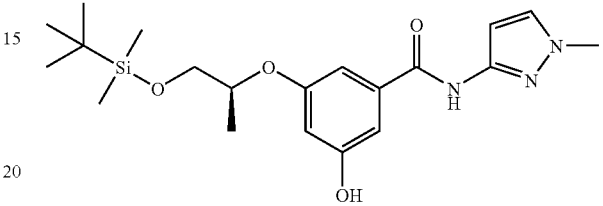

3-[((1S)-2-{[(1,1-dimethylethyl)(dimethyl)silyl]oxy}-1-methylethyl)oxy]-N-(1-methyl-1H-pyrazol-3-yl)-5-[(phenylmethyl)oxy]benzamide (1.8 g, 3.64 mmol) was dissolved in methanol (50 mL) and the flask evacuated and purged with nitrogen (3 times). 10% Palladium on carbon (0.2 g) was added and the flask further evacuated and finally purged with hydrogen gas. The reaction mixture was stirred at ambient temperature for 16 hours until completion. The reaction mixture was evacuated and purged with nitrogen (3 times). The catalyst was filtered off, and the filtrate concentrated in vacuo to give the desired compound (1.45 g). $^1$H NMR δ (d$_6$-DMSO): 0.02 (d, 6H), 0.83 (s, 9H), 1.18 (d, 3H), 3.66 (m, 2H), 3.72 (s, 3H), 4.51 (m, 1H), 6.42 (m, 1H), 6.52 (m, 1H), 6.90 (s, 1H), 7.02 (s, 1H), 7.55 (m, 1H), 9.58 (br s, 1H), 10.59 (br s, 1H). m/z 406 (M+H)$^+$

3-[((1S)-2-{[(1,1-Dimethylethyl)(dimethyl)silyl]oxy}-1-methylethyl)oxy]-N-(1-methyl-1H-pyrazol-3-yl)-5-[(phenylmethyl)oxy]benzamide

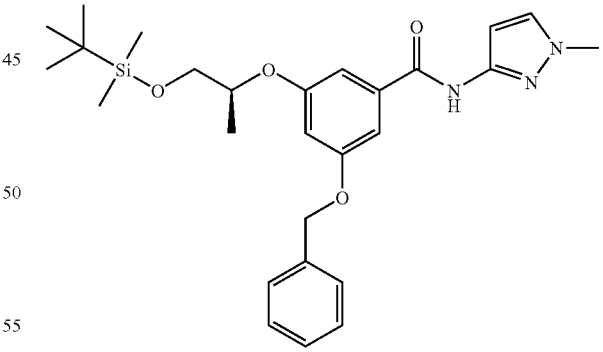

DIPEA (4.06 g, 23.4 mmol) was added to a suspension of 3-[((1S)-2-{[(1,1-dimethylethyl)(dimethyl)silyl]oxy}-1-methylethyl)oxy]-5-[(phenylmethyl)oxy]benzoic acid (2.43 g, 5.84 mmol), 3-amino-1-methylpyrazole (0.85 g, 8.76 mmol) and HATU (4.66 g, 12.3 mmol) in DMF (50 mL) and stirred at ambient temperature for 16 hours. The resultant mixture was partially reduced in vacuo, poured onto water (100 mL) and extracted with diethyl ether (2×50 mL). The extracts were washed with water and brine then dried (MgSO$_4$), filtered and reduced to an opaque gum which partially crystallized. The crude product was purified by column chromatography, eluting with 0-100% ethyl acetate in isohexane, to give the title compound as a colourless oil (1.87 g).

$^1$H NMR δ (d$_6$-DMSO): 0.02 (d, 6H), 0.84 (s, 9H), 1.21 (d, 3H), 3.68 (d, 2H), 3.76 (s, 3H), 4.58 (m, 1H), 5.13 (s, 2H), 6.56 (m, 1H), 6.70 (m, 1H), 7.18 (s, 1H), 7.24 (s, 1H), 7.29-7.46 (m, 5H), 7.57 (m, 1H), 10.74 (br s, 1H). m/z 496 (M+H)$^+$

3-[((1S)-2-{[(1,1-Dimethylethyl)(dimethyl)silyl]oxy}-1-methylethyl)oxy]-5-[(phenylmethyl)oxy]benzoic acid

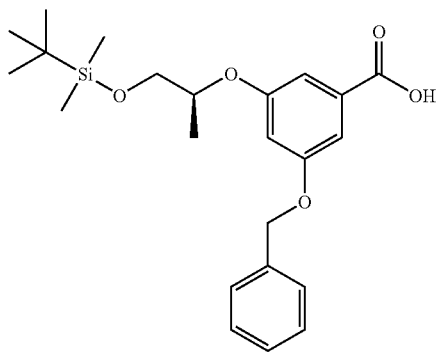

Methyl 3-[((1S)-2-{[(1,1-dimethylethyl)(dimethyl)silyl]oxy}-1-methylethyl)oxy]-5-[(phenylmethyl)oxy]benzoate (3.0 g, 6.98 mmol) was dissolved in THF (50 mL) and water (10 mL) and lithium hydroxide monohydrate (586 mg, 13.95 mmol) added. The resultant mixture was heated with stirring at 45° C. for 2 hours, then at ambient temperature for 16 hours, and at 45° C. for a further 4 hours. Water (40 mL) was added and the solvent removed in vacuo. The resultant solution was acidified carefully with 1M citric acid (2 equivalents), washed with water and brine then dried (MgSO$_4$), filtered and evaporated in vacuo to give the title compound as a colourless gum (2.58 g).

$^1$H NMR δ (d$_6$-DMSO): 0.02 (d, 6H), 0.84 (s, 9H), 1.17 (d, 3H), 3.66 (m, 2H), 4.43 (m, 1H), 5.05 (s, 2H), 6.56 (br s, 1H), 7.10 (br s, 1H), 7.17 (br s, 1H), 7.25-7.44 (m, 5H), 7.60 (br s, 1H).

Methyl 3-[((1S)-2-{[(1,1-dimethylethyl)(dimethyl)silyl]oxy}-1-methylethyl)oxy]-5-[(phenylmethyl)oxy]benzoate

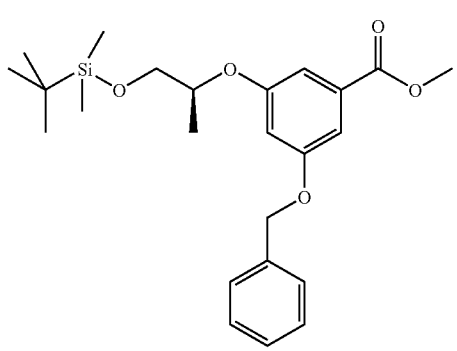

(2R)-1-{[(1,1-Dimethylethyl)(dimethyl)silyl]oxy}propan-2-ol (3.31 g, 17.4 mmol) was added to a solution of methyl 3-hydroxy-5-{[phenylmethyl]oxy}benzoate (3.00 g, 11.6 mmol) in THF (50 mL) at 0° C. followed by addition of triphenylphosphine (4.57 g, 17.4 mmol) then DIAD (3.43 mL, 17.4 mmol) and the reaction was warmed to RT and stirred for 16 h. The reaction was quenched with water (100 mL) and diethyl ether (400 mL) and the organic layer was separated then dried (MgSO$_4$) and evaporated. Purification by column chromatography, eluting with 1:15 to 1:5 ethyl acetate:hexane, afforded the title compound as a colourless oil (4.00 g, 80%).

$^1$H NMR δ (CDCl$_3$): 0.03 (s, 3H), 0.05 (s, 3H), 0.89 (s, 9H), 1.29 (d, 3H), 3.63 (dd, 1H), 3.78 (dd, 1H), 3.92 (s, 3H), 4.44 (m, 1H), 5.08 (s, 2H), 6.77 (m, 1H), 7.40 (m, 7H)

The preparation of methyl 3-hydroxy-5-{[phenylmethyl]oxy}benzoate was described earlier.

(2R)-1-{[(1,1-Dimethylethyl)(dimethyl)silyl]oxy}propan-2-ol

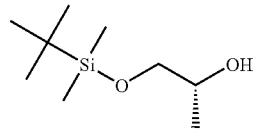

tert-Butyl(dimethyl)silyl chloride (5.90 g, 39.5 mmol) was added to a solution of (2R)-propane-1,2-diol (3.00 g, 39.5 mmol) in DCM (100 mL) followed by diisopropylethylamine (7.10 g, 55.3 mmol) and the reaction was stirred under argon for 72 h. The reaction was diluted with diethyl ether (500 mL) and water (140 mL) and the organic layer was separated then dried (MgSO$_4$), filtered and evaporated. Purification by column chromatography, eluting with 1:15 to 1:10 ethyl acetate:hexane, afforded the title compound as a colourless oil (6.00 g, 80%).

$^1$H NMR δ (CDCl$_3$): 0.10 (m, 6H), 0.92 (s, 9H), 1.14 (d, 3H), 2.42 (d, 1H), 3.38 (dd, 1H), 3.60 (dd, 1H), 3.82 (m, 1H).

The data matched that reported in the literature (*J. Org. Chem.*, 1998, 53, 2300).

EXAMPLE 8

3-{[3-Chloro-5-(morpholin-4-ylcarbonyl)pyridin-2-yl]oxy}-5-{[(1S)-2-hydroxy-1-methylethyl]oxy}-N-(1-methyl-1H-pyrazol-3-yl)benzamide

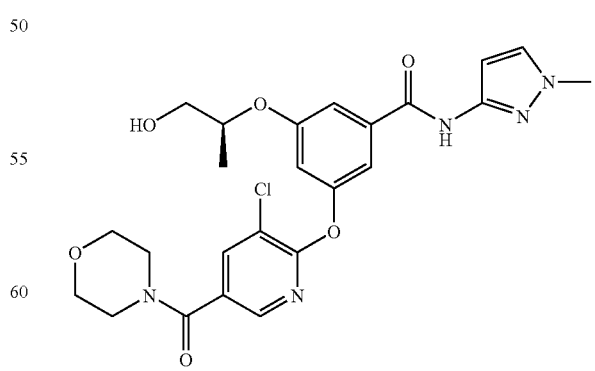

A solution 5-chloro-6-[(3-[((1S)-2-{[(1,1-dimethylethyl)(dimethyl)silyl]oxy}-1-methylethyl)oxy]-5-{[(1-methyl-1H-pyrazol-3-yl)amino]carbonyl}phenyl)oxy]pyridine-3- carboxylic acid (0.15 g, 0.267 mmol), morpholine (0.07 mL, 0.803 mmol), HATU (0.213 g, 0.560 mmol) and DIPEA (0.15 mL, 0.861 mmol) in DMF (7 mL) was stirred at RT for 2 days. Water (20 mL) was added and the solution extracted with ethyl acetate (50 mL). The ethyl acetate layer was separated, washed with brine and dried (MgSO$_4$), and evaporated to a residue which was chromatographed on silica, eluting with 1% methanol in ethyl acetate. 3.5M Hydrochloric acid (0.5 mL) was added to a solution of the residual solid taken up in methanol (5 mL) and allowed to stir at RT for 20 minutes. The solution was neutralised with saturated sodium bicarbonate solution and the methanol removed in vaccuo and the residual solution partitioned between water (20 mL) and ethyl acetate. The ethyl acetate layer was separated and washed with brine, dried (MgSO$_4$) and evaporated to give the desired product (34 mg). $^1$H NMR δ (d6-DMSO): 1.28 (d, 3H), 3.58 (m, 10H), 3.81 (s, 3H), 4.61 (sextet, 1H), 4.89 (t, 1H), 6.60 (d, 1H), 7.03 (t, 1H), 7.41 (s, 1H), 7.54 (s, 1H), 7.63 (d, 1H), 8.20 (q, 2H), 10.84 (s, 1H). m/z 516 (M+H)$^+$ The preparation of 5-chloro-6-[(3-[((1S)-2-{[(1,1-dimethylethyl)(dimethyl)silyl]oxy}-1-methylethyl)oxy]-5-{[(1-methyl-1H-pyrazol-3-yl)amino]carbonyl}phenyl)oxy]pyridine-3-carboxylic acid is described below:

5-Chloro-6-[(3-[((1S)-2-{[(1,1-dimethylethyl)(dimethyl)silyl]oxy}-1-methylethyl)oxy]-5-{[(1-methyl-1H-pyrazol-3-yl)amino]carbonyl}phenyl)oxy]pyridine-3-carboxylic acid

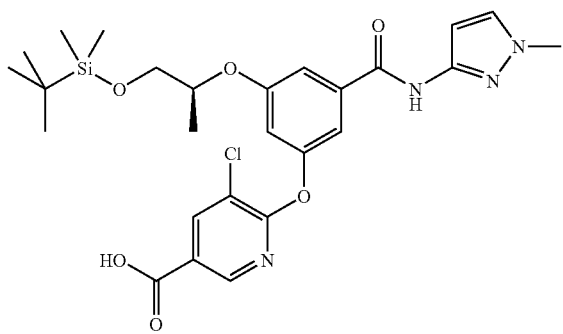

To a solution of methyl 5-chloro-6-[(3-[((1S)-2-{[(1,1-dimethylethyl)(dimethyl)silyl]oxy}-1-methylethyl)oxy]-5-{[(1-methyl-1H-pyrazol-3-yl)amino]carbonyl}phenyl)oxy]pyridine-3-carboxylate (1.2 g, 2.09 mmol) in THF (50 mL) was added a solution of lithium hydroxide monohydrate (0.219 g, 5.22 mmol) in water (30 mL). The mixture was allowed to stir under RT overnight. The THF was removed in vaccuo and the resulting solution was partitioned between water (50 mL) and ethyl acetate (75 mL), and the ethyl acetate layer separated, washed with brine and dried (MgSO$_4$). The aqueous layer was then adjusted to pH 7 by addition of 1N hydrochloric acid (5.2 mL) and partitioned between ethyl acetate (75 mL). The ethyl acetate layer was separated, washed with brine and dried (MgSO$_4$). The ethyl acetate layers were combined and evaporated to give the required product (1.1 g).
$^1$H NMR δ (d$_6$-DMSO): 0.01 (d, 6H), 0.82 (s, 9H), 1.22 (d, 3H), 3.73 (m, 2H), 3.76 (s, 3H), 4.55 (sextet, 1H), 6.55 (d, 1H), 6.90 (t, 1H), 7.30 (s, 1H), 7.44 (s, 1H), 7.58 (d, 1H), 8.36 (d, 1H), 8.19 (d, 1H), 8.51 (s, 1H). m/z (M+H)$^+$ Methyl 5-chloro-6-[(3-[((1S)-2-{[(1,1-dimethylethyl)(dimethyl)silyl]oxy}-1-methylethyl)oxy]-5-{[(1-methyl-1H-pyrazol-3-yl)amino]carbonyl}phenyl)oxy]pyridine-3-carboxylate

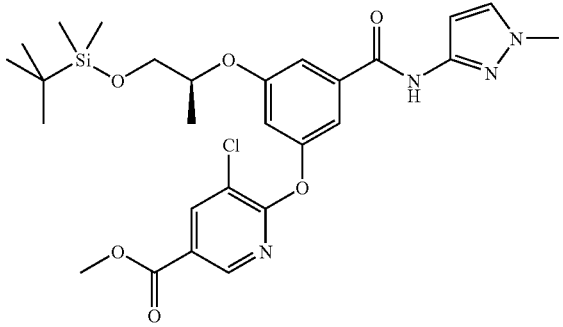

A solution of 3-[((1S)-2-{[(1,1-dimethylethyl)(dimethyl)silyl]oxy}-1-methylethyl)oxy]-5-hydroxy-N-(1-methyl-1H-pyrazol-3-yl)benzamide (1.0 g, 2.47 mmol), ethyl 5,6-dichloronicotinate (0.57 g, 2.59 mmol), and potassium carbonate (0.855 g, 6.14 mmol) in acetonitrile (15 mL) was heated at 160° C. for 4 hours using microwave heating. The acetonitrile was removed in vaccuo and the residual oil partitioned between water (50 mL) and ethyl acetate (75 mL). The ethyl acetate layer was separated, washed with brine, dried (MgSO$_4$), and evaporated to a residue which was chromatographed on silica, eluting with 50% ethyl acetate in hexane to give the desired compound (1.1 g). The analytical data indicated that transesterification had occurred at some stage in the procedure to furnish the methyl ester.
$^1$H NMR δ (CDCl$_3$): 0.05 (d, 6H), 0.87 (s, 9H), 1.30 (d, 3H), 3.72 (s, 3H), 3.73 (m, 1H), 3.93 (s, 3H), 4.47 (sextet, 1H), 6.80 (d, 1H), 6.93 (t, 1H), 7.19 (t, 1H), 7.25 (d, 1H), 7.26 (s, 1H), 7.34 (t, 1H), 8.35 (d, 1H), 8.61 (d, 1H), 8.97 (s, 1H); m/z (M+H)$^+$ 575

The preparation of 3-[((1S)-2-{[(1,1-dimethylethyl)(dimethyl)silyl]oxy}-1-methylethyl)oxy]-5-hydroxy-N-(1-methyl-1H-pyrazol-3-yl)benzamide is described earlier.

EXAMPLE 9

3-{[5-(Azetidin-1-ylcarbonyl)-3-chloropyridin-2-yl]oxy}-5-{[2-fluoro-1-(fluoromethyl)ethyl]oxy}-N-(1-methyl-1H-pyrazol-3-yl)benzamide

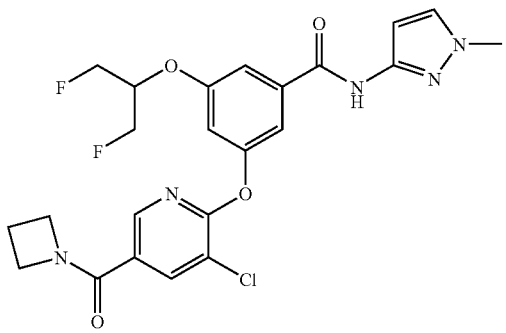

A mixture of 3-{[2-fluoro-1-(fluoromethyl)ethyl]oxy}-5-hydroxy-N-(1-methyl-1H-pyrazol-3-yl)benzamide (200 mg, 0.64 mmol), 5-(azetidin-1-ylcarbonyl)-2,3-dichloropyridine (164 mg, 0.71 mmol) and potassium carbonate (178 mg, 1.28 mmol) in acetonitrile (5 mL) was stirred in a 'Biotage initiator Microwave' at 120° C. for 4 hours. The solvent was removed in vacuo and the residue partitioned between ethyl acetate and water (100 mL), the organic layer washed with brine (50 mL), dried (MgSO₄), filtered and the solvent removed in vacuo to give a brown oil which was chromatographed on silica, eluting with a gradient of 50-100% ethyl acetate in isohexane, to give the desired compound (237 mg).

¹H NMR δ (CDCl₃): 2.39 (quintet, 2H), 3.74 (s, 3H), 4.25 (t, 2H), 4.37 (t, 2H), 4.63 (m, 2H), 4.74 (m, 3H), 6.81 (s, 1H), 7.01 (s, 1H), 7.29 (m, 1H), 7.31 (s, 1H), 7.42 (s, 1H), 8.17 (s, 1H), 8.23 (s, 1H), 9.26 (s, 1H). m/z 506 (M+H)⁺

The preparation of 5-(azetidin-1-ylcarbonyl)-2,3-dichloropyridine is described above.

The preparation of 3-{[2-fluoro-1-(fluoromethyl)ethyl]oxy}-5-hydroxy-N-(1-methyl-1H-pyrazol-3-yl)benzamide is described below:

3-{[2-Fluoro-1-(fluoromethyl)ethyl]oxy}-5-hydroxy-N-(1-methyl-1H-pyrazol-3-ylbenzamide

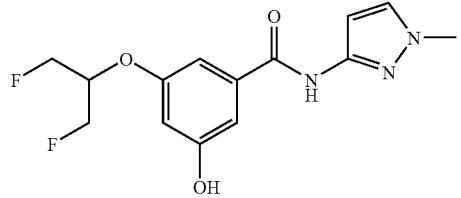

A solution of 3-{[2-fluoro-1-(fluoromethyl)ethyl]oxy}-N-(1-methyl-1H-pyrazol-3-yl)-5-[(phenylmethyl)oxy]benzamide (2.46 g, 6.13 mmol) and 10% by weight palladium on carbon (0.246 g) in ethanol (100 mL) was allowed to stir at RT, under a hydrogen atmosphere overnight. The solution was filtered through Celite® and the cake washed with methanol (100 mL). The solution was evaporated to give the desired compound (1.78 g). ¹H NMR δ (d₆-DMSO): 3.78 (s, 3H), 4.72 (m, 4H), 4.97 (m, 1H), 6.57 (d, 2H), 7.03 (s, 1H), 7.16 (s, 1H), 7.59 (s, 1H). m/z 312 (M+H)⁺

3-{[2-Fluoro-1-(fluoromethyl)ethyl]oxy}-N-(1-methyl-1H-pyrazol-3-yl)-5-[(phenylmethyl)oxy]benzamide

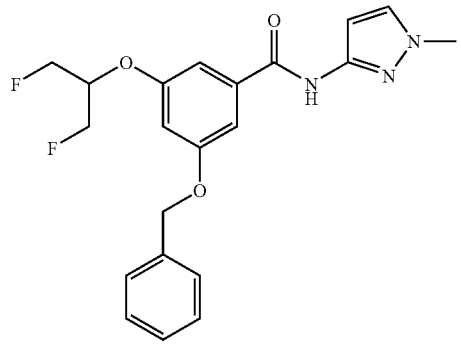

A solution 3-{[2-fluoro-1-(fluoromethyl)ethyl]oxy}-5-[(phenylmethyl)oxy]benzoic acid (3.00 g, 9.31 mmol), 3-amino-1-methylpyrazole (1.83 g, 18.6 mmol), HATU (4.60 g, 12.1 mmol) and DIPEA (3.25 mL, 18.6 mmol) in DMF (12 mL) was stirred at RT overnight. Water (150 mL) was added and the solution partitioned with ethyl acetate (250 mL). The ethyl acetate layer was separated, washed with brine and dried (MgSO₄), and evaporated to a residue which was chromatographed on silica, eluting with 50% ethyl acetate in isohexane, to give the desired product (2.46 g).

¹H NMR δ (CDCl₃): 3.69 (s, 3H), 4.57 (m, 5H), 5.00 (s, 2H), 6.70 (t, 1H), 6.74 (d, 1H), 7.01 (t, 1H), 7.08 (t, 1H), 7.21 (d, 1H), 7.30 (m, 5H), 8.68 (s, 1H); m/z 402 (M+H)⁺

3-{[2-Fluoro-1-(fluoromethyl)ethyl]oxy}-5-[(phenylmethyl)oxy]benzoic acid

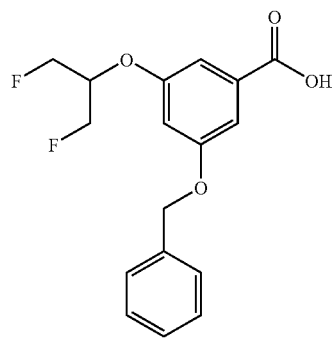

A solution of lithium hydroxide monohydrate (2.32 g, 55.1 mmol) in water (100 mL) was added to a solution of methyl 3-{[2-fluoro-1-(fluoromethyl)ethyl]oxy}-5-[(phenylmethyl)oxy]benzoate (7.41 g, 22.0 mmol) in THF (200 mL) and the mixture allowed to stir at RT overnight. The THF was removed in vacuo and the resulting solution partitioned between water (100 mL) and ethyl acetate (250 mL). The ethyl acetate layer was separated, washed with brine and dried (MgSO₄). The aqueous layer was then adjusted to pH 7 by addition of 1M hydrochloric acid and extracted with ethyl acetate (75 mL). The ethyl acetate layer was separated, washed with brine and dried (MgSO₄). The ethyl acetate layers were combined and evaporated to give the required product (6.404 g).

¹H NMR δ (d₆-DMSO): 4.74 (m, 4H), 5.08 (s, 2H), 6.67 (s, 1H), 6.67 (s, 1H), 7.23 (s, 1H), 7.37 (m, 5H). m/z 231 (M−H)⁻

Methyl 3-{[2-fluoro-1-(fluoromethyl)ethyl]oxy}-5-[(phenylmethyl)oxy]benzoate

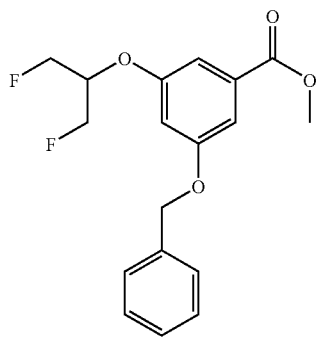

DIAD (7.63 mL, 38.7 mmol) was added in a dropwise fashion to a solution of methyl 3-hydroxy-5-{[phenylmethyl]oxy}benzoate (5.00 g, 19.4 mmol), 1,3-difluoropropan-2-ol (3 mL, 38.7 mmol), and triphenylphosphine (10.16 g, 38.7 mmol) in THF (100 mL) under an inert atmosphere at 0° C. The solution was allowed to reach RT and left to stir for 2 days. The THF was removed in vacuo and the residual oil slurried with a mixture of 20% ethyl acetate in isohexane. After allowing to stir for 90 minutes the mixture was filtered and the filtrate evaporated. The residual was oil chromatographed on silica, eluting with 30% ethyl acetate in isohexane, to give the desired compound (7.41 g).

$^1$H NMR δ (d$_6$-DMSO): 3.85 (s, 3H), 4.71 (m, 4H), 5.03 (m, 1H), 5.17 (s, 2H), 7.01 (t, 1H), 7.20 (m, 2H), 7.40 (m, 5H). m/z 335 (M–H)$^-$

The preparation of methyl 3-hydroxy-5-{[phenylmethyl]oxy}benzoate is described above.

EXAMPLE 10

3-{[5-(Azetidin-1-ylcarbonyl)-3-chloropyridin-2-yl]oxy}-5-{[(1S)-1-methylpropyl]oxy}-N-(1-methyl-1H-pyrazol-3-yl)benzamide

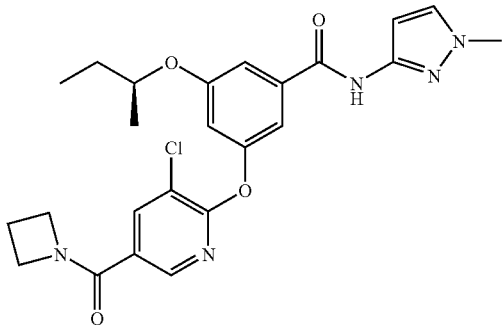

A solution of 3-hydroxy-5-{[(1S)-1-methylpropyl]oxy}-N-(1-methyl-1H-pyrazol-3-yl)benzamide (116 mg, 0.4 mmol) and the 5-(azetidin-1-ylcarbonyl)-2,3-dichloropyridine (111 mg, 0.48 mmol) in acetonitrile (2 mL) containing potassium carbonate (111 mg, 0.8 mmol) was heated with stirring in the microwave reactor for 6 hours at 160° C. The reaction mixture was filtered and the filtrate evaporated to dryness under reduced pressure and purified by chromatography on silica, eluting with 50-100% ethyl acetate in hexane, to give the required product (177 mg).

$^1$H NMR δ (CDCl$_3$): 0.91 (t, 3H), 1.25 (d, 3H), 1.52-1.75 (m, 2H), 2.32 (quin, 2H), 3.72 (s, 3H), 4.17 (t, 2H), 4.25-4.34 (m, 3H), 6.73 (d, 1H), 6.81 (t, 1H), 7.12 (s, 1H), 7.21 (d, 1H), 7.24 (s, 1H), 8.09 (d, 1H), 8.18 (d, 1H), 8.54 (s, 1H); m/z 484 (M+H)$^+$ The preparation of 5-(azetidin-1-ylcarbonyl)-2,3-dichloropyridine was described earlier.

The preparation of 3-hydroxy-5-{[(1S)-1-methylpropyl]oxy}-N-(1-methyl-1H-pyrazol-3-yl)benzamide is described below:

3-Hydroxy-5-{[(1S)-1-methylpropyl]oxy}-N-(1-methyl-1H-pyrazol-3-yl benzamide

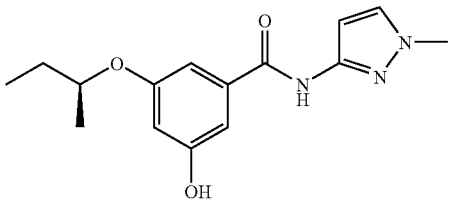

A solution of 3-{[(1S)-1-methylpropyl]oxy}-N-(1-methyl-1H-pyrazol-3-yl)-5-[(phenylmethyl)oxy]benzamide (900 mg) in THF (5 mL) and ethanol (5 mL) containing 10% palladium on carbon was stirred under an atmosphere of hydrogen overnight. The palladium on carbon was removed by filtration and the filtrate evaporated under reduced pressure to give the required compound as a white solid (683 mg).

$^1$H NMR δ (CDCl$_3$): 0.95 (t, 3H), 1.27 (d, 3H), 1.54-1.80 (m, 2H), 3.79 (s, 3H), 4.31 (q, 1H), 6.57 (t, 1H), 6.81 (d, 1H), 6.96 (s, 1H), 6.98 (s, 1H), 7.30 (s, 1H), 7.57 (s, 1H), 8.84 (s, 1H); m/z 290 (M+H)$^+$

3-{[(1S)-1-Methylpropyl]oxy}-N-(1-methyl-1H-pyrazol-3-yl)-5-[(phenylmethyl)oxy]benzamide

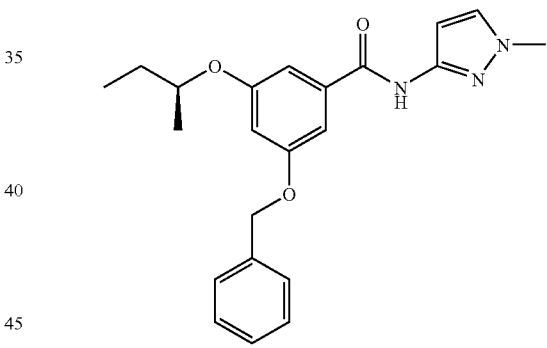

HATU (1.19 g, 3.13 mmol) was added to 3-{[(1S)-1-methylpropyl]oxy}-5-[(phenylmethyl)oxy]benzoic acid (750 mg, 2.5 mmol) and 3-amino-1 methylpyrazole (291 mg, 3 mmol) in DMF (5 mL) followed by addition of DIPEA (0.807 mL, 6.25 mmol) and the reaction was stirred for 16 hours. The reaction mixture was added to ethyl acetate (30 mL), washed with water (10 mL), 2N citric acid (10 mL), saturated aqueous sodium hydrogencarbonate (10 mL) and brine (10 mL), then dried (MgSO$_4$), filtered and evaporated to a gummy residue. The residue was taken up in 50% ether in ethylacetate (50 mL), washed with 2N hydrochloric acid (10 mL), water (10 mL), saturated aqueous sodium hydrogencarbonate (10 mL) and brine (10 mL) then dried (MgSO$_4$), filtered and evaporated to a foam (900 mg) which was used without further purification in the next step. $^1$H NMR δ (CDCl$_3$): 0.96 (t, 3H), 1.28 (d, 3H), 1.51-1.80 (m, 2H), 3.78 (s, 1H), 4.31 (q, 1H), 5.06 (s, 2H), 6.68 (t, 1H), 6.82 (d, 1H), 7.00 (s, 1H), 7.06 (s, 1H), 7.29 (s, 3H), 7.31-7.47 (m, 5H), 8.63 (s, 1H); m/z 380 (M+H)$^+$

3-{[(1S)-1-Methylpropyl]oxy}-5-[(phenylmethyl)oxy]benzoic acid

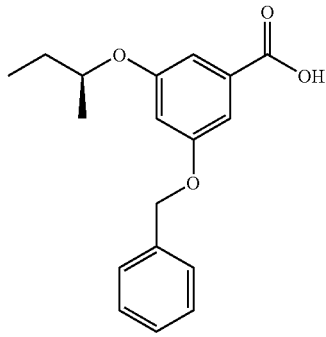

Methyl 3-{[(1S)-1-methylpropyl]oxy}-5-[(phenylmethyl)oxy]benzoate (14.87 g, 47.36 mmol) was vigorously stirred in a mixture of aqueous 1M sodium hydroxide (120 mL) and THF at approximately 45° C. for 4 hours. The bulk of the THF was removed under reduced pressure and the resultant solution partitioned between water and diethyl ether. The aqueous phase was acidified with 2M hydrochloric acid and then extracted with ethyl acetate. The organics were dried (MgSO$_4$) and concentrated in vacuo gave a white solid (11.5 g). $^1$H NMR δ (CDCl$_3$): 0.90 (t, 3H), 1.20 (d, 3H), 1.49-1.69 (m, 2H), 4.33-4.46 (m, 1H), 5.12 (s, 2H), 6.75-6.79 (m, 1H), 6.99-7.03 (m, 1H), 7.06-7.11 (m, 1H), 7.26-7.47 (m, 5H)

Methyl 3-{[(1S)-1-methylpropyl]oxy}-5-[(phenylmethyl)oxy]benzoate

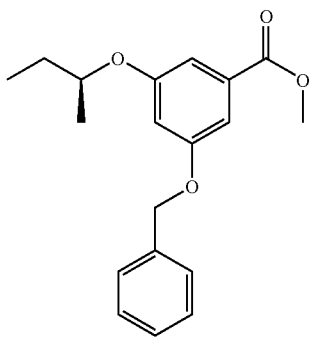

A solution of DIAD (16.6 mL, 84.0 mmol) in dry THF (100 mL) was added dropwise to a cooled (ice bath) stirred mixture of methyl 3-hydroxy-5-{[phenylmethyl]oxy}benzoate (14.5 g, 56.2 mmol); R-(−)-sec-butanol (5 g, 67.0 mmol) and solid-supported triphenylphosphine (28 g, of 3 mmol per g loading, 84.0 mmol) in dry THF (400 mL) whilst maintaining the temperature below 10° C. The mixture was allowed to stir for 3 hours, then diluted with diethyl ether (800 mL) and filtered. Removal of the solvent gave a pale coloured oil, which was purified by column chromatography on silica, eluting with 25% ethyl acetate in hexane; to give the desired product (14.87 g).
$^1$H NMR δ (CDCl$_3$): 0.99 (t, 3H), 1.28 (d, 3H), 1.53-1.80 (m, 2H), 3.89 (s, 3H), 4.25-4.42 (m, 1H), 5.07 (s, 2H), 6.68-6.81 (m, 1H), 7.17-7.53 (m, 7H); m/z 313 (M−H)$^−$ The preparation of methyl 3-hydroxy-5-{[phenylmethyl]oxy}benzoate was described earlier.

EXAMPLE 11

3-{[5-(Azetidin-1-ylcarbonyl)pyrazin-2-yl]oxy}-5-{[(1S)-1-methylpropyl]oxy}-N-(1-methyl-1H-pyrazol-3-yl)benzamide

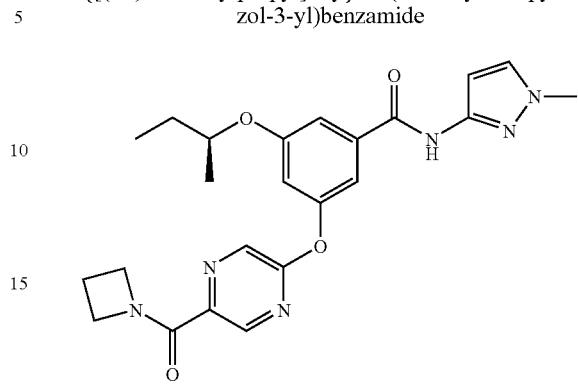

HATU (34 mg, 0.89 mmol) was added to 5-[(3-{[(1S)-1-methylpropyl]oxy}-5-{[(1-methyl-1H-pyrazol-3-yl)amino]carbonyl}phenyl)oxy]pyrazine-2-carboxylic acid (190 mg, 0.4 mmol) and azetidine hydrochloride (84 mg, 0.89 mmol) in DMF (5 mL). DIPEA (0.311 mL, 1.79 mmol) was added and the reaction was stirred for 16 hours. The reaction mixture was added to ethyl acetate (20 mL), washed with water (10 mL), 2N citric acid (10 mL), saturated aqueous sodium hydrogencarbonate (10 mL) and brine (10 mL), then dried (MgSO$_4$), filtered and evaporated under reduced pressure to a gummy residue. The residue was purified by chromatography on silica, eluting with 50-100% ethyl acetate in hexane, to give a gum which was taken up in 50% ethyl acetate in ether and washed twice with water, brine (10 mL) then dried (MgSO$_4$) to give the desired product as a foam (58 mg).
$^1$H NMR δ (CDCl$_3$): 0.91 (t, 3H), 1.25 (d, 3H), 1.51-1.75 (m, 2H), 2.31 (quin, 2H), 3.72 (s, 3H), 4.19 (t, 2H), 4.29 (q, 1H), 4.62 (t, 2H), 6.73 (d, 1H), 6.80 (t, 1H), 7.13 (t, 1H), 7.21 (d, 1H), 7.23 (t, 1H), 8.26 (s, 1H), 8.52 (s, 1H), 8.79 (s, 1H); m/z 451 (M+H)$^+$ The preparation of 5-[(3-{[(1S)-1-methylpropyl]oxy}-5-{[(1-methyl-1H-pyrazol-3-yl)amino]carbonyl}phenyl)oxy]pyrazine-2-carboxylic acid is described below:

5-[(3-{[(1S)-1-Methylpropyl]oxy}-5-{[(1-methyl-1H-pyrazol-3-yl)amino]carbonyl}phenyl)oxy]pyrazine-2-carboxylic acid

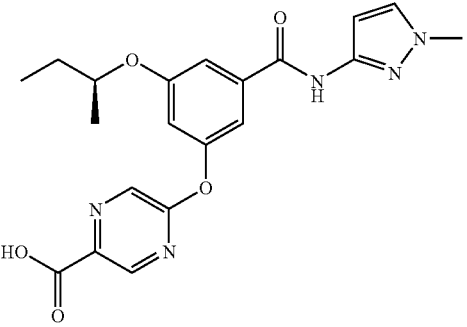

A solution of 3-hydroxy-5-{[(S)-1-methylpropyl]oxy}-N-(1-methyl-1H-pyrazol-3-yl)benzamide (116 mg, 0.4 mmol) and the methyl 5-chloropyrazine-2-carboxylate (83 mg, 0.48 mmol) in acetonitrile (2 mL) containing potassium carbonate (111 mg, 0.8 mmol) was heated with stirring in the microwave for 6 hours at 160° C. Analytical LC-MS showed formation of the acid but no ester. The reaction mixture was dissolved in water (10 mL), acidified with 2N citric acid and extracted with ethyl acetate (5×20 mL), washed with brine, dried (MgSO$_4$) and evaporated to dryness under reduced pressure to deliver the desired product (190 mg) which was used without purification in the next step. m/z 412 (M+H)$^+$ The preparation of 3-hydroxy-5-{[(S)-1-methylpropyl]oxy}-N-(1-methyl-1H-pyrazol-3-yl)benzamide was described earlier.

EXAMPLE 12

3-{[6-(azetidin-1-ylcarbonyl)pyridin-3-yl]oxy}-5-{[(1S)-1-methylpropyl]oxy}-N-(1-methyl-1H-pyrazol-3-yl)benzamide

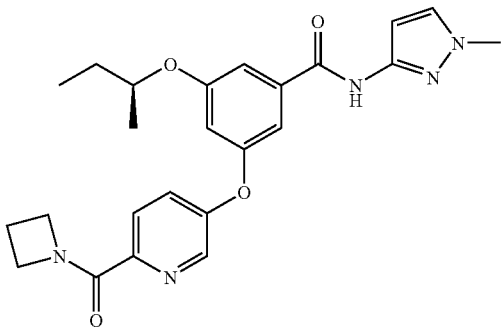

A mixture of 3-hydroxy-5-{[(1S)-1-methylpropyl]oxy}-N-(1-methyl-1H-pyrazol-3-yl)benzamide (0.116 g, 0.4 mmol), 2-(azetidin-1-ylcarbonyl)-5-bromopyridine (116 mg, 0.48 mmol), cesium carbonate (392 mg, 1.2 mmol) and bromotris(triphenylphosphine)copper(I) (38 mg, 0.04 mmol) in DMA (5 mL) was stirred in the microwave reactor at 160° C. for 4 hours. The product was dissolved in ethyl acetate (20 mL) and water (15 mL) and the layers separated. The organic layer was washed with brine (50 mL), dried (MgSO$_4$), filtered and the solvent removed in vacuo to give a brown oil which was chromatographed on silica, eluting with a gradient of 0-5% methanol in ethyl acetate, and then re-columned on silica, eluting with a gradient of 0-5% methanol in DCM, to give the desired compound as a white foam which crystallised on standing. The material was triturated with 50% ethyl acetate in hexane to give the required product as a white solid (95 mg). $^1$H NMR δ (CDCl$_3$): 0.90 (t, 3H), 1.23 (d, 3H), 1.51-1.72 (m, 2H), 2.28 (quin, 2H), 3.73 (s, 3H), 4.18 (t, 2H), 4.28 (q, 1H), 4.64 (t, 2H), 6.67 (t, 1H), 6.72 (d, 1H), 6.99 (s, 1H), 7.15 (s, 1H), 7.22 (d, 1H), 7.31 (d, 1H), 8.04 (d, 1H), 8.26 (s, 1H), 8.41 (s, 1H); m/z 450 (M+H)$^+$ The preparation of 3-hydroxy-5-{[(is)-1-methylpropyl]oxy}-N-(1-methyl-1H-pyrazol-3-yl)benzamide and 2-(azetidin-1-ylcarbonyl)-5-bromopyridine were described earlier.

EXAMPLE 13

3-{[2-(Azetidin-1-ylcarbonyl)pyrimidin-5-yl]oxy}-5-[(1-methylethyl)oxy]-N-(1-methyl-1H-pyrazol-3-yl)benzamide

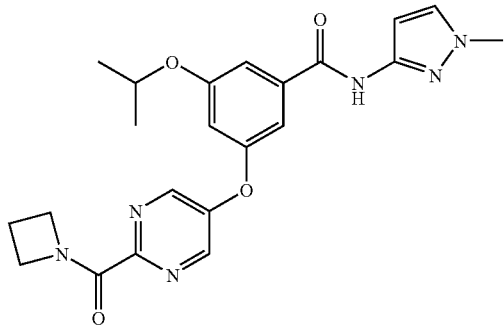

A mixture of 3-hydroxy-5-[(1-methylethyl)oxy]-N-(1-methyl-1H-pyrazol-3-yl)benzamide (250 mg, 0.91 mmol), 2-(azetidin-1-ylcarbonyl)-5-bromopyrimidine (242 mg, 1.0 mmol), cesium carbonate (886 mg, 2.72 mmol) and bromotris(triphenylphosphine)copper(I) (423 mg, 0.45 mmol) in DMA (5 mL) was stirred in a 'Biotage initiator Microwave' at 160° C. for 4 hours. The mixture was added to ethyl acetate (50 mL) and water (50 mL), the organic layer washed with brine (50 mL), dried (MgSO$_4$), filtered and the solvent removed in vacuo to give a brown oil. The residue was chromatographed on silica, eluting with a gradient of 0-10% methanol in ethyl acetate, to give the desired compound (199 mg).

$^1$H NMR δ (CDCl$_3$): 1.39 (d, 6H), 2.40 (quin, 2H), 3.82 (s, 3H), 4.35 (t, 2H), 4.62 (mult, 1H), 4.68 (t, 2H), 6.79 (s, 1H), 6.84 (s, 1H), 7.20 (s, 1H), 7.33 (mult, 2H), 8.60 (s, 2H), 8.97 (s, 1H); m/z 437 (M+H)$^+$ The following compound was synthesised in an analogous fashion from 3-hydroxy-5-[(1S)-2-methoxy-(1-methylethyl)oxy]-N-(1-methyl-1H-pyrazol-3-yl)benzamide.

| Example | Structure | m/z | NMR |
|---|---|---|---|
| 13a | 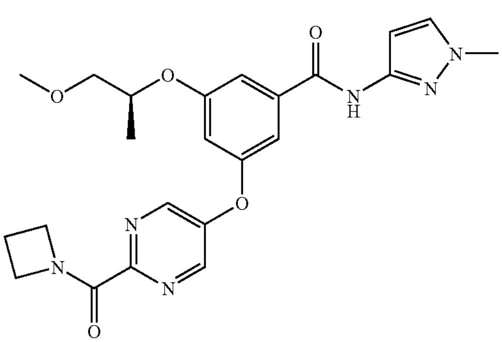 | 467 (M + H)$^+$ | $^1$H NMR δ (CDCl$_3$): 1.33 (d, 3H), 2.37 (quin, 2H), 3.41 (s, 3H), 3.48-3.60 (m, 2H), 3.78 (s, 3H), 4.30 (t, 2H), 4.58 (mult, 1H), 4.64 (t, 2H), 6.80 (d, 1H), 6.83 (t, 1H), 7.19 (s, 1H), 7.30 (d, 1H), 7.33 (s, 1H), 8.55 (s, 2H), 8.93 (s, 1H) |

The preparation of 3-hydroxy-5-[(1-methylethyl)oxy]-N-(1-methyl-1H-pyrazol-3-yl)benzamide and 3-hydroxy-5-[(1S)-2-methoxy-(1-methylethyl)oxy]-N-(1-methyl-1H-pyrazol-3-yl)benzamide were described earlier.

The preparation of 2-(azetidin-1-ylcarbonyl)-5-bromopyridine is described below:

2-(Azetidin-1-ylcarbonyl)-5-bromopyrimidine

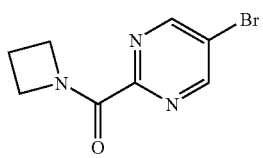

Oxalyl chloride (1.50 mL, 16.8 mmol) then DMF (2 drops) were added to a mixture of 5-bromopyrimidine-2-carboxylic acid (prepared according to literature procedure described in WO 2005/028452) (2.86 g, 14.0 mmol) in DCM (40 mL). The reaction mixture was stirred at RT for 2 hours, the volatiles removed in vacuo and the residue dissolved in DCM (40 mL). Azetidine hydrochloride (1.44 g, 15.4 mmol) followed by triethylamine (4.29 mL, 30.8 mmol) were added and the mixture stirred at RT for 72 hours. The mixture was concentrated in vacuo and ethyl acetate (100 mL) added to the residue. The organics were washed with water (100 mL), citric acid solution (50 mL), saturated sodium bicarbonate solution (50 mL), brine (50 mL), dried (MgSO$_4$), filtered and the solvent removed in vacuo to give a yellow solid which was chromatographed on silica, eluting with a gradient of 50-100% ethyl acetate in isohexane, to give the desired compound (0.86 g). $^1$H NMR δ (CDCl$_3$): 2.39 (quin, 2H), 4.32 (t, 2H), 4.63 (t, 2H), 8.92 (s, 2H); m/z 242, 244 (M+H)$^+$

EXAMPLE 14

3-{[6-(Azetidin-1-ylcarbonyl)pyridin-3-yl]oxy}-5-{[2-fluoro-1-(fluoromethyl)ethyl]oxy}-N-(1-methyl-1H-pyrazol-3-yl)benzamide

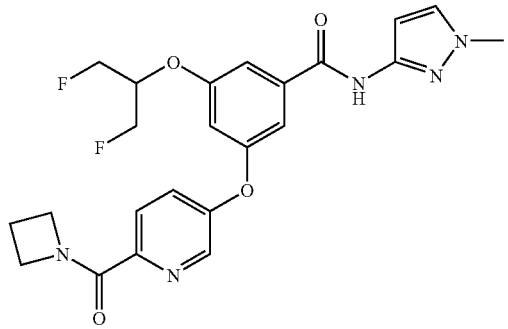

A mixture 3-{[2-fluoro-1-(fluoromethyl)ethyl]oxy}-5-hydroxy-N-(1-methyl-1H-pyrazol-3-yl)benzamide (100 mg, 0.32 mmol), 2-(azetidin-1-ylcarbonyl)-5-bromopyridine (86 mg, 0.35 mmol), cesium carbonate (209 mg, 0.64 mmol) and bromotris(triphenylphosphine)copper(I) (150 mg, 0.16 mmol) in DMA (5 mL) was stirred in a 'Biotage initiator Microwave' at 160° C. for 3 hours. The reaction mixture was added to ethyl acetate (50 mL) and water (50 mL), the organic layer washed with brine (50 mL), dried (MgSO$_4$), filtered and the solvent removed in vacuo to give a brown oil. The residue was chromatographed on silica, eluting with 0-100% ethyl acetate in isohexane, to give a colorless oil which appeared to be a mixture of product and eliminated product (3-{[6-(azetidin-1-ylcarbonyl)pyridin-3-yl]oxy}-5-{[1-(fluoromethyl)ethenyl]oxy}-N-(1-methyl-1H-pyrazol-3-yl)benzamide).

This mixture was dissolved in chloroform (5 mL), TFA (0.5 mL) added and the mixture stirred for 2 hours. Complete degradation of eliminated product was observed by LCMS and the mixture concentrated in vacuo then water added. The mixture was neutralised and extracted into ethyl acetate (2×30 mL), washed with brine (30 mL), dried (MgSO$_4$), filtered and reduced to give a yellow oil which was chromatographed on silica, eluting with 0-100% ethyl acetate in isohexane, to give the desired compound (13 mg).
$^1$H NMR δ (CDCl$_3$): 2.29 (quin, 2H), 3.76 (s, 3H), 4.19 (t, 2H), 4.55 (mult, 2H), 4.67 (mult, 5H), 6.72 (s, 1H), 6.80 (mult, 1H), 7.09 (s, 1H), 7.25 (mult, 2H), 7.32 (mult, 1H), 8.06 (d, 1H), 8.26 (d, 1H), 8.43 (s, 1H); m/z 472 (M+H)$^+$ The preparation of 3-{[2-fluoro-1-(fluoromethyl)ethyl]oxy}-5-hydroxy-N-(1-methyl-1H-pyrazol-3-yl)benzamide and 2-(azetidin-1-ylcarbonyl)-5-bromopyridine were described earlier.

EXAMPLE 15

3-{[5-(azetidin-1-ylcarbonyl)pyrazin-2-yl]oxy}-5-{[2-fluoro-1-(fluoromethyl)ethyl]oxy}-N-(1-methyl-1H-pyrazol-3-yl)benzamide

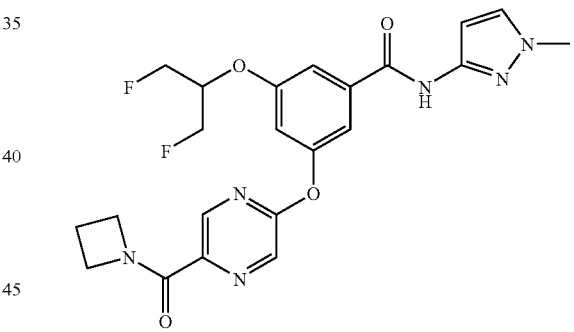

DIPEA (0.45 mL, 2.58 mmol) was added to a mixture of 5-[(3-{[2-fluoro-1-(fluoromethyl)ethyl]oxy}-5-{[(1-methyl-1H-pyrazol-3-yl)amino]carbonyl}phenyl)oxy]pyrazine-2-carboxylic acid (0.28 g, 0.65 mmol), azetidine hydrochloride (121 mg, 1.29 mmol) and HATU (516 mg, 1.36 mmol) in DMF (5 mL) and stirred at RT for 72 hours. Ethyl acetate (40 mL) was added and the organics washed with water (2×30 mL), brine (30 mL), dried (MgSO$_4$), filtered and reduced in vacuo to give a yellow oil which was chromatographed on silica, eluting with 0-100% ethyl acetate in isohexane, to give the desired compound (109 mg). $^1$H NMR δ (CDCl$_3$): 2.32 (quin, 2H), 3.70 (s, 3H), 4.19 (t, 2H), 4.54-4.72 (m, 7H), 6.73 (s, 1H), 6.93 (t, 1H), 7.22 (d, 1H), 7.25 (s, 1H), 7.34 (s, 1H), 8.28 (d, 1H), 8.78 (d, 1H), 8.80 (s, 1H); m/z 473 (M+H)$^+$ The following compound was synthesised in an analogous fashion from 5-[(3-[(1-methylethyl)oxy]-5-{[(1-methyl-1H-pyrazol-3-yl)amino]carbonyl}phenyl)oxy]pyrazine-2-carboxylic acid.

| Example | Structure | m/z | NMR |
|---|---|---|---|
| 15a | 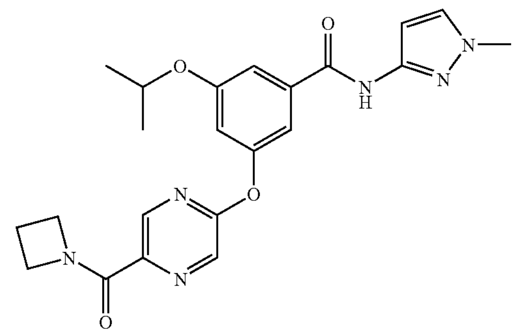 | 437 (M + H)⁺ | ¹H NMR δ (CDCl₃): 1.38 (d, 6H), 2.40 (quin, 2H), 3.83 (s, 3H), 4.28 (t, 2H), 4.62 (sept, 1H), 4.71 (t, 2H), 6.82 (s, 1H), 6.89 (t, 1H), 7.23 (s, 1H), 7.31 (m, 2H), 8.35 (s, 1H), 8.55 (s, 1H), 8.88 (s, 1H) |

The preparation of 5-[(3-{[2-fluoro-1-(fluoromethyl)ethyl]oxy}-5-{[(1-methyl-1H-pyrazol-3-yl)amino]carbonyl}phenyl)oxy]pyrazine-2-carboxylic acid is described below:

5-[(3-{[2-Fluoro-1-(fluoromethyl)ethyl]oxy}-5-{[(1-methyl-1H-pyrazol-3-yl)amino]carbonyl}phenyl)oxy]pyrazine-2-carboxylic acid

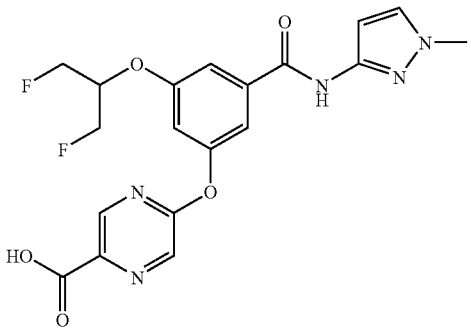

Lithium hydroxide monohydrate (77 mg, 1.82 mmol) in water (2 mL) was added to methyl 5-[(3-{[2-fluoro-1-(fluoromethyl)ethyl]oxy}-5-{[(1-methyl-1H-pyrazol-3-yl)amino]carbonyl}phenyl)oxy]pyrazine-2-carboxylate (325 mg, 0.73 mmol) in THF (4 mL) and the mixture stirred at RT for 20 hours. The THF was removed in vacuo and the aqueous residue washed with ethyl acetate to remove impurities then acidified with 1M citric acid. Ethyl acetate was added and a white solid removed by filtration and dried in vacuo to give the desired compound as a white solid (0.28 g). ¹H NMR δ (d₆-DMSO): 3.79 (s, 3H), 4.77 (m, 4H), 5.12 (t, 1H), 6.59 (s, 1H), 7.22 (s, 1H), 7.50 (s, 1H), 7.62 (s, 2H), 8.69 (s, 1H), 8.80 (s, 1H), 10.90 (s, 1H), 13.50 (s, 1H), m/z 434 (M+H)⁺

5-[(3-[(1-Methylethyl)oxy]-5-{[(1-methyl-1H-pyrazol-3-yl)amino]carbonyl}phenyl)oxy]pyrazine-2-carboxylic acid, used in the preparation of Example 15a, was prepared in an analogous fashion from methyl 5-[(3-[(1-methylethyl)oxy]-5-{[(1-methyl-1H-pyrazol-3-yl)amino]carbonyl}phenyl)oxy]pyrazine-2-carboxylate.

| Structure | m/z | NMR |
|---|---|---|
| | 398 (M + H)⁺ | |

The preparation of methyl 5-[(3-{[2-fluoro-1-(fluoromethyl)ethyl]oxy}-5-{[(1-methyl-1H-pyrazol-3-yl)amino]carbonyl}phenyl)oxy]pyrazine-2-carboxylate is described below:

Methyl 5-[(3-{[2-fluoro-1-(fluoromethyl)ethyl]oxy}-5-{[(1-methyl-1H-pyrazol-3-yl)amino]carbonyl}phenyl)oxy]pyrazine-2-carboxylate

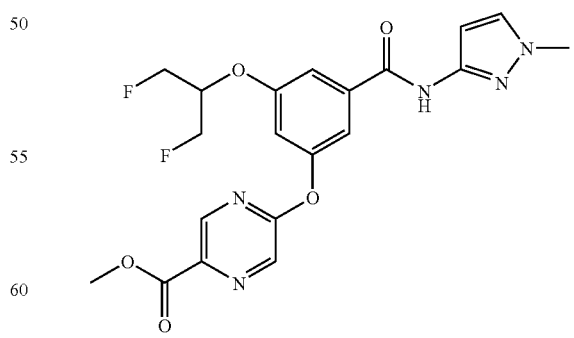

A mixture of 3-{[2-fluoro-1-(fluoromethyl)ethyl]oxy}-5-hydroxy-N-(1-methyl-1H-pyrazol-3-yl)benzamide (250 mg, 0.8 mmol), methyl 5-chloropyrazine-2-carboxylate (208 mg, 1.20 mmol) and potassium carbonate (222 mg, 1.61 mmol) in acetonitrile (5 mL) was stirred in a 'Biotage initiator Microwave' at 120° C. for 3 hours. The solvent was removed in vacuo and the residue dissolved in ethyl acetate (50 mL) and water (50 mL), the organic layer washed with brine (50 mL), dried (MgSO$_4$), filtered and the solvent removed in vacuo to give a yellow oil which was chromatographed on silica, eluting with 0-100% ethyl acetate in isohexane, to give the desired compound (0.325 g). $^1$H NMR δ (CDCl$_3$): 3.71 (s, 3H), 3.96 (s, 3H), 4.56 (m, 2H), 4.68 (m, 3H), 6.73 (s, 1H), 6.95 (s, 1H), 7.22 (s, 1H), 7.27 (s, 1H), 7.36 (s, 1H), 8.46 (s, 1H), 8.67 (s, 1H), 8.67 (s, 1H); m/z 448 (M+H)$^+$ Methyl 5-[(3-[(1-methylethyl)oxy]-5-{[(1-methyl-1H-pyrazol-3-yl)amino]carbonyl}phenyl)oxy]pyrazine-2-carboxylate, used in Example 15a, was prepared in an analogous fashion from 3-hydroxy-5-[(1-methylethyl)oxy]-N-(1-methyl-1H-pyrazol-3-yl)benzamide.

| Structure | m/z | NMR |
|---|---|---|
| 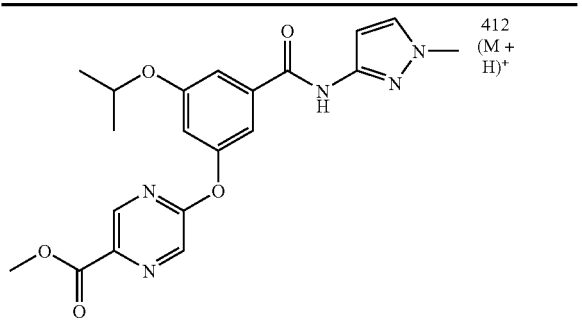 | 412 (M + H)$^+$ | |

The preparation of 3-{[2-fluoro-1-(fluoromethyl)ethyl]oxy}-5-hydroxy-N-(1-methyl-1H-pyrazol-3-yl)benzamide and 3-hydroxy-5-[(1-methylethyl)oxy]-N-(1-methyl-1H-pyrazol-3-yl)benzamide were described previously.

EXAMPLE 16

3-{[5-(Azetidin-1-ylcarbonyl)-3-chloropyridin-2-yl]oxy}-5-({(1S)-2-[(difluoromethyl)oxy]-1-methylethyl}oxy)-N-(1-methyl-1H-pyrazol-3-yl)benzamide

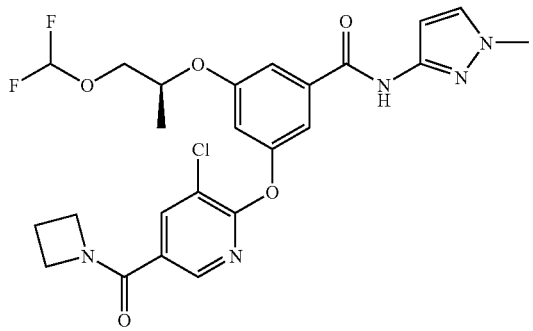

A mixture of 3-({(1S)-2-[(difluoromethyl)oxy]-1-methylethyl}oxy)-5-hydroxy-N-(1-methyl-1H-pyrazol-3-yl)benzamide (110 mg, 0.32 mmol), 5-(azetidin-1-ylcarbonyl)-2,3-dichloropyridine (75 mg, 0.32 mmol) and potassium carbonate (89 mg, 0.64 mmol) in acetonitrile (5 mL) was stirred in a 'Biotage initiator Microwave' at 160° C. for 3 hours. The solvent was removed in vacuo and ethyl acetate (50 mL) added to the residue which was washed with water (20 mL), brine (50 mL), dried (MgSO$_4$), filtered and the solvent removed in vacuo to give a yellow oil. The residue was chromatographed on silica, eluting with a gradient of 50-100% ethyl acetate in isohexane, to give the desired compound (92 mg). $^1$H NMR δ (CDCl$_3$): 1.40 (d, 3H), 2.41 (quin, 2H), 3.81 (s, 3H), 4.01 (mult, 2H), 4.26 (t, 2H), 4.38 (t, 2H), 4.67 (sextet, 1H), 6.29 (t, 1H), 6.82 (d, 1H), 6.96 (t, 1H), 7.27 (t, 1H), 7.31 (d, 1H), 7.38 (t, 1H), 8.18 (d, 1H), 8.26 (d, 1H), 8.77 (s, 1H), m/z 536 (M+H)$^+$ The following compound was made in an analogous fashion from 3-({(1S)-2-[(difluoromethyl)oxy]-1-methylethyl}oxy)-5-hydroxy-N-(1-methyl-1H-pyrazol-3-yl)benzamide and 5-(azetidin-1-ylcarbonyl)-2-chloropyridine.

| Example | Structure | m/z | NMR |
|---|---|---|---|
| 16a | 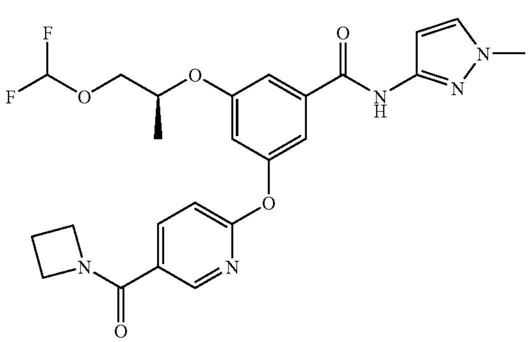 | 502 (M + H)$^+$ | $^1$H NMR δ (CDCl$_3$): 1.37 (d, 3H), 2.38 (quin, 2H), 3.73 (s, 3H), 3.98 (m, 2H), 4.25 (t, 2H), 4.36 (t, 2H), 4.62 (sextet, 1H), 6.27 (t, 1H), 6.81 (d, 1H), 6.90 (t, 1H), 7.00 (d, 1H), 7.24 (t, 1H), 7.27 (m, 1H), 7.33 (m, 1H), 8.08 (m, 1H), 8.42 (d, 1H), 9.12 (s, 1H) |

The preparation of 5-(azetidin-1-ylcarbonyl)-2,3-dichloropyridine and 5-(azetidin-1-ylcarbonyl)-2-chloropyridine were described earlier.

The preparation of 3-({(1S)-2-[(difluoromethyl)oxy]-1-methylethyl}oxy)-5-hydroxy-N-(1-methyl-1H-pyrazol-3-yl)benzamide is described below:

3-({(1S)-2-[(Difluoromethyl)oxy]-1-methylethyl}oxy)-5-hydroxy-N-(1-methyl-1H-pyrazol-3-yl)benzamide

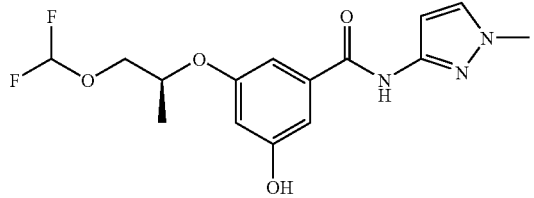

3-({(1S)-2-[(Difluoromethyl)oxy]-1-methylethyl}oxy)-N-(1-methyl-1H-pyrazol-3-yl)-5-[(phenylmethyl)oxy]benzamide (0.1 g, 0.23 mmol) was dissolved in ethanol (3 mL) and THF (3 mL) and the flask evacuated and purged with argon (3 times). 10% Palladium on carbon (0.01 g) was added and the flask further evacuated and finally purged with hydrogen gas. The reaction mixture was stirred at RT for 20 hours until completion. The reaction mixture was evacuated and purged with nitrogen (3 times). The catalyst was filtered off through celite and the filtrate concentrated in vacuo to give the desired compound (70 mg). $^1$H NMR δ (CDCl$_3$): 1.28 (d, 3H), 3.71 (s, 3H), 3.80-3.95 (m, 2H), 4.51 (sextet, 1H), 5.96-6.36 (t, 1H), 6.53 (s, 1H), 6.73 (s, 1H), 6.91 (s, 1H), 6.96 (s, 1H), 7.22 (s, 1H), 8.83 (s, 1H). m/z 342 (M+H)$^+$.

3-({(1S)-2-[(Difluoromethyl)oxy]-1-methylethyl}oxy)-N-(1-methyl-1H-pyrazol-3-yl)-5-[(phenylmethyl)oxy]benzamide

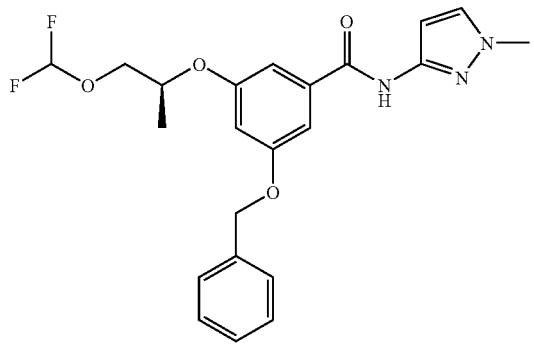

DIPEA (0.198 mL, 1.14 mmol) was added to a mixture of 3-({(1S)-2-[(difluoromethyl)oxy]-1-methylethyl}oxy)-5-[(phenylmethyl)oxy]benzoic acid (0.1 g, 0.28 mmol), 3-amino-1-methylpyrazole (39 mg, 0.4 mmol) and HATU (0.227 g, 0.6 mmol) in DMF (3 mL) and stirred at RT for 20 hours. Ethyl acetate (30 mL) was added and the mixture washed with water (30 mL), brine (30 mL), dried (MgSO$_4$), filtered and reduced in vacuo to give a yellow oil which was chromatographed on silica, eluting with a gradient of 0-100% ethyl acetate in isohexane, to give the desired compound (0.1 g).

$^1$H NMR δ (CDCl$_3$): 1.36 (d, 3H), 3.68 (s, 3H), 3.82-3.95 (m, 2H), 4.48 (sex, 1H), 5.00 (s, 2H), 6.19 (t, 1H), 6.63 (s, 1H), 6.73 (s, 1H), 6.93 (s, 1H), 7.03 (s, 1H), 7.28 (m, 1H), 7.35 (m, 5H), 8.59 (s, 1H). m/z 432 (M+H)$^+$.

3-({(1S)-2-[(Difluoromethyl)oxy]-1-methylethyl}oxy)-5-[(phenylmethyl)oxy]benzoic acid

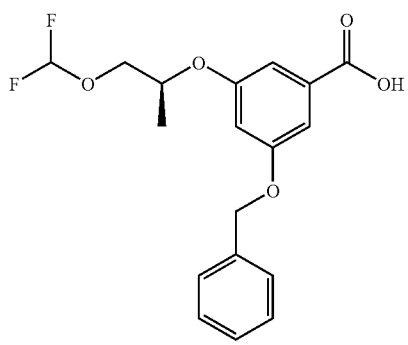

Lithium hydroxide monohydrate (19 mg, 0.45 mmol) in water (2 mL) was added to methyl 3-({(1S)-2-[(difluoromethyl)oxy]-1-methylethyl}oxy)-5-[(phenylmethyl)oxy]benzoate (0.11 g, 0.3 mmol) in THF (4 mL) and the mixture stirred at RT for 20 hours. The THF was removed in vacuo and the aqueous layer adjusted to pH3 with citric acid then extracted into ethyl acetate (2×30 mL). The organics were washed with water (30 mL), brine (30 mL), dried (MgSO$_4$), filtered and the solvent removed in vacuo to give the desired compound (0.1 g).

$^1$H NMR δ (d$_6$-DMSO): 1.27 (d, 3H), 4.00 (m, 2H), 4.75 (sextet, 1H), 5.15 (s, 2H), 6.72 (t, 1H), 7.08 (t, 1H), 7.16 (t, 1H), 7.41 (m, 5H), 12.95 (s, 1H). m/z 351 (M+H)$^+$.

Methyl 3-({(1S)-2-[(difluoromethyl)oxy]-1-methylethyl}oxy)-5-[(phenylmethyl)oxy]benzoate

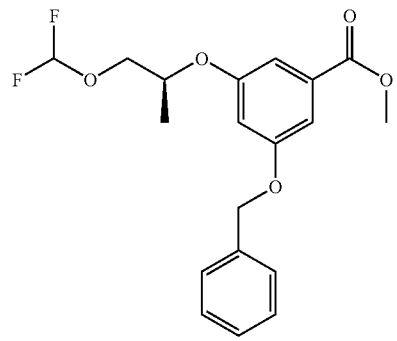

2-(Fluorosulphonyl)difluoroacetic acid (0.239 mL, 2.31 mmol) was added dropwise, with stirring, to a degassed mixture of methyl 3-{[(1S)-2-hydroxy-1-methylethyl]oxy}-5-[(phenylmethyl)oxy]benzoate (0.73 g, 2.31 mmol) and copper (I) iodide (88 mg, 0.46 mmol) in acetonitrile (10 mL) at 45° C. The reaction was stirred at 45° C. for 24 hours. The solvent was removed in vacuo and ethyl acetate (30 mL) added. The organics were washed with water (30 mL), brine (30 mL), dried (MgSO$_4$), filtered and the solvent removed in vacuo to give a yellow oil which was chromatographed on silica, eluting with a gradient of 0-30% ethyl acetate in isohexane, to give the desired compound (0.11 g).

¹H NMR δ (CDCl₃): 1.37 (d, 3H), 3.93 (s, 3H), 4.00 (m, 2H), 4.63 (sextet, 1H), 5.10 (s, 2H), 6.28 (t, 1H), 6.77 (t, 1H), 7.28 (t, 1H), 7.41 (m, 6H). m/z 367 (M+H)⁺.

Methyl 3-{[(1S)-2-hydroxy-1-methylethyl]oxy}-5-[(phenylethyl)oxy]benzoate

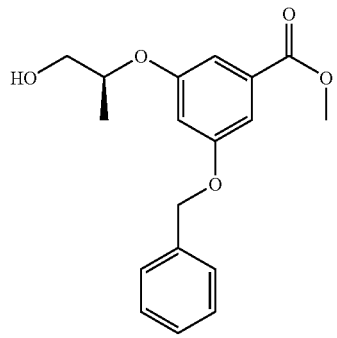

Benzyl bromide (1.89 g, 7.20 mmol) was added to a mixture of methyl 3-hydroxy-5-[(1S)-2-hydroxy-1-methylethoxy]benzoate (1.55 g, 6.86 mmol) and potassium carbonate (1.89 g, 0.014 mol) in DMF (16 mL) and the reaction stirred at RT for 20 hours. Ethyl acetate (40 mL) was added and the mixture washed with water (40 mL), saturated sodiumbicarbonate solution (40 mL), brine (40 mL), dried (MgSO₄), filtered and the solvent removed in vacuo to give a red oil which was chromatographed on silica, eluting with a gradient of 0-100% ethyl acetate in isohexane, to give the desired compound (1.7 g).

¹H NMR δ (CDCl₃): 1.30 (d, 3H), 1.95 (m, 1H), 3.76 (m, 2H), 3.92 (s, 3H), 4.53 (m, 1H), 5.11 (s, 2H), 6.78 (t, 1H), 7.25 (m, 1H), 7.32 (m, 1H), 7.45 (m, 5H). m/z 317 (M+H)⁺.

Methyl 3-hydroxy-5-[(1S)-2-hydroxy-1-methylethoxy]benzoate

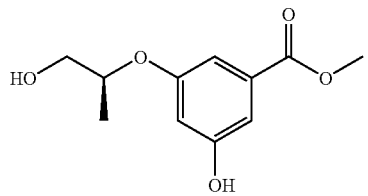

Trimethylsilyl iodide (115 mL, 0.79 mol) was added to a solution of methyl 3-hydroxy-5-[(1S)-2-methoxy-(1-methylethyl)oxy]benzoate (38.01 g, 0.158 mol) in acetonitrile (500 mL) and stirred for 24 hours. Methanol (300 mL) was added and the reaction stirred for 10 mins. 10% w/v Aqueous sodium thiosulfate pentahydrate (100 mL) was added to the mixture and stirred for 20 mins. The reaction mixture was neutralised with saturated aqueous sodium bicarbonate solution, the organic solvents removed in vacuo, and the product extracted into ethyl acetate (4×100 mL). The combined organic layers were dried (MgSO₄), filtered and the solvents removed in vacuo. The crude material was crystallised from ethyl acetate to give the title compound (16.80 g).

¹H NMR δ (d₆-DMSO): 1.18 (d, 3H), 3.40-3.55 (m, 2H), 3.80 (s, 3H), 4.35 (sex, 1H), 4.80 (t, 1H), 6.57 (m, 1H), 6.90 (m, 2H), 9.75 (s, 1H). m/z 304 (M+H)⁺

Methyl 3-Hydroxy-5-[(1S)-2-methoxy-(1-methylethyl)oxy]benzoate

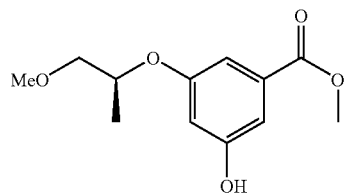

Methyl 3-[(1S)-2-methoxy-(1-methylethyl)oxy]-5-{[phenylmethyl]oxy}benzoate (50.0 g, 0.152 mmol) was dissolved in a mixture of THF:ethanol (600 mL) and the flask evacuated and purged with nitrogen (3 times). 10% Palladium on carbon (5.0 g) was added and the flask further evacuated and finally purged with hydrogen gas. The reaction mixture was stirred at ambient temperature for 20 hours until completion. The reaction mixture was evacuated and purged with nitrogen (3 times). The catalyst was filtered off, and the filtrate concentrated in vacuo to give the desired compound (36.7 g).

¹H NMR δ (d₆-DMSO): 1.2 (d, 3H), 3.25 (s, 3H), 3.44 (m, 2H), 3.82 (s, 3H), 4.55 (m, 1H), 6.6 (s, 1H), 6.9 (s, 1H), 6.95 (s, 1H), 9.8 (s, 1H).

The preparation of methyl 3-[(1S)-2-methoxy-(1-methylethyl)oxy]-5-{[phenylmethyl]oxy}benzoate was described previously.

EXAMPLE 17

3-{[6-(Azetidin-1-ylcarbonyl)pyridin-3-yl]oxy}-5-({(1S)-2-[(difluoromethyl)oxy]-1-methylethyl}oxy)-N-(1-methyl-1H-pyrazol-3-yl)benzamide

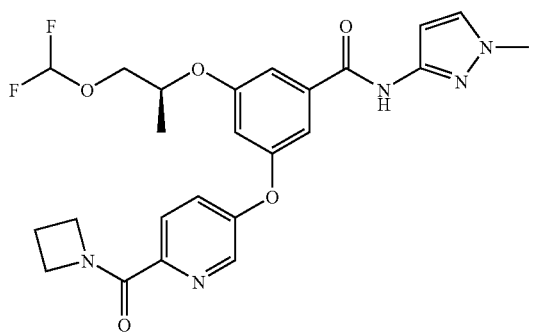

A mixture of 3-({(1S)-2-[(difluoromethyl)oxy]-1-methylethyl}oxy)-5-hydroxy-N-(1-methyl-1H-pyrazol-3-yl)benzamide (220 mg, 0.64 mmol), 2-(azetidin-1-ylcarbonyl)-5-bromopyridine (171 mg, 0.71 mmol), cesium carbonate (419 mg, 1.29 mmol) and bromotris(triphenylphosphine)copper(I) (300 mg, 0.32 mmol) in DMA (5 mL) was stirred in a 'Biotage initiator Microwave' at 160° C. for 4 hours. The reaction mixture was added to ethyl acetate (50 mL) and water (50 mL), the organic layer washed with brine (50 mL), dried (MgSO$_4$), filtered and the solvent removed in vacuo to give a brown oil. The residue was chromatographed on silica, eluting with 0-100% ethyl acetate in isohexane, to give the desired compound (102 mg).

$^1$H NMR δ (CDCl$_3$): 1.28 (d, 3H), 2.28 (quin, 2H), 3.68 (s, 3H), 3.90 (mult, 2H), 4.17 (t, 2H), 4.54 (sextet, 1H), 4.63 (t, 2H), 6.19 (t, 1H), 6.71 (t, 1H), 6.73 (s, 1H), 7.06 (s, 1H), 7.22 (mult, 2H), 7.30 (mult, 1H), 8.04 (d, 1H), 8.24 (d, 1H), 8.84 (s, 1H); m/z 502 (M+H)$^+$ The preparation of 3-({(1S)-2-[(difluoromethyl)oxy]-1-methylethyl}oxy)-5-hydroxy-N-(1-methyl-1H-pyrazol-3-yl)benzamide and 2-(azetidin-1-ylcarbonyl)-5-bromopyridine were described earlier.

EXAMPLE 18

3-{[5-(Azetidin-1-ylcarbonyl)pyrazin-2-yl]oxy}-5-({(1S)-2-[(difluoromethyl)oxy]-1-methylethyl}oxy)-N-(1-methyl-1H-pyrazol-3-yl)benzamide

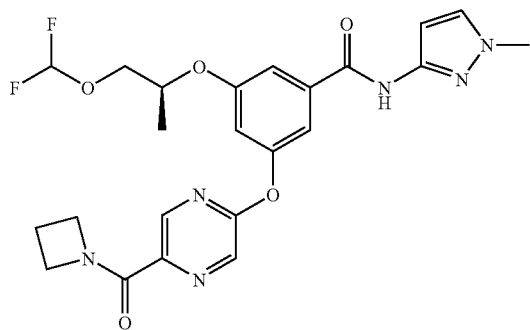

DIPEA (0.41 mL, 2.33 mmol) was added to a mixture of 5-[(3-({(1S)-2-[(difluoromethyl)oxy]-1-methylethyl}oxy)-5-{[(1-methyl-1H-pyrazol-3-yl)amino]carbonyl}phenyl)oxy]pyrazine-2-carboxylic acid (0.27 g, 0.58 mmol), azetidine hydrochloride (109 mg, 1.17 mmol) and HATU (466 mg, 1.22 mmol) in DMF (5 mL) and stirred at RT for 24 hours. Ethyl acetate (40 mL) was added and the organics washed with water (2×30 mL), brine (30 mL), dried (MgSO$_4$), filtered and concentrated in vacuo to give a yellow oil. The residue was chromatographed on silica, eluting with 0-5% methanol in ethyl acetate, to give the desired compound (124 mg).

$^1$H NMR δ (CDCl$_3$): 1.28 (d, 3H), 2.30 (quin, 2H), 3.65 (s, 3H), 3.90 (m, 2H), 4.18 (t, 2H), 4.53 (sextet, 1H), 4.61 (t, 2H), 6.19 (t, 1H), 6.73 (d, 1H), 6.84 (t, 1H), 7.18 (m, 2H), 7.28 (s, 1H), 8.25 (s, 1H), 8.76 (s, 1H), 9.14 (s, 1H); m/z 503 (M+H)$^+$.

The preparation of 5-[(3-({(1S)-2-[(difluoromethyl)oxy]-1-methylethyl}oxy)-5-{[(1-methyl-1H-pyrazol-3-yl)amino]carbonyl}phenyl)oxy]pyrazine-2-carboxylic acid is described below:

5-[(3-({(1S)-2-[(Difluoromethyl)oxy]-1-methylethyl}oxy)-5-{[(1-methyl-1H-pyrazol-3-yl)amino]carbonyl}phenyl)oxy]pyrazine-2-carboxylic acid

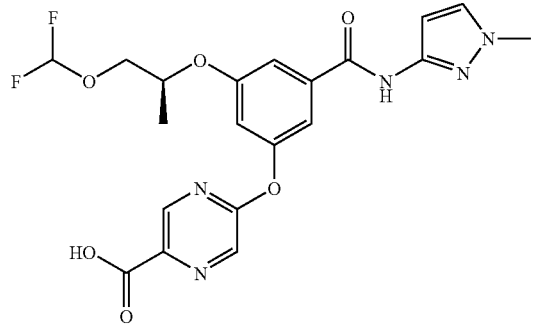

A mixture of 3-({(1S)-2-[(difluoromethyl)oxy]-1-methylethyl}oxy)-5-hydroxy-N-(1-methyl-1H-pyrazol-3-yl)benzamide (220 mg, 0.64 mmol), methyl 5-chloropyrazine-2-carboxylate (112 mg, 0.64 mmol) and potassium carbonate (178 mg, 1.29 mmol) in acetonitrile (5 mL) was stirred in a 'Biotage initiator Microwave' at 160° C. for 4 hours. The solvent was removed in vacuo and water (20 mL) added. The mixture was adjusted to pH3 with 1M citric acid and extracted into ethyl acetate (2×50 mL). The combined organics were washed with water (20 mL), brine (50 mL), dried (MgSO$_4$), filtered and the solvent removed in vacuo to give a yellow oil (0.19 g) which appeared to be a mixture of the acid and methyl ester. Lithium hydroxide monohydrate (26 mg, 0.60 mmol) in water (3 mL) was added to the mixture of acid and ester (0.19 g, 0.4 mmol) in THF (6 mL) and the mixture stirred at RT for 72 hours. The organics were removed in vacuo and the residue adjusted to pH3 with 1M citric acid, twice extracted into ethyl acetate and the combined organics, washed with water (30 mL), brine (30 mL), dried (MgSO$_4$), filtered and the solvent removed in vacuo to give the desired compound as a yellow solid (0.17 g). m/z 464 (M+H)$^+$ The preparation of 3-({(1S)-2-[(difluoromethyl)oxy]-1-methylethyl}oxy)-5-hydroxy-N-(1-methyl-1H-pyrazol-3-yl)benzamide was described earlier.

EXAMPLE 19

3-{[5-(azetidin-1-ylcarbonyl)-3-chloropyridin-2-yl]oxy}-5-{[(1R,2R)-2-hydroxy-1-methylpropyl]oxy}-N-(1-methyl-1H-pyrazol-3-yl)benzamide and 3-{[5-(azetidin-1-ylcarbonyl)-3-chloropyridin-2-yl]oxy}-5-{[(1S,2S)-2-hydroxy-1-methylpropyl]oxy}-N-(1-methyl-1H-pyrazol-3-yl)benzamide (1:1)

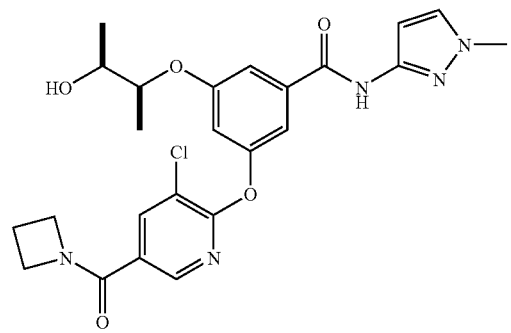

A solution of 5-(azetidin-1-ylcarbonyl)-2,3-dichloropyridine (95 mg, 0.44 mmol), a mixture of 3-hydroxy-5-{[(1R,2R)-2-hydroxy-1-methylpropyl]oxy}-N-(1-methyl-1H-pyrazol-3-yl)benzamide and 3-hydroxy-5-{[(1S,2S)-2-hydroxy-1-methylpropyl]oxy}-N-(1-methyl-1H-pyrazol-3-yl)benzamide (1:1) (129 mg, 0.42 mmol) and potassium carbonate (146 mg, 1.05 mmol) in acetonitrile (3 mL) was heated in a microwave reactor at 160° C. for 5 hours. The acetonitrile was removed in vacuo and the residue dissolved in ethyl acetate (25 mL). The organic solution was washed with water (25 mL), brine (25 mL), dried (MgSO$_4$) and evaporated to a residue which was chromatographed on alumina, eluting with a gradient of 0-5% methanol in ethyl acetate, to give the required product (56 mg).

$^1$H NMR δ (CDCl$_3$): 1.18 (m, 6H), 2.32 (m, 3H), 3.66 (s, 3H), 3.79 (quin, 1H), 4.15 (m, 3H), 4.28 (t, 2H), 6.72 (d, 1H), 6.85 (t, 1H), 7.17 (s, 1H), 7.19 (s, 1H), 7.29 (s, 1H), 8.08 (m, 1H), 8.15 (m, 1H), 9.10 (s, 1H); m/z 501 (M+H)$^+$ This mixture of diasteromers were separated by chiral preparatory HPLC on a Chiralpak IA (250 mm×20 mm) No. EG014 column, eluting with a mixture of isohexane/ethyl acetate/acetic acid/triethylamine (40/60/0.2/0.1) to give the first eluted isomer (43 mg), Example 19a, and the second eluted isomer (40 mg), Example 19b.

The preparation of 5-(azetidin-1-ylcarbonyl)-2,3-dichloropyridine was described earlier.

The preparation of 3-hydroxy-5-{[(1R,2R)-2-hydroxy-1-methylpropyl]oxy}-N-(1-methyl-1H-pyrazol-3-yl)benzamide and 3-hydroxy-5-{[(1S,2S)-2-hydroxy-1-methylpropyl]oxy}-N-(1-methyl-1H-pyrazol-3-yl)benzamide (1:1) is described below:

3-hydroxy-5-{[(1R,2R)-2-hydroxy-1-methylpropyl]oxy}-N-(1-methyl-1H-pyrazol-3-yl)benzamide and 3-hydroxy-5-{[(1S,2S)-2-hydroxy-1-methylpropyl]oxy}-N-(1-methyl-1H-pyrazol-3-yl)benzamide (1:1)

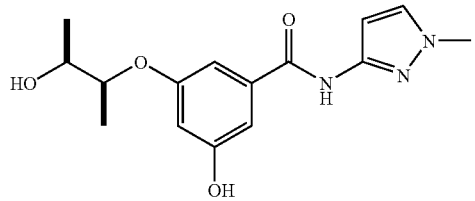

A solution of a mixture of 3-{[(1R,2R)-2-hydroxy-1-methylpropyl]oxy}-N-(1-methyl-1H-pyrazol-3-yl)-5-[(phenylmethyl)oxy]benzamide and 3-{[(1S,2S)-2-hydroxy-1-methylpropyl]oxy}-N-(1-methyl-1H-pyrazol-3-yl)-5-[(phenylmethyl)oxy]benzamide (1:1) (1.26 g, 3.19 mmol) and 10% by weight palladium on carbon (0.13 g) in ethanol (50 mL) was allowed to stir at RT under a hydrogen atmosphere for 16 hours. The solution was filtered through Celite® and washed through with methanol (100 mL). The solution was concentrated in vacuo to give the desired compound (1.03 g). $^1$H NMR δ (d$_6$-DMSO): 1.09 (d, 3H), 1.17 (d, 3H), 3.76 (m, 1H), 3.78 (s, 3H), 4.34 (quin, 1H), 6.48 (t, 1H), 6.56 (d, 1H), 6.93 (t, 1H), 7.05 (t, 1H), 7.60 (d, 1H), 9.66 (s, 1H), 10.67 (s, 1H); m/z 306 (M+H)$^+$ 3-{[(1R,2R)-2-hydroxy-1-methylpropyl]oxy}-N-(1-methyl-1H-pyrazol-3-yl)-5-[(phenylmethyl)oxy]benzamide and 3-{[(1S,2S)-2-hydroxy-1-methylpropyl]oxy}-N-(1-methyl-1H-pyrazol-3-yl)-5-[(phenylmethyl)oxy]benzamide (1:1)

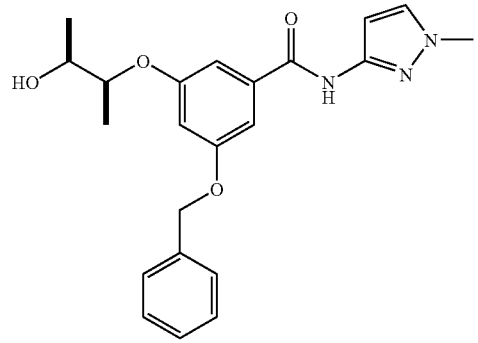

A solution of a mixture of 3-{[(1R,2R)-2-hydroxy-1-methylpropyl]oxy}-5-[(phenylmethyl)oxy]benzoic acid and 3-{[(1S,2S)-2-hydroxy-1-methylpropyl]oxy}-5-[(phenylmethyl)oxy]benzoic acid (1:1) (2.50 g, 7.92 mmol), 1-methyl-1H-pyrazol-3-amine (1.54 g, 15.8 mmol), HATU (3.92 g, 10.3 mmol) and DIPEA (2.76 mL, 15.8 mmol) in DMF (15 mL) was stirred at RT and under ambient atmosphere for 16 hours. Water (150 mL) was added and the solution extracted with ethyl acetate (250 mL). The ethyl acetate layer was washed with brine and dried (MgSO$_4$), and evaporated to a residue which was chromatographed on silica, eluting with 50% ethyl acetate in hexane, to give the desired product (1.26 g). $^1$H NMR δ (CDCl$_3$): 1.17 (s, 3H), 1.18 (s, 3H), 2.44 (d, 1H), 3.70 (s, 3H), 3.77 (m, 1H), 4.10 (quin, 1H), 4.99 (s, 2H), 6.64 (t, 1H), 6.75 (d, 1H), 6.96 (t, 1H), 7.03 (t, 1H), 7.22 (d, 1H), 7.31 (m, 5H), 8.68 (s, 1H); m/z 396 (M+H)$^+$ 3-{[(1R,2R)-2-Hydroxy-1-methylpropyl]oxy}-5-[(phenylmethyl)oxy]benzoic acid and 3-{[(1S,2S)-2-hydroxy-1-methylpropyl]oxy}-5-[(phenylmethyl)oxy]benzoic acid (1:1)

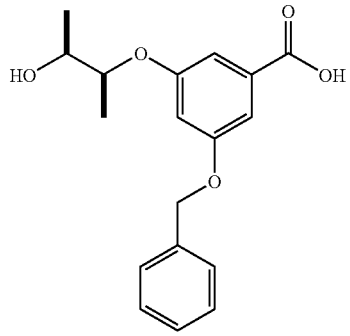

To a solution of a mixture of methyl 3-{[(1R,2R)-2-hydroxy-1-methylpropyl]oxy}-5-[(phenylmethyl)oxy]benzoate and methyl 3-{[(1S,2S)-2-hydroxy-1-methylpropyl]oxy}-5-[(phenylmethyl)oxy]benzoate (1:1) (2.52 g, 7.63 mmol) in THF (40 mL) was added a solution of lithium hydroxide monohydrate (0.80 g, 19.07 mmol) in water (10 mL). The mixture was allowed to stir at RT for 16 hours. The THF was removed in vaccuo and the resulting solution was partitioned between water (100 mL) and ethyl acetate (250 mL). The ethyl acetate layer was washed with brine (50 mL)

and dried (MgSO₄). The aqueous layer was then adjusted to pH 7 by addition of 1M hydrochloric acid and extracted with ethyl acetate (75 mL). The ethyl acetate layer was washed with brine and dried (MgSO₄). The ethyl acetate layers were combined and evaporated to give the required product (2.50 g).

¹H NMR δ (CDCl₃): 1.18 (s, 3H), 1.20 (s, 3H), 3.80 (quin, 1H), 4.14 (quin, 1H), 5.01 (s, 2H), 6.72 (t, 1H), 7.21 (m, 1H), 7.32 (m, 6H).

Methyl 3-{[(1R,2R)-2-hydroxy-1-methylpropyl]oxy}-5-[(phenylmethyl)oxy]benzoate and methyl 3-{[(1S,2S)-2-hydroxy-1-methylpropyl]oxy}-5-[(phenylmethyl)oxy]benzoate (1:1)

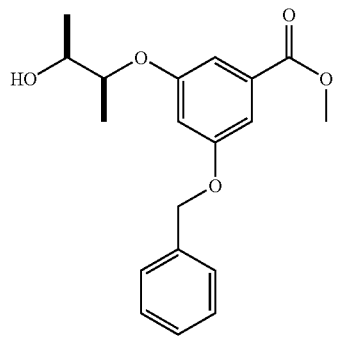

A solution of methyl 3-hydroxy-5-{[phenylmethyl]oxy}benzoate (3.00 g, 11.61 mmol), (2R,3S)-2,3-dimethyloxirane (3.04 mL, 34.8 mmol), and potassium carbonate (4.02 g, 29.0 mmol) in acetonitrile (60 mL) was heated in a microwave reactor at 150° C. for 3 hours. The acetonitrile was removed in vacuo and the residual oil dissolved in ethyl acetate (50 mL), washed with water (50 mL), brine (50 mL), dried (MgSO₄) and evaporated to a residual oil. The residue was chromatographed on silica, eluting with ethyl acetate, to give the desired compound (2.52 g). ¹H NMR δ (CDCl₃): 1.17 (d, 6H), 3.82 (s, 3H), 4.04 (q, 2H), 4.99 (s, 2H), 6.67 (t, 1H), 7.14 (s, 1H), 7.30 (m, 6H); m/z 330 (M−H)⁻

The preparation of methyl 3-hydroxy-5-{[phenylmethyl]oxy}benzoate was described earlier.

EXAMPLE 20

3-{[5-(Azetidin-1-ylcarbonyl)-3-chloropyridin-2-yl]oxy}-N-(1-ethyl-1H-pyrazol-3-yl)-5-{[(1S)-1-methyl-2-(methyloxy)ethyl]oxy}benzamide

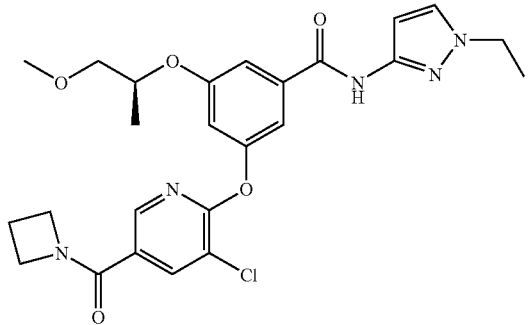

A solution of N-(1-ethyl-1H-pyrazol-3-yl)-3-hydroxy-5-{[(1S)-1-methyl-2-(methyloxy)ethyl]oxy}benzamide (128 mg, 0.4 mmol) and the 5-(azetidin-1-ylcarbonyl)-2,3-dichloropyridine (111 mg, 0.48 mmol) in acetonitrile (2 mL) containing potassium carbonate (111 mg, 0.8 mmol) was heated in a microwave reactor at 160° C. for 6 hours. The reaction mixture was filtered and the filtrate evaporated to dryness under reduced pressure and purified by chromatography on silica, eluting with 50-100% ethyl acetate in hexane to give the required product as a white foam (176 mg).

¹H NMR δ (CDCl₃): 1.28 (d, 3H), 1.41 (t, 3H), 2.32 (quin, 2H), 3.35 (s, 3H), 3.49 (m, 2H), 4.02 (q, 2H), 4.17 (t, 2H), 4.30 (t, 2H), 4.56 (q, 1H), 6.76 (d, 1H), 6.88 (t, 1H), 7.18 (s, 1H), 7.28 (d, 1H), 7.32 (t, 1H), 8.09 (d, 1H), 8.18 (d, 1H), 8.65 (s, 1H); m/z 514 (M+H)⁺

The preparation of N-(1-ethyl-1H-pyrazol-3-yl)-3-hydroxy-5-{[(1S)-1-methyl-2-(methyloxy)ethyl]oxy}benzamide is described below:

N-(1-Ethyl-1H-pyrazol-3-yl)-3-hydroxy-5-{[(1S)-1-methyl-2-(methyloxy)ethyl]oxy}benzamide

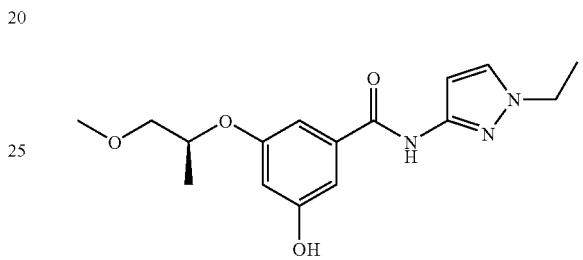

10% Palladium on carbon (1.9 g, 50% wet) was added under argon to N-(1-ethyl-1H-pyrazol-3-yl)-3-{[(1S)-1-methyl-2-(methyloxy)ethyl]oxy}-5-[(phenylmethyl)oxy]benzamide (19.1 g, 46.7 mmol) in dry THF (100 mL) and ethanol (100 mL). The reaction mixture was degassed, placed under a hydrogen balloon and stirred for 16 hours. The mixture was filtered through diatomaceous earth and the filtrate was evaporated to give a brown oil. The residue was purified by column chromatography on silica, eluting with 40-65% ethyl acetate in hexanes, to give the desired product as a clear oil which crystallised on standing (11.35 g).

¹H NMR δ (CDCl₃): 1.21 (d, 6H), 1.38 (t, 3H), 3.32 (s, 3H), 3.39-3.51 (m, 3H), 3.98 (q, 2H), 4.44-4.51 (m, 1H), 6.54 (s, 1H), 6.72 (d, 1H), 6.92 (s, 2H), 7.26 (d, 1H), 8.18 (s, 1H), 8.85 (s, 1H); m/z 320 (M+H)⁺ 318 (M−H)⁻

N-(1-Ethyl-1H-pyrazol-3-yl)-3-{[(1S)-1-methyl-2-(methyloxy)ethyl]oxy}-5-[(phenylmethyl)oxy]benzamide

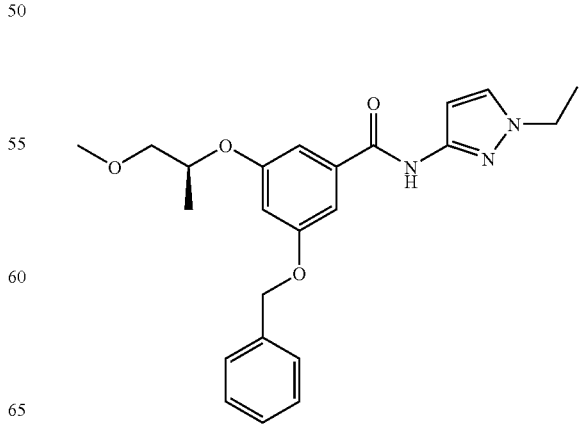

HATU (23.5 g, 61.83 mmol) was added to 3-[(1S)-2-methoxy-(1-methylethyl)oxy]-5-{[phenylmethyl]oxy}benzoic acid (16.28 g, 51.53 mmol) followed by addition of DMF (140 mL) and cooled to 0° C. 1-Ethyl-1H-pyrazol-3-amine (6.86 g, 61.8 mmol) was added followed by DIPEA (21.3 mL) and the reaction stirred under argon, at 0° C., for 3 hours. The solvent volume was reduced and the residue was dissolved in ethyl acetate (500 mL), washed with citric acid (200 mL), sodium hydrogen carbonate solution (150 mL) and saturated brine solution (2×150 mL). The organic layer was separated and dried (MgSO$_4$), filtered and evaporated. Purification by column chromatography on silica, eluting with 10-50% ethyl acetate in hexanes, afforded the title compound as a pale yellow oil (19.1 g).

$^1$H NMR δ (CDCl$_3$): 1.23 (d, 3H), 1.38 (t, 3H), 3.33 (s, 3H), 3.42 (dd, 1H), 3.50 (dd, 1H), 3.97 (q, 2H), 4.49 (sextet, 1H), 4.99 (s, 2H), 6.66 (t, 1H), 6.75 (d, 1H), 6.98 (s, 1H), 7.02 (s, 1H), 7.26 (d, 1H), 7.28-7.37 (m, 5H), 8.58 (s, 1H); m/z 410 (M+H)$^+$ The preparation of 3-[(1S)-2-methoxy-(1-methylethyl)oxy]-5-{[phenylmethyl]oxy}benzoic acid was described earlier.

The preparation of 1-ethyl-1H-pyrazol-3-amine is described in the literature [*Chem. Heterocycl. Compd.* (*Engl. Transl.*), 11, 1975, 212].

EXAMPLE 21

3-{[6-(Azetidin-1-ylcarbonyl)pyridin-3-yl]oxy}-N-(1-ethyl-1H-pyrazol-3-yl)-5-{[(1S)-1-methyl-2-(methyloxy)ethyl]oxy}benzamide

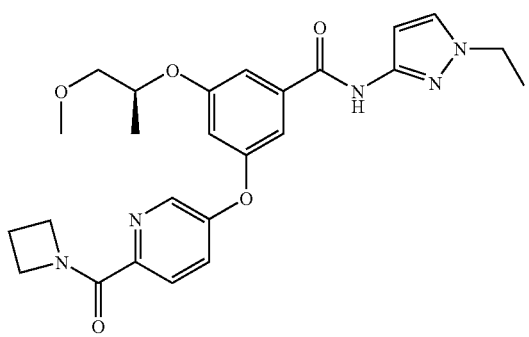

A mixture of N-(1-ethyl-1H-pyrazol-3-yl)-3-hydroxy-5-{[(1S)-1-methyl-2-(methyloxy)ethyl]oxy}benzamide (0.128 g, 0.4 mmol), 2-(azetidin-1-ylcarbonyl)-5-bromopyridine (116 mg, 0.48 mmol), cesium carbonate (392 mg, 1.2 mmol) and bromotris(triphenylphosphine)copper(I) (38 mg, 0.04 mmol) in DMA (5 mL) was stirred in a microwave reactor at 160° C. for 4 hours. The product was dissolved in ethyl acetate (20 mL) and water (15 mL) and the layers separated. The organic layer washed with brine (50 mL), dried (MgSO$_4$), filtered and the solvent removed in vacuo to give a brown oil which was chromatographed on silica, eluting with a gradient of 70-100% ethyl acetate in hexane to give the desired material as a clear foam (76 mg). $^1$H NMR δ (CDCl$_3$): 1.26 (d, 3H), 1.40 (t, 3H), 2.29 (quin, 2H), 3.34 (s, 3H), 3.42-3.53 (m, 2H), 4.01 (q, 2H), 4.18 (t, 2H), 4.54 (q, 1H), 4.64 (t, 2H), 6.74 (t, 2H), 7.04 (s, 1H), 7.22 (s, 1H), 7.27 (d, 1H), 7.30 (d, 1H), 8.04 (d, 1H), 8.25 (d, 1H), 8.47 (s, 1H); m/z 480 (M+H)$^+$ The preparation of N-(1-ethyl-1H-pyrazol-3-yl)-3-hydroxy-5-{[(1S)-1-methyl-2-(methyloxy)ethyl]oxy}benzamide and 2-(azetidin-1-ylcarbonyl)-5-bromopyridine was described earlier.

EXAMPLE 22

3-{[5-(Azetidin-1-ylcarbonyl)pyrazin-2-yl]oxy}-N-(1-ethyl-1H-pyrazol-3-yl)-5-{[(1S)-1-methyl-2-(methyloxy)ethyl]oxy}benzamide

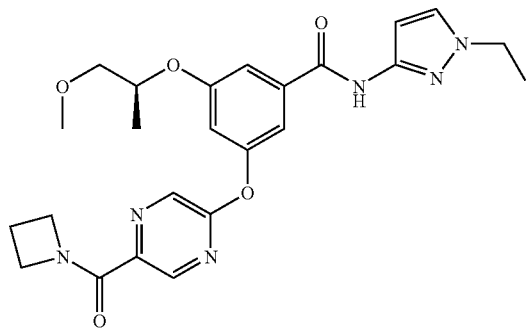

HATU (304 mg, 0.80 mmol) was added to 5-[(3-{[(1-ethyl-1H-pyrazol-3-yl)amino]carbonyl}-5-{[(1S)-1-methyl-2-(methyloxy)ethyl]oxy}phenyl)oxy]pyrazine-2-carboxylic acid (0.4 mmol) and azetidine hydrochloride (75 mg, 0.89 mmol) in DMF (5 mL) followed by addition of DIPEA (0.278 mL, 1.6 mmol) and the reaction was stirred for 16 hours. The reaction mixture was added to ethyl acetate (20 mL), the organic solution washed with water (10 mL), 2N citric acid (10 mL), saturated aqueous sodium hydrogencarbonate (10 mL) and brine (10 mL), then dried (MgSO$_4$), filtered and evaporated under reduced pressure to a gum. The residue was purified by chromatography on silica, eluting with 70-100% ethyl acetate in hexane, to give the desired compound as a white foam (98 mg). $^1$H NMR δ (CDCl$_3$): 1.27 (d, 3H), 1.40 (t, 3H), 2.31 (quin, 2H), 3.34 (s, 3H), 3.43-3.54 (m, 2H), 4.01 (q, 2H), 4.19 (t, 2H), 4.54 (q, 1H), 4.62 (t, 2H), 6.73 (d, 1H), 6.87 (t, 1H), 7.18 (t, 1H), 7.27 (d, 1H), 7.30 (t, 1H), 8.26 (d, 1H), 8.49 (s, 1H), 8.78 (d, 1H); m/z 481 (M+H)$^+$ The preparation of 5-[(3-{[(1-ethyl-1H-pyrazol-3-yl)amino]carbonyl}-5-{[(1S)-1-methyl-2-(methyloxy)ethyl]oxy}phenyl)oxy]pyrazine-2-carboxylic acid is described below:

5-[(3-{[(1-Ethyl-1H-pyrazol-3-yl)amino]carbonyl}-5-{[(1S)-1-methyl-2-(methyloxy)ethyl]oxy}phenyl)oxy]pyrazine-2-carboxylic acid

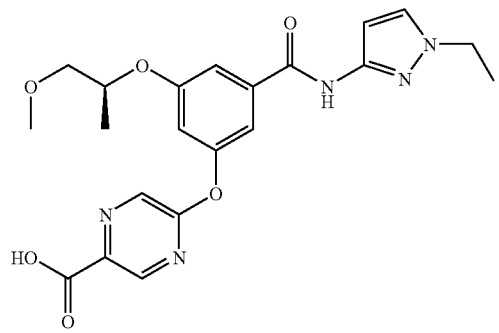

A solution of N-(1-ethyl-1H-pyrazol-3-yl)-3-hydroxy-5-{[(1S)-1-methyl-2-(methyloxy)ethyl]oxy}benzamide (128 mg, 0.4 mmol) and the methyl-5-chloropyrazine-2-carboxylate (83 mg, 0.48 mmol) in acetonitrile (2 mL), containing potassium carbonate (111 mg, 0.8 mmol), was heated in a microwave reactor at 160° C. for 6 hours. The reaction mixture was dissolved in water (10 mL), acidified with 2N citric acid and extracted with ethyl acetate (5×20 mL). The organic phase was washed with brine, dried (MgSO$_4$) and evaporated to dryness under reduced pressure to give the desired material a yellow solid (164 mg), which was used without purification in the next step. m/z 442 (M+H)$^+$ The preparation of N-(1-ethyl-1H-pyrazol-3-yl)-3-hydroxy-5-{[(1S)-1-methyl-2-(methyloxy)ethyl]oxy}benzamide was described earlier.

EXAMPLE 23

3-{[5-(Azetidin-1-ylcarbonyl)-3-chloropyridin-2-yl]oxy}-5-{[(1S)-2-hydroxy-1-methylethyl]oxy}-N-[1-(1-methylethyl)-1H-pyrazol-3-yl]benzamide

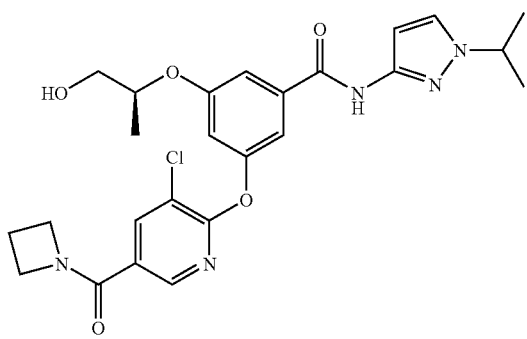

3-{[5-(Azetidin-1-ylcarbonyl)-3-chloropyridin-2-yl]oxy}-5-[((1S)-2-{[(1,1-dimethylethyl)(dimethyl)silyl]oxy}-1-methylethyl)oxy]-N-[1-(1-methylethyl)-1H-pyrazol-3-yl]benzamide (142 mg, 0.23 mmol) in methanol (2 mL) was stirred with 3.5M hydrochloric acid (0.2 mL, 0.68 mmol) for 1 hour. The solution was neutralised with saturated sodium bicarbonate solution and the organic solvent was removed under reduced pressure. The residue was extracted with ethyl acetate (3×10 mL), dried (MgSO$_4$), filtered and the solvent removed under reduced pressure. The residue was purified by chromatography on silica, eluting with 75-100% ethyl acetate in hexane, to give the required product as a white foam (99 mg).
$^1$H NMR δ (CDCl$_3$): 1.25 (d, 3H), 1.41 (d, 6H), 2.32 (quin, 2H), 3.67-3.71 (m, 2H), 4.17 (t, 2H), 4.26-4.35 (m, 3H), 4.52 (q, 1H), 6.73 (s, 1H), 6.87 (s, 1H), 7.19 (s, 1H), 7.30 (s, 1H), 7.32 (s, 1H), 8.10 (s, 1H), 8.18 (s, 1H), 8.56 (s, 1H); m/z 514 (M+H)$^+$ The preparation of 3-{[5-(azetidin-1-ylcarbonyl)-3-chloropyridin-2-yl]oxy}-5-[((1S)-2-{[(1,1-dimethylethyl)(dimethyl)silyl]oxy}-1-methylethyl)oxy]-N-[1-(1-methylethyl)-1H-pyrazol-3-yl]benzamide is described below:

3-{[5-(Azetidin-1-ylcarbonyl)-3-chloropyridin-2-yl]oxy}-5-[((1S)-2-{[(1,1-dimethylethyl)(dimethyl)silyl]oxy}-1-methylethyl)oxy]-N-[1-(1-methylethyl)-1H-pyrazol-3-yl]benzamide

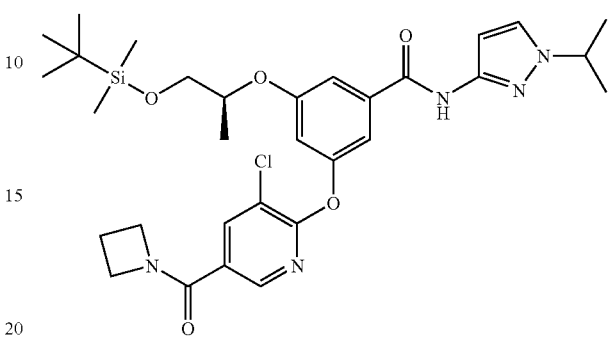

A solution of 3-[((1S)-2-{[(1,1-dimethylethyl)(dimethyl)silyl]oxy}-1-methylethyl)oxy]-5-hydroxy-N-[1-(1-methylethyl)-1H-pyrazol-3-yl]benzamide (103 mg, 0.24 mmol) and 5-(azetidin-1-ylcarbonyl)-2,3-dichloropyridine (66 mg, 0.29 mmol) in acetonitrile (2 mL), containing potassium carbonate (66 mg, 0.48 mmol), was heated in a microwave reactor at 160° C. for 6 hours. The reaction mixture was filtered and the filtrate evaporated to dryness under reduced pressure and purified by chromatography on silica, eluting with 50-100% ethyl acetate in hexane, to give the required product as a white foam (142 mg). m/z 628 (M+H)$^+$ 3-[((1S)-2-{[(1,1-Dimethylethyl)(dimethyl)silyl]oxy}-1-methylethyl)oxy]-5-hydroxy-N-[1-(1-methylethyl)-1H-pyrazol-3-yl]benzamide

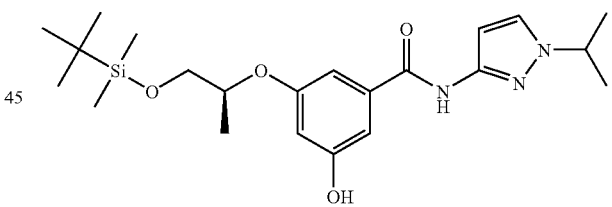

A solution of 3-[((1S)-2-{[(1,1-dimethylethyl)(dimethyl)silyl]oxy}-1-methylethyl)oxy]-N-[1-(1-methylethyl)-1H-pyrazol-3-yl]-5-[(phenylmethyl)oxy]benzamide (1.97 g, 3.77 mmol) and THF (70 mL) was evacuated and purged with Argon (×3). Palladium on carbon (10% w/w, 400 mg) was added and reaction mixture was evacuated and finally purged with hydrogen gas. Reaction mixture was left to stir at ambient temperature under hydrogen for 16 hours. The palladium on carbon was filtered off and concentrated in vacuo to give the product as a colourless oil (1.58 g, 97%).
$^1$H NMR δ (CDCl$_3$): 0.02 (s, 3H), 0.04 (s, 3H), 0.85 (s, 9H), 1.27 (d, 3H), 1.53 (s, 3H), 1.55 (s, 3H), 3.63 (dd, 1H), 3.77 (dd, 1H), 4.41 (m, 1H), 6.60 (s, 1H), 6.81 (s, 1H), 7.00 (s, 1H), 7.07 (s, 1H), 7.38 (s, 1H), 8.78 (br. s, 1H); m/z 434 (M+H)$^+$, 432 (M−H)$^−$.

3-[((1S)-2-{[(1,1-Dimethylethyl)(dimethyl)silyl]oxy}-1-methylethyl)oxy]-N-[1-(1 methylethyl)-1H-pyrazol-3-yl]-5-[(phenylmethyl)oxy]benzamide

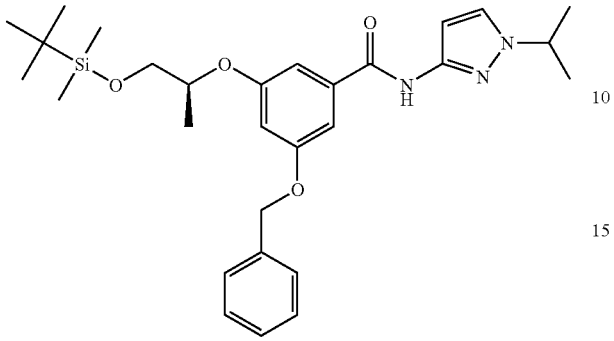

DIPEA (3.11 mL, 18.03 mmol) was added to a solution of 3-[((1S)-2-{[(1,1-dimethylethyl)(dimethyl)silyl]oxy}-1-methylethyl)oxy]-5-[(phenylmethyl)oxy]benzoic acid (3.00 g, 7.21 mmol), HATU (3.12 g, 8.21 mmol) and 1-(1-methylethyl)-1H-pyrazol-3-amine (1.13 g, 9.01 mmol) in DMF (10 mL). The resulting mixture was stirred at ambient temperature for 16 hours. The DMF was removed in vacuo. The solvent was evaporated and the residue was dissolved in 5% w/v citric acid (50 mL) and ethyl acetate (30 mL) and diethyl ether (30 mL) and the organic layer was further washed with saturated aqueous sodium bicarbonate solution (30 mL) and brine (30 mL). The organic layer was separated, then dried (MgSO$_4$), filtered and evaporated. Purification by column chromatography, eluting with 1:4 to 1:3 ethyl acetate:hexanes, afforded the title compound as a colourless oil (2.40 g, 65%). $^1$H NMR δ (CDCl$_3$): 0.01 (s, 3H), 0.03 (s, 3H), 0.86 (s, 9H), 1.24 (d, 3H), 1.49 (s, 3H), 1.51 (s, 3H), 3.64 (dd, 1H), 3.78 (dd, 1H), 4.39 (m, 1H), 4.46 (m, 1H), 5.09 (s, 2H), 6.70 (s, 1H), 6.78 (s, 1H), 7.02 (s, 1H), 7.08 (s, 1H), 7.35 (m, 6H), 8.32 (br. s, 1H); m/z 524 (M+H)$^+$, 522 (M−H)$^−$.

1-(1-Methylethyl)-1H-pyrazol-3-amine

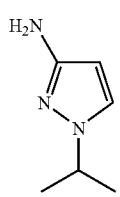

2-Chloroacrylonitrile (3.41 mL, 42.59 mmol) was added at RT to a stirring solution of N-isopropylhydrazine hydrochloride (4.71 g, 42.6 mmol), potassium carbonate (11.8 g, 85.2 mmol) in water (50 mL). The reaction was warmed to 45° C. for 4 hours before cooling back to RT. The aqueous layer was then extracted with ethyl acetate (5×30 mL) and the combined organic layers were dried (MgSO$_4$), treated with activated charcoal, filtered and evaporated. The residue was purified by chromatography, eluting with 67%-100% ethyl acetate in hexanes, to afford the title compound (3.08 g, 58%) as a 6:1 mixture of authentic product to regioisomeric product as an oil. The material was used without further purification. $^1$H NMR δ (CDCl$_3$): 1.42 (m, 6H), 3.58 (br. s, 2H), 4.25 (sept, 1H), 5.58 (d, 1H), 7.15 (d, 1H).

The preparation of 3-[((1S)-2-{[(1,1-dimethylethyl)(dimethyl)silyl]oxy}-1-methylethyl)oxy]-5-[(phenylmethyl)oxy] benzoic acid was described earlier.

EXAMPLE 24

3-{[5-(Azetidin-1-ylcarbonyl)pyridin-2-yl]oxy}-5-{[(1S)-1-methyl-2-(methyloxy)ethyl]oxy}-N-1H-pyrazol-3-ylbenzamide

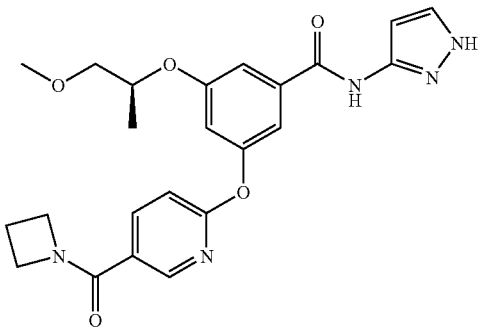

A solution of 1,1-dimethylethyl 3-{[(3-hydroxy-5-{[(1S)-1-methyl-2-(methyloxy)ethyl]oxy}phenyl)carbonyl]amino}-1H-pyrazole-1-carboxylate (157 mg, 0.4 mmol) and 5-(azetidin-1-ylcarbonyl)-2-chloropyridine (95 mg, 0.48 mmol) in acetonitrile (2 mL), containing potassium carbonate (111 mg, 0.8 mmol), was heated in a microwave reactor at 160° C. for 6 hours. The reaction mixture was filtered and the filtrate evaporated to dryness under reduced pressure and purified by chromatography on silica, eluting with 50-100% ethyl acetate in hexane to give a product which was further purified by chromatography on silica, eluting with 0-8% methanol in ethyl acetate, to give the required product as a white foam (21 mg).

$^1$H NMR δ (CDCl$_3$): 1.25 (d, 3H), 2.30 (quin, 2H), 3.33 (s, 3H), 3.42-3.54 (m, 2H), 4.12-4.29 (m, 4H), 4.54 (q, 1H), 6.77 (s, 1H), 6.81 (t, 1H), 6.97 (d, 1H), 7.20 (s, 1H), 7.27 (s, 1H), 7.33 (d, 1H), 8.01 (d, 2H), 8.28 (d, 1H), 10.27 (s, 1H); m/z 452 (M+H)$^+$ The preparation of 1,1-dimethylethyl 3-{[(3-hydroxy-5-{[(1S)-1-methyl-2-(methyloxy)ethyl]oxy}phenyl)carbonyl]amino}-1H-pyrazole-1-carboxylate is described below:

1,1-Dimethylethyl 3-{[(3-hydroxy-5-{[(1S)-1-methyl-2-(methyloxy)ethyl]oxy}phenyl)carbonyl]amino}-1H-pyrazole-1-carboxylate

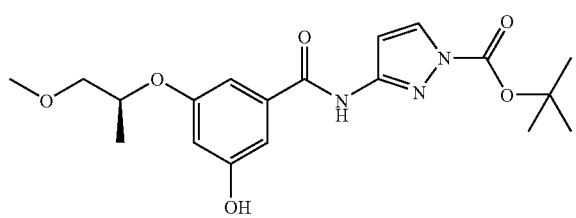

A solution of 1,1-dimethylethyl 3-[({3-{[(1S)-1-methyl-2-(methyloxy)ethyl]oxy}-5-[(phenylmethyl)oxy]phenyl}carbonyl)amino]-1H-pyrazole-1-carboxylate (23 g, 47.8 mmol) in THF (140 mL) and ethanol (140 mL) was evacuated and purged with nitrogen (×3). 10% Palladium on carbon (2.3 g; 10% w/w) was added and reaction mixture was evacuated and finally purged with hydrogen gas. The reaction mixture was left to stir at RT under a hydrogen balloon for 16 hours. The palladium on carbon was filtered through diatomaceous earth and the filtrate concentrated in vacuo to give a white foam (18 g, 97%).

$^1$H NMR δ (d$_6$-DMSO): 1.2 (d, 3H), 1.55 (s, 9H), 3.25 (s, 3H obscured by water peak), 3.4-3.5 (m, 2H), 4.7 (m, 1H), 6.5 (s, 1H), 6.95 (d, 1H), 7.0 (s, 1H), 7.1 (s, 1H), 8.2 (d, 1H), 9.65 (s, 1H), 11.2 (s, br, 1H); m/z 392 (M+H)$^+$ 1,1-Dimethylethyl 3-[({3-{[(1S)-1-methyl-2-(methyloxy)ethyl]oxy}-5-[(phenylmethyl)oxy]phenyl}carbonyl)amino]-1H-pyrazole-1-carboxylate

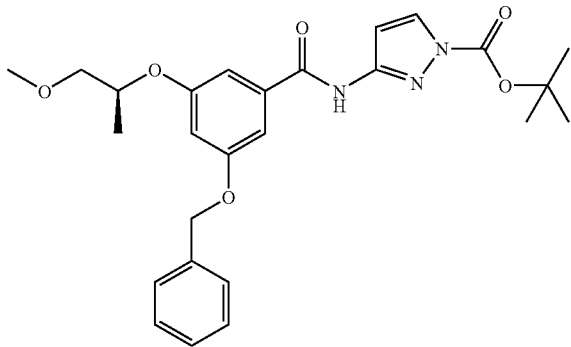

DIPEA (28.5 mL, 164 mmol) was added to a suspension of 3-[(1S)-2-methoxy-(1-methylethyl)oxy]-5-{[phenylmethyl]oxy}benzoic acid (20.7 g, 65.6 mmol), HATU (31.2 g, 82.0 mmol) and 1,1-dimethylethyl 3-amino-1H-pyrazole-1-carboxylate (15.0 g, 82.0 mmol) in DMF (30 mL) and the reaction mixture stirred for 16 hours at RT. Water (250 mL) was added and the reaction mixture extracted with diethyl ether (3×150 mL). The organic layer was washed with saturated brine solution and dried (MgSO$_4$). The filtrate was concentrated in vacuo and the residue crystallised on standing. The crystals were washed with isohexane to give to give the desired material as yellow crystals (23.4 g; 73%). m/z 482 (M+H)$^+$.

1,1-Dimethylethyl 3-amino-1H-pyrazole-1-carboxylate

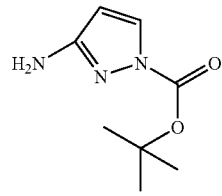

1H-Pyrazol-3-amine (428 mg, 5.15 mmol) was dissolved in DMF (5 mL) at 0° C. and treated with sodium hydride (206 mg, 5.15 mmol) followed by stirring for a further 30 min. Warmed di-tert-butyl dicarbonate (1.12 g, 5.15 mmol) was then slowly added via syringe over 5 min and the reaction was allowed to warm to room temperature and stirred for a further 2 h. The reaction was taken up in saturated aqueous sodium hydrogencarbonate (50 mL) and ethyl acetate (100 mL). The organic layer was separated then dried (MgSO$_4$), filtered and evaporated. Purification by column chromatography (eluting with 1:1 ethyl acetate:hexanes to neat ethyl acetate) afforded the title compound (117 mg) as a white solid. $^1$H NMR δ (CDCl$_3$): 1.62 (s, 9H), 4.00 (br. s, 2H), 5.81 (d, 1H), 7.82 (d, 1H) 1,1-Dimethylethyl 3-amino-1H-pyrazole-1-carboxylate was also made by reacting a solution of 1H-pyrazol-3-amine in THF (1 g in approximately 15.6 mL) with NaHMDS (2M in THF, 1.05 equivalents) then adding a solution of di-tert-butyl dicarbonate (1 equivalent) in THF (approximately 1 g of dicarbonate in 1.9 mL) and stirring at RT. The resulting material was crystallised from a mixture of ethyl acetate and isohexane.

The preparation of 3-[(1S)-2-methoxy-(1-methylethyl)oxy]-5-{[phenylmethyl]oxy}benzoic acid was described earlier.

EXAMPLE 25

3-{[5-(Azetidin-1-ylcarbonyl)-3-chloropyridin-2-yl]oxy}-N-(1-methyl-1H-pyrazol-3-yl)-5-[(3S)-tetrahydrofuran-3-yloxy]benzamide

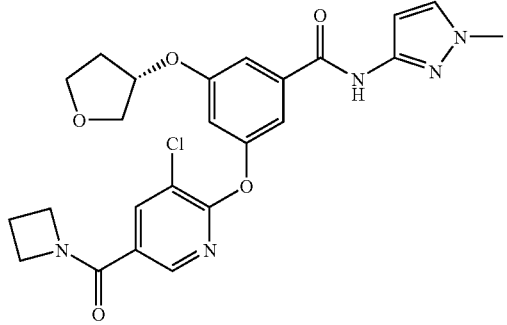

A mixture of 3-hydroxy-N-(1-methyl-1H-pyrazol-3-yl)-5-[(3S)-tetrahydrofuran-3-yloxy]benzamide (80 mg, 0.26 mmol), 5-(azetidin-1-ylcarbonyl)-2,3-dichloropyridine (61 mg, 0.26 mmol) and caesium carbonate (172 mg, 0.53 mmol) in acetonitrile (3 mL) was stirred in a Smith Creator microwave at 160° C. for 3 hours. The solvent was removed in vacuo and ethyl acetate (50 mL) added to the residue. The organic phase was washed with water (20 mL), brine (50 mL), dried (MgSO$_4$), filtered and the solvent removed in vacuo to give a yellow oil which was chromatographed on silica, eluting with a gradient of 0-10% methanol in DCM, to give the title compound as a yellow foam (52 mg).

$^1$H NMR δ (CDCl$_3$): 2.16-2.24 (2H, m), 2.34-2.44 (4H, m), 3.78 (3H, s), 3.89-4.01 (4H, m), 4.24 (2H, t), 4.37 (2H, t), 4.99 (1H, s), 6.80 (1H, s), 6.89 (1H, s), 7.23 (1H, s), 7.30 (2H, d), 8.16 (1H, s), 8.24 (1H, s), 8.73 (1H, s); m/z 498 (M+H)$^+$.

The preparation of 5-(azetidin-1-ylcarbonyl)-2,3-dichloropyridine was described earlier.

The preparation of 3-hydroxy-N-(1-methyl-1H-pyrazol-3-yl)-5-[(3S)-tetrahydrofuran-3-yloxy]benzamide is described below:

3-Hydroxy-N-(1-methyl-1H-pyrazol-3-yl)-5-[(3S)-tetrahydrofuran-3-yloxy]benzamide

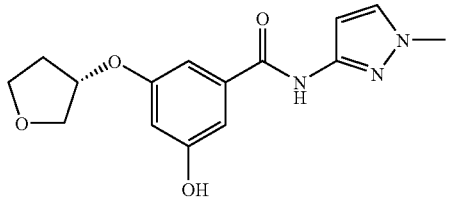

N-(1-Methyl-1H-pyrazol-3-yl)-3-[(phenylmethyl)oxy]-5-[(3S)-tetrahydrofuran-3-yloxy]benzamide (453 mg, 1.15 mmol) was dissolved in ethanol (5 mL) and ammonium formate (182 mg, 2.88 mmol) was added in one portion. The reaction was blanketed with argon and 10% palladium on activated carbon (30 mg) was added. This mixture was heated to 140° C. for 10 minutes in a Smith Creator microwave. The catalyst was filtered off and the volatiles removed in vacuo to give the title product as a white solid (339 mg).

$^1$H NMR δ (CDCl$_3$): 2.06-2.14 (1H, m), 2.15-2.22 (1H, m), 3.72-3.73 (3H, s), 3.84-3.89 (1H, m), 3.92-3.98 (3H, m), 4.88 (1H, m), 6.53 (1H, t), 6.78 (1H, d), 6.89 (1H, s), 6.95 (1H, s), 7.28 (1H, d), 9.27 (1H, s); m/z 304 (M+H)$^+$.

N-(1-Methyl-1H-pyrazol-3-yl)-3-[(phenylmethyl)oxy]-5-[(3S)-tetrahydrofuran-3-yloxy]benzamide

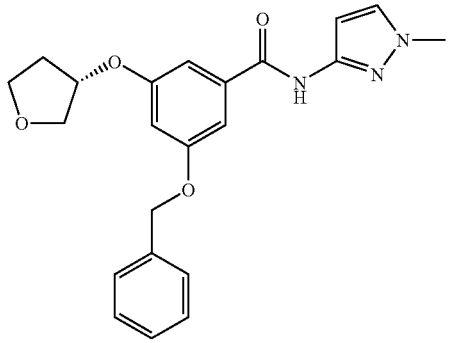

A suspension of 3-hydroxy-N-(1-methyl-1H-pyrazol-3-yl)-5-[(phenylmethyl)oxy]benzamide (450 mg, 1.39 mmol), (3R)-tetrahydrofuran-3-yl 4-methylbenzenesulfonate (507 mg, 2.09 mmol) and potassium carbonate (481 mg, 3.48 mmol) in acetonitrile (5 mL) was stirred in a Smith Creator microwave at 160° C. for 3 hours. The solvent was removed in vacuo and ethyl acetate added. The organics were washed with water (40 mL), brine (40 mL), dried (MgSO$_4$), filtered and the solvent removed in vacuo to give a yellow foam which was chromatographed on silica, eluting with a gradient of 0-100% ethyl acetate in iso-hexane, to give the title compound as a white foam (452 mg).

$^1$H NMR δ (CDCl$_3$): 2.09-2.14 (1H, m), 2.14-2.24 (1H, m), 3.68 (3H, s), 3.86-3.91 (1H, m), 3.94-3.98 (3H, m), 4.89 (1H, s), 5.03 (2H, s), 6.64 (1H, t), 6.85 (1H, s), 6.96 (1H, d), 7.07 (1H, t), 7.27 (1H, m), 7.33-7.41 (5H, m), 9.31 (1H, s); m/z 394 (M+H)$^+$.

(3R)-Tetrahydrofuran-3-yl 4-methylbenzenesulfonate

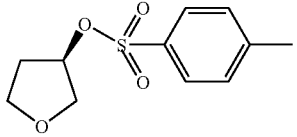

4-Toluene sulfonyl chloride (1.65 g, 8.63 mmol) was added to a solution of R-3-hydroxytetrahydrofuran (0.8 g, 9.08 mmol) and pyridine (0.88 mL, 10.9 mmol) in DCM (15 mL). The reaction was stirred at RT for 72 hours. Water (10 mL) and 1M hydrochloric acid (1 mL) were added and the mixture extracted with DCM (15 mL). The organic layer was washed with brine (20 mL), dried (MgSO$_4$), filtered and reduced in vacuo to give a yellow oil which was chromatographed on silica, eluting with a gradient of 0-50% ethyl acetate in iso-hexane, to give the desired compound (1.0 g). $^1$H NMR δ (CDCl$_3$): 2.13 (m, 2H), 2.47 (s, 3H), 3.80-3.95 (m, 4H), 5.15 (m, 1H), 7.37 (d, 2H), 7.81 (d, 2H).

3-Hydroxy-N-(1-methyl-1H-pyrazol-3-yl)-5-[(phenylmethyl)oxy]benzamide

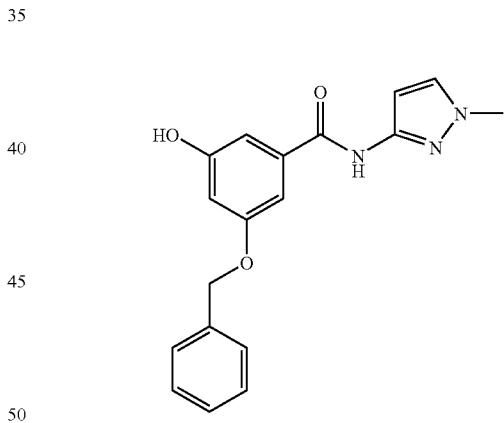

A suspension of N-(1-methyl-1H-pyrazol-3-yl)-3,5-bis[(phenylmethyl)oxy]benzamide (1.0 g, 2.42 mmol) was dissolved in ethanol (12 mL) and ammonium formate (229 mg, 3.63 mmol) was added in one portion. The reaction was blanketed with argon and 10% palladium on activated carbon (10 mg) was added. This mixture was heated to 140° C. for 5 minutes in a Smith Creator microwave. The catalyst was filtered off and the volatiles removed in vacuo, the residue was chromatographed on silica, eluting with a gradient of 30-100% ethyl acetate in iso-hexane, to give the title compound as a white solid (378 mg).

$^1$H NMR δ (d$_6$-DMSO): 3.78 (3H, s), 5.13 (2H, s), 6.55-6.57 (2H, m), 6.99 (1H, s), 7.17 (1H, s), 7.34-7.48 (5H, m), 7.60 (1H, d), 9.74 (1H, s), 10.70 (1H, s); m/z 324 (M+H)$^+$.

127

N-(1-Methyl-1H-pyrazol-3-yl)-3,5-bis[(phenylmethyl)oxy]benzamide

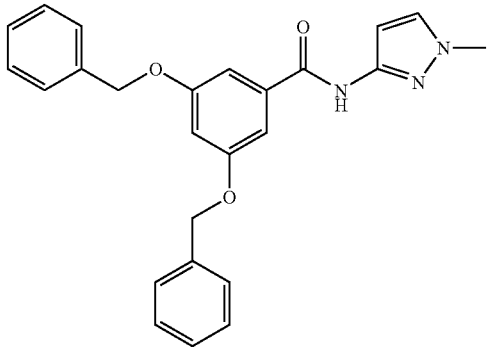

Oxalyl chloride (7.71 mL, 89.7 mmol) was added dropwise to a suspension of 3,5-dibenzyloxybenzoic acid (20.0 g, 59.8 mmol) in DCM (0.5 L) under argon. The reaction was stirred at RT for 6 hours after which time the volatiles were removed in vacuo. The residue was taken up in DCM (300 mL) and a solution of 1-methyl-1H-pyrazol-3-amine (5.81 g, 59.8 mmol) in DCM (50 mL) was added dropwise. The resulting solution was stirred for 16 hours at RT after which time a precipitate had formed. The solid was isolated by filtration and recrystallised from ethanol to give the title compound as a white solid (14.8 g). $^1$H NMR δ (d$_6$-DMSO): 3.84 (3H, s), 5.17 (4H, s), 6.59 (1H, d), 6.84 (1H, t), 7.33-7.46 (12H, m), 7.62 (1H, d), 10.83 (1H, s); m/z 414 (M+H)$^+$.

EXAMPLE 26

3-{[6-(Azetidin-1-ylcarbonyl)pyridin-3-yl]oxy}-N-(1-methyl-1H-pyrazol-3-yl)-5-[(3S)-tetrahydrofuran-3-yloxy]benzamide

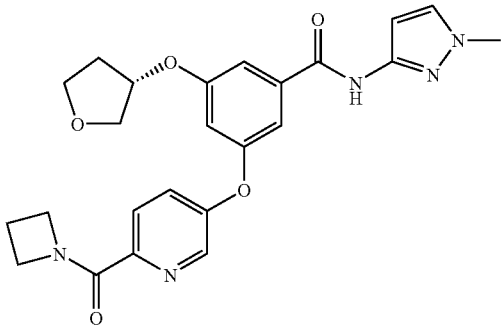

A mixture of 3-hydroxy-N-(1-methyl-1H-pyrazol-3-yl)-5-[(3S)-tetrahydrofuran-3-yloxy]benzamide (80 mg, 0.26 mmol), 2-(azetidin-1-ylcarbonyl)-5-bromopyridine (64 mg, 0.26 mmol), bromotris(triphenylphosphine)copper(I) (49 mg, 0.05 mmol) and caesium carbonate (257 mg, 0.78 mmol) in acetonitrile (3 mL) was stirred in a Smith Creator microwave at 160° C. for 6 hours. The solid was filtered off and the solvent was removed in vacuo and ethyl acetate (50 mL) added to the residue. The organic phase was washed with water (20 mL), brine (50 mL), dried (MgSO$_4$), filtered and the solvent removed in vacuo to give a yellow oil which was chromatographed on silica, eluting with a gradient of 0-10% methanol in DCM, to give the title compound as a colourless solid (58 mg). This compound was crystallised from ethyl acetate and isohexane using vapour diffusion techniques. $^1$H NMR δ (CDCl$_3$): 2.11-2.17 (1H, m), 2.20-2.29 (1H, m), 2.32-2.39 (2H, m), 3.78 (3H, s), 3.88-3.93 (1H, m), 3.96-4.02 (3H, m), 4.25 (2H, t), 4.71 (2H, t), 4.97 (1H, t), 6.73 (1H, t), 6.79 (1H, s), 7.11 (1H, s), 7.22 (1H, s), 7.27-7.30 (1H, m), 7.36-7.39 (1H, m), 8.12 (1H, d), 8.32 (1H, d), 8.73 (1H, s); m/z 464 (M+H)$^+$.

The preparation of 3-hydroxy-N-(1-methyl-1H-pyrazol-3-yl)-5-[(3S)-tetrahydrofuran-3-yloxy]benzamide and 2-(azetidin-1-ylcarbonyl)-5-bromopyridine was described earlier.

EXAMPLE 27

3-{[5-(Azetidin-1-ylcarbonyl)pyrazin-2-yl]oxy}-N-(1-methyl-1H-pyrazol-3-yl)-5-[(3S)-tetrahydrofuran-3-yloxy]benzamide

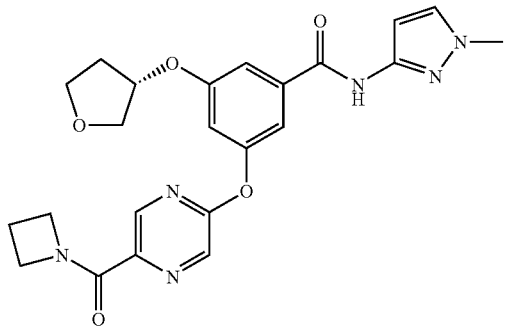

A mixture of 3-hydroxy-N-(1-methyl-1H-pyrazol-3-yl)-5-[(3S)-tetrahydrofuran-3-yloxy]benzamide (80 mg, 0.26 mmol), 2-(azetidin-1-ylcarbonyl)-5-chloropyrazine (52 mg, 0.26 mmol) and caesium carbonate (172 mg, 0.53 mmol) in acetonitrile (3 mL) was stirred in a Smith Creator microwave at 160° C. for 1 hr. The solvent was removed in vacuo and ethyl acetate (50 mL) added to the residue. The organic phase was washed with water (20 mL), brine (50 mL), dried (MgSO$_4$), filtered and the solvent removed in vacuo to give a yellow oil which was chromatographed on silica eluting with a gradient of 0-10% methanol in DCM to give the title compound (36 mg, 31%) as a white foam. This compound was crystallised from ethyl acetate and isohexane using vapour diffusion techniques. $^1$H NMR δ (CDCl$_3$): 2.12-2.19 (1H, m), 2.21-2.28 (1H, m), 2.34-2.42 (2H, m), 3.75 (3H, s), 3.88-3.93 (1H, m), 3.98-4.02 (3H, m), 4.23 (2H, t), 4.69 (2H, t), 4.95-4.97 (1H, m), 6.80 (1H, d), 6.87 (1H, t), 7.23 (1H, d), 7.27-7.30 (1H, m), 7.28-7.30 (1H, m), 8.34 (1H, d), 8.84 (1H, d), 8.98 (1H, s); m/z 465 (M+H)$^+$.

The preparation of 3-hydroxy-N-(1-methyl-1H-pyrazol-3-yl)-5-[(3S)-tetrahydrofuran-3-yloxy]benzamide was described earlier.

The preparation of 2-(azetidin-1-ylcarbonyl)-5-chloropyrazine is described below:

2-(Azetidin-1-ylcarbonyl-5-chloropyrazine

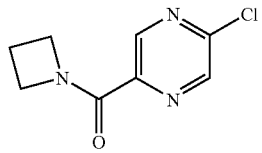

Oxalyl chloride (1.55 mL, 17.48 mmol), followed by DMF (2 drops), was added to a mixture of 5-chloropyrazine-2-carboxylic acid (2.31 g, 14.57 mmol) in DCM (40 mL). The reaction was stirred at RT for 2 hours after which time the volatiles were removed in vacuo. The residue was taken up DCM (40 mL) and azetidine (1.08 mL, 16.03 mmol) and triethylamine (4.46 mL, 32.06 mmol) added. The mixture was stirred at RT for 72 hours. The volatiles were removed in vacuo and ethyl acetate (100 mL) added to the residue. The organics were washed with water (100 mL), citric acid (50 mL), saturated sodium bicarbonate solution (50 mL), brine (50 mL), dried (MgSO$_4$), filtered and the solvent removed in vacuo to give a yellow solid. The residue was chromatographed on silica, eluting with a gradient of 50-100% ethyl acetate in iso-hexane, to give the desired compound as a yellow solid (2.38 g). $^1$H NMR δ (CDCl$_3$): 2.35-2.42 (2H, m), 4.26 (2H, t), 4.67 (2H, t), 8.52 (1H, d), 9.09 (1H, d); m/z 198 (M+H)$^+$.

5-Chloropyrazine-2-carboxylic acid

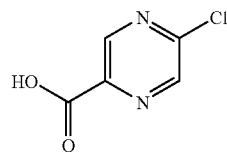

To a solution of methyl-5-chloropyrazine-2-carboxylate (120 mg, 0.70 mmol) in a mixture of acetonitrile (2 mL) and DMF (1 mL) was added lithium chloride (295 mg, 6.95 mmol). The suspension was heated to 160° C. for 5 mins in a Smith creator microwave after which time the reaction was diluted with water (10 mL). Saturated sodium bicarbonate solution (20 mL) was added and the aqueous layered extracted twice with ethyl acetate (30 mL). The combined organics were discarded and the aqueous layer adjusted to pH 4 with 1N hydrochloric acid. The aqueous phase was extracted twice with ethyl acetate (20 mL) and the combined organics washed with water (2×20 mL), brine (10 mL) and dried (MgSO$_4$). The volatiles were removed to give the title compound as a colourless solid (68 mg).
$^1$H NMR δ (CDCl$_3$): 7.20 (1H, br s), 8.72 (1H, s), 9.21-9.21 (1H, m); m/z 157 (M−H)$^+$.

EXAMPLE 28

3-{[4-(Azetidin-1-ylcarbonyl)-1,3-thiazol-2-yl]oxy}-5-{[(1S)-1-methyl-2-(methyloxy)ethyl]oxy}-N-(1-methyl-1H-pyrazol-3-yl)benzamide

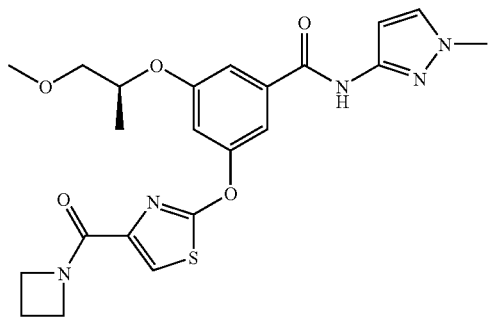

Cesium carbonate (488 mg, 1.5 mmol) was added to a solution of 3-hydroxy-5-[(1S)-2-methoxy-(1-methylethyl)oxy]-N-(1-methyl-1H-pyrazol-3-yl)benzamide (153 mg, 0.5 mmol) and 4-(azetidin-1-ylcarbonyl)-2-bromo-1,3-thiazole (206 mg, 0.75 mmol) in acetonitrile (5 mL) and the stirred mixture heated at 150° C. in a Biotage Initiator Microwave apparatus for 8 hours. The mixture was cooled to RT and pressure, poured onto water (75 mL) and extracted with ethyl acetate (3×25 mL). The combined organic layers were washed with brine, dried (MgSO$_4$) and evaporated to a residue which was chromatographed on silica, eluting with ethyl acetate, to give the desired material (95 mg).
$^1$H NMR δ (CDCl$_3$): 1.3 (d, 3H), 2.2 (m, 2H), 3.3 (s, 3H), 3.4-3.55 (m, 2H), 3.7 (s, 3H), 4.1 (t, 2H), 4.4 (t, 2H), 4.5 (m, 1H), 6.7 (s, 1H), 6.95 (s, 1H), 7.25 (s, 1H), 7.3 (s, 2H), 7.35 (s, 1H), 7.65 (s, 1H) and 8.8 (s, 1H); m/z 472 (M+H)$^+$.

The following compound was prepared in an analogous fashion from 4-(azetidin-1-ylcarbonyl)-2-bromo-1,3-thiazole and 3-hydroxy-5-[(1-methylethyl)oxy]-N-(1-methyl-1H-pyrazol-3-yl)benzamide

| Example | Structure | m/z | NMR |
|---|---|---|---|
| 28a | 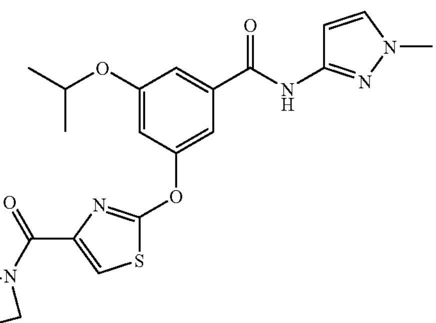 | 442 (M + H)$^+$ | $^1$H NMR δ (CDCl$_3$): 1.3 (d, 6H), 2.2 (m, 2H), 3.7 (s, 3H), 4.1 (m, 2H), 4.4 (m, 2H), 4.5 (m, 1H), 6.7 (s, 1H), 6.9 (s, 1H), 7.25 (d, 2H), 7.3 (s, 1H), 7.65 (s, 1H) and 9.0 (s, 1H). |

The preparation of 3-hydroxy-5-[(1S)-2-methoxy-(1-methylethyl)oxy]-N-(1-methyl-1H-pyrazol-3-yl)benzamide and 3-hydroxy-5-[(1-methylethyl)oxy]-N-(1-methyl-1H-pyrazol-3-yl)benzamide was described earlier The preparation of 4-(azetidin-1-ylcarbonyl)-2-bromo-1,3-thiazole is described below:

4-(Azetidin-1-ylcarbonyl)-2-bromo-1,3-thiazole

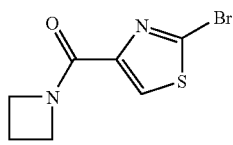

To a solution of 2-bromothiazole-5-carboxylic acid (752 mg, 3.62 mmol) in DCM (10 mL) was slowly added oxalyl chloride (0.38 mL, 4.34 mmol) and then DMF (1 drop). The mixture was stirred for 4 hours, following which the organics were removed in vacuo, and the residues azeotroped with toluene (10 mL). The crude material was dissolved in DCM (10 mL) and slowly added to a stirred suspension of azetidine hydrochloride (404 mg, 4.34 mmol) and triethylamine (1.8 mL, 13 mmol) in DCM (25 mL). The mixture was stirred at RT for 2 hours before the organics were removed in vacuo. The residue was partitioned between ethyl acetate (50 mL) and water (25 mL), the organic layer washed with brine (25 mL), dried (MgSO$_4$) and evaporated to a residue which was chromatographed on silica, eluting with 40% ethyl acetate in iso-hexane, to give the desired compound (500 mg).
$^1$H NMR δ (CDCl$_3$): 2.3 (m, 2H), 4.15 (m, 2H), 4.6 (m, 2H) and 8.0 (s, 1H); m/z 249 (M+H)$^+$.

EXAMPLE 29

3-{[5-(Azetidin-1-ylcarbonyl)pyrazin-2-yl]oxy}-5-{[(1S)-1-(hydroxymethyl)propyl]oxy}-N-(1-methyl-1H-pyrazol-3-yl)benzamide

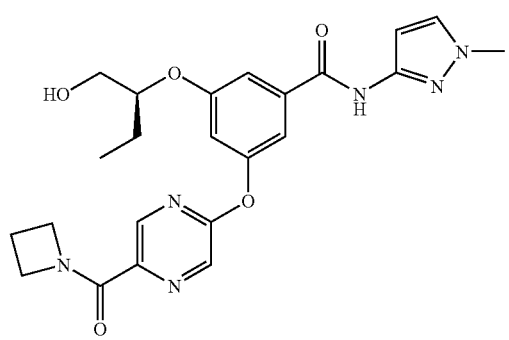

A solution of 5-[(3-{[(is)-1-(hydroxymethyl)propyl]oxy}-5-{[(1-methyl-1H-pyrazol-3-yl)amino]carbonyl}phenyl)oxy]pyrazine-2-carboxylic acid (12 mg, 0.03 mmol), azetidine hydrochloride (4 mg, 0.06 mmol), HATU (14 mg, 0.04 mmol) and DIPEA (0.02 mL, 0.11 mmol) in DMF (1 mL) was stirred at RT over the weekend. Water (15 mL) was added and the solution extracted with ethyl acetate (25 mL). The ethyl acetate layer was washed with brine (20 mL), dried (MgSO$_4$), and evaporated to a residue which was chromatographed by preparative HPLC on C18 reversed phase, eluting with 5-95% acetonitrile (+0.2% TFA) in water (+0.2% TFA), to give the required product along with 15% of a co-eluting impurity (5 mg). $^1$H NMR δ (CDCl$_3$): 0.92 (t, 3H), 0.97 (t, 0.45H), 1.69 (quin, 2H), 1.76 (m, 0.3H), 2.34 (quin, 2H), 3.76 (m, 2H), 3.86 (s, 3H), 4.23 (t, 2H), 4.49 (sextet, 1H), 4.66 (t, 2H), 4.77 (m, 0.15H), 6.93 (t, 1H), 6.99 (d, 1H), 7.34 (s, 1H), 7.46 (s, 1H), 7.50 (s, 1H), 8.29 (s, 1H), 8.78 (s, 1H), 10.68 (s, 1H), 10.78 (s, 0.15H); m/z 468 (M+H)$^+$ The spectroscopic data is consistent with 15% of the following impurity 3-{[5-(azetidin-1-ylcarbonyl)pyrazin-2-yl]oxy}-5-{[(2S)-2-hydroxybutyl]oxy}-N-(1-methyl-1H-pyrazol-3-yl)benzamide.

The preparation of 5-[(3-{[(1S)-1-(hydroxymethyl)propyl]oxy}-5-{[(1-methyl-1H-pyrazol-3-yl)amino]carbonyl}phenyl)oxy]pyrazine-2-carboxylic acid is described below:

5-[(3-{[(1S)-1-(Hydroxymethyl)propyl]oxy}-5-{[(1-methyl-1H-pyrazol-3-yl)amino]carbonyl}phenyl)oxy]pyrazine-2-carboxylic acid

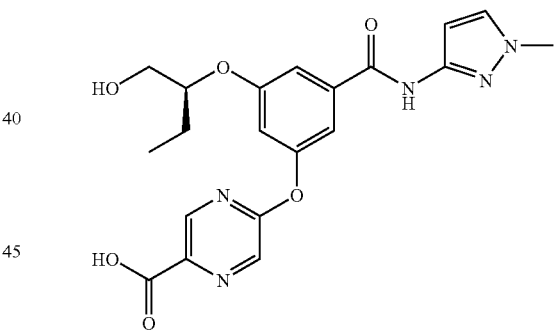

Lithium hydroxide monohydrate (6 mg, 0.14 mmol) in water (1 mL) was added to a solution of methyl 5-[(3-{[(1S)-1-(hydroxymethyl)propyl]oxy}-5-{[(1-methyl-1H-pyrazol-3-yl)amino]carbonyl}phenyl)oxy]pyrazine-2-carboxylate (25 mg, 0.06 mmol) in THF (1 mL). The mixture was allowed to stir at RT for 16 hours. The THF was removed in vacuo and the resulting solution was partitioned between water (10 mL) and ethyl acetate (25 mL), the ethyl acetate layer was washed with brine (10 mL) and dried (MgSO$_4$). The aqueous layer was then adjusted to pH 7 by addition of 1M hydrochloric acid and extracted with ethyl acetate (25 mL). The ethyl acetate layer was washed with brine (10 mL) and dried (MgSO$_4$). The ethyl acetate extracts were combined and evaporated to give the required product (12 mg). m/z 428.44 (M+H)$^+$

133

Methyl 5-[(3-{[(1S)-1-(hydroxymethyl)propyl]oxy}-5-{[(1-methyl-1H-pyrazol-3-yl)amino]carbonyl}phenyl)oxy]pyrazine-2-carboxylate

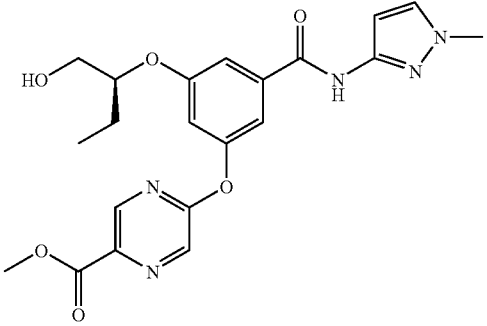

Methyl 5-chloropyrazine-2-carboxylate (104 mg, 0.60 mmol) and cesium carbonate (467 mg, 1.43 mmol) were added to a solution of 3-hydroxy-5-{[(1S)-1-(hydroxymethyl)propyl]oxy}-N-(1-methyl-1H-pyrazol-3-yl)benzamide (175 mg, 0.570 mmol), in acetonitrile (5 mL) and the mixture heated in a microwave reactor at 160° C. for 330 minutes. The acetonitrile was removed in vacuo and the residue dissolved in ethyl acetate (25 mL), washed with water (20 mL), brine (20 mL), dried (MgSO$_4$) and evaporated to a residue which was chromatographed by preparative HPLC on C18 reversed phase, eluting with 5-95% acetonitrile (+0.2% TFA) in water (+0.2% TFA), to give the required product (41 mg). $^1$H NMR δ (CDCl$_3$): 0.97 (t, 3H), 1.78 (quin, 2H), 3.82 (s, 3H), 3.91 (s, 3H), 4.52 (m, 3H), 4.66 (quin, 1H), 6.59 (t, 1H), 6.89 (d, 1H), 7.05 (t, 1H), 7.15 (t, 1H), 8.19 (d, 1H), 8.79 (d, 1H), 9.86 (s, 1H); m/z 442 (M+H)$^+$ 3-Hydroxy-5-{[(1S)-1-(hydroxymethyl)propyl]oxy}-N-(1-methyl-1H-pyrazol-3-ylbenzamide

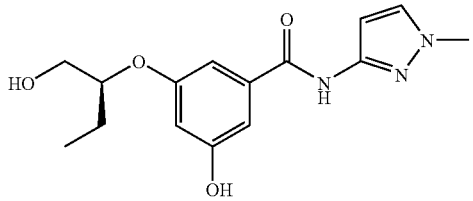

To a solution of 3-hydroxy-5-({(1S)-1-[(methyloxy)methyl]propyl}oxy)-N-(1-methyl-1H-pyrazol-3-yl)benzamide (500 mg, 1.6 mmol) in acetonitrile (25 mL), iodotrimethylsilane (1.11 mL, 7.8 mmol) was added and the resulting mixture stirred for 16 hours. Saturated sodium hydrogencarbonate solution (10 mL) was added, the solution stirred for 10 mins, saturated aqueous sodium thiosulfate (5 mL) was added then the acetonitrile was removed in vacuo. The residual aqueous layer was extracted with ethyl acetate (3×40 mL) and the organic layers combined, dried (MgSO$_4$), filtered and evaporated and purified by column chromatography, eluting with 85% ethyl acetate in isohexane, to give the title compound as a colourless foam (405 mg). $^1$H NMR δ (d$_6$-DMSO): 0.95 (t, 3H), 1.5-1.8 (m, 2H), 3.5 (m, 2H), 3.8 (s, 3H), 4.3 (m, 1H), 4.8 (t, 1H), 6.45 (s, 1H), 6.55 (s, 1H), 6.9 (s, 1H), 7.05 (s, 1H), 7.55 (s, 1H), 9.6 (s, 1H); m/z 306 (M+H)$^+$

134

3-Hydroxy-5-({(1S)-1-[(methyloxy)methyl]propyl}oxy)-N-(1-methyl-1H-pyrazol-3-yl)benzamide

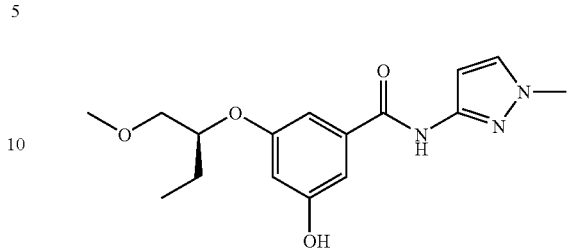

To a solution of 3-({(1S)-1-[(methyloxy)methyl]propyl}oxy)-N-(1-methyl-1H-pyrazol-3-yl)-5-[(phenylmethyl)oxy]benzamide (4.6 g, 11 mmol) in 1:1 THF:methanol (100 mL) was added 10% w/w palladium on carbon (450 mg) and the resulting mixture was stirred under an atmosphere of hydrogen for 6 hours. The atmosphere was replaced with argon and the mixture was filtered and evaporated to afford the title compound as a white solid (3.6 g).

$^1$H NMR δ (CDCl$_3$): 0.95 (t, 3H), 1.7 (m, 2H), 3.4 (s, 3H), 3.55 (m, 2H), 3.8 (s, 3H), 4.3 (m, 1H), 6.65 (s, 1H), 6.8 (s, 1H), 7.0 (m, 2H), 7.2 (m, 1H), 7.3 (s, 1H), 8.7 (s, 1H); m/z 320 (M+H)$^+$ 3-({(1S)-1-[(Methyloxy)methyl]propyl}oxy)-N-(1-methyl-1H-pyrazol-3-yl)-5-[(phenylmethyl)oxy]benzamide

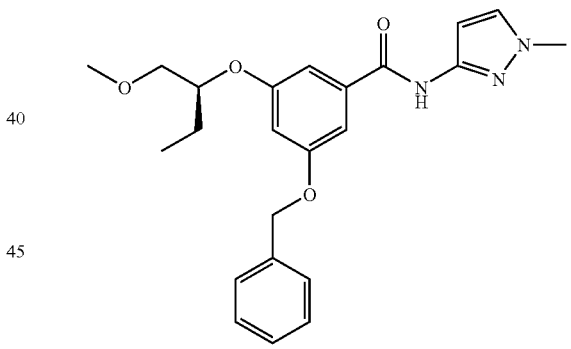

To a solution of 3-({(is)-1-[(methyloxy)methyl]propyl}oxy)-5-[(phenylmethyl)oxy]benzoic acid (4.75 g, 14.4 mmol) and 3-amino-1-methyl-1H-pyrazole (2.04 g, 21 mmol) in DMF (25 mL) was added HATU (8.53 g, 22.4 mmol) then DIPEA (7.0 mL, 40 mmol) and the resulting mixture was stirred for 16 hours. The mixture was partitioned between ethyl acetate (100 mL) and water (30 mL). The organic layer was separated, washed with 1N citric acid (30 mL), water (30 mL), saturated sodium bicarbonate (30 mL), water (30 mL) and brine (30 mL) then dried (MgSO$_4$) and evaporated. The residue was purified by column chromatography, eluting with 50% ethyl acetate in isohexane, to give the title compound as a colourless oil (4.57 g).

$^1$H NMR δ (CDCl$_3$): 0.95 (t, 3H), 1.7 (m, 2H), 3.4 (s, 3H), 3.55 (m, 2H), 3.8 (s, 3H), 4.3 (m, 1H), 5.05 (s, 2H), 6.75 (s, 1H), 6.8 (s, 1H), 7.05 (d, 2H), 7.25 (s, 1H), 7.4 (m, 5H), 8.45 (s, 1H); m/z 410 (M+H)$^+$

3-({(1S)-1-[(Methyloxy)methyl]propyl}oxy)-5-[(phenylmethyl)oxy]benzoic acid

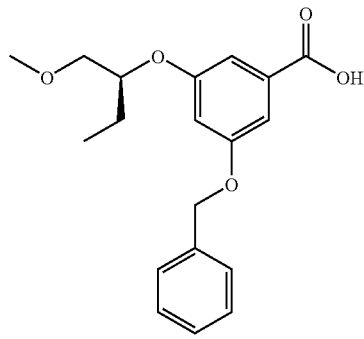

To a solution of methyl 3-({(1S)-1-[(methyloxy)methyl]propyl}oxy)-5-[(phenylmethyl)oxy]benzoate (6.85 g, 20 mmol) in 3:1 THF:methanol (100 mL) was added 1N lithium hydroxide solution in water (40 mL, 40 mmol), then a further 100 mL water was added portionwise at intervals while the resulting mixture was stirred for 2 hours. The organic solvents were removed by evaporation and the cloudy solution filtered. The pH of the filtrate was adjusted to 3 by the addition of 2 M hydrochloric acid. This was extracted with ethyl acetate (3×70 mL). The combined organic extracts were dried (MgSO$_4$) and evaporated to afford the title compound as a colourless oil which solidified (6.36 g).

$^1$H NMR δ (CDCl$_3$): 0.95 (t, 3H), 1.7 (m, 2H), 3.4 (s, 3H), 3.55 (m, 2H), 4.3 (m, 1H), 5.05 (s, 2H), 6.8 (s, 1H), 7.3-7.5 (m, 7H); m/z 329 (M−H)$^-$

Methyl 3-({(1S)-1-[(methyloxy)methyl]propyl}oxy)-5-[(phenylmethyl)oxy]benzoate

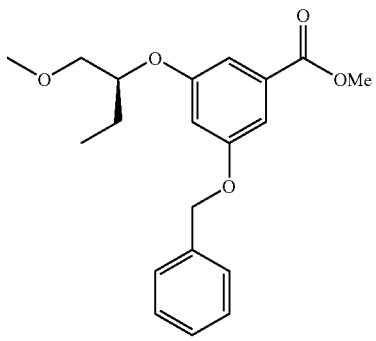

A stirred solution of methyl 3-hydroxy-5-{[phenylmethyl]oxy}benzoate (7.5 g, 29 mmol), (R)-1-methoxy-butan-2-ol (3.76 g, 36.25 mmol) and triphenylphosphine (9.5 g, 36.25 mmol) in dry THF (75 mL) was cooled in an ice-bath and a solution of 40% DEAD in toluene (15.8 mL, 36.25 mmol) was added dropwise over 30 minutes. The reaction mixture was allowed to warm slowly to 10° C. and stirred for 16 hours. The THF was evaporated and the residue was dissolved in 30% ethyl acetate in isohexane and cooled in ice. The resultant precipitate was removed by filtration and washed with 10% ethyl acetate in isohexane. The filtrate was evaporated and purified by column chromatography, eluting with 10% ethyl acetate in isohexane, to give the title compound as a colourless oil (6.85 g).

$^1$H NMR δ (CDCl$_3$): 0.95 (t, 3H), 1.7 (m, 2H), 3.35 (s, 3H), 3.55 (m, 2H), 3.9 (s, 3H), 4.3 (m, 1H), 5.05 (s, 2H), 6.8 (s, 1H), 7.25 (m, 2H), 7.4 (m, 5H); m/z 345 (M+H)$^+$

The preparation of (R)-1-methoxy-butan-2-ol was described in the literature [Coke, J. L.; Shue, R. S., *J. Org. Chem.* 38, (1973), 2210-2211].

The preparation of methyl 3-hydroxy-5-{[phenylmethyl]oxy}benzoate was described earlier.

EXAMPLE 30

3-{[2-(Azetidin-1-ylcarbonyl)pyrimidin-5-yl]oxy}-5-{[(1S)-1-methyl-2-(methyloxy)ethyl]oxy}-N-1,3-thiazol-2-ylbenzamide

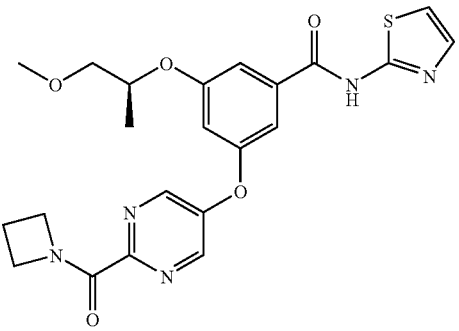

A mixture of 3-hydroxy-5-{[(1S)-2-methoxy-(1-methylethyl)oxy}-N-1,3-thiazol-2-ylbenzamide (130 mg, 0.42 mmol), 2-(azetidin-1-ylcarbonyl)-5-bromopyrimidine (113 mg, 0.46 mmol), cesium carbonate (412 mg, 1.26 mmol) and bromotris(triphenylphosphine)copper(I) (118 mg, 0.13 mmol) in DMA (5 mL) was stirred in the a microwave reactor at 160° C. for 4 hours. Ethyl acetate (50 mL) was added to the residue and the organics washed with water (20 mL), brine (50 mL), dried (MgSO$_4$), filtered and the solvent removed in vacuo to give a brown oil. The residue was chromatographed on silica, eluting with a gradient of 0-10% methanol in ethyl acetate, to give the desired compound (67 mg). $^1$H NMR δ (CDCl$_3$): 1.34 (d, 3H), 2.38 (quintet, 2H), 3.40 (s, 3H), 3.49-3.61 (m, 2H), 4.29 (t, 2H), 4.59-4.67 (m, 3H), 6.92 (t, 1H), 6.98 (d, 1H), 7.23 (d, 1H), 7.44 (t, 1H), 7.49 (t, 1H), 8.54 (s, 2H), 11.96 (s, 1H); m/z 470 (M+H)$^+$ The preparation of 3-hydroxy-5-{[(1S)-2-methoxy-(1-methylethyl)oxy}-N-1,3-thiazol-2-ylbenzamide was described earlier.

The preparation of 2-(azetidin-1-ylcarbonyl)-5-bromopyrimidine is described below:

2-(Azetidin-1-ylcarbonyl)-5-bromopyrimidine

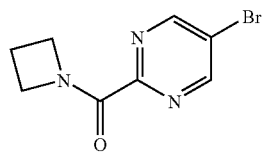

Oxalyl chloride (1.50 mL, 16.79 mmol), followed by DMF (2 drops), were added to a mixture of 5-bromopyrimidine-2-carboxylic acid (2.86 g, 14.0 mmol) in DCM (40 mL). The reaction was stirred at RT for 2 hours, the volatiles removed in vacuo and the residue dissolved in DCM (40 mL). Azetidine hydrochloride (1.44 g, 15.39 mmol), followed by triethylamine (4.29 mL, 30.78 mmol), were added and the mixture stirred at RT for 72 hours. The mixture was concentrated in vacuo and ethyl acetate (100 mL) added to the residue. The organics were washed with water (100 mL), citric acid (50 mL), saturated sodium bicarbonate solution (50 mL), brine (50 mL), dried (MgSO$_4$), filtered and the solvent removed in vacuo to give a yellow solid. The solid was chromatographed on silica, eluting with a gradient of 50-100% ethyl acetate in isohexane, to give the desired compound as a yellow solid (0.86 g).

hours at 120° C. in a microwave reactor. The mixture was cooled, filtered and concentrated in vacuo. The crude product was chromatographed on silica, eluting with 0-5% methanol in DCM, to give the required product as a white foam (282 mg).

$^1$H NMR δ (d$_6$-DMSO): 1.61 (m, 2H), 1.74 (m, 4H), 1.94 (m, 2H), 2.30 (m, 2H), 3.78 (s, 3H), 4.10 (t, 2H), 4.57 (t, 2H), 4.94 (m, 1H), 6.57 (d, 1H), 7.01 (t, 1H), 7.42 (m, 1H), 7.47 (m, 1H), 7.60 (d, 1H), 8.55 (d, 1H), 8.68 (d, 1H), 10.80 (s, 1H). m/z 463 (M+H)$^+$

The following compound was made in an analogous fashion from 3-(cyclopentyloxy)-5-hydroxy-N-(1-methyl-1H-pyrazol-3-yl)benzamide and 5-(azetidin-1-ylcarbonyl)-2,3-dichloropyridine.

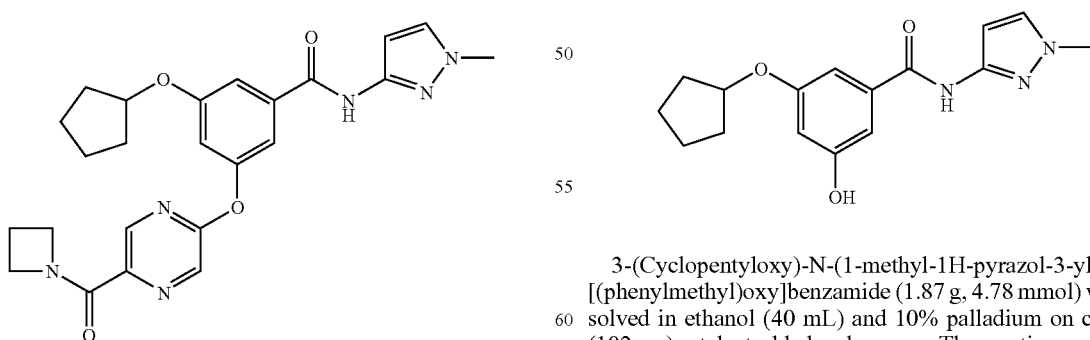

| Example | Structure | m/z | $^1$H NMR (d$_6$-DMSO) |
|---|---|---|---|
| 31a | 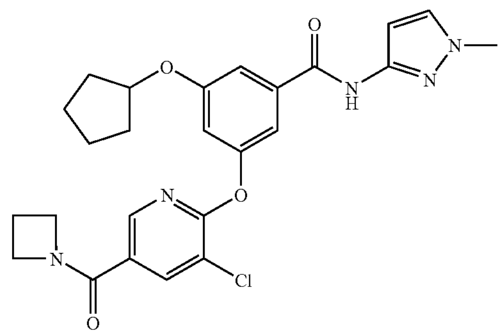 | 496 (M + H)$^+$ | δ: 1.69 (m, 2H), 1.82 (m, 4H), 2.03 (m, 2H), 2.34 (m, 2H), 3.99 (s, 3H), 4.14 (t, 2H), 4.45 (t, 2H), 5.03 (m, 1H), 6.65 (d, 1H), 7.06 (t, 1H), 7.47 (t, 1H), 7.54 (t, 1H), 7.68 (d, 1H), 8.30 (d, 1H), 8.42 (d, 1H), 10.87 (s, 1H). |

The preparation of 5-bromopyrimidine-2-carboxylic acid is described in the literature (International Patent Application WO 2005/028452).

EXAMPLE 31

3-{[5-(Azetidin-1-ylcarbonyl)pyrazin-2-yl]oxy}-5-(cyclopentyloxy)-N-(1-methyl-1H-pyrazol-3-yl)benzamide 3-(Cyclopentyloxy)-5-hydroxy-N-(1-methyl-1H-pyrazol-3-yl)benzamide (200 mg, 0.67 mmol), 2-(azetidin-1-ylcarbonyl)-5-chloropyrazine (159 mg, 0.80 mmol) and potassium carbonate (184 mg, 1.33 mmol) were dissolved/suspended in acetonitrile (3.5 mL). The reaction mixture was heated for 4

The preparations of 2-(azetidin-1-ylcarbonyl)-5-chloropyrazine and 5-(azetidin-1-ylcarbonyl)-2,3-dichloropyridine were described earlier.

The preparation of 3-(cyclopentyloxy)-5-hydroxy-N-(1-methyl-1H-pyrazol-3-yl)benzamide is described below:

3-(Cyclopentyloxy)-5-hydroxy-N-(1-methyl-1H-pyrazol-3-yl)benzamide 3-(Cyclopentyloxy)-N-(1-methyl-1H-pyrazol-3-yl)-5-[(phenylmethyl)oxy]benzamide (1.87 g, 4.78 mmol) was dissolved in ethanol (40 mL) and 10% palladium on charcoal (102 mg) catalyst added under argon. The reaction was stirred under an atmosphere of hydrogen for 86 hours, then filtered through Celite® and concentrated in vacuo to a light brown solid (1.31 g). $^1$H NMR δ (d$_6$-DMSO): 1.54 (m, 2H), 1.76 (m, 4H), 1.96 (m, 2H), 2.75 (s, 1H), 3.83 (s, 3H), 4.91 (m, 1H), 6.49 (m, 1H), 6.61 (m, 1H), 6.98 (m, 1H), 7.06 (m, 1H), 7.65 (s, 1H), 9.73 (br s, 1H); m/z 302 (M+H)$^+$

3-(Cyclopentyloxy)-N-(1-methyl-1H-pyrazol-3-yl)-5-[(phenylmethyl)oxy]benzamide

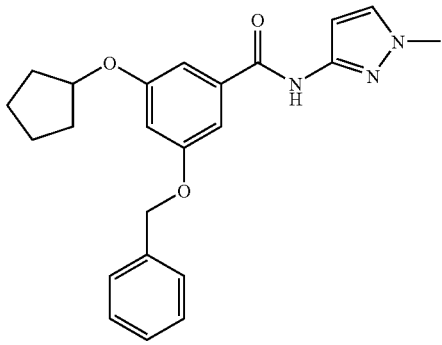

3-(Cyclopentyloxy)-5-[(phenylmethyl)oxy]benzoic acid (3.14 g, 10.0 mmol), 1-methyl-1H-pyrazol-3-amine (1.95 g, 20 mmol) and HATU (4.95 g, 13 mmol) were dissolved in DMF (12.5 mL) then DIPEA (3.49 mL, 20 mmol) was added. The resultant mixture was stirred at RT for 20 hours. The mixture was quenched with water (150 mL) and extracted with ethyl acetate (2×75 mL), washed with brine, dried (MgSO$_4$), filtered and concentrated in vacuo to leave a yellow oil. The residue was chromatographed on silica, eluting with 0-30% ethyl acetate in isohexane, to give the desired product as a clear gum (1.87 g).

$^1$H NMR δ (CDCl$_3$): 1.59 (m, 4H), 1.83 (m, 4H), 3.79 (s, 3H), 4.76 (m, 1H), 5.08 (s, 2H), 6.66 (t, 1H), 6.82 (m, 1H), 7.01 (m, 1H), 7.08 (m, 1H), 7.26 (m, 1H), 7.33 (m, 1H), 7.35-7.45 (m, 4H), 8.67 (s, 1H); m/z 392 (M+H)$^+$

3-(Cyclopentyloxy)-5-[(phenylmethyl)oxy]benzoic acid

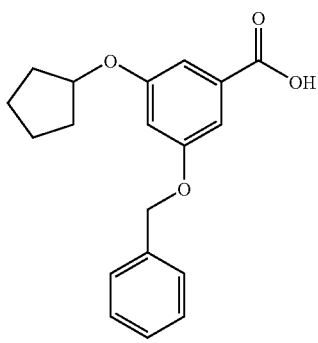

Methyl 3-(cyclopentyloxy)-5-[(phenylmethyl)oxy]benzoate (9.25 g, 28.34 mmol) was dissolved in THF (120 mL) and a solution of lithium hydroxide mono hydrate (3.49 g, 85.0 mmol) in water (60 mL) added. The bi-phasic solution was stirred at RT for 16 hours (LCMS indicated reaction 80% complete), methanol (15 mL) added and the mixture stirred for a further 4 hours. The THF was removed in vacuo then water (40 mL) added and the pH adjusted to 7 with hydrochloric acid. The solid was collected and washed thoroughly with cold water (8.85 g).

$^1$H NMR δ (d$_6$-DMSO): 1.64 (m, 2H), 1.76 (m, 4H), 1.96 (m, 2H), 4.89 (m, 1H), 5.19 (s, 2H), 6.80 (s, 1H), 7.07 (s, 1H), 7.16 (s, 1H), 7.34-7.53 (m, 5H); m/z 311 (M+H)$^+$

Methyl 3-(cyclopentyloxy)-5-[(phenylmethyl)oxy]benzoate

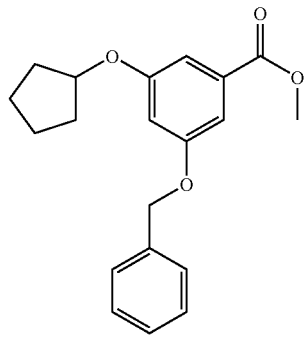

Methyl 3-hydroxy-5-{[phenylmethyl]oxy}benzoate (10 g, 38.7 mmol), 1-cyclopentanol (6.135 mL, 58.07 mmol) and triphenylphosphine (15.24 g, 58.07 mmol) were stirred under argon in THF (166 mL) and cooled in an ice bath to 5° C. DEAD (25.3 mL, 58.1 mmol) was added dropwise to the mixture, maintaining the internal temperature in the range 5-10° C. Stirring was continued for 16 hours. The mixture was concentrated in vacuo, re-dissolved in ethyl acetate (60 mL) and isohexane (60 mL), the resultant precipitate removed and the solution concentrated in vacuo to give a yellow oil. The residue was chromatographed on silica, eluting with 0-30% ethyl acetate in isohexane, to give a colourless oil which crystallised to a white solid under vacuum.

$^1$H NMR δ (CDCl$_3$): 1.62 (m, 2H), 1.71-1.98 (m, 6H), 3.90 (s, 3H), 4.76 (m, 1H), 5.08 (s, 2H), 6.69 (m, 1H), 7.16 (m, 1H), 7.23 (m, 1H), 7.29-7.44 (m, 5H); m/z 325 (M+H)$^+$

The preparation of methyl 3-hydroxy-5-{[phenylmethyl]oxy}benzoate was described earlier.

EXAMPLE 32

3-{[6-(Azetidin-1-ylcarbonyl)pyridin-3-yl]oxy}-5-(cyclopentyloxy)-N-(1-methyl-1H-pyrazol-3-yl)benzamide

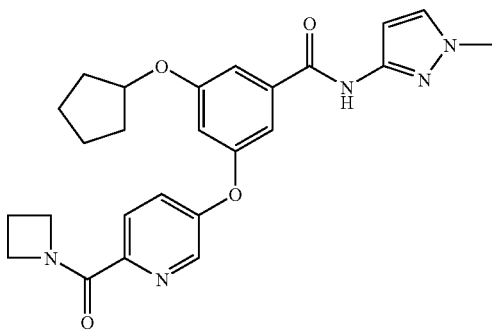

3-(Cyclopentyloxy)-5-hydroxy-N-(1-methyl-1H-pyrazol-3-yl)benzamide (200 mg, 0.67 mmol), 2-(azetidin-1-ylcarbonyl)-5-bromopyridine (193 mg, 0.80 mmol), bromotris(triphenylphosphine)copper (186 mg, 0.2 mmol) and caesium carbonate (230 mg, 0.70 mmol) were dissolved/suspended in DMA (3.5 mL). The reaction mixture was heated for 40 mins at 200° C. in a microwave reactor then allowed to cool, filtered and reduced in vacuo. The crude product was purified by chromatography on silica, eluting with 0-100% ethyl acetate in isohexane, to give the desired compound as a slightly yellow foam (176 mg). $^1$H NMR δ (d$_6$-DMSO): 1.61 (m, 2H), 1.73 (m, 4H), 1.94 (m, 2H), 2.28 (m, 2H), 3.78 (s, 3H), 4.08 (t, 2H), 4.59 (t, 2H), 4.95 (m, 1H), 6.56 (d, 1H), 6.88 (t, 1H), 7.28 (m, 1H), 7.43 (t, 1H), 7.56 (m, 1H), 7.59 (d, 1H), 7.99 (d, 1H), 8.41 (m, 1H), 10.85 (s, 1H); m/z 462 (M+H)$^+$

EXAMPLE 33

3-{[5-(Azetidin-1-ylcarbonyl)pyrazin-2-yl]oxy}-5-{[(1R,2R)-2-hydroxy-1-methylpropyl]oxy}-N-(1-methyl-1H-pyrazol-3-yl)benzamide and 3-{[5-(Azetidin-1-ylcarbonyl)pyrazin-2-yl]oxy}-5-{[(1S,2S)-2-hydroxy-1-methylpropyl]oxy}-N-(1-methyl-1H-pyrazol-3-yl)benzamide (1:1)

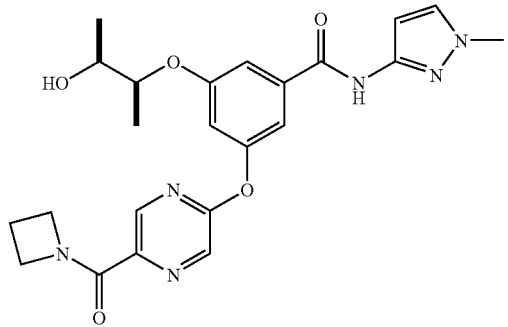

DIPEA (0.26 mL, 1.5 mmol) was added to a mixture of 5-[(3-{[(1R,2R)-2-hydroxy-1-methylpropyl]oxy}-5-{[(1-methyl-1H-pyrazol-3-yl)amino]carbonyl}phenyl)oxy]pyrazine-2-carboxylic acid and 5-[(3-{[(1S,2S)-2-hydroxy-1-methylpropyl]oxy}-5-{[(1-methyl-1H-pyrazol-3-yl)amino]carbonyl}phenyl)oxy]pyrazine-2-carboxylic acid (1:1) (0.16 g, 0.37 mmol), azetidine hydrochloride (71 mg, 0.75 mmol) and HATU (299 mg, 0.79 mmol) in DMF (5 mL) and stirred at RT for 72 hours. Ethyl acetate (40 mL) was added and the mixture washed with water (2×30 mL), brine (30 mL), dried (MgSO$_4$), filtered and reduced in vacuo to give a yellow oil which was chromatographed on silica, eluting with 0-100% ethyl acetate in isohexane to give the titled mixture of diastereoisomers as a colourless oil. The mixture was separated by chiral preparatory HPLC on a Chiralpak IA (250 mm×20 mm) EG014 column, eluting with 30% ethanol in tertbutylmethyl ether. The first diastereomer eluted, Example 33a, was isolated as a white foam (18 mg).

$^1$H NMR δ (CDCl$_3$): 1.19 (d, 3H), 1.23 (d, 3H), 2.26-2.34 (m, 3H), 3.74 (s, 3H), 3.77-3.85 (m, 1H), 4.13-4.23 (m, 3H), 4.63 (t, 2H), 6.72 (d, 1H), 6.86 (t, 1H), 7.16-7.22 (m, 2H), 7.27-7.30 (m, 1H), 8.27 (d, 1H), 8.31 (s, 1H), 8.79 (d, 1H); m/z 467 (M+H)$^+$

The second diastereomer eluted, Example 33b, was isolated as a white foam (19 mg).

$^1$H NMR δ (CDCl$_3$): 1.19 (d, 3H), 1.22 (d, 3H), 2.27-2.36 (m, 3H), 3.73 (s, 3H), 3.76-3.84 (m, 1H), 4.13-4.22 (m, 3H), 4.62 (t, 2H), 6.72 (d, 1H), 6.86 (t, 1H), 7.17-7.19 (m, 1H), 7.21 (d, 1H), 7.28 (t, 1H), 8.26 (d, 1H), 8.40 (s, 1H), 8.79 (d, 1H); m/z 467 (M+H)$^+$

The preparation of a mixture of 5-[(3-{[(1R,2R)-2-hydroxy-1-methylpropyl]oxy}-5-{[(1-methyl-1H-pyrazol-3-yl)amino]carbonyl}phenyl)oxy]pyrazine-2-carboxylic acid and 5[(3-{[(1S,2S)-2-hydroxy-1-methylpropyl]oxy}-5-{[(1-methyl-1H-pyrazol-3-yl)amino]carbonyl}phenyl)oxy]pyrazine-2-carboxylic acid (1:1) is described below:

5-[(3-{[(1R,2R)-2-Hydroxy-1-methylpropyl]oxy}-5-{[(1-methyl-1H-pyrazol-3-yl)amino]carbonyl}phenyl)oxy]pyrazine-2-carboxylic acid and 5-[(3-{[(1S,2S)-2-Hydroxy-1-methylpropyl]oxy}-5-{[(1-methyl-1H-pyrazol-3-yl)amino]carbonyl}phenyl)oxy]pyrazine-2-carboxylic acid (1:1)

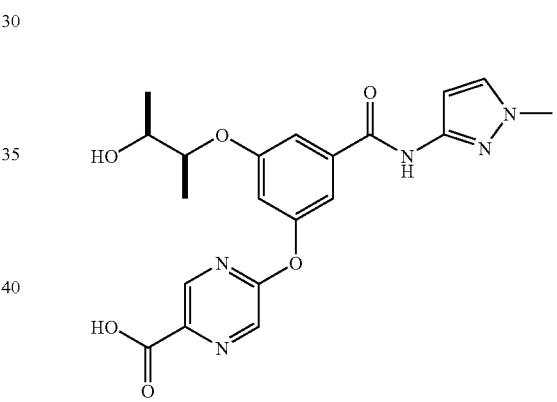

Lithium hydroxide monohydrate (38 mg, 0.88 mmol) in water (3 mL) was added to methyl 5-[(3-{[(1R,2R)-2-hydroxy-1-methylpropyl]oxy}-5-{[(1-methyl-1H-pyrazol-3-yl)amino]carbonyl}phenyl)oxy]pyrazine-2-carboxylate and methyl 5-[(3-{[(1S,2S)-2-hydroxy-1-methylpropyl]oxy}-5-{[(1-methyl-1H-pyrazol-3-yl)amino]carbonyl}phenyl)oxy]pyrazine-2-carboxylate (1:1) (0.26 g, 0.59 mmol) in THF (6 mL) and the mixture stirred at RT for 72 hours. The THF was removed in vacuo and the aqueous residue adjusted to pH3 with citric acid, then extracted into ethyl acetate, washed with water (30 mL), brine (30 mL), dried (MgSO$_4$), filtered and the solvent removed in vacuo to give the desired compound as a white solid (0.16 g).

$^1$H NMR δ (d$_6$-DMSO): 1.16 (d, 3H), 1.26 (d, 3H), 3.84 (s, 3H), 4.20 (m, 1H), 4.49 (m, 1H), 4.89 (d, 1H), 6.64 (d, 1H), 7.13 (t, 1H), 7.49 (s, 1H), 7.59 (s, 1H), 7.67 (d, 1H), 8.72 (d, 1H), 8.85 (d, 1H), 10.93 (s, 1H), 13.53 (s, 1H); m/z 426 (M−H)$^−$

Methyl 5-[(3-{[(1R,2R)-2-hydroxy-1-methylpropyl]oxy}-5-{[(1-methyl-1H-pyrazol-3-yl)amino]carbonyl}phenyl)oxy]pyrazine-2-carboxylate and Methyl 5-[(3-{[(1S,2S)-2-hydroxy-1-methylpropyl]oxy}-5-{[(1-methyl-1H-pyrazol-3-yl)amino]carbonyl}phenyl)oxy]pyrazine-2-carboxylate (1:1)

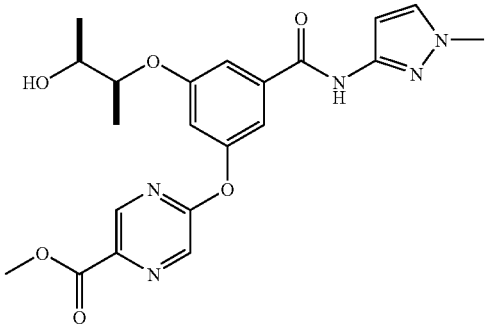

A mixture of 3-hydroxy-5-{[(1R,2R)-2-hydroxy-1-methylpropyl]oxy}-N-(1-methyl-1H-pyrazol-3-yl)benzamide and 3-hydroxy-5-{[(1S,2S)-2-hydroxy-1-methylpropyl]oxy}-N-(1-methyl-1H-pyrazol-3-yl)benzamide (1:1) (230 mg, 0.75 mmol), methyl 5-chloropyrazine-2-carboxylate (195 mg, 1.13 mmol) and potassium carbonate (208 mg, 1.51 mmol) in acetonitrile (5 mL) was stirred in a microwave reactor at 130° C. for 3 hours. The solvent was removed in vacuo and water added. The mixture was acidified, extracted into ethyl acetate and the combined organics washed with brine, dried (MgSO$_4$), filtered and reduced in vacuo to give a yellow foam (265 mg), which was used in the next step without further purification. $^1$H NMR δ (CDCl$_3$): 1.29 (m, 6H), 1.99 (s, 1H), 3.80 (s, 3H), 3.90 (quintet, 1H), 4.05 (s, 3H), 4.25 (quintet, 1H), 6.82 (d, 1H), 6.95 (t, 1H), 7.30 (m, 2H), 7.39 (s, 1H), 8.55 (s, 1H), 8.55 (s, 1H), 8.86 (s, 1H); m/z 442 (M+H)$^+$ The preparation of 3-hydroxy-5-{[(1R,2R)-2-hydroxy-1-methylpropyl]oxy}-N-(1-methyl-1H-pyrazol-3-yl)benzamide and 3-hydroxy-5-{[(1S,2S)-2-hydroxy-1-methylpropyl]oxy}-N-(1-methyl-1H-pyrazol-3-yl)benzamide (1:1) was described earlier.

EXAMPLE 34

3-{[5-(Azetidin-1-ylcarbonyl)-1,3-thiazol-2-yl]oxy}-5-{[(1S)-1-methyl-2-(methyloxy)ethyl]oxy}-N-(5-methylpyrazin-2-yl)benzamide

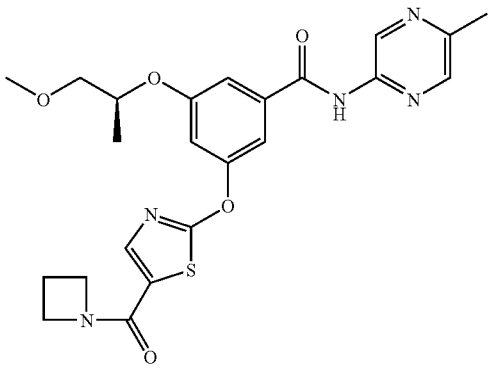

Cesium carbonate (489 mg, 1.5 mmol) was added to a solution of 3-hydroxy-5-{[(1S)-1-methyl-2-(methyloxy)ethyl]oxy}-N-(5-methylpyrazin-2-yl)benzamide (159 mg, 0.5 mmol) and 5-(azetidin-1-ylcarbonyl)-2-chloro-1,3-thiazole (152 mg, 0.75 mmol) in acetonitrile (5 mL) and the stirred mixture heated at 120° C. in a microwave reactor for 1 hour. The mixture was cooled to RT and ambient pressure, the acetonitrile evaporated in vacuo, the residue partitioned between water (25 mL) and ethyl acetate (50 mL), the organic layer washed with brine, dried (MgSO$_4$) and evaporated to a residue which was chromatographed on silica, eluting with ethyl acetate, to give the desired product (181 mg).

$^1$H NMR δ (CDCl$_3$): 1.3 (d, 3H), 2.35 (m, 2H), 2.5 (s, 3H), 3.3 (s, 3H), 3.45-3.55 (m, 2H), 4.1-4.4 (m, 4H), 4.55 (m, 1H), 7.0 (d, 1H), 7.35 (d, 1H), 7.45 (s, 1H), 7.45 (s, 1H), 8.05 (s, 1H), 8.4 (s, 1H) and 9.45 (s, 1H). m/z 484 (M+H)$^+$.

The following compounds were synthesised in an analogous fashion from either 3-hydroxy-5-{[(1S)-1-methyl-2-(methyloxy)ethyl]oxy}-N-(5-methylpyrazin-2-yl)benzamide or 3-hydroxy-5-[(1S)-2-methoxy-(1-methylethyl)oxy]-N-(1-methyl-1H-pyrazol-3-yl)benzamide and the appropriate halogenated heterocycle:

| Example | Structure | m/z | NMR |
|---|---|---|---|
| 34a | 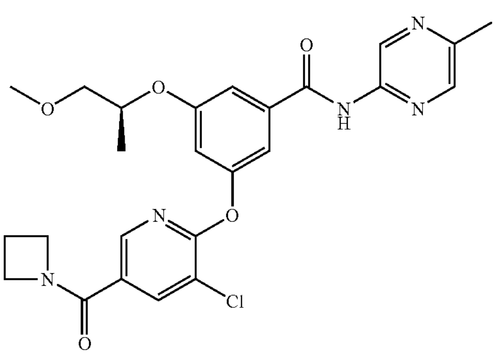 | 512 (M + H)$^+$ | $^1$H NMR δ (CDCl$_3$): 1.3 (d, 3H), 2.3 (m, 2H), 2.5 (s, 3H), 3.3 (s, 3H), 3.45-3.55 (m, 2H), 4.1-4.35 (m, 4H), 4.55 (m, 1H), 6.9 (d, 1H), 7.2 (d, 1H), 7.35 (s, 1H), 8.05 (s, 1H), 8.1 (s, 1H), 8.2 (d, 1H), 8.3 (s, 1H) and 9.45 (s, 1H). |

| Example | Structure | m/z | NMR |
|---|---|---|---|
| 34b*** | 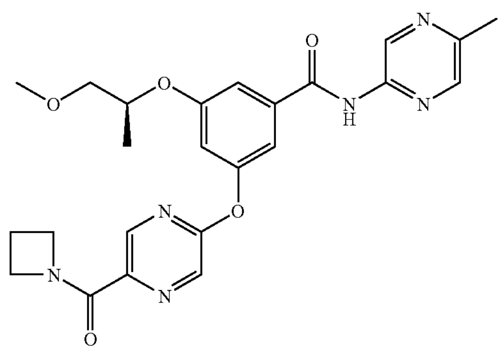 | 479 (M + H)+ | ¹H NMR δ (CDCl₃): 1.3 (d, 3H), 2.3 (m, 2H), 2.5 (s, 3H), 3.3 (s, 3H), 3.45-3.55 (m, 2H), 4.2 (t, 2H), 4.55 (m, 1H), 4.65 (t, 2H), 6.9 (d, 1H), 7.25 (d, 1H), 7.35 (d, 1H), 8.05 (s, 1H), 8.3 (s, 1H), 8.45 (s, 1H) 8.8 (s, 1H) and 9.45 (s, 1H). |
| 34c | 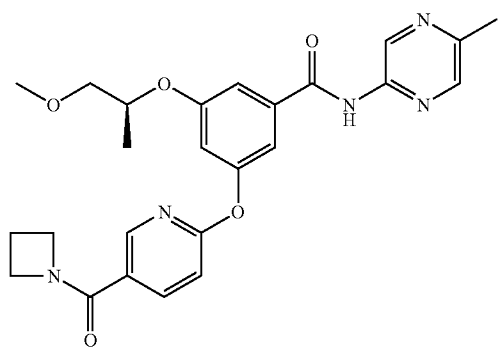 | 478 (M + H) | ¹H NMR δ (CDCl₃): 1.3 (d, 3H), 2.3 (m, 2H), 2.5 (s, 3H), 3.3 (s, 3H), 3.45 3.55 (m, 2H), 4.15-4.35 (m, 4H), 4.55 (m, 1H), 6.8 (d, 1H), 6.95 (d, 1H), 7.2 (s, 1H), 7.35 (s, 1H), 8.0 (dd, 1H), 8.05 (s, 1H), 8.35 (d, 1H), 8.5 (s, 1H) and 9.5 (s, 1H). |
| 34d | 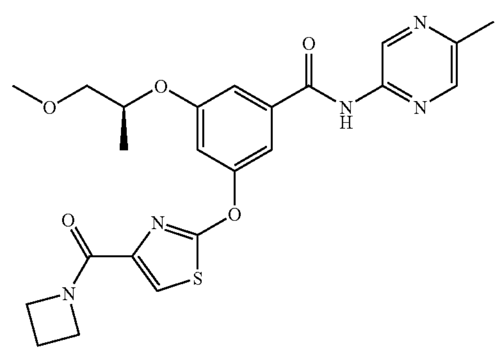 | 484 (M + H)+ | ¹H NMR δ (CDCl₃): 1.3 (d, 3H), 2.2 (m, 2H), 2.5 (s, 3H), 3.3 (s, 3H), 3.45-3.55 (m, 2H), 4.15 (t, 2H), 4.4 (t, 2H), 4.55 (m, 1H), 7.0 (d, 1H), 7.3 (d, 1H), 7.45 (s, 1H), 7.65 (s, 1H), 8.05 (s, 1H), 8.4 (s, 1H) and 9.45 (s, 1H). |
| 34e | 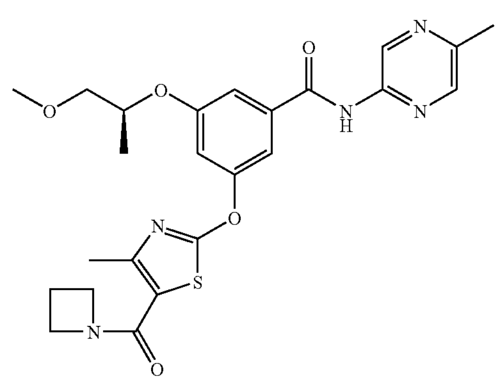 | 498 (M + H)+ | ¹H NMR δ (CDCl₃): 1.3 (d, 3H), 2.25 (m, 2H), 2.45 (s, 3H), 2.5 (s, 3H), 3.3 (s, 3H), 3.45-3.55 (m, 2H), 4.1-4.2 (t, 4H), 4.55 (m, 1H), 7.0 (d, 1H), 7.35 (d, 2H), 8.05 (s, 1H), 8.4 (s, 1H) and 9.45 (s, 1H). |

| Example | Structure | m/z | NMR |
|---|---|---|---|
| 34f** | 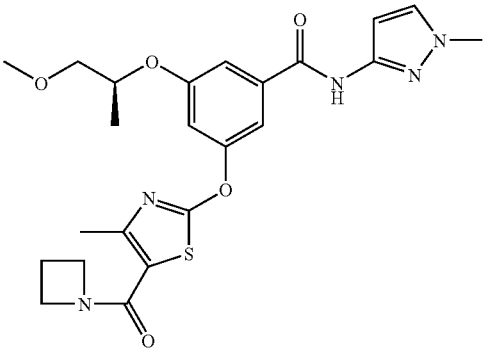 | 486 (M + H)+ | ¹H NMR δ (CDCl₃): 1.3 (d, 3H), 2.25 (m, 2H), 2.5 (s, 3H), 3.3 (s, 3H), 3.4-3.55 (m, 2H), 3.7 (s, 3H), 4.1-4.2 (t, 4H), 4.5 (m, 1H), 6.7 (s, 1H), 6.95 (s, 1H), 7.2 (d, 1H), 7.3 (d, 2H) and 8.6 (s, 1H). |

**The compound was partially crystallised from diethyl ether; mpt: melting onset 80.7° C.

***Example 34b, 3-{[5-(azetidin-1-ylcarbonyl)pyrazin-2-yl]oxy}-5-{[(1S)-1-methyl-2-(methyloxy)ethyl]oxy}-N-(5-methylpyrazin-2-yl)benzamide, was also prepared in the following manner.

A mixture of 3-hydroxy-5-{[(1S)-1-methyl-2-(methyloxy)ethyl]oxy}-N-(5-methylpyrazin-2-yl)benzamide (25.4 g, 80.0 mmol), 2-(azetidin-1-ylcarbonyl)-5-chloropyrazine (17.4 g, 88.0 mmol) and potassium carbonate (33.1 g, 240 mmol) in acetonitrile (254 mL) was heated at 60° C. for 24 hours. The solvent was removed by evaporation and the residue partitioned between ethyl acetate (15 vol) and water (10 vol). The layers were separated, the aqueous layer further extracted into ethyl acetate (2×10 vol) and the combined organics washed with water (2×5 vol), brine (5 vol), dried (MgSO₄), filtered, concentrated in vacuo. The residue was chromatographed on silica, eluting with ethyl acetate, to give the desired compound as a foam (33.7 g). The pure material was dissolved in hot tert-butylmethyl ether (30 vols), seeded with genuine crystalline sample (the seeds were isolated from a small scale crystallisation where material was dissolved in a minimum amount of hot tert-butylmethyl ether then isohexane added and the flask scratched to promote crystallisation) and stirred overnight. The mixture was cooled and the crystalline material (melting onset 110.3° C.) collected by filtration (29.1 g).

¹H NMR δ (d₆-DMSO): 1.27 (d, 3H), 2.30 (quin, 2H), 2.49 (s, 3H), 3.31 (s, 3H), 3.47-3.56 (m, 2H), 4.10 (t, 2H), 4.57 (t, 2H), 4.79 (td, 1H), 7.13 (t, 1H), 7.48 (td, 1H), 7.57 (td, 1H), 8.36 (d, 1H), 8.56 (d, 1H), 8.69 (d, 1H), 9.26 (d, 1H), 11.00 (s, 1H); m/z 479 (M+H)+

This crystalline form could be converted to a different crystalline form by placing approximately 30 mg of material in a vial with a magnetic flea, and adding approximately 1 mL of water. A few (3) drops of methanol were added to this, and the vial was sealed with a lid. The slurry was then left to stir on a magnetic plate at RT (25° C.). After 3 days, the sample was removed from the plate, the lid removed and the slurry left to dry under ambient conditions. The new crystalline form (melting onset 110.2° C.) was shown to be different by XRPD analysis.

The title compound may also be crystallised by stirring a slurry of the compound in water.

The preparation of 3-hydroxy-5-{[(1S)-1-methyl-2-(methyloxy)ethyl]oxy}-N-(5-methylpyrazin-2-yl)benzamide is described below:

3-Hydroxy-5-j{[(1S)-1-methyl-2-(methyloxy)ethyl]oxy}-N-(5-methylpyrazin-2-yl)benzamide

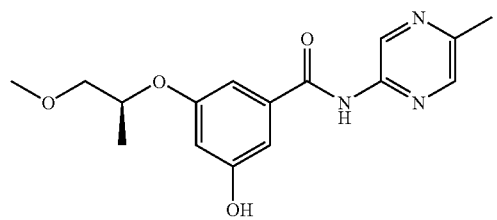

10% Palladium on charcoal (700 mg) was added to a solution of 3-{[(1S)-1-methyl-2-(methyloxy)ethyl]oxy}-N-(5-methylpyrazin-2-yl)-5-[(phenylmethyl)oxy]benzamide (7.0 g, 17.2 mmol) in ethanol (125 mL) and the mixture stirred at RT under a hydrogen atmosphere for 4 hours. The catalyst was removed by filtration and the ethanol evaporated in vacuo. The residue was crystallised from ethyl acetate to give the desired compound (4.22 g). ¹H NMR δ (CDCl₃): 1.25 (d, 3H), 2.5 (s, 3H), 3.3 (s, 3H), 3.4-3.5 (m, 2H), 4.5 (m, 1H), 6.3 (br, 1H), 6.55 (s, 1H), 6.9 (s, 1H), 6.95 (s, 1H), 8.05 (s, 1H), 8.45 (s, 1H) and 9.5 (s, 1H). m/z 318 (M+H)+.

This reaction was also carried out using methanol as solvent and using 5 bar pressure of hydrogen.

3-{[((s)-1-Methyl-2-(methyloxy ethyl]oxy}-N-(5-methylpyrazin-2-yl)-5-[(phenylmethyl)oxy]benzamide

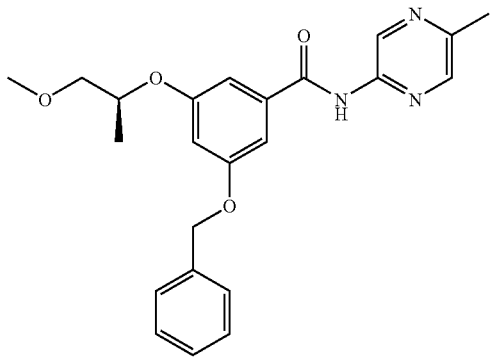

Oxalyl chloride (2.1 mL, 24.0 mmol) was added to a solution of 3-[(1S)-2-methoxy-(1-methylethyl)oxy]-5-{[phenylmethyl]oxy}benzoic acid (6.32 g, 20.0 mmol) in DCM (100 mL) and the mixture stirred at RT for 4 hours. The mixture was evaporated in vacuo to a residue, which was taken up in DCM (25 mL) and added to a stirred mixture of 2-amino-5-methylpyrazine (2.29 g, 21.0 mmol) and pyridine (1.94 mL, 24.0 mmol) in DCM (100 mL) at 5° C.-10° C. The mixture was stirred at RT for 18 hours, the DCM evaporated in vacuo. The residue was partitioned between water (50 mL) and ethyl acetate (150 mL), the organic layer washed with brine, dried (MgSO$_4$) and evaporated to a residue, which was chromatographed on silica, eluting with 50% ethyl acetate in isohexane, to give the desired compound (7.0 g). $^1$H NMR δ (CDCl$_3$): 1.3 (d, 3H), 2.5 (s, 3H), 3.3 (s, 3H), 3.4-3.5 (m, 2H), 4.5 (m, 1H), 5.0 (s, 2H), 6.7 (s, 1H), 7.0 (s, 1H), 7.05 (s, 1H), 7.35 (m, 5H), 8.05 (s, 1H), 8.3 (s, 1H) and 9.5 (s, 1H). m/z 408 (M+H)$^+$.

The preparation of 2-amino-5 methylpyrazine is described in the literature [*Tetrahedron Lett.* 2002, 9287].

The preparation of 3-[(1S)-2-methoxy-(1-methylethyl)oxy]-5-{[phenylmethyl]oxy}benzoic acid was described earlier.

The preparation of 3-hydroxy-5-[(1S)-2-methoxy-(1-methylethyl)oxy]-N-(1-methyl-1H-pyrazol-3-yl)benzamide was described earlier.

The preparations of the halogenated heterocycles 5-(azetidin-1-ylcarbonyl)-2-chloro-1,3-thiazole, 5-(azetidin-1-ylcarbonyl)-2,3-dichloropyridine, 2-(azetidin-1-ylcarbonyl)-5-chloropyrazine, 5-(azetidin-1-ylcarbonyl)-2-chloropyridine and 4-(azetidin-1-ylcarbonyl)-2-bromo-1,3-thiazole were described earlier.

The preparation of 5-(azetidin-1-ylcarbonyl)-2-bromo-4-methyl-1,3-thiazole, used in Examples 34e-f, is described below:

5-(Azetidin-1-ylcarbonyl)-2-bromo-4-methyl-1,3-thiazole

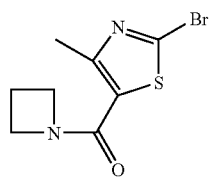

Oxalyl chloride (0.47 mL; 5.41 mmol) was added to a solution of 2-bromo-4-methyl-1,3-thiazole-5-carboxylic acid (1.0 g; 4.5 mmol) in DCM (25 mL). The mixture was stirred at RT for 18 hours, the DCM was evaporated in vacuo, the residue azeotroped with toluene (2×5 mL) and added to a solution of azetidine hydrochloride (503 mg; 5.41 mmol) and triethylamine (2.3 mL; 16.2 mmol) in DCM (50 mL). The mixture was stirred at RT for 18 hours, the DCM evaporated in vacuo, and the residue partitioned between water (75 mL) and ethyl acetate (150 mL). The organic layer was washed with brine, dried (MgSO$_4$) and evaporated to a residue which was chromatographed on silica, eluting with 40% ethyl acetate in isohexane, to give a solid which was crystallised from ethyl acetate/isohexane to give the desired compound (490 mg). $^1$H NMR δ (CDCl$_3$): 2.35 (m, 2H), 2.55 (s, 3H) and 4.1 (t, 4H).

EXAMPLE 35

3-{[5-(Azetidin-1-ylcarbonyl)-3-chloropyridin-2-yl]oxy}-5-[(1-methylethyl)oxy]-N-(5-methylpyrazin-2-yl)benzamide

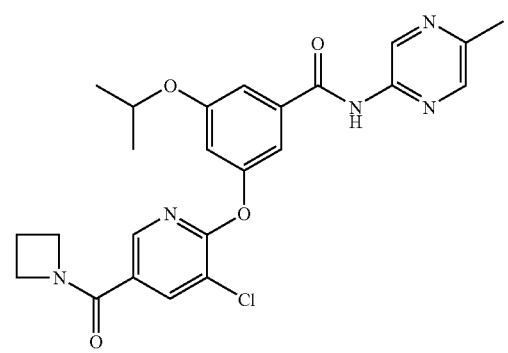

Cesium carbonate (489 mg, 1.5 mmol) was added to a solution of 3-hydroxy-5-[(1-methylethyl)oxy]-N-(5-methylpyrazin-2-yl)benzamide (144 mg, 0.5 mmol) and 5-(azetidin-1-ylcarbonyl)-2,3-dichloropyridine (173 mg, 0.75 mmol) in acetonitrile (5 mL) and the stirred mixture heated at 120° C. in a microwave reactor for 1 hour. The mixture was cooled to RT and ambient pressure, the acetonitrile evaporated in vacuo, the residue partitioned between water (25 mL) and ethyl acetate (50 mL). The organic layer was washed with brine, dried (MgSO$_4$) and evaporated to a residue which was chromatographed on silica, eluting with 75% ethyl acetate in isohexane, to give the desired compound (167 mg). $^1$H NMR δ (CDCl$_3$): 1.3 (d, 6H), 2.3 (m, 2H), 2.5 (s, 3H), 4.1-4.3 (m, 4H), 4.55 (m, 1H), 6.85 (d, 1H), 7.2 (d, 1H), 7.3 (s, 1H), 8.05 (s, 1H), 8.1 (s, 1H), 8.2 (s, 1H) 8.3 (s, 1H) and 9.45 (s, 1H). m/z 482 (M+H)$^+$.

The following compounds were prepared in an analogues fashion from 3-hydroxy-5-[(1-methylethyl)oxy]-N-(5-methylpyrazin-2-yl)benzamide and the appropriate halogenated heterocycle:

| Example | Structure | m/z | NMR |
|---|---|---|---|
| 35a | 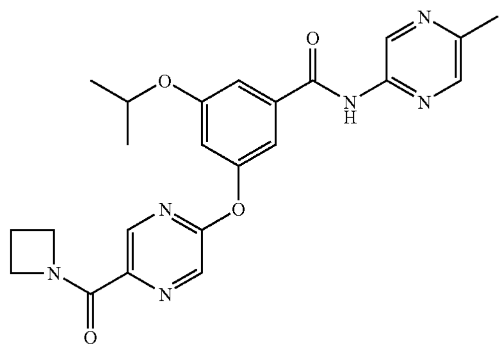 | 449 (M + H)+ | 1H NMR δ (CDCl3): 1.3 (d, 6H), 2.3 (m, 2H), 2.5 (s, 3H), 4.2 (t, 4H), 4.55 (m, 1H), 4.6 (t, 2H), 6.8 (d, 1H),7.2 (s, 1H), 7.35 (s, 1H), 8.05 (s, 1H), 8.25 (s, 1H), 8.35 (s, 1H), 8.8 (s, 1H) and 9.45 (s, 1H). |
| 35b | 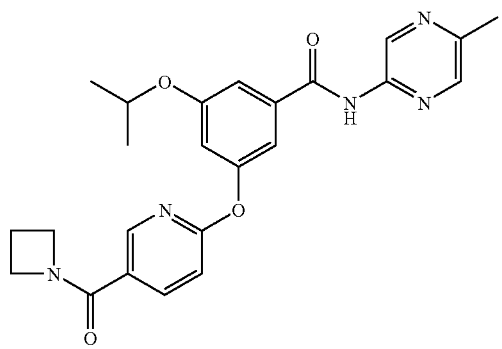 | 448 (M + H)+ | 1H NMR δ (CDCl3): 1.3 (d, 6H), 2.3 (m, 2H), 2.5 (s, 3H), 4.15 (t, 2H), 4.3 (t, 2H), 4.55 (m, 1H), 6.8 (d, 1H), 6.95 (d, 1H), 7.2 (d, 1H), 7.25 (d, 1H), 8.0 (dd, 1H), 8.1 (s, 1H), 8.35 (s, 1H) 8.4 (s, 1H) and 9.45 (s, 1H). |
| 35c* | 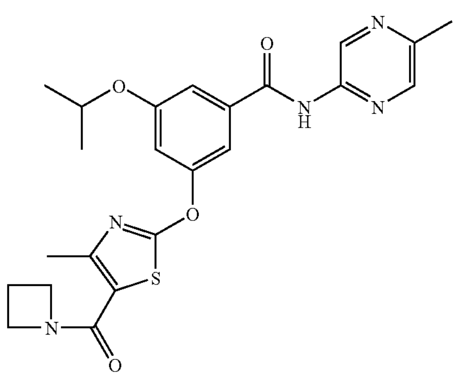 | 468 (M + H)+ | 1H NMR δ (DMSO d6): 1.3 (d, 6H), 2.25 (m, 2H), 2.45 (s, 3H), 3.3 (s, 3H), 4.0-4.2 (br, 4H), 4.8 (m, 1H), 7.2 (d, 1H), 7.6 (d, 2H), 8.35 (s, 1H), 9.25 (s, 1H) and 11.0 (s, 1H). |

*Compound was crystallised from ethyl acetate and isohexane; mpt: melting onset 140.4° C.

The preparation of 3-hydroxy-5-[(1-methylethyl)oxy]-N-(5-methylpyrazin-2-yl)benzamide is described below:

3-Hydroxy-5-[(1-methylethyl)oxy]-N-(5-methylpyrazin-2-yl)benzamide

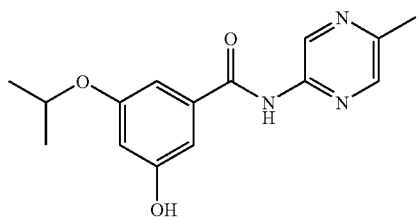

10% Palladium on charcoal (550 mg) was added to a solution of 3-[(1-methylethyl)oxy]-N-(5-methylpyrazin-2-yl)-5-[(phenylmethyl)oxy]benzamide (5.5 g, 14.6 mmol) in ethanol (75 mL) and THF (50 mL) and the mixture stirred at RT under a hydrogen atmosphere for 24 hours. The catalyst was removed by filtration and the filtrates evaporated in vacuo to a residue which was crystallised from ethyl acetate to give the desired compound (3.42 g).

1H NMR δ (CDCl3): 1.3 (d, 6H), 2.5 (s, 3H), 4.5 (m, 1H), 5.8 (br, 1H), 6.5 (d, 1H), 6.9 (d, 1H), 6.95 (d, 1H), 8.05 (s, 1H), 8.4 (s, 1H) and 9.5 (s, 1H). m/z 288 (M+H)+.

3[(1-Methylethyl)oxy]-N-(5-methylpyrazin-2-yl)-5-[(phenylmethyl)oxy]benzamide

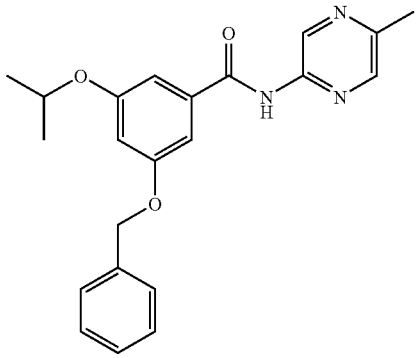

Oxalyl chloride (2.1 mL, 24.0 mmol) was added to a solution of 3-[(1-methylethyl)oxy]-5-[(phenylmethyl)oxy]benzoic acid (5.72 g, 20.0 mmol) in DCM (100 mL) and the mixture stirred at ambient RT for 4 hours. The mixture was evaporated in vacuo to a residue, which was taken up in DCM (25 mL) and added to a stirred mixture of 2-amino-5-methylpyrazine (2.29 g, 21.0 mmol) and pyridine (1.94 mL, 24.0 mmol) in DCM (100 mL) at 5° C.-10° C. The mixture was stirred at RT for 18 hours, the DCM evaporated in vacuo to a residue, which was partitioned between water (50 mL) and ethyl acetate (150 mL). The organic layer was washed with brine, dried (MgSO$_4$) and evaporated to a residue which was chromatographed on silica, eluting with 30% ethyl acetate in isohexane, and crystallised from ethyl acetate/isohexane to give the desired compound (5.52 g).

$^1$H NMR δ (CDCl$_3$): 1.3 (d, 6H), 2.5 (s, 3H), 4.5 (m, 1H), 5.0 (s, 2H), 6.6 (s, 1H), 6.95 (s, 1H), 7.0 (s, 1H), 7.35 (m, 5H), 8.05 (s, 1H), 8.3 (s, 1H) and 9.5 (s, 1H). m/z 378 (M+H)$^+$.

The preparations of 3-[(1-methylethyl)oxy]-5-[(phenylmethyl)oxy]benzoic acid and 2-amino-5-methylpyrazine were described earlier.

The preparations of the halogenated heterocycles 5-(azetidin-1-ylcarbonyl)-2,3-dichloropyridine, 2-(azetidin-1-ylcarbonyl)-5-chloropyrazine, 5-(azetidin-1-ylcarbonyl)-2-chloropyridine and 5-(azetidin-1-ylcarbonyl)-2-bromo-4-methyl-1,3-thiazole were described earlier.

EXAMPLE 36

3-{[6-(Azetidin-1-ylcarbonyl)pyridin-3-yl]oxy}-5-{[(1S)-1-methyl-2-(methyloxy)ethyl]oxy}-N-(5-methylpyrazin-2-yl)benzamide

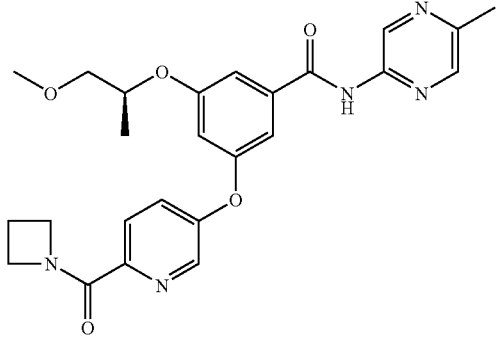

Cesium carbonate (489 mg, 1.5 mmol) was added to a solution of 3-hydroxy-5-{[(1S)-1-methyl-2-(methyloxy)ethyl]oxy}-N-(5-methylpyrazin-2-yl)benzamide (159 mg, 0.5 mmol) and 2-(azetidin-1-ylcarbonyl)-5-bromopyridine (181 mg, 0.75 mmol) and bromotris(triphenylphosphine)copper (93 mg, 0.1 mmol) in DMA (5 mL) and the stirred mixture heated at 160° C. in a microwave reactor for 4 hours. The mixture was cooled to RT and ambient pressure, partitioned between water (75 mL) and ethyl acetate (50 mL), the organic layer washed with brine, dried (MgSO$_4$) and evaporated in vacuo. The residue was chromatographed on silica, eluting with ethyl acetate, to give the desired compound that was crystallised from ether (45 mg, melting onset 113.8° C.). The compound may also be crystallised from ethyl acetate, giving rise to an alternative crystalline form (melting onset 132.7° C.). $^1$H NMR δ (CDCl$_3$): 1.3 (d, 3H), 2.3 (m, 2H), 2.5 (s, 3H), 3.3 (s, 3H), 3.45-3.55 (m, 2H), 4.2 (t, 2H), 4.55 (m, 1H), 4.65 (t, 2H), 6.75 (d, 1H), 7.05 (d, 1H), 7.25 (s, 1H), 7.3 (d, 1H), 8.0 (s, 1H), 8.05 (d, 1H), 8.25 (d, 1H), 8.3 (s, 1H) and 9.45 (s, 1H). m/z 478 (M+H)$^+$.

The preparations of 2-(azetidin-1-ylcarbonyl)-5-bromopyridine and 3-hydroxy-5-{[(1S)-1-methyl-2-(methyloxy)ethyl]oxy}-N-(5-methylpyrazin-2-yl)benzamide were described earlier.

EXAMPLE 37

3-{[6-(Azetidin-1-ylcarbonyl)pyridin-3-yl]oxy}-5-[(1-methylethyl)oxy]-N-(5-methylpyrazin-2-yl)benzamide

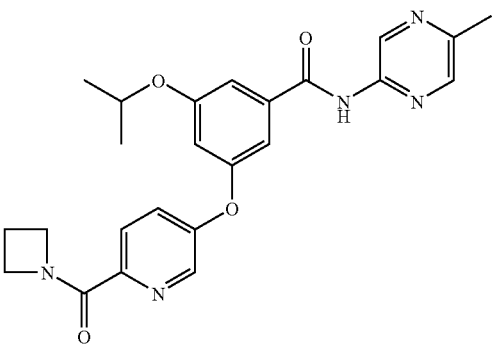

Cesium carbonate (489 mg, 1.5 mmol) was added to a solution of 3-hydroxy-5-[(1-methylethyl)oxy]-N-(5-methylpyrazin-2-yl)benzamide (144 mg, 0.5 mmol) and 2-(azetidin-1-ylcarbonyl)-5-bromopyridine (181 mg, 0.75 mmol) and bromotris(triphenylphosphine)copper (93 mg, 0.1 mmol) in DMA (5 mL) and the stirred mixture heated at 160° C. in a microwave reactor for 4 hours. The mixture was cooled to RT and ambient pressure, partitioned between water (75 mL) and ethyl acetate (50 mL), the organic layer washed with brine, dried (MgSO$_4$) and evaporated in vacuo. The residue was chromatographed on silica, eluting with 75% ethyl acetate in isohexane, to give the desired compound (crystallised from ether) (72 mg). $^1$H NMR δ (CDCl$_3$): 1.3 (d, 6H), 2.3 (m, 2H), 2.5 (s, 3H), 4.2 (t, 2H), 4.5 (m, 1H), 4.65 (t, 2H), 6.7 (s, 1H), 7.05 (s, 1H), 7.2 (s, 1H), 7.3 (d, 1H), 8.0 (br, 2H), 8.3 (br, 2H) and 9.45 (s, 1H). m/z 448 (M+H)$^+$. Mpt (melting onset) 125.7° C.

The preparations of 2-(azetidin-1-ylcarbonyl)-5-bromopyridine and 3-hydroxy-5-[(1-methylethyl)oxy]-N-(5-methylpyrazin-2-yl)benzamide were described earlier.

EXAMPLE 38

3-{[5-(Azetidin-1-ylcarbonyl)-3-chloropyridin-2-yl]oxy}-5-{[(1S)-methyl-2-(methyloxy)ethyl]oxy}-N-1H-pyrazol-3-ylbenzamide

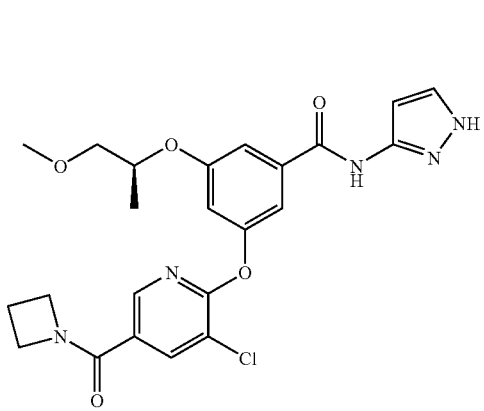

A mixture of 1,1-dimethylethyl 3-{[(3-hydroxy-5-{[(1S)-1-methyl-2-(methyloxy)ethyl]oxy}phenyl)carbonyl]amino}-1H-pyrazole-1-carboxylate (196 mg, 0.5 mmol), 5-(azetidin-1-ylcarbonyl)-2,3-dichloropyridine (128 mg, 0.55 mmol) and potassium carbonate (138 mg, 1.0 mmol) in acetonitrile (5 mL) was stirred in a microwave reactor at 120° C. for 4 hours. The solvent was removed in vacuo and the residue partitioned between ethyl acetate and water. The organic layer was washed with brine (50 mL), dried (MgSO$_4$), filtered and the solvent removed in vacuo to give a brown oil which was chromatographed on silica, eluting with a gradient of 50-100% ethyl acetate in isohexane, to give the desired compound as a white foam (142 mg).

$^1$H NMR δ (CDCl$_3$): 1.26 (d, 3H), 2.31 (quin, 2H), 3.33 (s, 3H), 3.43-3.53 (m, 2H), 4.11-4.33 (m, 4H), 4.54 (q, 1H), 6.78 (s, 1H), 6.86 (s, 1H), 7.24 (s, 1H), 7.33 (s, 1H), 7.42 (s, 1H), 8.06 (d, 1H), 8.12 (s, 1H), 9.98 (s, 1H); m/z 486 (M+H)$^+$ The preparations of 1,1-dimethylethyl 3-{[(3-hydroxy-5-{[(1S)-1-methyl-2-(methyloxy)ethyl]oxy}phenyl)carbonyl]amino}-1H-pyrazole-1-carboxylate and 5-(azetidin-1-ylcarbonyl)-2,3-dichloropyridine were described earlier.

EXAMPLE 39

3-{[5-(Azetidin-1-ylcarbonyl)-3-chloropyridin-2-yl]oxy}-5-{[(1S)-1-methyl-2-(methyloxy)ethyl]oxy}-N-1,3-thiazol-2-ylbenzamide

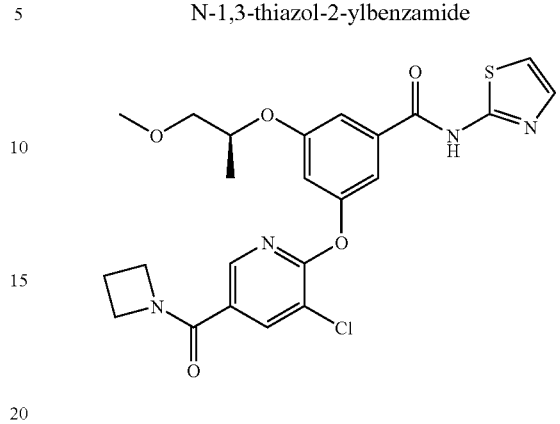

DIPEA (0.129 mL) was added to a suspension of 3-{[5-(azetidin-1-ylcarbonyl)-3-chloropyridin-2-yl]oxy}-5-{[(1S)-1-methyl-2-(methyloxy)ethyl]oxy}benzoic acid (168 mg), HATU (190 mg) and 2-aminothiazole (40 mg) in DMF (2 mL) and the mixture stirred at RT for 16 hours. Water (30 mL) was added and the mixture extracted with ethyl acetate (3×20 mL). The combined organic extracts were washed with brine, dried (MgSO$_4$), and evaporated to a residue which was chromatographed on silica, eluting with 50-100% ethyl acetate in isohexane, to give the desired compound (75 mg).

$^1$H NMR δ (CDCl$_3$): 1.27 (d, 3H), 2.31 (quin, 2H), 3.33 (s, 3H), 3.41-3.55 (m, 2H), 4.12-4.33 (m, 4H), 4.55 (q, 1H), 6.91 (d, 1H), 6.95 (s, 1H), 7.30 (s, 1H), 7.31 (d, 1H), 7.40 (s, 1H), 8.08 (s, 1H), 8.16 (s, 1H); m/z 503 (M+H)$^+$ The following compounds were made in an analogous fashion from either 3-{[5-(azetidin-1-ylcarbonyl)-3-chloropyridin-2-yl]oxy}-5-{[(is)-1-methyl-2-(methyloxy)ethyl]oxy}benzoic acid, 3-{[5-(azetidin-1-ylcarbonyl)-3-chloropyridin-2-yl]oxy}-5-[(1-methylethyl)oxy]benzoic acid, 3-{[5-(azetidin-1-ylcarbonyl)pyrazin-2-yl]oxy}-5-[(1-methylethyl)oxy]benzoic acid, 3-{[5-(azetidin-1-ylcarbonyl)pyrazin-2-yl]oxy}-5-{[(1S)-1-methyl-2-(methyloxy)ethyl]oxy}benzoic acid, 3-{[6-(azetidin-1-ylcarbonyl)pyridin-3-yl]oxy}-5-{[(is)-1-methyl-2-(methyloxy)ethyl]oxy}benzoic acid or 3-{[6-(azetidin-1-ylcarbonyl)pyridin-3-yl]oxy}-5-[(1-methylethyl)oxy]benzoic acid and the appropriate aminoheterocycle.

| Example | Structure | m/z | NMR |
|---|---|---|---|
| 39a | 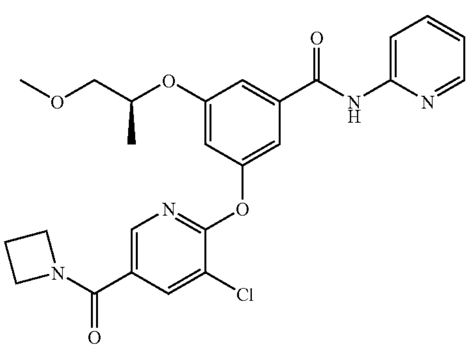 | 497 (M + H)$^+$ | $^1$H NMR δ (CDCl$_3$): 1.28 (d, 3H), 2.32 (quin, 2H), 3.34 (s, 3H), 3.41-3.56 (m, 2H), 4.11-4.34 (m, 4H), 4.55 (q, 1H), 6.90 (s, 1H), 7.00 (t, 1H), 7.22 (s, 1H), 7.34 (s, 1H), 7.68 (t, 1H), 8.08 (s, 1H), 8.19 (s, 1H), 8.23 (s, 1H), 8.27 (d, 1H), 8.37-8.56 (m, 1H) |

-continued

| Example | Structure | m/z | NMR |
|---|---|---|---|
| 39b | 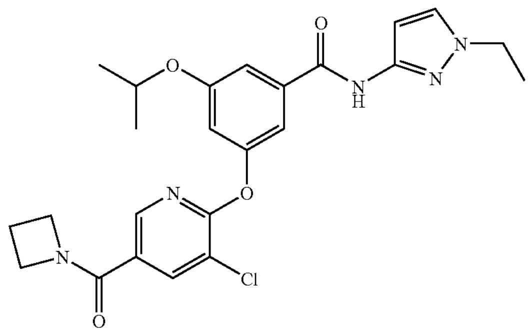 | 484 (M + H)+ | ¹H NMR δ (CDCl₃): 1.29 (d, 6H), 1.39 (t, 3H), 2.31 (quin, 2H), 4.00 (q, 2H), 4.11-4.34 (m, 4H), 4.54 (quin, 1H), 6.73 (s, 1H), 6.81 (s, 1H), 7.14 (s, 1H), 7.24 (s, 2H), 8.09 (s, 1H), 8.18 (s, 1H), 8.39 (s, 1H) |
| 39c | 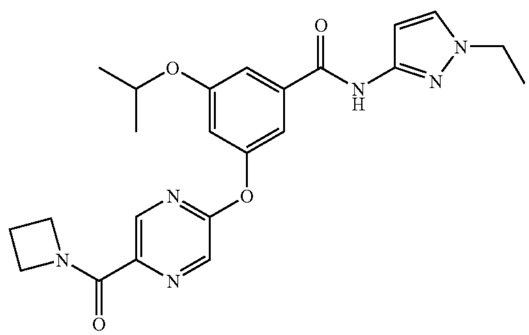 | 451 (M + H)+ | ¹H NMR δ (CDCl₃): 1.29 (d, 6H), 1.39 (t, 3H), 2.31 (quin, 2H), 3.99 (q, 2H), 4.19 (t, 2H), 4.53 (quin, 1H), 4.61 (t, 2H), 6.72 (s, 1H), 6.80 (s, 1H), 7.14 (s, 1H), 7.25 (s, 2H), 8.25 (s, 1H), 8.36 (s, 1H), 8.79 (s, 1H) |
| 39d | 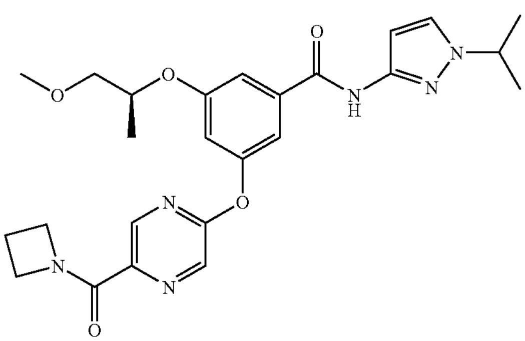 | 495 (M + H)+ | ¹H NMR δ (CDCl₃): 1.27 (d, 3H), 1.41 (d, 6H), 2.31 (quin, 2H), 3.33 (s, 3H), 3.41-3.55 (m, 2H), 4.19 (t, 2H), 4.30 (quin, 1H), 4.54 (q, 1H), 4.62 (t, 2H), 6.71 (s, 1H), 6.86 (s, 1H), 7.18 (s, 1H), 7.28 (s, 1H), 7.30 (s, 1H), 8.25 (s, 1H), 8.33 (s, 1H), 8.79 (s, 1H) |
| 39e | 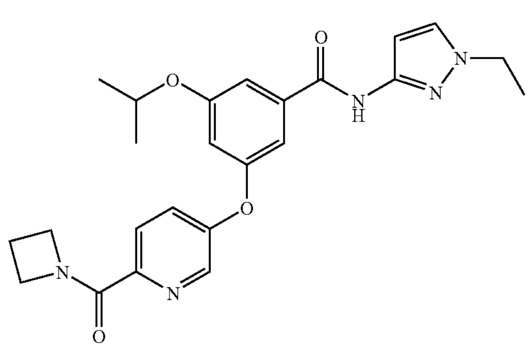 | 450 (M + H)+ | ¹H NMR δ (CDCl₃): 1.28 (d, 6H), 1.39 (t, 3H), 2.28 (quin, 2H), 4.00 (q, 2H), 4.18 (t, 2H), 4.52 (quin, 1H), 4.64 (t, 2H), 6.65 (s, 1H), 6.71 (s, 1H), 7.00 (s, 1H), 7.16 (s, 1H), 7.25 (s, 1H), 7.30 (d, 1H), 8.04 (d, 1H), 8.25 (s, 1H), 8.32 (s, 1H) |

-continued

| Example | Structure | m/z | NMR |
|---|---|---|---|
| 39f | 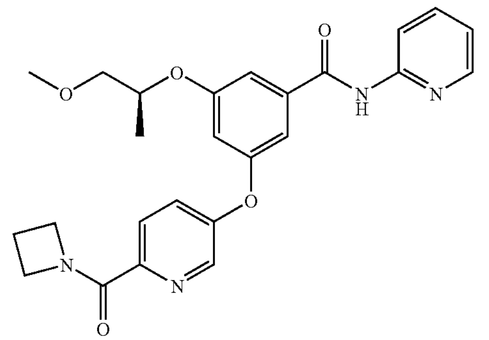 | 463 (M + H)+ | ¹H NMR δ (CDCl₃): 1.27 (d, 3H), 2.28 (quin, 2H), 3.34 (s, 3H), 3.43-3.54 (m, 2H), 4.18 (t, 2H), 4.56 (q, 1H), 4.64 (t, 2H), 6.76 (s, 1H), 7.03 (q, 1H), 7.10 (s, 1H), 7.27 (s, 1H), 7.31 (d, 1H), 7.71 (t, 1H), 8.05 (d, 1H), 8.23 (s, 1H), 8.26 (s, 1H), 8.29 (d, 1H), 8.59 (s, 1H) |
| 39g | 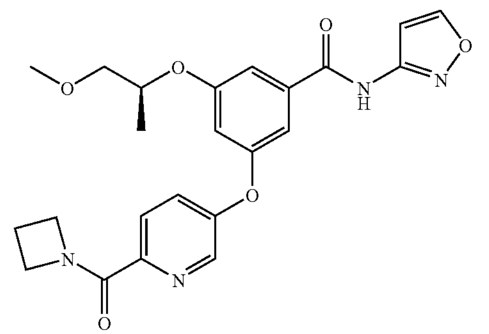 | 453 (M + H)+ | ¹H NMR δ (CDCl₃): 1.25 (d, 3H), 2.27 (quin, 2H), 3.32 (s, 3H), 3.41-3.53 (m, 2H), 4.17 (t, 2H), 4.54 (q, 1H), 4.63 (t, 2H), 6.78 (s, 1H), 7.11 (s, 1H), 7.15 (s, 1H), 7.27 (s, 1H), 7.29 (d, 1H), 8.03 (d, 1H), 8.18 (s, 1H), 8.25 (s, 1H), 9.43 (s, 1H) |
| 39h | 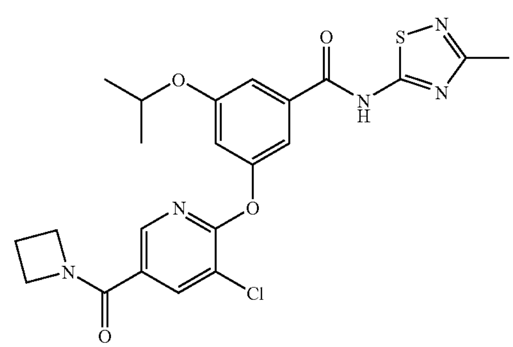 | 488 (M + H)+ | ¹H NMR δ (d₆-DMSO): 1.22 (d, 6H), 2.16 (quin, 2H), 2.41 (s, 3H), 3.95 (t, 2H), 4.26 (t, 2H), 4.67 (quin, 1H), 7.05 (s, 1H), 7.43 (s, 1H), 7.52 (s, 1H), 8.15 (s, 1H), 8.25 (s, 1H), 13.32 (s, 1H) |
| 39i* | 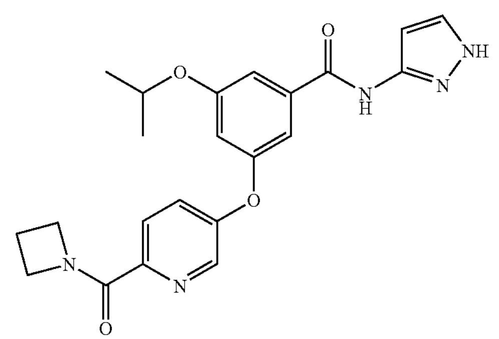 | 422 (M + H)+ | ¹H NMR δ (CDCl₃): 1.28 (d, 6H), 2.27 (quin, 2H), 4.16 (t, 2H), 4.51 (quin, 1H), 4.62 (t, 2H), 6.68 (s, 1H), 6.72 (s, 1H), 7.08 (s, 1H), 7.23 (s, 1H), 7.28 (d, 1H), 7.46 (s, 1H), 7.99 (d, 1H), 8.24 (s, 1H), 9.25 (s, 1H) |

-continued

| Example | Structure | m/z | NMR |
|---|---|---|---|
| 39j*+ | 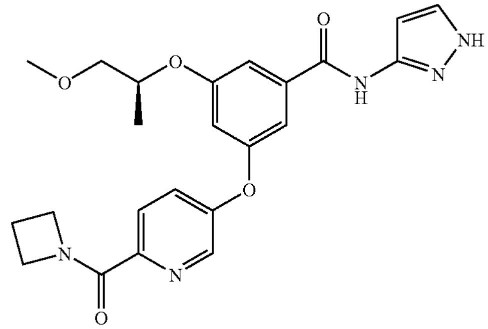 | 452 (M + H)+ | ¹H NMR δ (CDCl₃): 1.25 (d, 3H), 2.28 (quin, 2H), 3.33 (s, 3H), 3.42-3.55 (m, 2H), 4.16 (t, 2H), 4.54 (q, 1H), 4.62 (t, 2H), 6.73 (s, 1H), 6.75 (s, 1H), 7.12 (s, 1H), 7.28 (d, 1H), 7.32 (s, 1H), 7.43 (s, 1H), 8.00 (d, 1H), 8.24 (s, 1H), 9.78 (s, 1H) |
| 39k*++ | 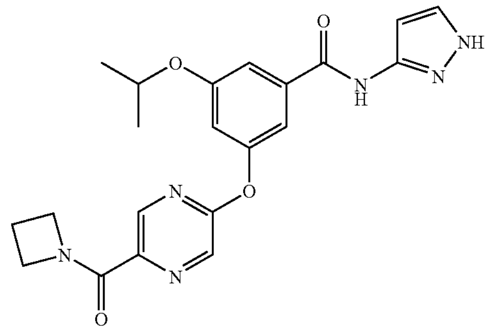 | 423 (M + H)+ | ¹H NMR δ (CDCl₃): 1.28 (d, 6H), 2.31 (quin, 2H), 4.19 (t, 2H), 4.52 (quin, 1H), 4.61 (t, 2H), 6.76-6.78 (m, 2H), 7.19 (s, 1H), 7.27 (s, 1H), 7.37 (s, 1H), 8.29 (s, 1H), 8.74 (s, 1H), 10.03 (s, 1H) |
| 39l* | 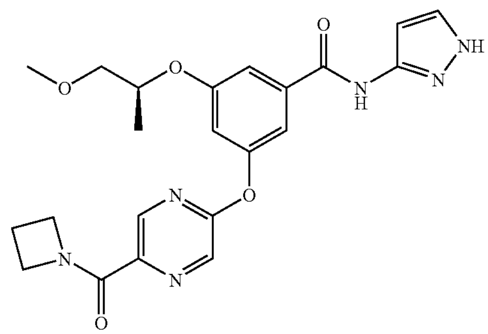 | 453 (M + H)+ | ¹H NMR δ (CDCl₃): 1.25 (d, 3H), 2.31 (quin, 2H), 3.33 (s, 3H), 3.42-3.54 (m, 2H), 4.18 (t, 2H), 4.53 (q, 1H), 4.61 (t, 2H), 6.78 (s, 1H), 6.83 (s, 1H), 7.22 (s, 1H), 7.35 (s, 2H), 8.31 (s, 1H), 8.73 (s, 1H), 10.38 (s, 1H) |
| 39m* | 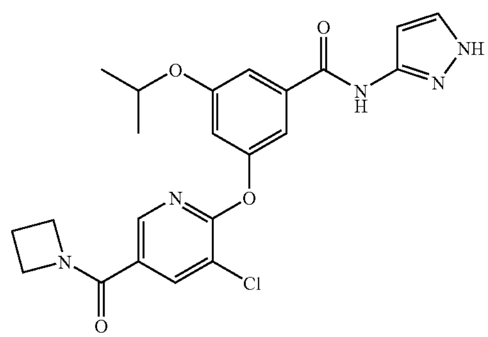 | 456 (M + H)+ | ¹H NMR δ (CDCl₃): 1.28 (d, 6H), 2.31 (quin, 2H), 4.15 (t, 2H), 4.25 (t, 2H), 4.53 (quin, 1H), 6.79 (s, 2H), 7.20 (s, 1H), 7.26 (s, 1H), 7.33 (s, 1H), 8.08 (s, 1H), 8.10 (s, 1H), 10.44 (s, 1H) |

*The reactions were carried out using 1,1-dimethylethyl 3-amino-1H-pyrazole-1-carboxylate as the amino heterocycle, the resultant products were dissolved in acetonitrile (4 mL) and ethanol (0.5 mL) and heated in a microwave reactor at 150° C. for 12 minutes. The mixtures were allowed to cool then concentrated in vacuo to give the desired products.

+This compound was crystallised from ethyl acetate and isohexane using vapour diffusion techniques.

++This compound was crystallised from acetonitrile, melting point (melting onset) 108.5° C.

The preparation of 1,1-dimethylethyl 3-amino-1H-pyrazole-1-carboxylate was described earlier. The preparation of 3-{[5-(azetidin-1-ylcarbonyl)-3-chloropyridin-2-yl]oxy}-5-{[(1S)-1-methyl-2-(methyloxy)ethyl]oxy}benzoic acid is given below:

3-{[5-(Azetidin-1-ylcarbonyl)-3-chloropyridin-2-yl]oxy}-5-{[(1S)-1-methyl-2-(methyloxy)ethyl]oxy}benzoic acid

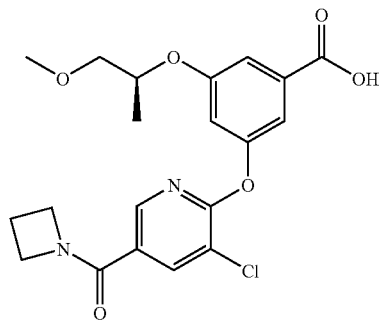

A mixture of methyl 3-hydroxy-5-[(1S)-2-methoxy-(1-methylethyl)oxy]benzoate (240 mg, 0.1 mmol), 5-(azetidin-1-ylcarbonyl)-2,3-dichloropyridine (278 mg, 1.2 mmol) and potassium carbonate (276 mg, 2.0 mmol) in DMA (5 mL) was stirred at 120° C. for 16 hours. The solution was poured into water (30 mL) and acidified with 1N hydrochloric acid before being extracted with ethyl acetate (3×20 mL). The combined organics were washed with brine (20 mL), dried (MgSO$_4$), filtered and the solvent removed in vacuo to give methyl 3-{[5-(azetidin-1-ylcarbonyl)-3-chloropyridin-2-yl]oxy}-5-{[(1S)-1-methyl-2-(methyloxy)ethyl]oxy}benzoate (as evidenced by LCMS data only m/z 435 (M+H)$^+$) as a brownish oil (550 mg). The crude methyl 3-{[5-(azetidin-1-ylcarbonyl)-3-chloropyridin-2-yl]oxy}-5-{[(1S)-1-methyl-2-(methyloxy)ethyl]oxy}benzoate (434 mg, 1 mmol) was dissolved in THF (15 mL) and methanol (5 mL) then 1N aqueous Lithium hydroxide solution (2 mL) added followed by the dropwise addition of water until a clear solution obtained. The mixture was stirred was stirred for 4 hours at RT and the organics removed by evaporation. The aqueous solution was filtered, extracted with ethyl acetate (10 mL) and the aqueous layer acidified with 2N hydrochloric acid. The acidified layer was extracted with ethyl acetate (3×30 mL) and the combined organic extracts washed with water (10 mL), brine (10 mL) and concentrated in vacuo to give the desired compound as a pale oil (375 mg). $^1$H NMR δ (CDCl$_3$): 1.27 (d, 3H), 2.32 (quin, 2H), 3.34 (s, 3H), 3.42-3.55 (m, 2H), 4.13-4.34 (m, 4H), 4.54 (q, 1H), 6.93 (s, 1H), 7.40 (s, 1H), 7.48 (s, 1H), 8.08 (s, 1H), 8.19 (s, 1H), m/z 421 (M+H)$^+$ 3-{[5-(Azetidin-1-ylcarbonyl)-3-chloropyridin-2-yl]oxy}-5-[(1-methylethyl)oxy]benzoic acid, 3-{[5-(azetidin-1-ylcarbonyl)pyrazin-2-yl]oxy}-5-[(1-methylethyl)oxy]benzoic acid and 3-{[5-(azetidin-1-ylcarbonyl)pyrazin-2-yl]oxy}-5-{[(1S)-1-methyl-2-(methyloxy)ethyl]oxy}benzoic acid were made in an analogous fashion from either methyl 3-hydroxy-5-[(1S)-2-methoxy-(1-methylethyl)oxy]benzoate or methyl 3-hydroxy-5-[(1-methylethyl)oxy]benzoate and the appropriate halogenated heterocycle.

| Structure | m/z | NMR |
|---|---|---|
| 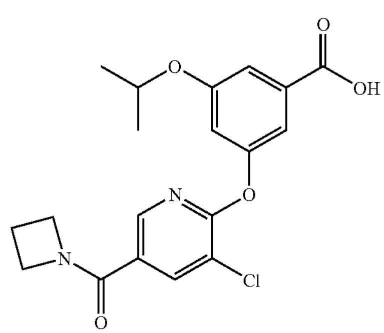 | 391 (M + H)$^+$ | $^1$H NMR δ (CDCl$_3$): 1.29 (d, 6H), 2.31 (quin, 2H), 4.11-4.35 (m, 4H), 4.53 (quin, 1H), 6.87 (s, 1H), 7.37 (s, 1H), 7.42 (s, 1H), 8.09 (s, 1H), 8.19 (s, 1H) |
| 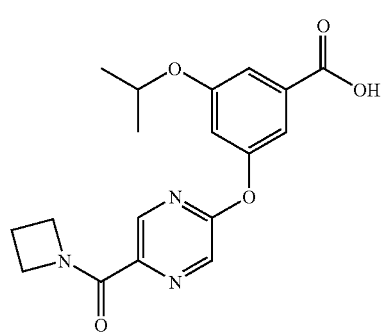 | 358 (M + H)$^+$ | $^1$H NMR δ (d$_6$-DMSO): 1.28 (6H, d), 2.26-2.34 (2H, quin), 4.10 (2H, t), 4.56 (2H, t), 4.65-4.71 (1H, quin), 7.11 (1H, t), 7.29(1H, s), 7.33 (1H, s), 8.53 (1H, s), 8.66 (1H, s) |

| Structure | m/z | NMR |
|---|---|---|
| 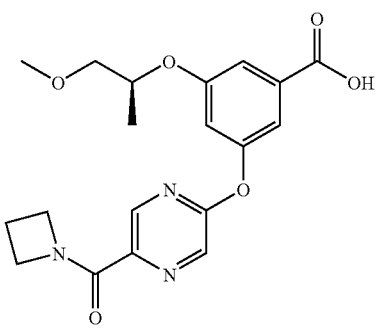 | 388 (M + H)+ | ¹H NMR δ (CDCl₃): 1.27 (d, 3H), 2.31 (quin, 2H), 3.33 (s, 3H), 3.41-3.55 (m, 2H), 4.20 (t, 2H), 4.50-4.57 (m, 1H), 4.62 (t, 2H), 6.92 (t, 1H), 7.39 (s, 1H), 7.49 (s, 1H), 8.25 (s, 1H), 8.78 (s, 1H) |

The preparation of 3-{[6-(azetidin-1-ylcarbonyl)pyridin-3-yl]oxy}-5-[(1-methylethyl)oxy]benzoic acid is described below:

3-{[6-(Azetidin-1-ylcarbonyl)pyridin-3-yl]oxy}-5-[(1-methylethyl)oxy]benzoic acid

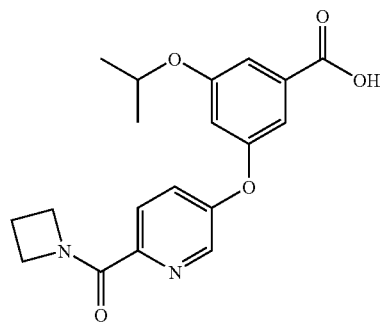

A mixture of methyl 3-hydroxy-5-[(1-methylethyl)oxy]benzoate (0.84 g, 4 mmol), 2-(azetidin-1-ylcarbonyl)-5-bromopyridine (1.16 g, 4.8 mmol), cesium carbonate (3.92 g, 1.2 mmol) and bromotris(triphenylphosphine)copper(I) (744 mg, 0.8 mmol) in DMA (20 mL) was stirred in a microwave reactor at 160° C. for 6 hours. The mixture was diluted with water (100 mL), washed with ethyl acetate (2×20 mL) and the aqueous layer filtered then acidified with 2N hydrochloric acid. The acidic layer was extracted with ethyl acetate (3×50 mL), the combined organics washed with water (2×20 mL), brine (20 mL), dried (MgSO₄), and the solvent removed in vacuo. The residue was triturated with ether to give the desired compound as a white solid (1.06 g). ¹H NMR δ (d₆-DMSO): 1.28 (d, 6H), 2.28 (quin, 2H), 4.08 (t, 2H), 4.59 (t, 2H), 4.69 (quin, 1H), 6.98 (t, 1H), 7.10 (s, 1H), 7.28 (s, 1H), 7.56 (d, 1H), 7.99 (d, 1H), 8.41 (s, 1H); m/z 357 (M+H)⁺

3-{[6-(Azetidin-1-ylcarbonyl)pyridin-3-yl]oxy}-5-{[(1S)-1-methyl-2-(methyloxy)ethyl]oxy}benzoic acid was prepared in an analogous fashion from 2-(azetidin-1-ylcarbonyl)-5-bromopyridine and methyl 3-hydroxy-5-[(1S)-2-methoxy-(1-methylethyl)oxy]benzoate.

| Structure | m/z | NMR |
|---|---|---|
| 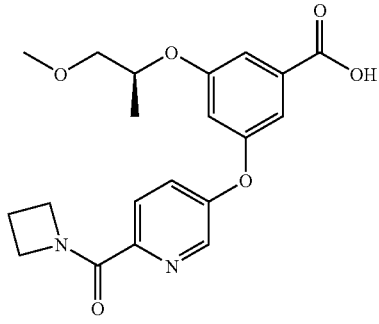 | 387 (M + H)+ | ¹H NMR δ (CDCl₃): 1.25 (d, 3H), 2.28 (quin, 2H), 3.33 (s, 3H), 3.40-3.54 (m, 2H), 4.20 (t, 2H), 4.53 (quin, 1H), 4.64 (t, 2H), 6.79 (t, 1H), 7.25 (s, 1H), 7.42 (s, 1H), 7.99-8.11 (m, 1H), 8.19-8.35 (m, 1H) |

The preparations of methyl 3-hydroxy-5-[(1S)-2-methoxy-(1-methylethyl)oxy]benzoate, methyl 3-hydroxy-5-[(1-methylethyl)oxy]benzoate and the appropriate halogenated heterocycles were described earlier.

3-{[5-(Azetidin-1-ylcarbonyl)pyrazin-2-yl]oxy}-5-[(1-methylethyl)oxy]-N-1H-pyrazol-3-ylbenzamide, Example 39k, was also prepared in the following manner from 1,1-dimethylethyl 3-[({3-hydroxy-5-[(1-methylethyl)oxy]phenyl}carbonyl)amino]-1H-pyrazole-1-carboxylate.

1,1-Dimethylethyl 3-[({3-hydroxy-5-[(1-methylethyl)oxy]phenyl}carbonyl)amino]-1H-pyrazole-1-carboxylate (56.3 g, 0.16 mol) was dissolved in acetonitrile (500 mL) and charged to a 3 L fixed vessel. Potassium carbonate—325 mesh—(64.5 g, 0.47 mol) was added, followed by 2-(azetidin-1-ylcarbonyl)-5-chloropyrazine (33.5 g, 0.17 mol) with a 100 mL acetonitrile charge wash. The mixture was stirred rapidly and warmed to 60° C. under nitrogen. Additional acetonitrile (250 mL) was added followed, after 1.5 hours, by the addition of DMF (150 mL) to dissolve residual solid material. The reaction was stirred overnight then allowed to cool to RT and filtered. The filtrate was concentrated under vacuum to remove the acetonitrile and the residual solution poured into water (1500 mL) with stirring. The precipitated solid was filtered, dissolved in DCM (560 mL), washed with 1:1 brine/saturated aqueous solution of sodium hydrogen carbonate (2×500 mL) and dried (MgSO$_4$). The organic solution was filtered and TFA (50 mL). The solution was stirred at RT for 3 hours. Additional TFA (50 mL) was added and the mixture stirred at 30° C. for a further 3 hours then at RT overnight. The solvent was removed under vacuum and the residue azeotroped with toluene. The orange oily residue was dissolved in ethyl acetate (500 mL) and washed with a saturated solution of sodium hydrogen carbonate (2×500 mL), brine (500 mL), dried (MgSO$_4$) and concentrated to leave a pale yellow waxy solid (64 g). The solid was triturated with ethyl acetate (200 mL) at 45° C. for 2 hours, filtered, washed with ethyl acetate and dried in a vacuum oven at 40° C. overnight to leave a white solid (52 g). The crude solid was columned on silica, eluting with a mixture of a 7N ammonia in methanol solution in DCM (0.5-6.5% methanol gradient), to give pure desired material [pure 1] (23.6 g, 99.1% pure by HPLC) and less pure material recovered from mixed fractions and previous liquors (34.5 g, 82.8% pure by HPLC). The impure material was dissolved in DCM (50 mL) and a white solid crystallised out. The solid was removed by filtration and washed with DCM to give pure desired material [pure 2] (6.5 g, 98.3% pure by HPLC). The filtrate was columned on silica, eluting with 7N ammonia in methanol solution in DCM (0-5% methanol gradient), to give the desired material [pure 3] (18.3 g, 98.7% pure by HPLC). Pures 1, 2 & 3 were combined (48.4 g) and charged to a 3 L fixed vessel. Ethyl acetate (500 mL, 10 vol) was added and the mixture was heated to reflux with stirring, additional ethyl acetate (400 mL, 8 vol) was added and the remaining solid material removed by hot filtration. The filtrate was cooled to 60° C. and isohexane (250 mL) added dropwise. The slurry was cooled to 20° C. over approx 1 hour and then stirred at RT overnight. The slurry was filtered and the solid washed with isohexane (2×200 mL) then dried in a vacuum oven at 40° C. to leave a white solid (34.8 g). This solid was further dried in a vacuum oven at 60° C. overnight to leave the desired compound as a white powder (33.1 g). This is a different crystal form to that previously described, melting point (melting onset) 113.8° C.

The preparation of 2-(azetidin-1-ylcarbonyl)-5-chloropyrazine was described earlier.

The preparation of 1,1-dimethylethyl 3-[({3-hydroxy-5-[(1-methylethyl)oxy]phenyl}carbonyl)amino]-1H-pyrazole-1-carboxylate is described below.

1,1-Dimethylethyl 3-[({3-hydroxy-5-[(1-methylethyl)oxy]phenyl}carbonyl)amino]-1H-pyrazole-1-carboxylate

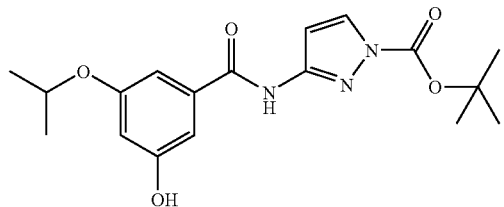

1,1-Dimethylethyl 3-[({3-[(1-methylethyl)oxy]-5-[(phenylmethyl)oxy]phenyl}carbonyl)amino]-1H-pyrazole-1-carboxylate (76.4 g, 0.17 mol) was dissolved in ethanol (750 mL, 10 vol) and 10% palladium on charcoal (water wet) (7.5 g) added. The mixture was hydrogenated for 18 hours at 25° C. and a pressure of 5 bar. The catalyst was removed by filtration through Celite® and the cake washed with methanol (250 mL). The combined filtrate was concentrated under vacuum to leave a beige foamy solid which was chromatographed on silica, eluting with 10-70% ethyl acetate in isohexane, to give the desired material as a white foam solid (56.4 g). $^1$H NMR δ (CDCl$_3$): 1.30 (d, 6H), 1.64 (s, 9H), 4.49-4.55 (m, 1H), 6.67 (t, 1H), 6.98 (d, 2H), 7.10 (d, 1H), 8.02 (d, 1H), 9.21 (s, 1H); m/z 360 (M–H)$^-$ 1,1-Dimethylethyl 3-[({3-[(1-methylethyl)oxy]-5-[(phenylmethyl)oxy]phenyl}carbonyl)amino]-1H-pyrazole-1-carboxylate

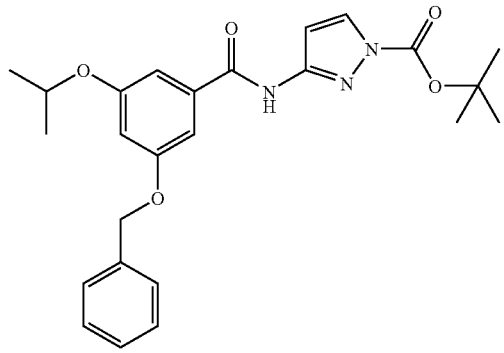

A solution of oxalyl chloride (76 mL, 0.87 mol) in DCM (125 mL) was added dropwise to a slurry of 3-[(1-methylethyl)oxy]-5-[(phenylmethyl)oxy]benzoic acid (50 g, 0.17 mol) and DMF (1 mL) in DCM (300 mL). The reaction was stirred at RT for 2 hours then the solvent removed under vacuum and the residue azeotroped with toluene (200 mL). The oily residue was dissolved in dry pyridine (100 mL) and the mixture added, over 5 minutes, to a solution of 1,1-dimethylethyl 3-amino-1H-pyrazole-1-carboxylate (38.4 g, 0.21 mol) in dry pyridine (325 mL) under nitrogen. The reaction was stirred at RT for 1 hour, the solvent removed under vacuum and the residue azeotroped with toluene. The residue was partitioned between DCM (500 mL) and water (500 mL) and the organic layer washed with a saturated aqueous solution of sodium hydrogen carbonate (500 mL), brine (500 mL) and dried (MgSO$_4$). The organic solution was concentrated under vacuum and the residue twice azeotroped with toluene to leave an orange resin (88.8 g). The resin was chromatographed on silica, eluting with 25-50% ethyl acetate in isohexane, to give the desired material as a pale yellow foam (76.4 g). $^1$H NMR δ (CDCl$_3$): 1.33 (d, 6H), 1.56 (s, 9H), 4.49-4.55 (m, 1H), 5.04 (s, 2H), 6.69 (t, 1H), 7.00 (t, 1H), 7.06-7.07 (m, 1H), 7.17 (d, 1H), 7.32-7.45 (m, 5H), 8.04 (d, 1H), 9.48 (s, 1H); m/z 450 (M−H)$^-$ The preparations of 3-[(1-methylethyl)oxy]-5-[(phenylmethyl)oxy]benzoic acid and 1,1-dimethylethyl 3-amino-1H-pyrazole-1-carboxylate were described earlier.

EXAMPLE 40

3-{[5-(Azetidin-1-ylcarbonyl)-3-chloropyridin-2-yl]oxy}-N-(1,5-dimethyl-1H-pyrazol-3-yl)-5-{[(1S)-1-methyl-2-(methyloxy)ethyl]oxy}benzamide

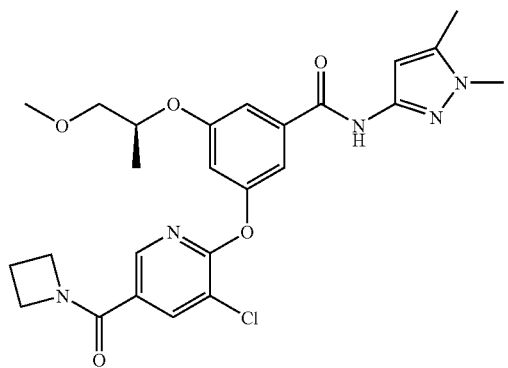

A solution of N-(1,5-dimethyl-1H-pyrazol-3-yl)-3-hydroxy-5-{[(1S)-1-methyl-2-(methyloxy)ethyl]oxy}benzamide (0.62 mmol) in acetonitrile (5 mL), was treated with potassium carbonate (1.24 mmol) and 5-(azetidin-1-ylcarbonyl)-2,3-dichloropyridine (0.68 mmol), before being heated to 120° C. in a microwave reactor for 4.5 hours. The mixture was evaporated in vacuo, before being partitioned between DCM (20 mL) and water (20 mL). The organics were evaporated in vacuo then chromatographed on silica, eluting with 0-10% methanol in ethyl acetate, to give the desired compound as a white foam (160 mg).

$^1$H NMR δ (d$_6$-DMSO): 1.25 (d, 3H), 2.24 (s, 3H), 2.26 (m, 2H), 3.30 (s, 3H), 3.50 (m, 2H), 3.66 (s, 3H), 4.05 (t, 2H), 4.37 (t, 2H), 4.78 (m, 1H), 6.42 (s, 1H), 7.03 (t, 1H), 7.38 (t, 1H), 7.51 (t, 1H), 8.23 (d, 1H), 8.34 (d, 1H), 10.76 (s, 1H); m/z 514, 516 (M+H)$^+$

The preparation of 5-(azetidin-1-ylcarbonyl)-2,3-dichloropyridine was described earlier.

The preparation of N-(1,5-dimethyl-1H-pyrazol-3-yl)-3-hydroxy-5-{[(1S)-1-methyl-2-(methyloxy)ethyl]oxy}benzamide is described below:

N-(1,5-Dimethyl-1H-pyrazol-3-yl)-3-hydroxy-5-{[(1S)-1-methyl-2-(methyloxy)ethyl]oxy}benzamide

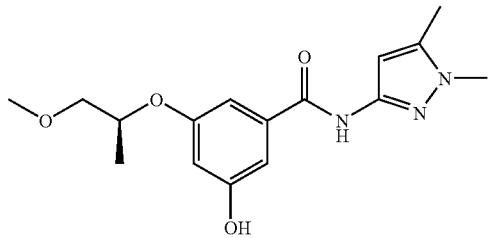

A solution of N-(1,5-dimethyl-1H-pyrazol-3-yl)-3-{[(1S)-1-methyl-2-(methyloxy)ethyl]oxy}-5-[(phenylmethyl)oxy]benzamide (2.57 mmol) in ethanol (40 mL), under argon was treated with 10% palladium on carbon (100 mg, wetted with 0.1 mL water and 1 mL ethanol). The flask was evacuated and filled with hydrogen, this procedure was repeated 4 times. The mixture was left to stir at RT overnight under an atmosphere of hydrogen then the reaction filtered through Celite® and the cake washed with ethanol (50 mL) and ethyl acetate (50 mL). The combined organic layers were evaporated in vacuo to give the desired compound as a white foam (597 mg). $^1$H NMR δ (d$_6$-DMSO): 1.23 (d, 3H), 2.25 (s, 3H), 3.31 (s, 3H), 3.47 (m, 2H), 3.66 (s, 3H), 4.66 (m, 1H), 6.40 (s, 1H), 6.46 (t, 1H), 6.95 (t, 1H), 7.06 (t, 1H), 9.60 (s, 1H), 10.49 (s, 1H); m/z 320 (M+H)$^+$ N-(1,5-Dimethyl-1H-pyrazol-3-yl)-3-{[(1S)-1-methyl-2-(methyloxy)ethyl]oxy}-5-[(phenylmethyl)oxy]benzamide

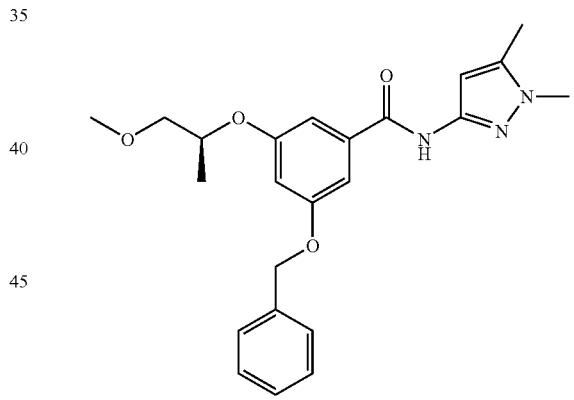

A solution of 3-[(1S)-2-methoxy-(1-methylethyl)oxy]-5-{[phenylmethyl]oxy}benzoic acid (4.11 mmol) in DMF (10 mL) was treated with the 1,5-dimethyl-1H-pyrazol-3-ylamine (4.52 mmol), DIPEA (5.93 mmol) and HATU (3.85 mmol) and stirred at RT overnight, under an argon atmosphere. The mixture was poured onto water (100 mL) and extracted with ethyl acetate (3×100 mL). The organic layer was washed with brine (20 mL) and evaporated in vacuo before chromatography on silica, eluting with 20-80% ethyl acetate in isohexane, to afford the desired compound as a yellow oil (1.05 g).

$^1$H NMR δ (d$_6$-DMSO): 1.23 (d, 3H), 2.25 (s, 3H), 3.30 (s, 3H), 3.48 (m, 2H), 3.67 (s, 3H), 4.71 (m, 1H), 5.16 (s, 2H), 6.42 (s, 1H), 6.73 (t, 1H), 7.20 (t, 1H), 7.26 (t, 1H), 7.34 (m, 1H), 7.41 (m, 2H), 7.46 (m, 2H), 10.62 (s, 1H); m/z 410 (M+H)$^+$

The preparation of 3-[(1S)-2-methoxy-(1-methylethyl)oxy]-5-{[phenylmethyl]oxy}benzoic acid was described earlier.

The 1,5-dimethyl-1H-pyrazol-3-ylamine was prepared according to the literature route [*J. Het. Chem.*, (1982), 19, 1267].

EXAMPLE 41

3-{[5-(Azetidin-1-ylcarbonyl)-3-chloropyridin-2-yl]oxy}-N-(1,5-dimethyl-1H-pyrazol-3-yl)-5-{[2-fluoro-1-(fluoromethyl)ethyl]oxy}benzamide

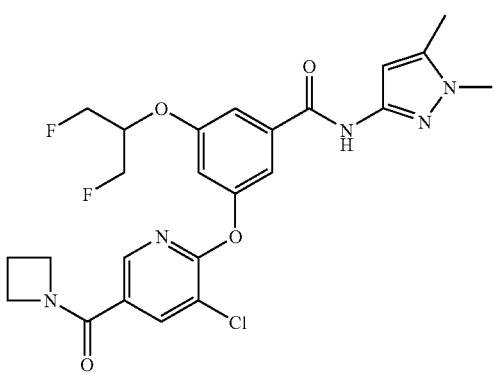

A solution of N-(1,5-dimethyl-1H-pyrazol-3-yl)-3-{[2-fluoro-1-(fluoromethyl)ethyl]oxy}-5-hydroxybenzamide (0.61 mmol) in acetonitrile (5 mL), was treated with the potassium carbonate (1.23 mmol) and 5-(azetidin-1-ylcarbonyl)-2,3-dichloropyridine (0.68 mmol), before being heated to 120° C. in a microwave reactor for 4 hours. The mixture was filtered and evaporated in vacuo before being chromatographed on silica, eluting with 0-5% methanol in ethyl acetate, to give the desired compound as a white foam (175 mg).

$^1$H NMR δ (d$_6$-DMSO): 2.27 (m, 5H), 3.66 (s, 3H), 4.06 (t, 2H), 4.37 (t, 2H), 4.65 (m, 1H), 4.73 (m, 1H), 4.77 (m, 1H), 4.85 (m, 1H), 5.10 (m, 1H), 6.42 (s, 1H), 7.16 (t, 1H), 7.45 (t, 1H), 7.60 (t, 1H), 8.23 (d, 1H), 8.35 (d, 1H), 10.71 (s, 1H) m/z 520 (M+H)$^+$

The preparation of 5-(azetidin-1-ylcarbonyl)-2,3-dichloropyridine was described earlier.

The preparation of N-(1,5-dimethyl-1H-pyrazol-3-yl)-3-{[2-fluoro-1-(fluoromethyl)ethyl]oxy}-5-hydroxybenzamide is described below:

N-(1,5-Dimethyl-1H-pyrazol-3-yl)-3-{[2-fluoro-1-(fluoromethyl)ethyl]oxy}-5-hydroxybenzamide

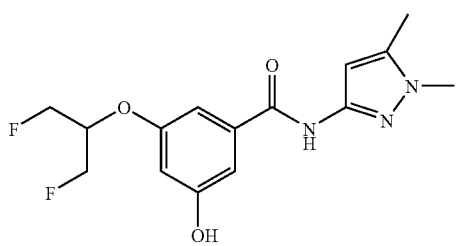

A solution of N-(1,5-dimethyl-1H-pyrazol-3-yl)-3-{[2-fluoro-1-(fluoromethyl)ethyl]oxy}-5-[(phenylmethyl)oxy]benzamide (1.89 mmol) in ethanol (30 mL) was treated with 10% palladium on carbon (78 mg, wetted with 1 mL ethanol). The flask was evacuated and filled with hydrogen and this procedure repeated a further 4 times. The mixture was left to stir at RT overnight under an atmosphere of hydrogen then the mixture filtered through Celite® and the cake washed with ethanol (50 mL) and ethyl acetate (50 mL). The combined organics were evaporated in vacuo to give the desired compound as a white foam (613 mg).

$^1$H NMR δ (d$_6$-DMSO): 2.52 (s, 3H), 3.66 (s, 3H), 4.66 (m, 2H), 4.77 (m, 2H), 4.97 (m, 1H), 6.41 (s, 1H), 6.56 (t, 1H), 7.02 (m, 1H), 7.15 (t, 1H), 10.52 (s, 1H); m/z 326 (M+H)$^+$

N-(1,5-Dimethyl-1H-pyrazol-3-yl)-3-{[2-fluoro-1-(fluoromethyl)ethyl]oxy}-5-[(phenylmethyl)oxy]benzamide

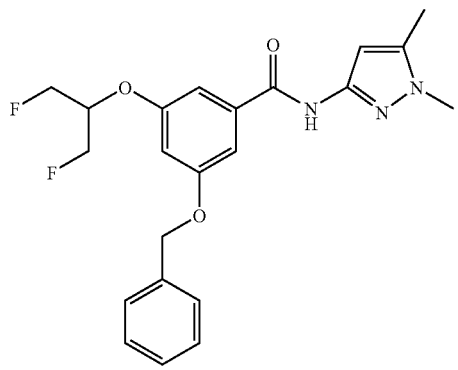

A solution of 3-{[2-fluoro-1-(fluoromethyl)ethyl]oxy}-5-[(phenylmethyl)oxy]benzoic acid (2.96 mmol) in DMF (5 mL) was treated with 1,5-dimethyl-1H-pyrazol-3-ylamine (3.11 mmol), DIPEA (5.93 mmol) and HATU (3.85 mmol) and stirred at RT overnight. The mixture was poured into water (100 mL) and extracted with ethyl acetate (3×75 mL). The organics were washed with brine, dried (MgSO$_4$) and evaporated in vacuo before chromatography on solica, eluting with 50-100% ethyl acetate in isohexane, to give the desired compound as a colourless glass (784 mg). $^1$H NMR δ (d$_6$-DMSO): 2.81 (s, 3H), 3.67 (s, 3H), 4.66 (m, 2H), 4.78 (m, 2H), 5.04 (m, 1H), 5.69 (s, 2H), 6.43 (s, 1H), 6.85 (t, 1H), 7.28 (m, 1H), 7.32 (m, 1H), 7.35 (m, 1H), 7.41 (m, 2H), 7.47 (m, 2H), 10.64 (s, 1H); m/z 416 (M+H)$^+$ The preparations of 3-{[2-fluoro-1-(fluoromethyl)ethyl]oxy}-5-[(phenylmethyl)oxy]benzoic acid and 1,5-dimethyl-1H-pyrazol-3-ylamine were described earlier.

EXAMPLE 42

3-{[6-(Azetidin-1-ylcarbonyl)pyridazin-3-yl]oxy}-5-{[(1S)-1-methyl-2-(methyloxy)ethyl]oxy}-N-(1-methyl-1H-pyrazol-3-yl)benzamide

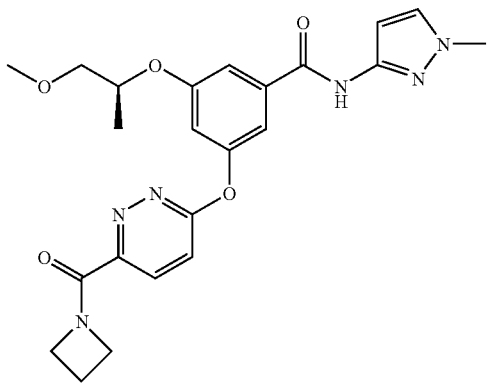

A mixture of 3-(azetidin-1-ylcarbonyl)-6-chloropyridazine (45 mg, 0.23 mmol), 3-hydroxy-5-[(1S)-2-methoxy-(1-methylethyl)oxy]-N-(1-methyl-1H-pyrazol-3-yl)benzamide (70 mg, 0.23 mmol) and potassium carbonate (63 mg, 0.46 mmol) in acetonitrile (3 mL) was stirred in a Smith Creator microwave at 130° C. for 1 hour. The solid was filtered off and the solvent was removed in vacuo. The residue was purified by reverse phase preparative HPLC, eluting with 5-95% acetonitrile in water (+0.2% TFA), followed by passage through a Silicycle Si-Carbonate cartridge, eluting with methanol, to give the desired product as a colourless solid (97 mg). $^1$H NMR δ (CDCl$_3$): 1.34 (3H, d), 1.66 (3H, s), 2.33-2.41 (2H, m), 3.40 (3H, s), 3.48-3.52 (1H, m), 3.56-3.60 (1H, m), 3.79 (3H, s), 4.27 (2H, d), 4.58-4.62 (1H, m), 4.76 (2H, t), 6.79 (1H, d), 6.97 (1H, t), 7.25-7.29 (3H, m), 7.35-7.36 (1H, m), 8.26-8.28 (1H, m), 8.49 (1H, s); m/z 467 (M+H)$^+$.

The preparation of 3-hydroxy-5-[(1S)-2-methoxy-(1-methylethyl)oxy]-N-(1-methyl-1H-pyrazol-3-yl)benzamide was described earlier.

The preparation of 3-(azetidin-1-ylcarbonyl)-6-chloropyridazine is described below:

3-(Azetidin-1-ylcarbonyl)-6-chloropyridazine

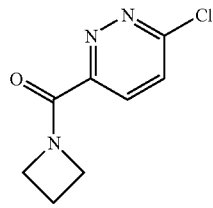

Phosphorus oxychloride (50 mL) was added to 6-hydroxypyridazine-3-carboxylic acid (9.82 g, 70.05 mmol) and the resulting solution heated to reflux. After 45 mins the solution was allowed to cool and the excess of phosphorus oxychloride was removed under reduced pressure. THF (50 mL) was added to the black residue and the resulting solution cooled to 0° C. Triethylamine (9.77 mL, 70.05 mmol) and azetidine (4.0 g, 70.05 mmol) were added dropwise. The resulting mixture was allowed to warm to RT and stirred overnight. The volatiles were removed under reduced pressure and water (50 mL) added, then the residue was adjusted to pH8 using sodium hydroxide solution. The aqueous layer was extracted five times with ethyl acetate, the combined organics dried (MgSO$_4$) and the solvent removed to give the crude product as a dark oil. A sample was purified by preparative HPLC, eluting with 5-95% acetonitrile in water (+0.2% TFA), and gave the title compound as a colorless solid (135 mg).

$^1$H NMR δ (CDCl$_3$): 2.39-2.47 (2H, m), 4.30 (2H, t), 4.82 (2H, t), 7.64 (1H, d), 8.21 (1H, d); m/z 198 (M+H)$^+$.

EXAMPLE 43

3-{[5-(Azetidin-1-ylcarbonyl)pyrazin-2-yl]oxy}-N-(4-methyl-1,3-thiazol-2-yl)-5-[(3S)-tetrahydrofuran-3-yloxy]benzamide

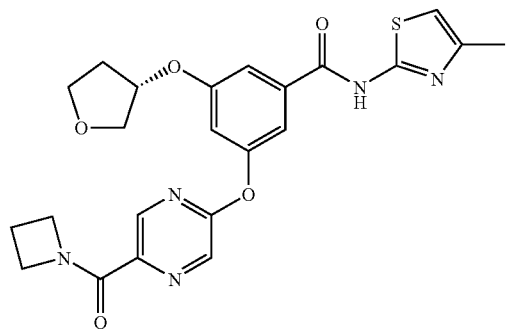

3-{[5-(Azetidin-1-ylcarbonyl)pyrazin-2-yl]oxy}-5-[(3S)-tetrahydrofuran-3-yloxy]benzoic acid (200 mg, 0.52 mmol), HATU (475 mg, 1.25 mmol) and 2-amino-4-methylthiazole (119 mg, 1.04 mmol) were suspended in DMF (2 mL). DIPEA (0.220 mL, 1.26 mmol) was then added and the reaction mixture stirred at RT for 16 hours. The DMF was removed in vacuo and water (15 mL) added. The mixture was extracted with ethyl acetate (3×20 mL) and the extracts combined, washed with water (15 mL), 1N hydrochloric acid (10 mL), water (10 mL), a saturated aqueous solution of sodium bicarbonate (10 mL), brine (10 mL), dried (MgSO$_4$), filtered, and evaporated in vacuo. The residue was chromatographed on silica, eluting with a gradient of 60-100% ethyl acetate in isohexane, to give the desired compound (70 mg).

$^1$H NMR δ (CDCl$_3$): 2.13-2.29 (m, 2H), 2.32 (s, 3H), 2.34-2.42 (m, 2H), 3.89-4.02 (m, 4H), 4.26 (t, 2H), 4.69 (t, 2H), 4.96-4.99 (m, 1H), 6.57 (d, 1H), 6.94 (t, 1H), 7.29 (t, 1H), 7.33 (t, 1H), 8.35 (d, 1H), 8.85 (d, 1H), 9.72 (s, 1H); m/z 482 (M+H)$^+$, 480 (M−H)$^-$

The following compounds were prepared in an analogous fashion from 3-{[5-(azetidin-1-ylcarbonyl)pyrazin-2-yl]oxy}-5-[(3S)-tetrahydrofuran-3-yloxy]benzoic acid and the appropriate aminoheterocycle.

| Example | Structure | m/z | NMR |
|---|---|---|---|
| 43a | 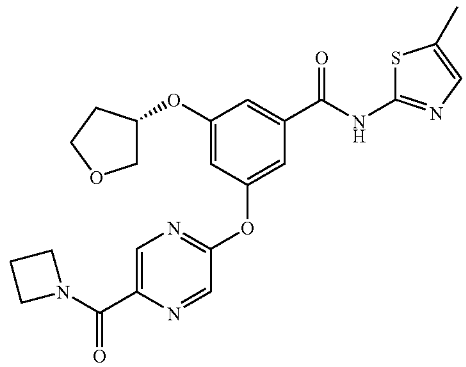 | 482 (M + H)⁺ | ¹H NMR δ (CDCl₃): 2.12-2.29 (m, 2H), 2.34-2.42 (m, 2H), 2.38 (s, 3H), 3.88-4.02 (m, 4H), 4.26 (t, 2H), 4.68 (t, 2H), 4.96-5.00 (m, 1H), 6.93 (t, 1H), 6.98 (s, 1H), 7.34 (t, 1H), 7.37 (t, 1H), 8.34 (d, 1H), 8.84 (d, 1H) |
| 43b | 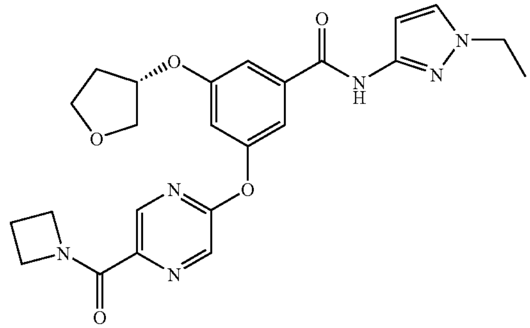 | 479 (M + H)⁺ | ¹H NMR δ (CDCl₃): 1.46 (t, 3H), 2.13-2.29 (m, 2H), 2.34-2.42 (m, 2H), 3.88-4.02 (m, 4H), 4.06 (q, 2H), 4.26 (t, 2H), 4.69 (t, 2H), 4.96-5.00 (m, 1H), 6.78 (d, 1H), 6.88 (t, 1H), 7.24 (t, 1H), 7.30-7.31 (m, 1H), 7.32 (d, 1H), 8.34 (d, 1H), 8.36 (s, 1H), 8.86 (d, 1H) |
| 43c | 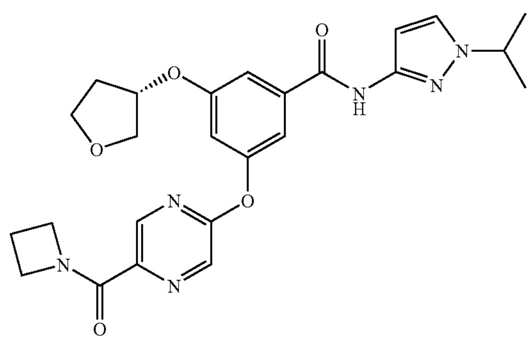 | 493 (M + H)⁺ 491 (M − H)⁻ | ¹H NMR δ (CDCl₃): 1.48 (d, 6H), 2.13-2.29 (m, 2H), 2.34-2.42 (m, 2H), 3.88-4.02 (m, 4H), 4.26 (t, 2H), 4.36 (septet, 1H), 4.69 (t, 2H), 4.97-5.00 (m, 1H), 6.77 (d, 1H), 6.88 (t, 1H), 7.24-7.25 (m, 1H), 7.31-7.31 (m, 1H), 7.35 (d, 1H), 8.33 (d, 1H), 8.34 (s, 1H), 8.86 (d, 1H) |
| 43d* | 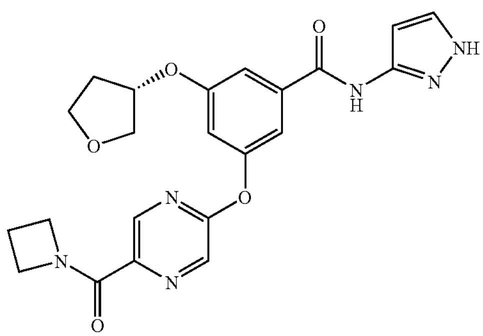 | 451 (M + H)⁺ 449 (M − H)⁻ | ¹H NMR δ (CDCl₃): 2.13-2.29 (m, 2H), 2.34-2.42 (m, 2H), 3.88-4.02 (m, 4H), 4.26 (t, 2H), 4.69 (t, 2H), 4.96-5.00 (m, 1H), 6.84 (s, 1H), 6.87 (t, 1H), 7.28 (t, 1H), 7.31 (t, 1H), 7.46 (d, 1H), 8.36 (d, 1H), 8.83 (d, 1H), 9.45 (s, 1H), 10.05 (s, 1H) |

| Example | Structure | m/z | NMR |
|---|---|---|---|
| 43e | 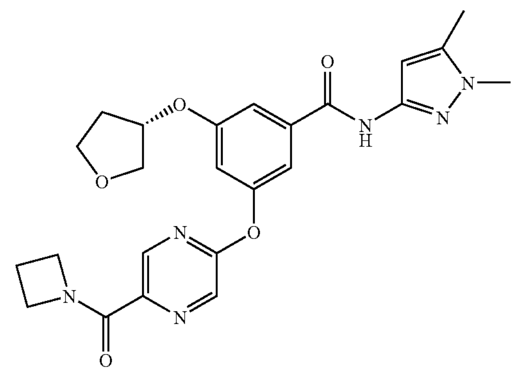 | 479 (M + H)+ 477 (M − H)− | ¹H NMR δ (CDCl₃): 2.11-2.24 (m, 2H), 2.26 (s, 3H), 2.33-2.41 (m, 2H), 3.61 (s, 3H), 3.87-4.00 (m, 4H), 4.25 (t, 2H), 4.68 (t, 2H), 4.93-4.97 (m, 1H), 6.58 (s, 1H), 6.86 (t, 1H), 7.24 (t, 1H), 7.28 (s, 1H), 8.32 (d, 1H), 8.84 (d, 1H), 8.85 (s, 1H) |

*The reaction was carried out using 1,1-dimethylethyl 3-amino-1H-pyrazole-1-carboxylate as the amino heterocycle, the resultant product was dissolved in acetonitrile and heated in a microwave reactor at 150° C. for 5-10 minutes. The mixtures were allowed to cool then concentrated in vacuo to give the desired products. The preparation of 1,1-dimethylethyl 3-amino-1H-pyrazole-1-carboxylate was described earlier.

The preparation of 3-{[5-(azetidin-1-ylcarbonyl)pyrazin-2-yl]oxy}-5-[(3S)-tetrahydrofuran-3-yloxy]benzoic acid is described below:

3-{[5-(Azetidin-1-ylcarbonyl)pyrazin-2-yl]oxy}-5-[(3S)-tetrahydrofuran-3-yloxy]benzoic acid

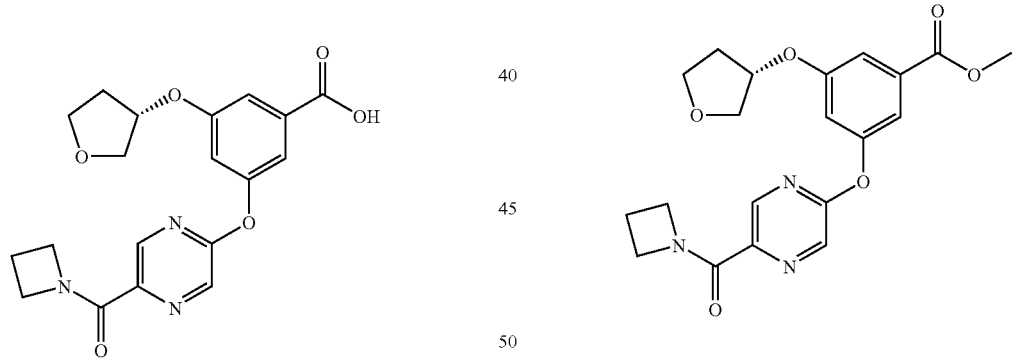

Methyl 3-{[5-(azetidin-1-ylcarbonyl)pyrazin-2-yl]oxy}-5-[(3S)-tetrahydrofuran-3-yloxy]benzoate (7.02 mmol) was dissolved in THF (50 mL), 1N sodium hydroxide (7.0 mL) was added followed by water (50 mL) and the resultant solution stirred at RT for 4 hours. The organics were removed in vacuo, the aqueous solution filtered and extracted with ethyl acetate (30 mL). The aqueous layer was acidified with 2N hydrochloric acid, extracted with ethyl acetate (3×50 mL), and the organic extracts washed with water (10 mL), brine (10 mL) then evaporated to dryness to give the desired material as a white foam (2.33 g). ¹H NMR δ (CDCl₃): 2.14-2.30 (m, 2H), 2.34-2.42 (m, 2H), 3.89-3.94 (m, 2H), 3.97-4.02 (m, 2H), 4.28 (t, 2H), 4.69 (t, 2H), 4.97-5.00 (m, 1H), 6.94 (t, 1H), 7.48 (t, 2H), 8.34 (d, 1H), 8.85 (d, 1H); m/z 386 (M+H)+, 384 (M−H)−

Methyl 3-{[5-(azetidin-1-ylcarbonyl)pyrazin-2-yl]oxy}-5-[(3S)-tetrahydrofuran-3-yloxy]benzoate A solution of methyl 3-hydroxy-5-[(3S)-tetrahydrofuran-3-yloxy]benzoate (2.5 g, 10.5 mmol), potassium carbonate (2.9 g, 21.0 mmol) and 2-(azetidin-1-ylcarbonyl)-5-chloropyrazine (2.48 g, 12.6 mmol) in DMA (25 mL) was heated at 120° C. for 2 hours. The solution was diluted with ethyl acetate (150 mL), washed with water (3×50 mL), brine (20 mL), dried (MgSO₄), filtered and the solvent removed in vacuo. The residue was purified by chromatography on silica, eluting with 0-50% ethyl acetate in isohexane, to give the desired compound as a colourless oil (2.8 g). ¹H NMR δ (CDCl₃): 2.13-2.29 (m, 2H), 2.34-2.41 (m, 2H), 3.88-4.04 (m, 4H), 3.90 (s, 3H), 4.25 (t, 2H), 4.68 (t, 2H), 4.96-5.00 (m, 1H), 6.91 (t, 1H), 7.43 (d, 2H), 8.32 (d, 1H), 8.85 (d, 1H); m/z 386 (M+H)+, 384 (M−H)−

Methyl 3-hydroxy-5-[(3S)-tetrahydrofuran-3-yloxy]benzoate

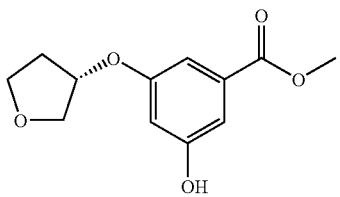

Methyl 3-[(phenylmethyl)oxy]-5-[(3S)-tetrahydrofuran-3-yloxy]benzoate (25.0 g, 76.2 mmol) was dissolved in THF (150 mL) and ethanol (150 mL). 10% Palladium on carbon (30 mg) was added and the mixture placed under a hydrogen atmosphere and left to stir at RT until the reaction was complete. The catalyst was removed by filtration through diatomaceous earth and the filtrate was concentrated in vacuo to give an orange oil which crystallised on standing. The solid was filtered off and washed with diethyl ether to give the desired product as a white solid (13.75 g).

$^1$H NMR δ (CDCl$_3$): 2.1-2.3 (2H, m), 3.9 (3H, s), 3.9-3.95 (2H, m), 3.97-4.05 (2H, m), 4.95 (1H, s), 5.6 (1), 6.6 (1H, t), 7.1 (1H, t), 7.13 (1H, t); m/z 237 (M+H)$^+$

Methyl 3-[(phenylmethyl)oxy]-5-[(3S)-tetrahydrofuran-3-yloxy]benzoate

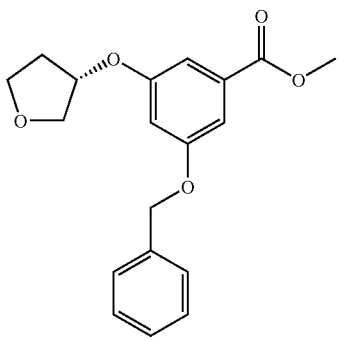

A mixture of methyl 3-hydroxy-5-{[phenylmethyl]oxy}benzoate (18.8 g, 72.75 mmol), (3R)-tetrahydrofuran-3-yl 4-methylbenzenesulfonate (18.5 g, 76.4 mmol) and potassium carbonate (20.08 g, 145.5 mmol) in butyronitrile (250 mL) was heated to 130° C. for 3 hours. The solvent was removed in vacuo and ethyl acetate added. The organics were washed with water (40 mL), 0.5M sodium hydroxide solution (40 mL), brine (40 mL), dried (MgSO$_4$), filtered and the solvent removed in vacuo. The residue was chromatographed on silica, eluting with a gradient of 0-5% methanol in DCM, to give the desired compound as a colourless oil (20.1 g). $^1$H NMR δ (CDCl$_3$): 2.08-2.26 (m, 2H), 3.78-4.01 (m, 4H), 3.90 (s, 3H), 4.92-4.96 (m, 1H), 5.08 (s, 2H), 6.69 (t, 1H), 7.15 (t, 1H), 7.29 (t, 1H), 7.34-7.44 (m, 5H); m/z 327 (M+H)$^+$ The preparations of methyl 3-hydroxy-5-{[phenylmethyl]oxy}benzoate and (3R)-tetrahydrofuran-3-yl 4-methylbenzenesulfonate were described earlier.

EXAMPLE 44

3-{[5-(Azetidin-1-ylcarbonyl)-3-chloropyridin-2-yl]oxy}-N-(4-methyl-1,3-thiazol-2-yl)-5-[(3S)-tetrahydrofuran-3-yloxy]benzamide

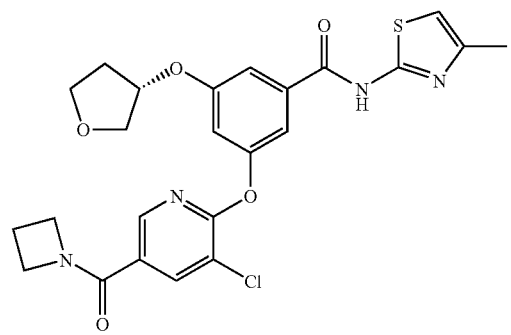

1-Chloro-N,N,2-trimethyl-1-propenylamine (0.70 mL, 0.53 mmol) was added to a solution of 3-{[5-(azetidin-1-ylcarbonyl)-3-chloropyridin-2-yl]oxy}-5-[(3S)-tetrahydrofuran-3-yloxy]benzoic acid (200 mg, 0.48 mmol) in DCM (6 mL) and stirred at RT for 2 hours. 2-Amino-4-methylthiazole (110 mg, 0.96 mmol) and pyridine (0.078 mL, 0.96 mmol) were added and the reaction stirred at RT for 16 hours. The solvent was removed in vacuo, water (20 mL) added and the mixture extracted with ethyl acetate (3×20 mL). The extracts were combined and washed with 2N hydrochloric acid (20 mL), saturated aqueous sodium bicarbonate solution (20 mL), water (20 mL), brine (20 mL), dried (MgSO$_4$), filtered, and evaporated in vacuo. The residue was chromatographed on silica, eluting with a gradient of 50-100% ethyl acetate in isohexane, to give the desired compound (78 mg).

$^1$H NMR δ (CDCl$_3$): 2.13-2.28 (m, 2H), 2.31 (s, 3H), 2.35-2.43 (m, 2H), 3.88-4.02 (m, 4H), 4.21-4.28 (m, 2H), 4.31-4.39 (m, 2H), 4.96-5.00 (m, 1H), 6.56 (d, 1H), 6.94 (t, 1H), 7.28 (t, 1H), 7.34 (t, 1H), 8.16 (d, 1H), 8.25 (d, 1H), 9.83 (s, 1H); m/z 515 (M+H)$^+$, 513 (M–H)$^-$

The following compounds were prepared in an analogous fashion from 3-{[5-(azetidin-1-ylcarbonyl)-3-chloropyridin-2-yl]oxy}-5-[(3S)-tetrahydrofuran-3-yloxy]benzoic acid and the appropriate aminoheterocycle.

| Example | Structure | m/z | NMR |
|---|---|---|---|
| 44a | 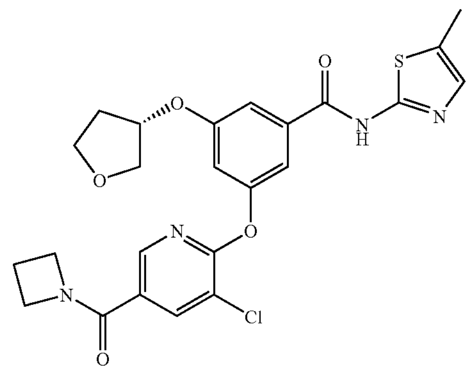 | 515 (M + H)+ 513 (M − H)− | ¹H NMR δ (CDCl₃): 2.13-2.29 (m, 2H), 2.34-2.42 (m, 2H), 2.38 (s, 3H), 3.88-4.02 (m, 4H), 4.24-4.34 (m, 4H), 4.96-4.99 (m, 1H), 6.94 (t, 1H), 6.97 (d, 1H), 7.34 (t, 1H), 7.36-7.37 (m, 1H), 8.15 (d, 1H), 8.24 (d, 1H), 10.82 (s, 1H) |
| 44b | 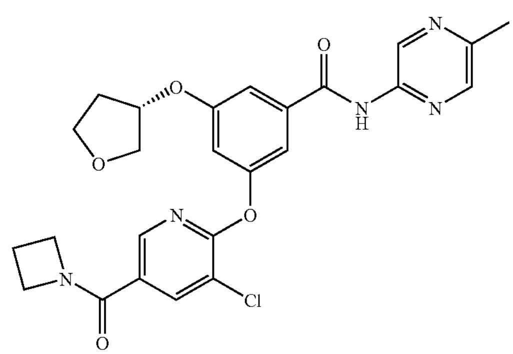 | 510 (M + H)+ 508 (M − H)− | ¹H NMR δ (CDCl₃): 2.15-2.31 (m, 2H), 2.35-2.43 (m, 2H), 2.56 (s, 3H), 3.89-4.03 (m, 4H), 4.20-4.39 (m, 4H), 4.99-5.03 (m, 1H), 6.93 (t, 1H), 7.29 (t, 1H), 7.35 (t, 1H), 8.14 (s, 1H), 8.16 (d, 1H), 8.26 (d, 1H), 8.36 (s, 1H), 9.54 (d, 1H) |
| 44c | 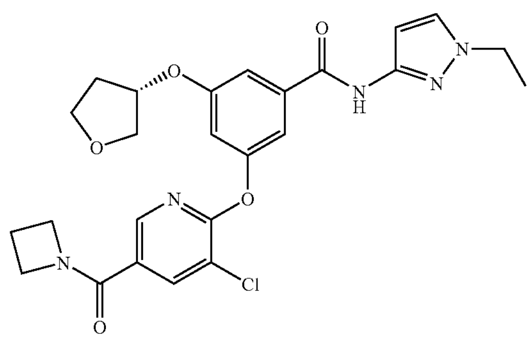 | 512 (M + H)+ 510 (M − H)− | ¹H NMR δ (CDCl₃): 1.46 (t, 3H), 2.14-2.30 (m, 2H), 2.35-2.43 (m, 2H), 3.88-4.02 (m, 4H), 4.06 (q, 2H), 4.20-4.28 (m, 2H), 4.31-4.39 (m, 2H), 4.97-5.01 (m, 1H), 6.78 (d, 1H), 6.89 (t, 1H), 7.23 (t, 1H), 7.30-7.31 (m, 1H), 7.32 (d, 1H), 8.16 (d, 1H), 8.25 (d, 1H), 8.37 (s, 1H) |
| 44d | 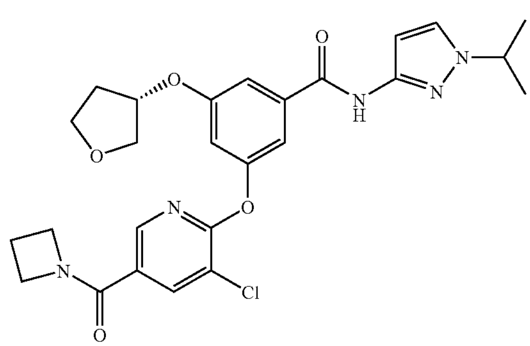 | 526 (M + H)+ 524 (M − H)− | ¹H NMR δ (CDCl₃): 1.48 (d, 6H), 2.14-2.29 (m, 2H), 2.35-2.43 (m, 2H), 3.88-4.02 (m, 4H), 4.20-4.28 (m, 2H), 4.30-4.40 (m, 2H), 4.36 (septet, 1H), 4.98-5.01 (m, 1H), 6.78 (d, 1H), 6.89 (t, 1H), 7.24 (t, 1H), 7.32 (t, 1H), 7.35 (d, 1H), 8.16 (d, 1H), 8.25 (d, 1H), 8.35 (s, 1H) |

-continued

| Example | Structure | m/z | NMR |
|---|---|---|---|
| 44e* | 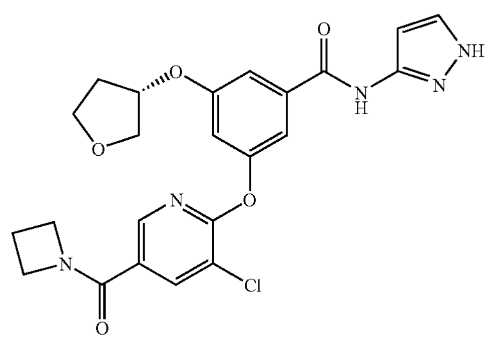 | 484 (M + H)+ 482 (M − H)− | ¹H NMR δ (CDCl₃): 2.12-2.29 (m, 2H), 2.34-2.42 (m, 2H), 3.87-4.02 (m, 4H), 4.20-4.28 (m, 2H), 4.29-4.37 (m, 2H), 4.97-5.00 (m, 1H), 6.85 (s, 1H), 6.88 (t, 1H), 7.29-7.30 (m, 1H), 7.31-7.31 (m, 1H), 7.44 (d, 1H), 8.15 (d, 1H), 8.21 (d, 1H), 9.76 (s, 1H), 10.17 (s, 1H) |

*The reaction was carried out using 1,1-dimethylethyl 3-amino-1H-pyrazole-1-carboxylate as the amino heterocycle, the resultant product was dissolved in acetonitrile and heated in a microwave reactor at 150° C. for 5-10 minutes. The mixtures were allowed to cool then concentrated in vacuo to give the desired products. The preparation of 1,1-dimethylethyl 3-amino-1H-pyrazole-1-carboxylate was described earlier.

The preparation of 3-{[5-(azetidin-1-ylcarbonyl)-3-chloropyridin-2-yl]oxy}-5-[(3S)-tetrahydrofuran-3-yloxy]benzoic acid is described below:

3-{[5-(Azetidin-1-ylcarbonyl)-3-chloropyridin-2-yl]oxy}-5-[(3S)-tetrahydrofuran-3-yloxy]benzoic acid

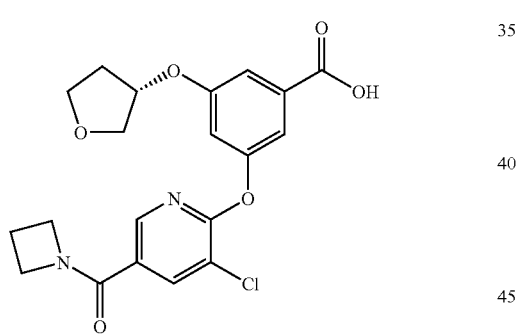

Methyl 3-{[5-(azetidin-1-ylcarbonyl)-3-chloropyridin-2-yl]oxy}-5-[(3S)-tetrahydrofuran-3-yloxy]benzoate

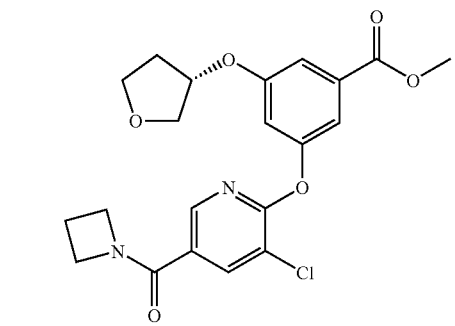

Methyl 3-{[5-(azetidin-1-ylcarbonyl)-3-chloropyridin-2-yl]oxy}-5-[(3S)-tetrahydrofuran-3-yloxy]benzoate (3.75 g, 8.68 mmol) was dissolved in THF (40 mL), 1N sodium hydroxide (8.68 mL, 8.68 mmol) was added followed by water (40 mL) and methanol (1 drop) and the resultant solution stirred at RT for 3 hours. The organics were removed in vacuo, the aqueous solution filtered and extracted with ethyl acetate (30 mL). The aqueous layer was acidified with 2N hydrochloric acid, extracted with ethyl acetate (3×50 mL), and the organic extracts washed with water (10 mL), brine (10 mL) then evaporated to dryness to give the desired material as a white foam (3.53 g).

¹H NMR δ (CDCl₃): 2.14-2.30 (m, 2H), 2.35-2.43 (m, 2H), 3.89-3.94 (m, 2H), 3.96-4.02 (m, 2H), 4.22-4.38 (m, 4H), 4.97-5.01 (m, 1H), 6.95 (t, 1H), 7.46-7.47 (m, 1H), 7.49-7.50 (m, 1H), 8.15 (d, 1H), 8.26 (d, 1H); m/z 419 (M+H)+, 417 (M−H)−.

A solution of methyl 3-hydroxy-5-[(3S)-tetrahydrofuran-3-yloxy]benzoate (2.5 g, 10.5 mmol), potassium carbonate (2.9 g, 21.0 mmol) and 5-(azetidin-1-ylcarbonyl)-2,3-dichloropyridine (2.9 g, 12.6 mmol) in DMA (25 mL) was heated at 120° C. for 5 hours. The solution was diluted with ethyl acetate (150 mL), washed with water (3×50 mL), brine (20 mL), dried (MgSO₄), filtered and the solvent removed in vacuo. The residue was purified by chromatography on silica, eluting with 20-50% ethyl acetate in isohexane, to give the desired compound as a colourless oil (3.75 g). ¹H NMR δ (CDCl₃): 2.13-2.29 (m, 2H), 2.38 (quin, 2H), 3.85-4.04 (m, 4H), 3.90 (s, 3H), 4.19-4.37 (m, 4H), 4.96-5.00 (m, 1H), 6.91 (t, 1H), 7.42-7.45 (m, 2H), 8.14 (d, 1H), 8.25 (d, 1H); m/z 433 (M+H)+.

The preparations of methyl 3-hydroxy-5-[(3S)-tetrahydrofuran-3-yloxy]benzoate and 5-(azetidin-1-ylcarbonyl)-2,3-dichloropyridine were described earlier.

EXAMPLE 45

3-{[6-(Azetidin-1-ylcarbonyl)pyridin-3-yl]oxy}-N-(5-methylpyrazin-2-yl)-5-[(3S)-tetrahydrofuran-3-yloxy]benzamide

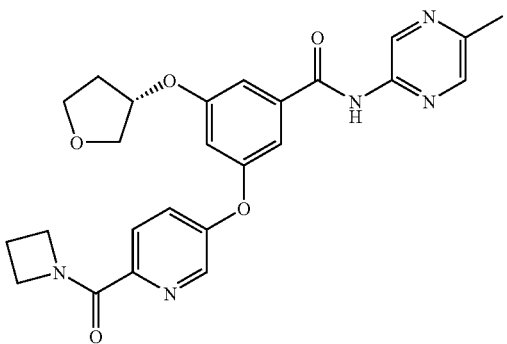

1-Chloro-N,N,2-trimethyl-1-propenylamine (0.133 mL, 1.0 mmol) was added to a suspension of 3-{[6-(azetidin-1-ylcarbonyl)pyridin-3-yl]oxy}-5-[(3S)-tetrahydrofuran-3-yloxy]benzoic acid (350 mg, 0.94 mmol) in DCM (10 mL) and stirred at RT for 30 min. 2-Amino-5-methylpyrazine (196 mg, 1.82 mmol) and pyridine (0.148 mL, 1.82 mmol) were added and the reaction stirred at RT for 2 hours. The solvent was removed in vacuo and water (30 mL) added. The mixture was extracted with ethyl acetate (3×20 mL), washed with 2N hydrochloric acid (20 mL), water (10 mL), saturated aqueous sodium bicarbonate solution (20 mL), water (10 mL) and brine (20 mL). The combined organic extracts were dried (MgSO$_4$), filtered and evaporated in vacuo. The residue was purified by chromatography, eluting with 0-10% methanol in DCM, to give the desired product as a colourless oil (150 mg).
$^1$H NMR δ (CDCl$_3$): 2.12-2.18 (1H, m), 2.22-2.29 (1H, m), 2.31-2.40 (2H, m), 2.56 (3H, s), 3.89-4.03 (4H, m), 4.25 (2H, t), 4.71 (2H, t), 4.97-5.00 (1H, m), 6.76 (1H, t), 7.15 (1H, t), 7.25 (1H, d), 7.38-7.40 (1H, m), 8.12 (1H, s), 8.14 (1H, d), 8.32 (1H, s), 8.34 (1H, d), 9.52 (1H, d); m/z 476 (M+H)$^+$, 474 (M−H)$^−$ The following compound was prepared in an analogous fashion from 3-{[5-(azetidin-1-ylcarbonyl)pyrazin-2-yl]oxy}-5-[(3S)-tetrahydrofuran-3-yloxy]benzoic acid or 3-{[6-(azetidin-1-ylcarbonyl)pyridin-3-yl]oxy}-5-[(3S)-tetrahydrofuran-3-yloxy]benzoic acid and the appropriate aminoheterocycle.

| Example | Structure | m/z | NMR |
|---|---|---|---|
| 45a | 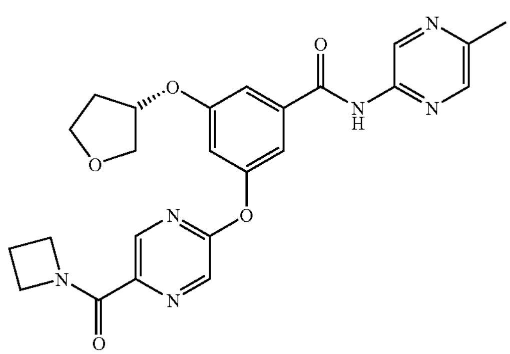 | 477 (M + H)$^+$ | $^1$H NMR δ (CDCl$_3$): 2.16-2.31 (m, 2H), 2.34-2.42 (m, 2H), 2.56 (s, 3H), 3.89-4.02 (m, 4H), 4.26 (t, 2H), 4.69 (t, 2H), 4.98-5.02 (m, 1H), 6.92 (s, 1H), 7.30 (s, 1H), 7.35 (s, 1H), 8.15 (s, 1H), 8.36 (s, 2H), 8.86 (s, 1H), 9.54 (s, 1H) |
| 45b | 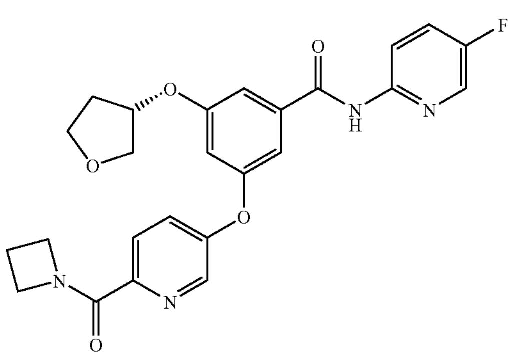 | 479 (M + H)$^+$ 477 (M − H)$^−$ | $^1$H NMR δ (CDCl$_3$): 2.12-2.31 (m, 2H), 2.32-2.40 (m, 2H), 3.90-4.04 (m, 4H), 4.26 (t, 2H), 4.71 (t, 2H), 4.97-5.01 (m, 1H), 6.76 (t, 1H), 7.13 (t, 1H), 7.23 (t, 1H), 7.39 (dd, 1H), 7.48-7.53 (m, 1H), 8.14 (d, 1H), 8.16 (d, 1H), 8.33-8.38 (m, 2H), 8.47 (s, 1H) |

-continued

| Example | Structure | m/z | NMR |
|---|---|---|---|
| 45c | 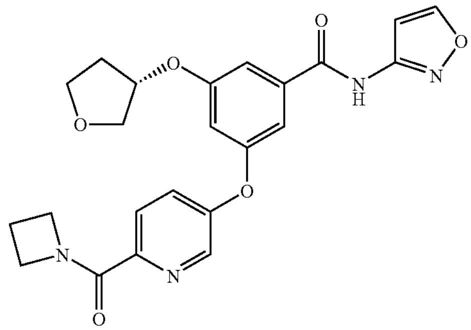 | 451 (M + H)+ 449 (M − H)− | ¹H NMR δ (CDCl₃): 2.13 -2.31 (m, 2H), 2.32-2.39 (m, 2H), 3.89-4.03 (m, 4H), 4.25 (t, 2H), 4.71 (t, 2H), 4.97-5.01 (m, 1H), 6.79 (t, 1H), 7.18 (d, 1H), 7.22 (t, 1H), 7.27 (t, 1H), 7.37 (dd, 1H), 8.11 (d, 1H), 8.28 (d, 1H), 8.33 (d, 1H), 9.47 (s, 1H) |
| 45d | 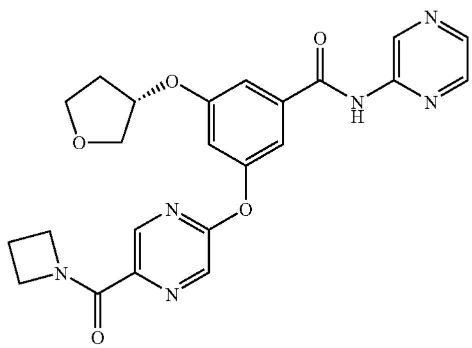 | 463 (M + H)+ 461 (M − H)− | ¹H NMR δ (CDCl₃): 2.15-2.32 (m, 2H), 2.35-2.43 (m, 2H), 3.90-4.06 (m, 4H), 4.27 (t, 2H), 4.70 (t, 2H), 5.00-5.05 (m, 1H), 6.93 (t, 1H), 7.31 (t, 1H), 7.36 (t, 1H), 8.29 (t, 1H), 8.38-8.38 (m, 1H), 8.40-8.41 (m, 1H), 8.46 (s, 1H), 8.86 (d, 1H), 9.68 (s, 1H) |
| 45e | 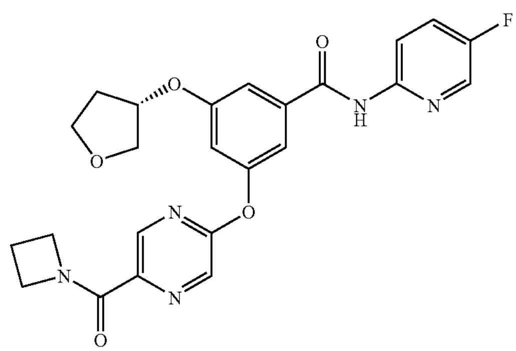 | 480 (M + H)+ 478 (M − H)− | ¹H NMR δ (CDCl₃): 2.15-2.31 (m, 2H), 2.35-2.43 (m, 2H), 3.90-4.03 (m, 4H), 4.27 (t, 2H), 4.69 (t, 2H), 4.99-5.02 (m, 1H), 6.91 (t, 1H), 7.28 (t, 1H), 7.33 (t, 1H), 7.48-7.53 (m, 1H), 8.16 (d, 1H), 8.35-8.39 (m, 1H), 8.37 (d, 1H), 8.51 (s, 1H), 8.86 (d, 1H) |

The preparation of 3-{[5-(azetidin-1-ylcarbonyl)pyrazin-2-yl]oxy}-5-[(3S)-tetrahydrofuran-3-yloxy]benzoic acid was described earlier.

The preparation of 3-{[6-(azetidin-1-ylcarbonyl)pyridin-3-yl]oxy}-5-[(3S)-tetrahydrofuran-3-yloxy]benzoic acid is described below:

3-{[6-(Azetidin-1-ylcarbonyl)pyridin-3-yl]oxy}-5-[(3S)-tetrahydrofuran-3-yloxy]benzoic acid

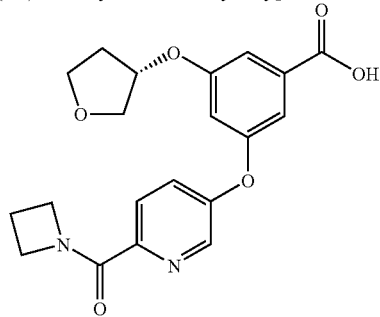

Methyl 3-hydroxy-5-[(3S)-tetrahydrofuran-3-yloxy]benzoate (875 mg, 3.68 mmol), 2-(azetidin-1-ylcarbonyl)-5-bromopyridine (1.06 g, 4.41 mmol), caesium carbonate (3.59 g, 11.03 mmol), and bromotris(triphenylphosphine)copper (0.69 g, 0.735 mmol) were added together in DMA (16 mL) and heated in a microwave reactor at 160° C. for 9 hours. The mixture was taken up in water (25 mL) and washed with ethyl acetate (2×20 mL). The aqueous layer was acidified with 1N hydrochloric acid (30 mL) and extracted with ethyl acetate (5×30 mL). The combined organic extract was washed with water (30 mL), brine (30 mL), dried (MgSO₄), filtered and evaporated to give a brown solid which was triturated with diethyl ether to give the desired compound as a beige solid (820 mg).

¹H NMR δ (d₆-DMSO): 2.00-2.06 (m, 1H), 2.23-2.37 (m, 3H), 3.78-3.95 (m, 4H), 4.13 (t, 2H), 4.64 (t, 2H), 5.16-5.19 (m, 1H), 7.05 (t, 1H), 7.18-7.19 (m, 1H), 7.33-7.34 (m, 1H), 7.62 (dd, 1H), 8.04 (d, 1H), 8.46 (d, 1H); m/z 385 (M+H)+, 383 (M−H)−

The preparations of methyl 3-hydroxy-5-[(3S)-tetrahydrofuran-3-yloxy]benzoate and 2-(azetidin-1-ylcarbonyl)-5-bromopyridine were described earlier.

EXAMPLE 46

3-{[3-Chloro-5-(pyrrolidin-1-ylcarbonyl)pyridin-2-yl]oxy}-5-[(1-methylethyl)oxy]-N-(5-methylpyrazin-2-yl)benzamide

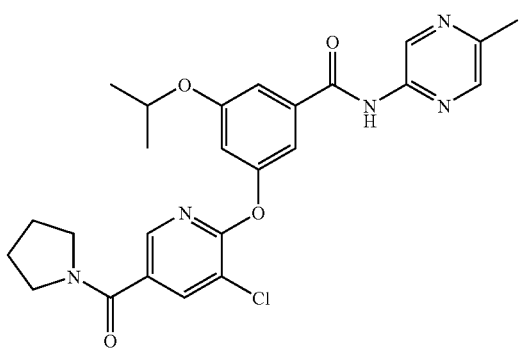

Cesium carbonate (782 mg, 2.4 mmol) was added to a solution of 3-hydroxy-5-[(1-methylethyl)oxy]-N-(5-methylpyrazin-2-yl)benzamide (230 mg, 0.8 mmol) and 2,3-dichloro-5-(pyrrolidin-1-ylcarbonyl)pyridine (234 mg, 0.96 mmol) in acetonitrile (5 mL) and the stirred mixture heated in a microwave reactor at 120° C. for 2 hours. The mixture was cooled to RT and the acetonitrile evaporated in vacuo. The residue was partitioned between water (25 mL) and ethyl acetate (50 mL), the organic layer washed with brine, dried ($MgSO_4$) and evaporated to a residue which was chromatographed on silica, eluting with 75% ethyl acetate in isohexane, to give the desired compound (290 mg).

$^1$H NMR δ ($CDCl_3$): 1.3 (d, 6H), 1.9 (m, 4H), 2.5 (s, 3H), 3.4-3.7 (m, 4H), 4.55 (m, 1H), 6.85 (d, 1H), 7.2 (d, 1H), 7.25 (d, 1H), 7.9 (d, 1H), 8.1 (dd, 1H), 8.2 (s, 1H), 8.35 (s, 1H) and 9.45 (s, 1H); m/z 496 (M+H)$^+$.

The following compounds were prepared in an analogous fashion from 2,3-dichloro-5-(pyrrolidin-1-ylcarbonyl)pyridine and either 3-hydroxy-5-{[(1S)-1-methyl-2-(methyloxy)ethyl]oxy}-N-(5-methylpyrazin-2-yl)benzamide or 3-hydroxy-N-(1-methyl-1H-pyrazol-3-yl)-5-[(3S)-tetrahydrofuran-3-yloxy]benzamide.

| Example | Structure | m/z | NMR |
|---|---|---|---|
| 46a | 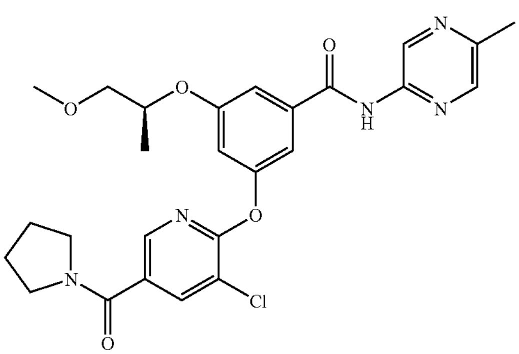 | 526 (M + H)$^+$ | $^1$H NMR δ ($CDCl_3$): 1.3 (d, 3H), 1.9 (m, 4H), 2.5 (s, 3H), 3.3 (s, 3H), 3.4-3.6 (m, 6H), 4.55 (m, 1H), 6.9 (d, 1H), 7.2 (s, 1H), 7.35 (s, 1H), 7.95 (d, 1H), 8.05 (s, 1H), 8.15 (d, 1H), 8.35 (s, 1H), 9.5 (s, 1H). |
| 46b | 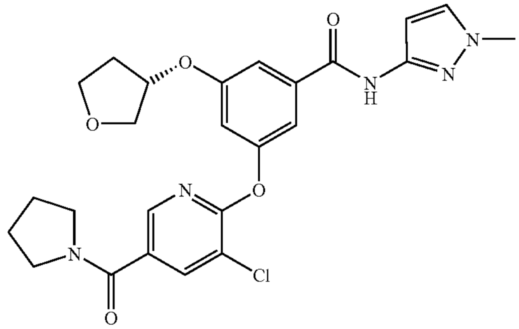 | 512 (M + H)$^+$ | $^1$H NMR δ ($CDCl_3$): 1.8-1.95 (m, 4H), 2.1 (m, 2H), 3.45 (t, 2H), 3.6 (t, 2H), 3.7 (s, 3H), 3.85 (m, 2H), 3.95 (d, 2H), 4.9 (m, 1H), 6.7 (d, 1H), 6.8 (d, 1H), 7.15 (d, 1H), 7.25 (d, 2H), 7.95 (d, 1H), 8.1 (d, 1H), 8.9 (s, 1H) |

The preparation of 2,3-dichloro-5-(pyrrolidin-1-ylcarbonyl)pyridine is described below:

2,3-Dichloro-5-(pyrrolidin-1-ylcarbonyl)pyridine

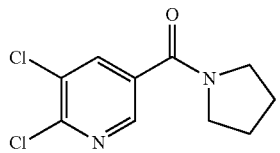

Oxalyl chloride (3.2 mL; 36.0 mmol) was added to a solution of 5,6 dichloronicotinic acid (5.76 g; 30.0 mmol) and 4M hydrogen chloride in dioxan (7.5 mL; 30.0 mmol) in DCM (50 mL). The mixture was stirred at RT for 18 hours, the DCM evaporated in vacuo, the residue azeotroped with toluene (2×15 mL) then added to a solution of pyrrolidine (3.0 mL; 36.0 mmol) and triethylamine (10.0 mL; 72 mmol) in DCM (150 mL). The mixture was stirred at RT for 6 hours, the DCM evaporated in vacuo, the residue partitioned between water (75 mL) and ethyl acetate (100 mL), the organic layer washed with brine, dried (MgSO$_4$) and evaporated in vacuo. The residue was chromatographed on silica, eluting with 50% ethyl acetate in isohexane, to give the desired compound which was further purified by crystallisation from ethyl acetate and isohexane (6.88 g). $^1$H NMR δ (CDCl$_3$): 1.9 (m, 4H), 3.4 (m, 2H), 3.6 (s, 3H), 7.9 (s, 1H) and 8.4 (s, 1H); m/z 245 (M+H)$^+$.

The preparations of 3-hydroxy-5-[(1-methylethyl)oxy]-N-(5-methylpyrazin-2-yl)benzamide and 3-hydroxy-5-{[(1S)-1-methyl-2-(methyloxy)ethyl]oxy}-N-(5-methylpyrazin-2-yl)benzamide were described earlier.

EXAMPLE 47

3-{[5-(Azetidin-1-ylcarbonyl)pyrazin-2-yl]oxy}-N-(1-methyl-1H-pyrazol-3-yl)-5-(tetrahydro-2H-pyran-4-yloxy)benzamide

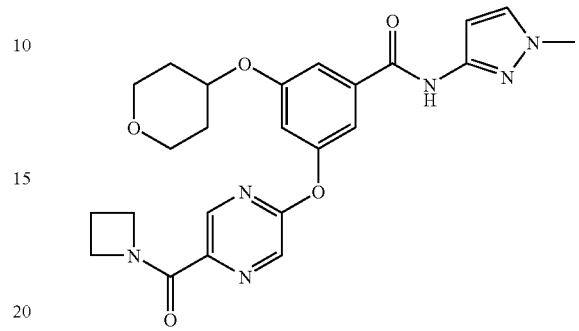

3-Hydroxy-N-(1-methyl-1H-pyrazol-3-yl)-5-(tetrahydro-2H-pyran-4-yloxy)benzamide (209 mg, 0.66 mmol), 2-(azetidin-1-ylcarbonyl)-5-chloropyrazine (159 mg, 0.80 mmol) and potassium carbonate (184 mg, 1.33 mmol) were dissolved/suspended in acetonitrile (3.5 mL). The reaction mixture was heated in a microwave reactor for 4 hours at 120° C. then cooled, filtered and reduced in vacuo. The crude product was purified by chromatography on silica, eluting with 0-5% methanol in DCM, to give the required product as a white foam (39 mg). $^1$H NMR δ (d$_6$-DMSO): 1.57-1.68 (m, 2H), 1.97-2.05 (m, 2H), 2.26-2.36 (m, 2H), 3.47-3.55 (m, 2H), 3.78 (s, 3H), 3.84-3.91 (m, 2H), 4.10 (t, 2H), 4.57 (t, 2H), 4.67-4.75 (m, 1H), 6.58 (d, 1H), 7.11 (t, 1H), 7.43 (t, 1H), 7.54 (t, 1H), 7.60 (d, 1H), 8.56 (d, 1H), 8.68 (d, 1H), 10.80 (s, 1H); m/z 479 (M+H)$^+$ The following compounds were made in an analogous fashion from the either 3-hydroxy-N-(1-methyl-1H-pyrazol-3-yl)-5-(tetrahydro-2H-pyran-4-yloxy)benzamide or 3-hydroxy-N-(5-methylpyrazin-2-yl)-5-(tetrahydro-2H-pyran-4-yloxy)benzamide and the appropriate halogenated heterocycle.

| Example | Structure | m/z | NMR |
|---|---|---|---|
| 47a | 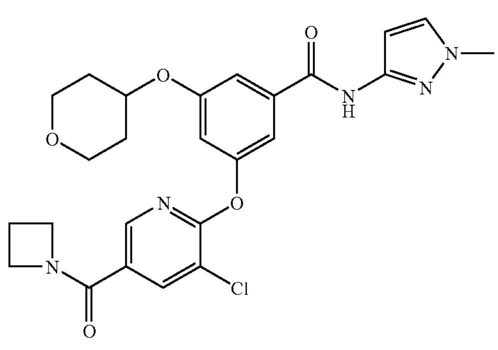 | 512 (M + H)$^+$ | $^1$H NMR δ (d$_6$-DMSO): 1.57-1.67 (m, 2H), 1.98-2.06 (m, 2H), 2.21-2.32 (m, 2H), 3.47-3.55 (m, 2H), 3.78 (s, 3H), 3.84-3.91 (m, 2H), 4.01-4.10 (m, 2H), 4.33-4.41 (m, 2H), 4.67-4.75 (m, 1H), 6.57 (d, 1H), 7.09 (t, 1H), 7.40 (t, 1H), 7.52 (t, 1H), 7.60 (d, 1H), 8.23 (d, 1H), 8.34 (d, 1H), 10.79 (s, 1H) |

-continued

| Example | Structure | m/z | NMR |
|---------|-----------|-----|-----|
| 47b | 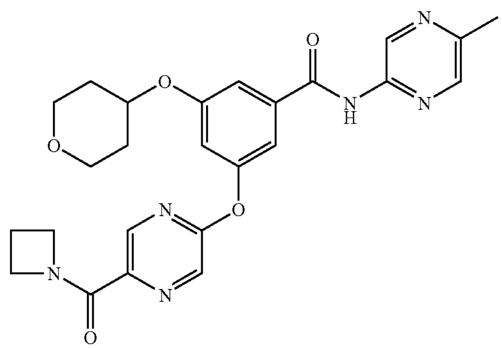 | 491 (M + H)⁺ | ¹H NMR δ (d₆-DMSO): 1.58-1.68 (m, 2H), 1.99-2.06 (m, 2H), 2.26-2.35 (m, 2H), 2.49 (s, 3H), 3.47-3.55 (m, 2H), 3.84-3.91 (m, 2H), 4.10 (t, 2H), 4.57 (t, 2H), 4.69-4.77 (m, 1H), 7.18 (t, 1H), 7.49 (t, 1H), 7.58 (t, 1H), 8.36 (d, 1H), 8.57 (d, 1H), 8.68 (d, 1H), 9.25 (d, 1H), 10.98 (s, 1H) |
| 47c | 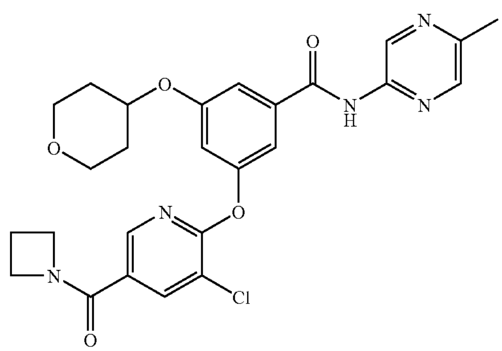 | 524 (M + H)⁺ | ¹H NMR δ (d₆-DMSO): 1.63 (m, 2H), 2.02 (m, 2H), 2.27 (m, 2H), 2.49 (s, 3H), 3.51 (m, 2H), 3.87 (m, 2H), 4.06 (t, 2H), 4.36 (t, 2H), 4.74 (m, 1H), 7.16 (t, 1H), 7.47 (t, 1H), 7.57 (t, 1H), 8.23 (d, 1H), 8.34 (d, 1H), 8.36 (m, 1H), 9.25 (d, 1H), 10.98 (s, 1H) |

The preparations of 2-(azetidin-1-ylcarbonyl)-5-chloropyrazine and 5-(azetidin-1-ylcarbonyl)-2,3-dichloropyridine were described earlier.

The preparation of 3-hydroxy-N-(1-methyl-1H-pyrazol-3-yl)-5-(tetrahydro-2H-pyran-4-yloxy)benzamide is described below:

3-Hydroxy-N-(1-methyl-1H-pyrazol-3-yl)-5-(tetrahydro-2H-pyran-4-yloxy benzamide

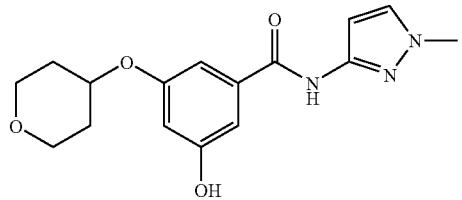

N-(1-Methyl-1H-pyrazol-3-yl)-3-[(phenylmethyl)oxy]-5-(tetrahydro-2H-pyran-4-yloxy)benzamide (1.85 g, 4.54 mmol) was dissolved in ethanol (40 mL) and 10% palladium on charcoal (97 mg) catalyst added under argon. The reaction was stirred under an atmosphere of hydrogen for 16 hours then filtered through Celite® and the filtrate concentrated in vacuo give the desired compound as a light brown solid (1.30 g).
¹H NMR δ (d₆-DMSO): 1.54-1.65 (m, 2H), 1.94-2.03 (m, 2H), 3.44-3.54 (m, 2H), 3.78 (s, 3H), 3.83-3.90 (m, 2H), 4.56-4.65 (m, 1H), 6.51 (t, 1H), 6.56 (d, 1H), 6.97 (t, 1H), 7.08 (t, 1H), 7.59 (d, 1H), 9.63 (s, 1H), 10.59 (s, 1H); m/z 318 (M+H)⁺

N-(1-Methyl-1H-pyrazol-3-yl)-3-[(phenylmethyl)oxy]-5-(tetrahydro-2H-pyran-4-yloxy)benzamide

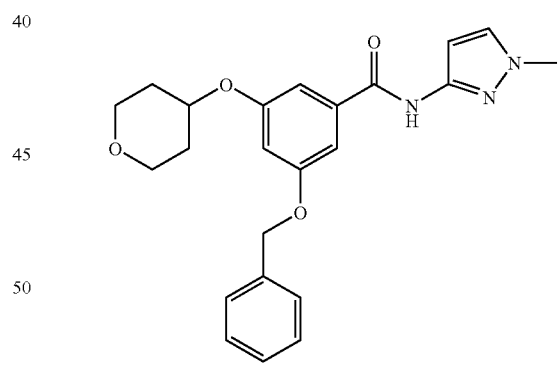

3-[(Phenylmethyl)oxy]-5-(tetrahydro-2H-pyran-4-yloxy) benzoic acid (3.14 g, 9.5 mmol), 1-methyl-1H-pyrazol-3-amine (1.85 g, 19.0 mmol) and HATU (4.70 g, 12.35 mmol) were dissolved in DMF (12.5 mL) and DIPEA (3.31 mL, 19.0 mmol) added. The resultant mixture was stirred at RT for 20 hours. The mixture was quenched with water (150 mL), extracted with ethyl acetate (2×75 mL), washed with brine, dried (MgSO₄) and concentrated in vacuo. The residue was chromatographed on silica, eluting with 0-50% ethyl acetate in isohexane, to give the desired compound as a pale yellow gum (1.85 g).

3-[(Phenylmethyl)oxy]-5-(tetrahydro-2H-pyran-4-yloxy)benzoic acid

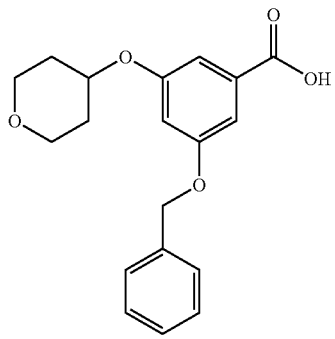

Methyl 3-[(phenylmethyl)oxy]-5-(tetrahydro-2H-pyran-4-yloxy)benzoate (9.00 g, 26.3 mmol) was dissolved in THF (120 mL) and methanol (30 mL) added a solution of lithium hydroxide monohydrate (3.24 g, 78.9 mmol) in water (60 mL). The bi-phasic solution was stirred at RT for 3 hours until complete conversion was indicated by LCMS. The organics were removed in vacuo and water (40 mL) added. The pH of the mixture was adjusted to 7 by the addition of hydrochloric acid and the resulting precipitate filtered and washed with cold water to give the desired compound as a white solid (8.03 g). $^1$H NMR δ (d$_6$-DMSO): 1.57 (m, 2H), 1.94 (m, 2H), 3.50 (m, 2H), 3.84 (m, 2H), 4.62 (m, 1H), 5.15 (s, 2H), 6.87 (t, 1H), 7.09 (m, 1H), 7.14 (m, 1H), 7.34 (t, 1H), 7.40 (t, 2H), 7.46 (d, 2H), 12.99 (s, 1H); m/z 327 (M+H)$^+$

Methyl 3-[(phenylmethyl)oxy]-5-(tetrahydro-2H-pyran-4-yloxy)benzoate

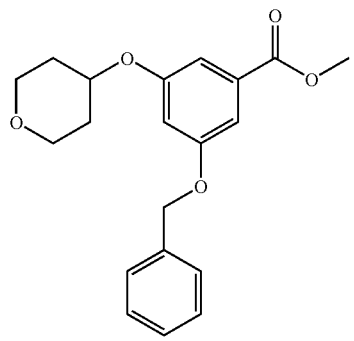

Methyl 3-hydroxy-5-{[phenylmethyl]oxy}benzoate (7.75 g, 30.0 mmol), tetrahydro-4H-pyran-4-ol (4.28 mL, 45.0 mmol) and triphenylphosphine (11.8 g, 45.0 mmol) were stirred under argon in THF (166 mL) and cooled to 5° C. in an ice bath. DEAD (19.6 mL, 45.0 mmol) was added dropwise to the mixture, maintaining the internal temperature below 10° C. Stirring was continued for 16 hours then the reaction mixture reduced in vacuo and the residue redissolved in ethyl acetate (60 mL) and isohexane (60 mL). The precipitate was removed, the filtrate concentrated in vacuo and purified by chromatography on silica, eluting with 0-25% ethyl acetate in isohexane (a small quantity of DCM used to assist column loading), to give the desired compound as a colourless oil (9.0 g).

$^1$H NMR δ (d$_6$-DMSO): 1.58 (m, 2H), 1.94 (m, 2H), 3.49 (m, 2H), 3.84 (m, 5H), 4.65 (m, 1H), 5.16 (s, 2H), 6.92 (t, 1H), 7.10 (m, 1H), 7.15 (m, 1H), 7.34 (t, 1H), 7.40 (t, 2H), 7.46 (d, 2H); m/z 343 (M+H)$^+$

The preparation of methyl 3-hydroxy-5-{[phenylmethyl]oxy}benzoate was described earlier. The preparation of 3-hydroxy-N-(5-methylpyrazin-2-yl)-5-(tetrahydro-2H-pyran-4-yloxy)benzamide is described below:

3-Hydroxy-N-(5-methylpyrazin-2-yl)-5-(tetrahydro-2H-pyran-4-yloxy)benzamide

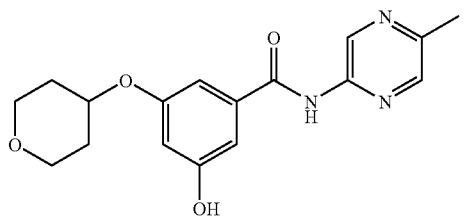

N-(5-Methylpyrazin-2-yl)-3-[(phenylmethyl)oxy]-5-(tetrahydro-2H-pyran-4-yloxy)benzamide (1.70 g, 4.05 mmol) was dissolved in ethanol (40 mL) and 10% palladium on charcoal (86 mg) catalyst added under argon. The reaction was stirred under an atmosphere of hydrogen for 4 days then filtered and the filtrate concentrated in vacuo to give the desired compound as a cream-coloured solid (1.20 g). m/z 330 (M+H)$^+$

N-(5-Methylpyrazin-2-yl)-3-[(phenylmethyl)oxy]-5-(tetrahydro-2H-pyran-4-yloxy)benzamide

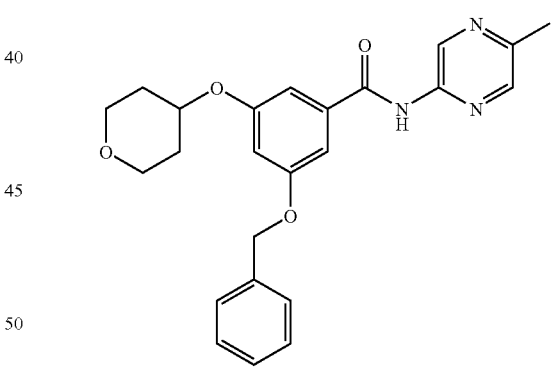

3-[(Phenylmethyl)oxy]-5-(tetrahydro-2H-pyran-4-yloxy)benzoic acid (3.14 g, 9.5 mmol), 2-amino-5 methylpyrazine (2.08 g, 19.0 mmol) and HATU (4.70 g, 12.35 mmol) were dissolved in DMF (12.5 mL) and DIPEA (3.31 mL, 19.0 mmol) added. The resultant mixture was stirred at RT for 20 hours. The mixture was quenched with water (150 mL) and extracted with ethyl acetate (2×75 mL), washed with brine, dried (MgSO$_4$) and concentrated in vacuo. The residue was chromatographed on silica, eluting with 0-50% ethyl acetate in isohexane, to give the desired compound as a pale yellow gum (1.70 g). m/z 420 (M+H)$^+$ The preparations of 3-[(phenylmethyl)oxy]-5-(tetrahydro-2H-pyran-4-yloxy)benzoic acid and 2-amino-5 methylpyrazine were described earlier.

EXAMPLE 48

3-{[6-(Azetidin-1-ylcarbonyl)pyridin-3-yl]oxy}-N-(1-methyl-1H-pyrazol-3-yl)-5-(tetrahydro-2H-pyran-4-yloxy)benzamide

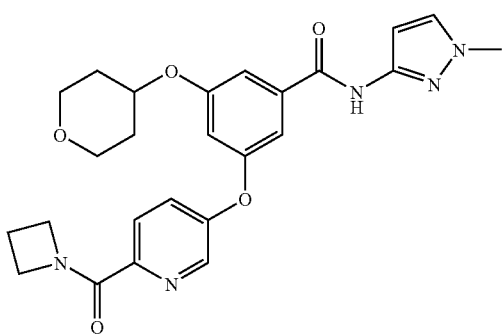

3-Hydroxy-N-(1-methyl-1H-pyrazol-3-yl)-5-(tetrahydro-2H-pyran-4-yloxy)benzamide (200 mg, 0.63 mmol), 2-(azetidin-1-ylcarbonyl)-5-bromopyridine (184 mg, 0.76 mmol), bromotris(triphenylphosphine)copper (186 mg, 0.2 mmol) and caesium carbonate (411 mg, 1.26 mmol) were dissolved/suspended in DMA (3.5 mL). The reaction mixture was heated in a microwave reactor for 1 hour at 200° C. then allowed to cool, filtered and reduced in vacuo. Water (25 mL) was added and the product extracted with ethyl acetate (2×25 mL), the organics dried (MgSO$_4$) then purified by chromatography on silica, eluting with 0-10% methanol in DCM, to give the desired compound as a pale yellow foam (65 mg). $^1$H NMR δ (d$_6$-DMSO): 1.57-1.67 (m, 2H), 1.97-2.05 (m, 2H), 2.23-2.34 (m, 2H), 3.51 (t, 2H), 3.78 (s, 3H), 3.83-3.90 (m, 2H), 4.08 (t, 2H), 4.59 (t, 2H), 4.69-4.76 (m, 1H), 6.56 (d, 1H), 7.00 (t, 1H), 7.29 (t, 1H), 7.49 (t, 1H), 7.54-7.58 (m, 1H), 7.60 (d, 1H), 8.00 (d, 1H), 8.41 (d, 1H), 10.83 (s, 1H); m/z 478 (M+H)$^+$ The following compound was made in an analogous fashion from 2-(azetidin-1-ylcarbonyl)-5-bromopyridine and 3-hydroxy-N-(5-methylpyrazin-2-yl)-5-(tetrahydro-2H-pyran-4-yloxy)benzamide.

The preparations of 2-(azetidin-1-ylcarbonyl)-5-bromopyridine, 3-hydroxy-N-(1-methyl-1H-pyrazol-3-yl)-5-(tetrahydro-2H-pyran-4-yloxy)benzamide and 3-hydroxy-N-(5-methylpyrazin-2-yl)-5-(tetrahydro-2H-pyran-4-yloxy)benzamide were described earlier.

EXAMPLE 49

3-{[6-(Azetidin-1-ylcarbonyl)pyridin-3-yl]oxy}-N-(1-methyl-1H-pyrazol-3-yl)-5-[(3R)-tetrahydrofuran-3-yloxy]benzamide

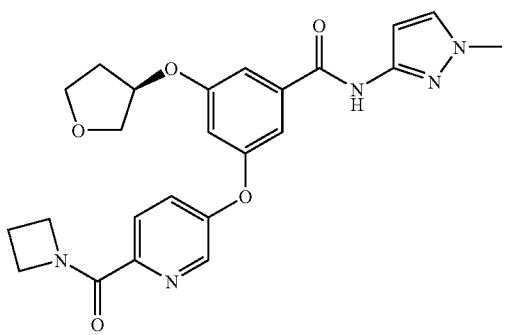

A mixture of 3-hydroxy-N-(1-methyl-1H-pyrazol-3-yl)-5-[(3R)-tetrahydrofuran-3-yloxy]benzamide (150 mg, 0.49 mmol), 2-(azetidin-1-ylcarbonyl)-5-bromopyridine (120 mg, 0.49 mmol), bromotris(triphenylphosphine)copper (92 mg, 0.10 mmol) and caesium carbonate (484 mg, 1.48 mmol) in acetonitrile (7 mL) was stirred in a microwave reactor at 160° C. for 6 hours. The solid was filtered off, the solvent was removed in vacuo and ethyl acetate (50 mL) added to the residue. The organic phase was washed with water (10 mL), brine (20 mL), dried (MgSO$_4$), filtered and the solvent removed in vacuo. The residue was chromatographed on silica, eluting with a gradient of 0-10% methanol in DCM, to give the title compound as a white solid (86 mg). $^1$H NMR δ (CDCl$_3$): 2.10-2.17 (m, 1H), 2.19-2.25 (m, 1H), 2.32-2.38 (m, 2H), 3.76 (s, 3H), 3.87-3.92 (m, 1H), 3.95-4.01 (m, 3H), 4.24 (t, 2H), 4.71 (t, 2H), 4.97 (t, 1H), 6.73 (t, 1H), 6.81 (s,

| Example | Structure | m/z | NMR |
|---|---|---|---|
| 48a | 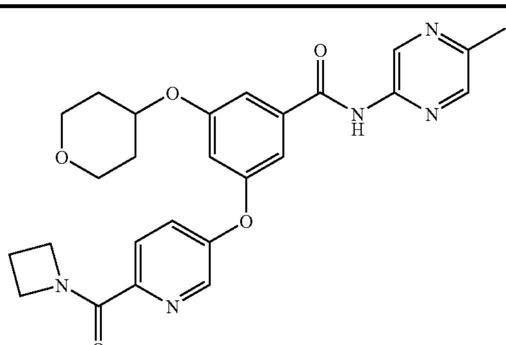 | 490 (M + H)$^+$ | $^1$H NMR δ (d$_6$-DMSO): 1.62 (m, 2H), 2.01 (m, 2H), 2.28 (m, 2H), 2.48 (s, 3H), 3.50 (m, 2H), 3.86 (m, 2H), 4.07 (t, 2H), 4.59 (t, 2H), 4.75 (m, 1H), 7.08 (t, 1H), 7.49 (s, 1H), 7.53 (s, 1H), 7.56 (q, 1H), 8.00 (d, 1H), 8.36 (s, 1H), 8.43 (d, 1H), 9.24 (d, 1H), 11.09 (s, 1H) |

1H), 7.11 (s, 1H), 7.24 (s, 1H), 7.27-7.30 (m, 1H), 7.36-7.39 (m, 1H), 8.12 (d, 1H), 8.31 (d, 1H), 8.72 (s, 1H); m/z 464 (M+H)⁺.

The preparation of 2-(azetidin-1-ylcarbonyl)-5-bromopyridine was described earlier.

The preparation of 3-hydroxy-N-(1-methyl-1H-pyrazol-3-yl)-5-[(3R)-tetrahydrofuran-3-yloxy]benzamide is described below:

3-hydroxy-N-(1-methyl-1H-pyrazol-3-yl)-5-[(3R)-tetrahydrofuran-3-yloxy]benzamide

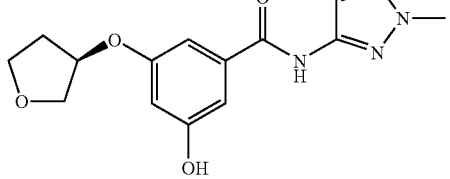

A suspension of 3-hydroxy-N-(1-methyl-1H-pyrazol-3-yl)-5-[(phenylmethyl)oxy]benzamide (450 mg, 1.39 mmol), (3S)-tetrahydrofuran-3-yl 4-methylbenzenesulfonate (507 mg, 2.09 mmol) and potassium carbonate (481 mg, 3.48 mmol) in acetonitrile (5 mL) was stirred in a microwave reactor at 160° C. for 3 hours. The solvent was removed in vacuo and ethyl acetate added. The organics were washed with water (40 mL), brine (40 mL), dried (MgSO₄), filtered and the solvent removed in vacuo. The residue was chromatographed on silica, eluting with a gradient of 0-100% ethyl acetate in isohexane, to give N-(1-methyl-1H-pyrazol-3-yl)-3-[(phenylmethyl)oxy]-5-[(3R)-tetrahydrofuran-3-yloxy] benzamide as a white foam. This was dissolved in ethanol (5 mL) and ammonium formate (182 mg, 2.88 mmol) added in one portion. The reaction was blanketed with argon and 10% palladium on activated carbon (30 mg) was added. This mixture was heated in a microwave reactor at 140° C. for 10 minutes, the catalyst filtered off and the volatiles removed in vacuo to give the title product as a white solid (305 mg).

¹H NMR δ (d₆-DMSO): 1.96-2.00 (m, 1H), 2.20-2.25 (m, 1H), 3.74-3.85 (m, 6H), 3.87-3.91 (m, 1H), 5.06-5.08 (m, 1H), 6.46 (t, 1H), 6.57 (d, 1H), 6.97 (s, 1H), 7.02 (s, 1H), 7.60 (d, 1H), 9.74 (s, 1H), 10.70 (s, 1H); m/z 304 (M+H)⁺.

The preparation of 3-hydroxy-N-(1-methyl-1H-pyrazol-3-yl)-5-[(phenylmethyl)oxy]benzamide was described earlier. (3S)-Tetrahydrofuran-3-yl 4-methylbenzenesulfonate was prepared in an analogous fashion to (3R)-tetrahydrofuran-3-yl 4-methylbenzenesulfonate, as described in Example 25.

EXAMPLE 50

3-{[5-(Azetidin-1-ylcarbonyl)pyrazin-2-yl]oxy}-5-{[(1S)-1-methyl-2-(methyloxy)ethyl]oxy}-N-pyridin-2-ylbenzamide

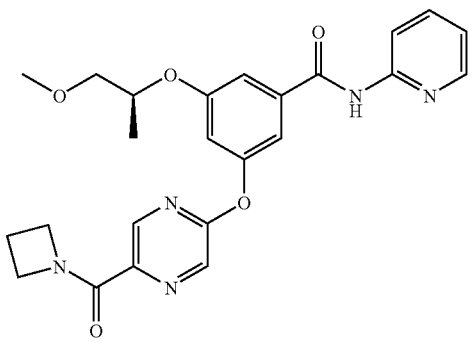

1-Chloro-N,N,2-trimethyl-1-propenylamine (0.080 mL, 0.6 mmol) was added to a solution of 3-{[5-(azetidin-1-ylcarbonyl)pyrazin-2-yl]oxy}-5-{[(1S)-1-methyl-2-(methyloxy)ethyl]oxy}benzoic acid (193 mg, 0.50 mmol) in DCM (10 mL) and stirred at RT for 30 minutes. 2-Aminopyridine (57 mg, 0.6 mmol) and pyridine (0.082 mL, 1 mmol) were added and the reaction stirred for a further 16 hours. The solvent was removed in vacuo and the residue was taken up in ethyl acetate (50 mL). The organic phase was washed with water (2×20 mL), 1N citric acid (10 mL), water (10 mL), a saturated aqueous solution of sodium bicarbonate (10 mL) and brine (100 mL), then dried (MgSO₄), filtered, and evaporated in vacuo. The residue was chromatographed on silica, eluting with a gradient of 50-80% ethyl acetate in isohexane, to give the desired compound as a white foam (42 mg). ¹H NMR δ (CDCl₃): 1.28 (d, 3H), 2.31 (quin, 2H), 3.34 (s, 3H), 3.43-3.56 (m, 2H), 4.19 (t, 2H), 4.57 (q, 1H), 4.62 (t, 2H), 6.90 (s, 1H), 7.03 (t, 1H), 7.20 (s, 1H), 7.36 (s, 1H), 7.71 (t, 1H), 8.23 (d, 1H), 8.28 (s, 1H), 8.30 (d, 1H), 8.64 (s, 1H), 8.79 (s, 1H); m/z 464 (M+H)⁺

The following compounds were prepared in an analogous fashion from the appropriate benzoic acid and the appropriate aminoheterocycle.

| Example | Structure | m/z | NMR |
|---------|-----------|-----|-----|
| 50a | 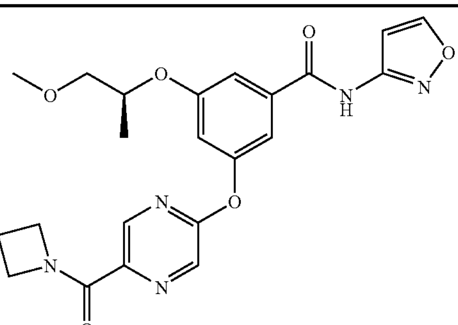 | 454 (M + H)⁺ | ¹H NMR δ (CDCl₃): 1.27 (d, 3H), 2.26-2.38 (m, 2H), 3.34 (s, 3H), 3.42-3.57 (m, 2H), 4.19 (t, 2H), 4.51-4.70 (m, 3H), 6.92 (s, 1H), 7.12 (s, 1H), 7.27 (s, 1H), 7.36 (s, 1H), 8.20 (s, 1H), 8.27 (s, 1H), 8.78 (s, 1H), 9.33 (s, 1H) |

-continued

| Example | Structure | m/z | NMR |
|---------|-----------|-----|-----|
| 50b | 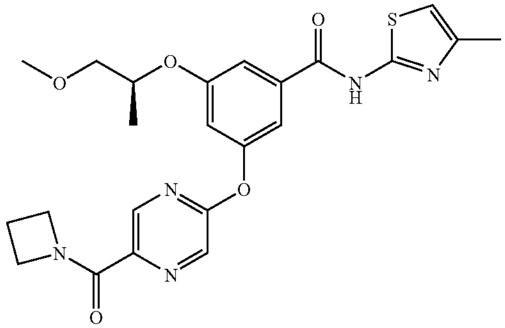 | 484 (M + H)⁺ | ¹H NMR δ (CDCl₃): 1.26 (d, 3H), 2.22 (s, 3H), 2.27-2.39 (m, 2H), 3.33 (s, 3H), 3.41-3.57 (m, 2H), 4.19 (t, 2H), 4.50-4.58 (m, 1H), 4.62 (t, 2H), 6.50 (s, 1H), 6.92 (s, 1H), 7.23 (s, 1H), 7.35 (s, 1H), 8.27 (s, 1H), 8.78 (s, 1H) |
| 50c | 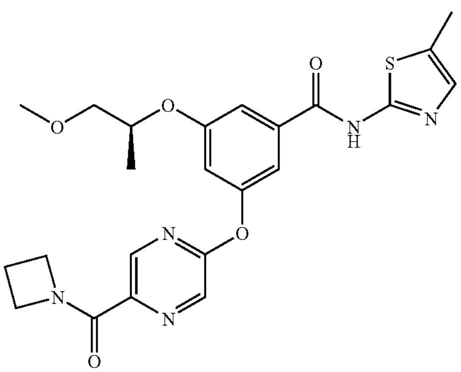 | 484 (M + H)⁺ | ¹H NMR δ (CDCl₃): 1.26 (d, 3H), 2.25-2.36 (m, 5H), 3.32 (s, 3H), 3.40-3.54 (m, 2H), 4.19 (t, 2H), 4.52 (q, 1H), 4.61 (t, 2H), 6.81 (s, 1H), 6.92 (s, 1H), 7.28 (s, 1H), 7.38 (s, 1H), 8.25 (s, 1H), 8.77 (s, 1H) |
| 50d | 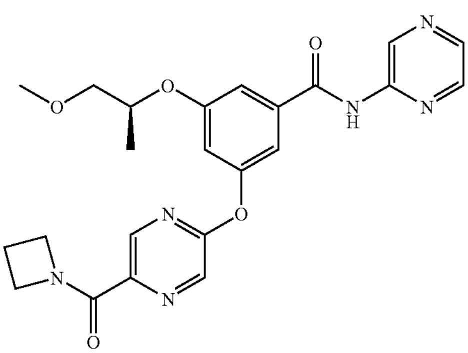 | 465 (M + H)⁺ | ¹H NMR δ (CDCl₃): 1.29 (d, 3H), 2.32 (quin, 2H), 3.34 (s, 3H), 3.44-3.56 (m, 2H), 4.19 (t, 2H), 4.56 (q, 1H), 4.62 (t, 2H), 6.92 (s, 1H), 7.23 (s, 1H), 7.35 (s, 1H), 8.21 (s, 1H), 8.29 (s, 1H), 8.33 (s, 1H), 8.43 (s, 1H), 8.79 (s, 1H), 9.61 (s, 1H) |
| 50e | 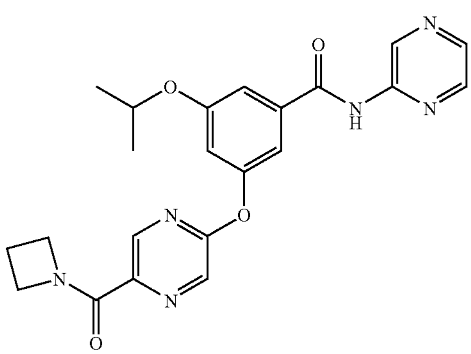 | 435 (M + H)⁺ | ¹H NMR δ (CDCl₃): 1.31 (d, 6H), 2.32 (quin, 2H), 4.19 (t, 2H), 4.56 (quin, 1H), 4.62 (t, 2H), 6.85 (s, 1H), 7.20 (s, 1H), 7.30 (s, 1H), 8.21 (s, 1H), 8.29 (s, 1H), 8.33 (s, 1H), 8.40 (s, 1H), 8.80 (s, 1H), 9.61 (s, 1H) |

| Example | Structure | m/z | NMR |
|---|---|---|---|
| 50f | 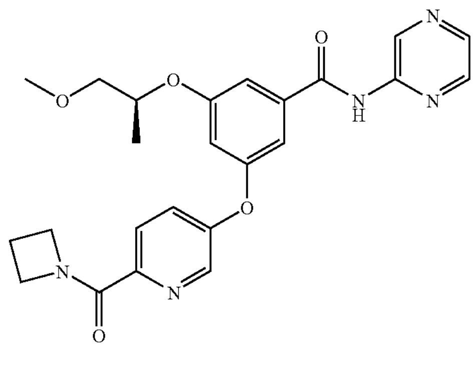 | 464 (M + H)+ | ¹H NMR δ (CDCl₃): 1.27 (d, 3H), 2.29 (quin, 2H), 3.34 (s, 3H), 3.43-3.55 (m, 2H), 4.18 (t, 2H), 4.56 (q, 1H), 4.64 (t, 2H), 6.78 (s, 1H), 7.09 (s, 1H), 7.26 (s, 1H), 7.32 (d, 1H), 8.06 (d, 1H), 8.22 (s, 1H), 8.27 (s, 1H), 8.34 (s, 1H), 8.36 (s, 1H), 9.60 (s, 1H) |
| 50g* | 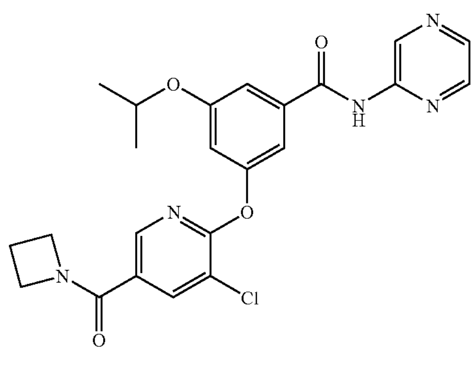 | 468 (M + H)+ | ¹H NMR δ (CDCl₃): 1.31 (d, 6H), 2.32 (quin, 2H), 4.17 (t, 2H), 4.29 (t, 2H), 4.57 (quin, 1H), 6.87 (s, 1H), 7.20 (s, 1H), 7.29 (s, 1H), 8.10 (s, 1H), 8.19 (s, 1H), 8.21 (s, 1H), 8.32 (s, 1H), 8.42 (s, 1H), 9.62 (s, 1H) |
| 50h | 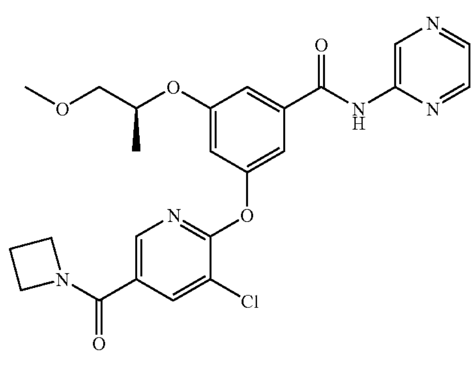 | 498 (M + H)+ | ¹H NMR δ (CDCl₃): 1.29 (d, 3H), 2.32 (quin, 2H), 3.35 (s, 3H), 3.43-3.57 (m, 2H), 4.17 (t, 2H), 4.29 (t, 2H), 4.57 (q, 1H), 6.93 (s, 1H), 7.24 (s, 1H), 7.35 (s, 1H), 8.10 (s, 1H), 8.19 (s, 1H), 8.21 (s, 1H), 8.32 (s, 1H), 8.42 (s, 1H), 9.62 (s, 1H) |

*The isolated sample was contaminated with approximately 15% of an unknown impurity following initial chromatography.

The preparations of 3-{[5-(azetidin-1-ylcarbonyl)pyrazin-2-yl]oxy}-5-{[(1S)-1-methyl-2-(methyloxy)ethyl]oxy}benzoic acid, 3-{[5-(azetidin-1-ylcarbonyl)pyrazin-2-yl]oxy}-5-[(1-methylethyl)oxy]benzoic acid, 3-{[6-(azetidin-1-ylcarbonyl)pyridin-3-yl]oxy}-5-{[(1S)-1-methyl-2-(methyloxy)ethyl]oxy}benzoic acid, 3-{[5-(azetidin-1-ylcarbonyl)-3-chloropyridin-2-yl]oxy}-5-[(1-methylethyl)oxy]benzoic acid, and 3-{[5-(azetidin-1-ylcarbonyl)-3-chloropyridin-2-yl]oxy}-5-{[(1S)-1-methyl-2-(methyloxy)ethyl]oxy}benzoic acid were described earlier.

EXAMPLE 51

3-{[3-Chloro-5-(morpholin-4-ylcarbonyl)pyridin-2-yl]oxy}-N-(1-methyl-1H-pyrazol-3-yl)-5-[(3S)-tetrahydrofuran-3-yloxy]benzamide

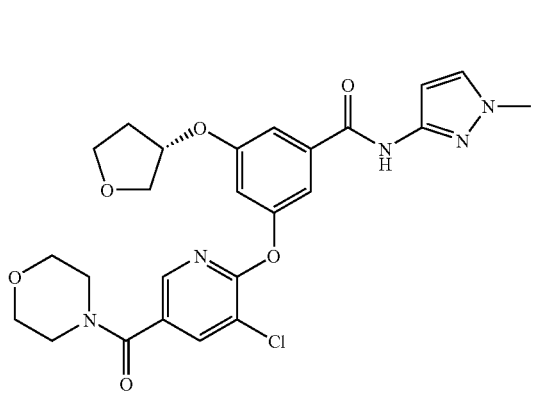

Cesium carbonate (489 mg, 1.5 mmol) was added to a solution of 3-hydroxy-N-(1-methyl-1H-pyrazol-3-yl)-5-[(3S)-tetrahydrofuran-3-yloxy]benzamide (152 mg, 0.5 mmol) and 4-[(5,6-dichloropyridin-3-yl)carbonyl]morpholine (143 mg, 0.55 mmol) in acetonitrile (5 mL) and the mixture heated at 120° C. in a microwave reactor for 2 hours. The acetonitrile was evaporated in vacuo and the residue partitioned between water (25 mL) and ethyl acetate (50 mL). The organic layer was washed with brine, dried (MgSO$_4$) and evaporated to a residue which was chromatographed on silica, eluting with ethyl acetate, to give the desired compound (203 mg). $^1$H NMR δ (CDCl$_3$): 2.05-2.2 (m, 2H), 3.4-3.7 (m, 8H), 3.7 (s, 3H), 3.85 (m, 2H), 3.95 (d, 2H), 4.9 (m, 1H), 6.7 (d, 1H), 6.8 (d, 1H), 7.15 (d, 1H), 7.25 (d, 2H), 7.85 (d, 1H), 8.0 (d, 1H), 8.95 (s, 1H); m/z 512 (M+H)$^+$.

The following compound was prepared in an analogous fashion from 3-hydroxy-N-(1-methyl-1H-pyrazol-3-yl)-5-[(3S)-tetrahydrofuran-3-yloxy]benzamide and 7-[(5,6-dichloropyridin-3-yl)carbonyl]-7-azabicyclo[2.2.1]heptane The preparation of 3-hydroxy-N-(1-methyl-1H-pyrazol-3-yl)-5-[(3S)-tetrahydrofuran-3-yloxy]benzamide was described earlier.

The preparation of 4-[(5,6-dichloropyridin-3-yl)carbonyl]morpholine is described below:

4-[(5,6-Dichloropyridin-3-yl)carbonyl]morpholine

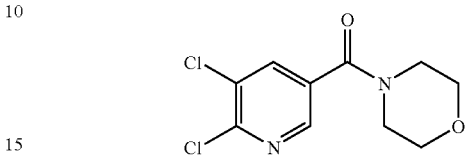

Oxalyl chloride (3.2 mL; 36.0 mmol) was added to a solution of 5,6 dichloronicotinic acid (5.76 g; 30.0 mmol) and 4M hydrogen chloride in dioxane (7.5 mL; 30 mmol) in DCM (50 mL). The mixture was stirred at RT for 18 hours, the DCM evaporated in vacuo, the residue azeotroped with toluene (2×15 mL) and added to a solution of morpholine (3.1 mL; 36.0 mmol) and triethylamine (10.0 mL; 72 mmol) in DCM (150 mL). The mixture was stirred at RT for 18 hours, the DCM evaporated in vacuo, and the residue partitioned between water (75 mL) and ethyl acetate (100 mL). The organic layer was washed with brine, dried (MgSO$_4$) and evaporated to a residue which was chromatographed on silica, eluting with 50% ethyl acetate in isohexane, to give the desired compound (7.1 g).

$^1$H NMR δ (CDCl$_3$): 3.3-3.8 (br, 8H), 7.8 (s, 1H), 8.25 (s, 1H); m/z 261 (M+H)$^+$.

The preparation of 7-[(5,6-dichloropyridin-3-yl)carbonyl]-7-azabicyclo[2.2.1]heptane is described below:

7-[(5,6-Dichloropyridin-3-yl)carbonyl]-7-azabicyclo[2.2.1]heptane

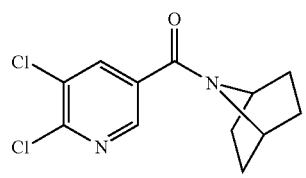

| Example | Structure | m/z | NMR |
|---|---|---|---|
| 51a | 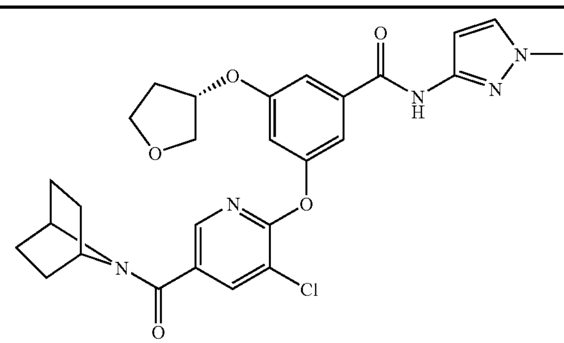 | 538 (M + H)$^+$ | $^1$H NMR δ (CDCl$_3$): 1.5 (m, 4H), 1.7-1.9 (m, 4H), 2.05-2.2 (m, 2H), 3.7 (s, 3H), 3.85 (m, 2H), 3.95 (d, 2H), 4.1 (m, 1H), 4.7 (m, 1H), 4.9 (m, 1H), 6.75 (d, 1H), 6.85 (d, 1H), 7.2 (d, 1H), 7.25 (d, 2H), 8.0 (d, 1H), 8.2 (d, 1H) and 9.0 (s, 1H). |

Oxalyl chloride (3.2 mL; 36.0 mmol) was added to a solution of 5,6 dichloronicotinic acid (5.76 g, 30.0 mmol) and 4M hydrogen chloride in dioxane (7.5 mL; 30.0 mmol) in DCM (50 mL). The mixture was stirred at RT for 18 hours, the DCM evaporated in vacuo, the residue azeotroped with toluene (2×15 mL) and added to a solution of 7-azabicyclo[2.2.1]heptane hydrochloride (4.75 g; 36.0 mmol) and triethylamine (15.1 mL; 108 mmol) in DCM (150 mL). The mixture was stirred at RT for 18 hours, the DCM evaporated in vacuo and the residue partitioned between water (75 mL) and ethyl acetate (150 mL). The organic layer was washed with brine, dried (MgSO$_4$) and evaporated to give a solid which was crystallised from ethyl acetate to give the desired compound (5.45 g).

$^1$H NMR δ (CDCl$_3$): 1.5 (m, 4H), 1.85 (m, 4H), 4.0 (br, 1H), 4.65 (br, 1H), 7.9 (s, 1H), 8.4 (s, 1H); m/z 271 (M+H)$^+$.

EXAMPLE 52

3-{[5-(Azetidin-1-ylcarbonyl)-4-methyl-1,3-thiazol-2-yl]oxy}-N-(1-methyl-1H-pyrazol-3-yl)-5-[(3S)-tetrahydrofuran-3-yloxy]benzamide

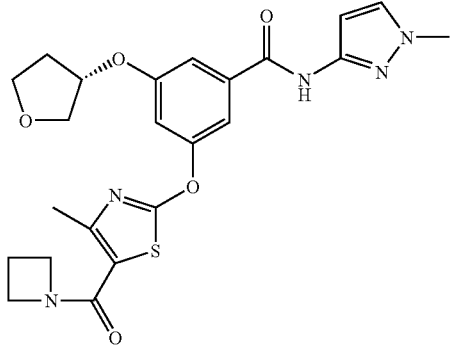

Cesium carbonate (489 mg, 1.5 mmol) was added to a solution of 3-hydroxy-N-(1-methyl-1H-pyrazol-3-yl)-5-[(3S)-tetrahydrofuran-3-yloxy]benzamide (152 mg, 0.5 mmol) and 5-(azetidin-1-ylcarbonyl)-2-bromo-4-methyl-1,3-thiazole (144 mg, 0.55 mmol) in acetonitrile (5 mL) and the stirred mixture heated at 120° C. in a microwave reactor for 2 hours. The mixture was allowed to cool, the acetonitrile evaporated in vacuo, and the residue partitioned between water (25 mL) and ethyl acetate (50 mL). The organic layer was washed with brine, dried (MgSO$_4$) and evaporated to a residue which was chromatographed on silica, eluting with ethyl acetate, to give the desired compound as a solid which was further crystallised from an ethyl acetate/isohexane mixture (122 mg).

$^1$H NMR δ (CDCl$_3$): 2.0-2.15 (m, 2H), 2.2-2.3 (m, 2H), 2.5 (s, 3H), 3.75 (s, 3H), 3.85 (m, 2H), 3.95 (d, 2H), 4.1-4.3 (m, 4H), 4.9 (m, 1H), 6.75 (d, 1H), 6.95 (d, 1H), 7.25 (d, 2H), 7.3 (d, 1H) and 8.8 (s, 1H); m/z 484 (M+H)$^+$.

The preparations of 3-hydroxy-N-(1-methyl-1H-pyrazol-3-yl)-5-[(3S)-tetrahydrofuran-3-yloxy]benzamide and 5-(azetidin-1-ylcarbonyl)-2-bromo-4-methyl-1,3-thiazole were described earlier.

EXAMPLE 53

3-{[6-(Azetidin-1-ylcarbonyl)pyridin-3-yl]oxy}-5-{[(1S)-2-hydroxy-1-methylethyl]oxy}-N-(5-methylpyrazin-2-yl)benzamide

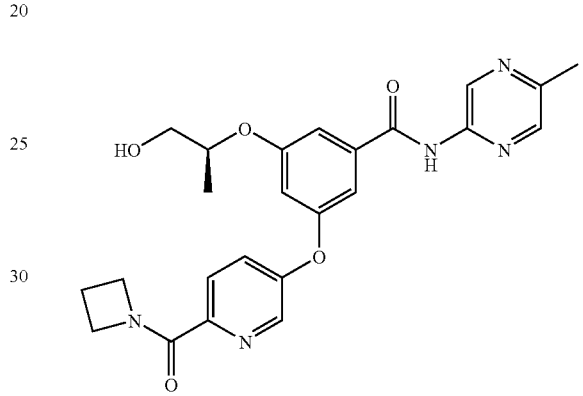

1M Hydrochloric acid (5 mL) was added to a solution of 3-{[6-(azetidin-1-ylcarbonyl)pyridin-3-yl]oxy}-5-[((1S)-2-{[(1,1-dimethylethyl)(dimethyl)silyl]oxy}-1-methylethyl)oxy]-N-(5-methylpyrazin-2-yl)benzamide (82 mg, 0.14 mmol) in methanol (5 mL) and stirred at RT for 1 hour. The methanol was removed in vacuo and the residue taken to pH6, extracted into ethyl acetate (3×50 mL) and the combined organics washed with brine (50 mL), dried (MgSO$_4$), filtered and reduced in vacuo. The crude yellow oil was chromatographed on silica, eluting with 0-5% methanol in ethyl acetate, to give the desired compound as a white foam (36 mg). The compound could be crystallised from a mixture of tert-butylmethyl ether and methanol. $^1$H NMR δ (CDCl$_3$): 1.24 (d, 3H), 1.81 (s, 1H), 2.28 (quin, 2H), 2.48 (s, 3H), 3.67-3.72 (m, 2H), 4.17 (t, 2H), 4.47-4.54 (m, 1H), 4.63 (t, 2H), 6.73 (t, 1H), 7.09 (t, 1H), 7.25 (t, 1H), 7.27-7.30 (m, 1H), 8.01-8.06 (m, 2H), 8.24 (d, 1H), 8.58 (s, 1H), 9.44 (d, 1H); m/z 464 (M+H)$^+$ The following compound was synthesised in an analogous fashion from 3-{[6-(azetidin-1-ylcarbonyl)pyridin-3-yl]oxy}-5-[((1S)-2-{[(1,1-dimethylethyl)(dimethyl)silyl]oxy}-1-methylethyl)oxy]-N-(3-methyl-1,2,4-thiadiazol-5-yl)benzamide.

| Example | Structure | m/z | NMR |
|---|---|---|---|
| 53a | 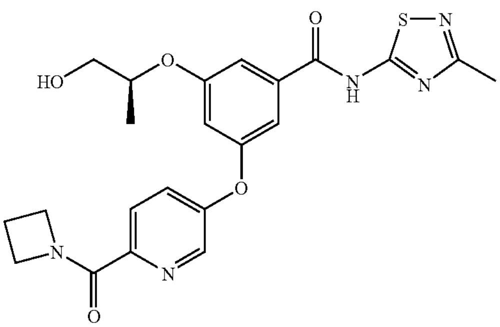 | 470 (M + H)+ | 1H NMR δ (CDCl3): 1.22 (d, 3H), 2.28 (quin, 2H), 2.40 (s, 3H), 3.00 (s, 1H), 3.70 (d, 2H), 4.16 (t, 2H), 4.51 (sextet, 1H), 4.64 (t, 2H), 6.74 (t, 1H), 7.20-7.27 (m, 3H), 7.97 (d, 1H), 8.23 (d, 1H), 11.55 (s, 1H) |

The preparation of 3-{[6-(azetidin 1-ylcarbonyl)pyridin-3-yl]oxy}-5-[((1S)-2-{[(1,1-dimethylethyl)(dimethyl)silyl]oxy}-1-methylethyl)oxy]-N-(5-methylpyrazin-2-yl)benzamide is described below.

3-{[6-(Azetidin-1-ylcarbonyl)pyridin-3-yl]oxy}-5-[((1S)-2-{[(1,1-dimethylethyl)(dimethyl)silyl]oxy}-1-methylethyl)oxy]-N-(5-methylpyrazin-2-yl)benzamide

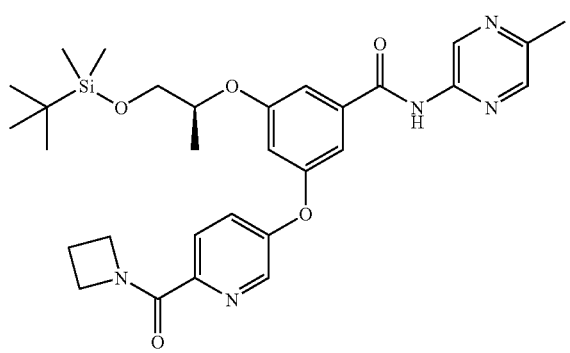

1-Chloro-N,N,2-trimethyl-1-propenylamine (0.11 mL, 0.80 mmol) was added to a solution of 3-{[6-(azetidin-1-ylcarbonyl)pyridin-3-yl]oxy}-5-[((1S)-2-{[(1,1-dimethylethyl)(dimethyl)silyl]oxy}-1-methylethyl)oxy]benzoic acid (0.3 g, 0.62 mmol) in DCM (10 mL) and stirred for 1 hour. 2-Amino-5-methylpyrazine (135 mg, 1.23 mmol), then pyridine (0.1 mL, 1.23 mmol), were added and the mixture stirred for a further 30 mins before being reduced in vacuo and partitioned between ethyl acetate (50 mL) and water (50 mL). The aqueous layer was further extracted into ethyl acetate (50 mL) and the combined organics washed with water (50 mL), brine (50 mL), dried (MgSO4), filtered and reduced in vacuo. The crude oil was chromatographed on silica, eluting with 40-100% ethyl acetate in isohexane, to give the desired compound as a colourless oil (82 mg).

1H NMR δ (CDCl3): 0.00 (s, 3H), 0.03 (s, 3H), 0.83 (s, 9H), 1.28 (d, 3H), 2.32 (quin, 2H), 2.53 (s, 3H), 3.64-3.77 (m, 2H), 4.22 (t, 2H), 4.47-4.51 (m, 1H), 4.68 (t, 2H), 6.81 (t, 1H), 7.10 (t, 1H), 7.27 (t, 1H), 7.33-7.35 (m, 1H), 8.08-8.11 (m, 2H), 8.30 (d, 1H), 8.37 (s, 1H), 9.50 (d, 1H); m/z 578 (M+H)+

3-{[6-(Azetidin-1-ylcarbonyl)pyridin-3-yl]oxy}-5-[((1S)-2-{[(1,1-dimethylethyl)(dimethyl)silyl]oxy}-1-methylethyl)oxy]-N-(3-methyl-1,2,4-thiadiazol-5-yl)benzamide was prepared in an analogous fashion from 3-{[6-(azetidin-1-ylcarbonyl)pyridin-3-yl]oxy}-5-[((1S)-2-{[(1,1-dimethylethyl)(dimethyl)silyl]oxy}-1-methylethyl)oxy]benzoic acid

| Structure | m/z |
|---|---|
| 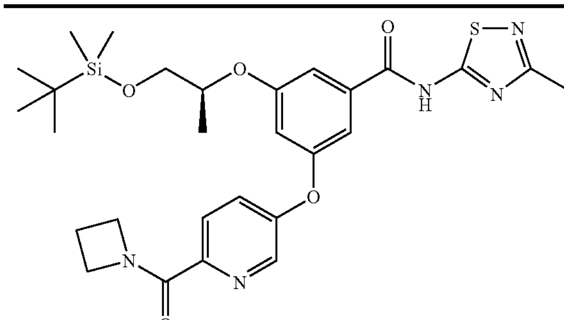 | 584 (M + H)+ |

The preparation of 2-amino-5-methylpyrazine was described earlier.

The preparation of 3-{[6-(azetidin-1-ylcarbonyl)pyridin-3-yl]oxy}-5-[((1S)-2-{[(1,1-dimethylethyl)(dimethyl)silyl]oxy}-1-methylethyl)oxy]benzoic acid is described below.

3-{[6-(Azetidin-1-ylcarbonyl)pyridin-3-yl]oxy}-5-[((1S)-2-{[(1,1-dimethylethyl)(dimethyl)silyl]oxy}-1-methylethyl)oxy]benzoic acid

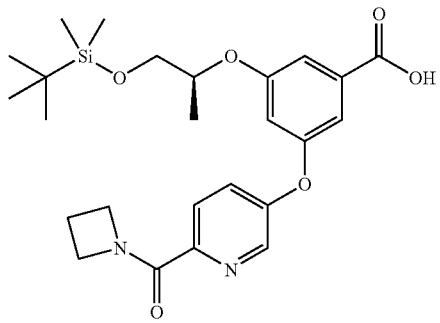

tert-Butyldimethylsilyl chloride (1.11 g, 7.36 mmol) was added to a mixture of 3-{[6-(azetidin-1-ylcarbonyl)pyridin-3-yl]oxy}-5-{[(1S)-2-hydroxy-1-methylethyl]oxy}benzoic acid (1.37 g, 3.68 mmol) and 1,8-diazabicyclo(5,4,0)undec-7-ene (1.11 mL, 7.36 mmol) in acetonitrile (20 mL) and stirred at RT for 24 hours. The solvent was removed in vacuo and water (80 mL) added to the resultant oil. The mixture was adjusted to pH 10 with 1M sodium bicarbonate solution then washed with ether (80 mL) to remove impurities. The aqueous layer was adjusted to pH 3 with 1M citric acid and extracted into ethyl acetate (2×100 mL) and the combined organics washed with brine (50 mL), dried (MgSO$_4$), filtered and reduced in vacuo. The crude material was chromatographed on an Isolute NH2 cartridge, eluting with methanol then ammonia in methanol, to give a beige foam. This material was subsequently triturated with ethyl acetate to give the desired compound as a beige foam (1.0 g). $^1$H NMR δ (CDCl$_3$): 0.01 (s, 3H), 0.03 (s, 3H), 0.83 (s, 9H), 1.27 (d, 3H), 2.26-2.35 (m, 2H), 3.58-3.79 (m, 2H), 4.15-4.25 (m, 2H), 4.43-4.49 (m, 1H), 4.60-4.69 (m, 2H), 6.77-6.82 (m, 1H), 7.28 (m, 2H), 7.42-7.44 (m, 1H), 8.02-8.07 (m, 1H), 8.27-8.29 (m, 1H); m/z 487 (M+H)$^+$ 3-{[6-(Azetidin-1-ylcarbonyl)pyridin-3-yl]oxy}-5-{[(1S)-2-hydroxy-1-methylethyl]oxy}benzoic acid

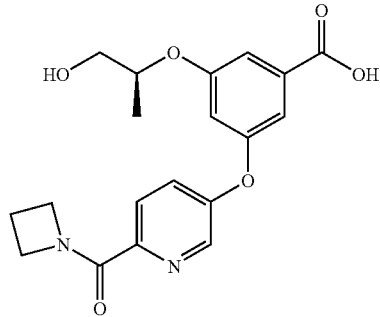

A mixture of methyl 3-hydroxy-5-[(1S)-2-hydroxy-1-methylethoxy]benzoate (2.35 g, 10.39 mmol), 2-(azetidin-1-ylcarbonyl)-5-bromopyridine (2.51 g, 10.39 mmol), cesium carbonate (10.16 g, 31.16 mmol) and bromotris(triphenylphosphine)copper (1.93 g, 2.08 mmol) in DMA (20 mL) was stirred in a microwave reactor at 160° C. for 8 hours. The mixture was partitioned between ethyl acetate (50 mL) and water (50 mL). The aqueous layer was acidified with 1M citric acid and extracted into ethyl acetate (2×100 mL), washed with brine, dried (MgSO$_4$) and the solvent removed in vacuo. The crude oil was chromatographed on an Isolute NH2 cartridge, eluting with methanol then ammonia in methanol, to give the desired material as a beige foam (1.37 g). m/z 373 (M+H)$^+$ The preparations of methyl 3-hydroxy-5-[(1S)-2-hydroxy-1-methylethoxy]benzoate and 2-(azetidin-1-ylcarbonyl)-5-bromopyridine were described earlier.

EXAMPLE 54

3-{[5-(Azetidin-1-ylcarbonyl)-3-chloropyridin-2-yl]oxy}-5-{[(1S)-2-hydroxy-1-methylethyl]oxy}-N-(5-methylpyrazin-2-yl)benzamide

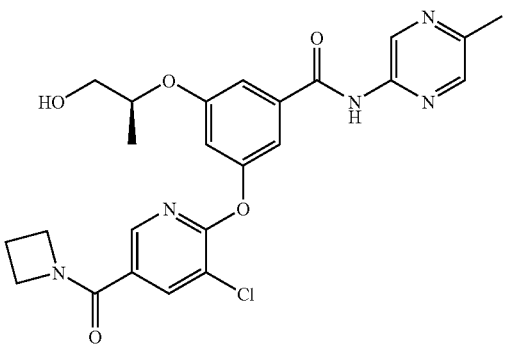

1M Hydrochloric acid (10 mL) was added to a solution of 3-{[5-(azetidin-1-ylcarbonyl)-3-chloropyridin-2-yl]oxy}-5-[((1S)-2-{[(1,1-dimethylethyl)(dimethyl)silyl]oxy}1-methylethyl)oxy]-N-(5-methylpyrazin-2-yl)benzamide (180 mg, 0.29 mmol) in methanol (10 mL) and stirred at RT for 1 hour. The methanol was removed in vacuo and the residue adjusted to pH 6 then extracted into ethyl acetate (3×50 mL). The combined organics were washed with brine (50 mL), dried (MgSO$_4$), and reduced in vacuo to give a yellow oil which was chromatographed on silica, eluting with 0-5% methanol in ethyl acetate, to give the desired compound as a white foam (134 mg). The compound was crystallised from ethyl acetate and methanol.

$^1$H NMR δ (CDCl$_3$): 1.33 (d, 3H), 2.40 (quin, 2H), 2.56 (s, 3H), 3.76-3.81 (m, 2H), 4.25 (t, 2H), 4.38 (t, 2H), 4.57-4.64 (m, 1H), 6.98 (t, 1H), 7.31 (t, 1H), 7.42 (t, 1H), 8.14 (s, 1H), 8.17 (d, 1H), 8.26 (d, 1H), 8.64 (s, 1H), 9.55 (s, 1H); m/z 498 (M+H)$^+$ The following compounds were prepared in an analogous fashion:

| Example | Structure | m/z | NMR |
|---|---|---|---|
| 54a | 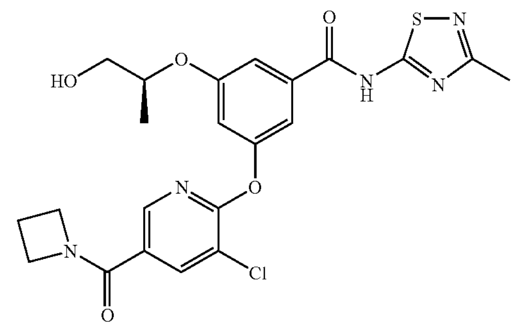 | 504 (M + H)+ | ¹H NMR δ (CDCl₃): 1.30 (d, 3H), 2.40 (quin, 2H), 2.47 (s, 3H), 3.23 (s, 1H), 3.78-3.79 (m, 2H), 4.25 (t, 2H), 4.38 (t, 2H), 4.58 (sextet, 1H), 6.97 (t, 1H), 7.39-7.40 (m, 2H), 8.15 (d, 1H), 8.22 (d, 1H), 11.68 (s, 1H) |
| 54b | 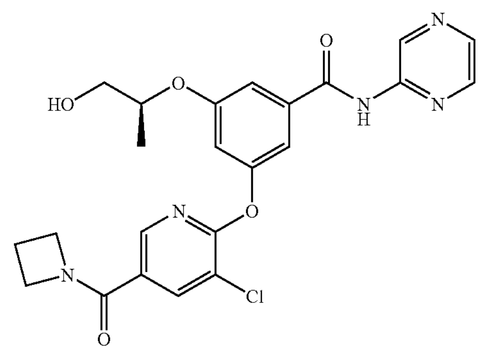 | 484 (M + H)+ | ¹H NMR δ (CDCl₃): 1.27 (d, 3H), 2.02 (t, 1H), 2.33 (quin, 2H), 3.70-3.73 (m, 2H), 4.17 (t, 2H), 4.30 (t, 2H), 4.52-4.56 (m, 1H), 6.93 (t, 1H), 7.24 (t, 1H), 7.35 (t, 1H), 8.10 (d, 1H), 8.19 (d, 1H), 8.21-8.22 (m, 1H), 8.33 (d, 1H), 8.43 (s, 1H), 9.61 (d, 1H) |
| 54c | 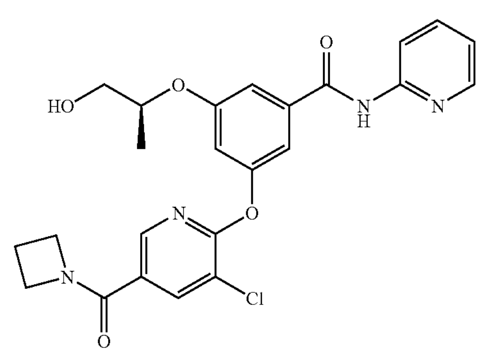 | 483 (M + H)+ | ¹H NMR δ (CDCl₃): 1.26 (d, 3H), 2.17 (t, 1H), 2.32 (quin, 2H), 3.67-3.74 (m, 2H), 4.17 (t, 2H), 4.30 (t, 2H), 4.49-4.56 (m, 1H), 6.89 (t, 1H), 7.00-7.03 (m, 1H), 7.23 (t, 1H), 7.34 (t, 1H), 7.67-7.71 (m, 1H), 8.10 (d, 1H), 8.18 (d, 1H), 8.22-8.23 (m, 1H), 8.28 (d, 1H), 8.54 (s, 1H) |

The preparation of 3-{[5-(azetidin-1-ylcarbonyl)-3-chloropyridin-2-yl]oxy}-5-[((1S)-2-{[(1,1-dimethylethyl)(dimethyl)silyl]oxy}-1-methylethyl)oxy]-N-(5-methylpyrazin-2-yl)benzamide is described below.

3-{[5-(Azetidin-1-ylcarbonyl)-3-chloropyridin-2-yl]oxy}-5-[((1S)-2-{[(1,1-dimethylethyl)(dimethyl)silyl]oxy}-1-methylethyl)oxy]-N-(5-methylpyrazin-2-yl)benzamide

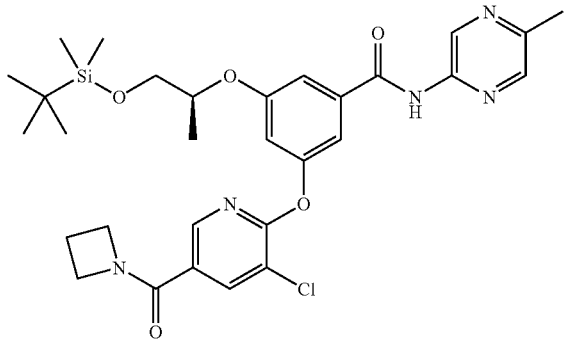

1-Chloro-N,N,2-trimethyl-1-propenylamine (0.1 mL, 0.75 mmol) was added to a solution of 3-{[5-(azetidin-1-ylcarbonyl)-3-chloropyridin-2-yl]oxy}-5-[((1S)-2-{[(1,1-dimethylethyl)(dimethyl)silyl]oxy}-1-methylethyl)oxy]benzoic acid (0.3 g, 0.58 mmol) in DCM (10 mL) and stirred for 1 hour. 2-Amino-5-methylpyrazine (126 mg, 1.15 mmol) then pyridine (0.094 mL, 1.15 mmol) were added and the mixture stirred for a further 30 mins before being reduced in vacuo and partitioned between ethyl acetate (50 mL) and water (50 mL). The aqueous layer was further extracted into ethyl acetate (50 mL) and the combined organics washed with water (50 mL), brine (50 mL), dried (MgSO$_4$), and reduced in vacuo. The crude oil was chromatographed on silica, eluting with 40-100% ethyl acetate in isohexane, to give the title compound as an oil (180 mg).

$^1$H NMR δ (CDCl$_3$): 0.00 (s, 3H), 0.03 (s, 3H), 0.82 (s, 9H), 1.28 (d, 3H), 2.35 (quin, 2H), 2.51 (s, 3H), 3.63-3.78 (m, 2H), 4.19 (t, 2H), 4.32 (t, 2H), 4.47-4.51 (m, 1H), 6.95 (t, 1H), 7.23-7.24 (m, 1H), 7.35 (t, 1H), 8.08 (s, 1H), 8.12 (d, 1H), 8.21 (d, 1H), 8.45 (s, 1H), 9.51 (d, 1H); m/z 612 (M+H)$^+$ The following intermediates used in the preparation of Examples 54a-c were prepared in an analogous fashion.

| Structure | m/z | NMR |
|---|---|---|
| 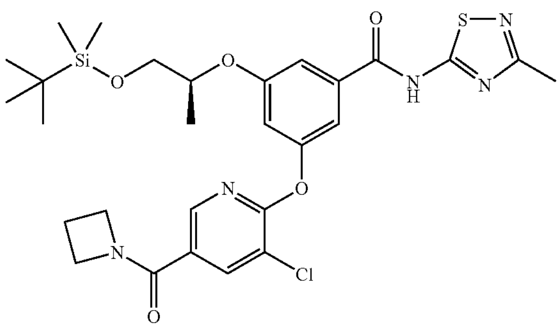 | 618 (M + H)$^+$ | $^1$H NMR δ (CDCl$_3$): 0.00 (s, 3H), 0.03 (s, 3H), 0.84 (s, 9H), 1.37 (d, 3H), 2.30-2.38 (m, 5H), 3.61-3.79 (m, 2H), 4.19 (t, 2H), 4.30 (t, 2H), 4.41-4.47 (m, 1H), 6.84-6.86 (m, 1H), 7.62-7.62 (m, 1H), 7.72-7.73 (m, 1H), 8.10-8.11 (m, 1H), 8.19-8.20 (m, 1H), 9.89 (s, 1H) |
| 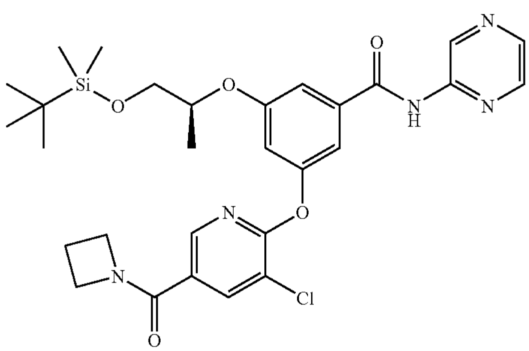 | 598 (M + H)$^+$ | $^1$H NMR δ (CDCl$_3$): 0.00 (s, 3H), 0.03 (s, 3H), 0.83 (s, 9H), 1.29 (d, 3H), 2.35 (quin, 2H), 3.64-3.79 (m, 2H), 4.19 (t, 2H), 4.32 (t, 2H), 4.47-4.51 (m, 1H), 6.96 (s, 1H), 7.25 (s, 1H), 7.36 (s, 1H), 8.12 (d, 1H), 8.21 (d, 1H), 8.23 (s, 1H), 8.34 (d, 1H), 8.52 (s, 1H), 9.64 (s, 1H) |
| 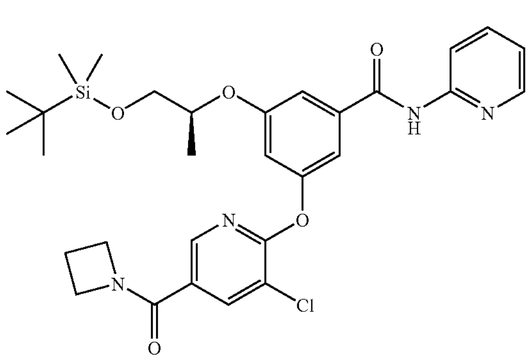 | 597 (M + H)$^+$ | $^1$H NMR δ (CDCl$_3$): 0.00 (s, 3H), 0.03 (s, 3H), 0.84 (s, 9H), 1.28 (d, 3H), 2.35 (quin, 2H), 3.63-3.78 (m, 2H), 4.19 (t, 2H), 4.32 (t, 2H), 4.46-4.50 (m, 1H), 6.93 (t, 1H), 7.01-7.05 (m, 1H), 7.23-7.23 (m, 1H), 7.34 (t, 1H), 7.69-7.73 (m, 1H), 8.12 (d, 1H), 8.21 (d, 1H), 8.24 (d, 1H), 8.31 (d, 1H), 8.56 (s, 1H) |

The preparation of 3-{[5-(azetidin-1-ylcarbonyl)-3-chloropyridin-2-yl]oxy}-5-[((1S)-2-{[(1,1-dimethylethyl)(dimethyl)silyl]oxy}-1-methylethyl)oxy]benzoic acid is described below.

3-{[5-(Azetidin-1-ylcarbonyl)-3-chloropyridin-2-yl]oxy}-5-[((1S)-2-{[(1,1-dimethylethyl)(dimethyl)silyl]oxy}-1-methylethyl)oxy]benzoic acid

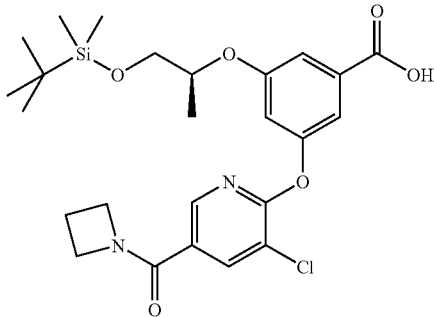

tert-Butyldimethylsilyl chloride (2.78 g, 18.4 mmol) was added to a mixture of 3-{[5-(azetidin-1-ylcarbonyl)-3-chloropyridin-2-yl]oxy}-5-{[(1S)-2-hydroxy-1-methylethyl]oxy}benzoic acid (3.74 g, 9.19 mmol) and 1,8-diazabicyclo(5,4,0)undec-7-ene (2.75 mL, 7.36 mmol) in acetonitrile (40 mL) and stirred at RT for 24 hours. The solvent was removed in vacuo and water (80 mL) added to the resultant oil. The mixture was adjusted to pH 10 with 1M sodium bicarbonate solution and washed with ether to remove any impurities. The aqueous layer was adjusted to pH 3 with 1M citric acid and extracted into ethyl acetate (2×100 mL). The combined organics were washed with brine (50 mL), dried (MgSO$_4$), filtered and reduced in vacuo to give the desired compound as a white foam (2.9 g).
$^1$H NMR δ (CDCl$_3$): 0.00 (s, 3H), 0.03 (s, 3H), 0.83 (s, 9H), 1.28 (d, 3H), 2.35 (quin, 2H), 3.62-3.78 (m, 2H), 4.21 (t, 1H), 4.32 (t, 1H), 4.43-4.50 (m, 1H), 6.95-6.98 (m, 1H), 7.42-7.45 (m, 1H), 7.50-7.53 (m, 1H), 8.12 (d, 1H), 8.22 (d, 1H); m/z 521 (M+H)$^+$ 3-{[5-(Azetidin-1-ylcarbonyl)-3-chloropyridin-2-yl]oxy}-5-{[(1S)-2-hydroxy-1-methylethyl]oxy}benzoic acid

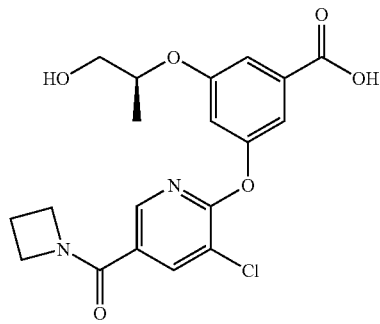

Lithium hydroxide monohydrate (529 mg, 12.59 mmol) in water (25 mL) was added to a solution of methyl 3-{[5-(azetidin-1-ylcarbonyl)-3-chloropyridin-2-yl]oxy}-5-{[(1S)-2-hydroxy-1-methylethyl]oxy}benzoate (5.3 g, 12.6 mmol) in THF (50 mL) and stirred at RT for 3 hours. The THF was removed in vacuo and the aqueous layer was washed with ethyl acetate (50 mL) to remove any impurities. The aqueous layer was acidified and extracted into ethyl acetate (2×50 mL), and the organics washed with brine, dried (MgSO$_4$), and concentrated in vacuo to give the desired compound as a white foam (3.74 g).
$^1$H NMR δ (CDCl$_3$): 1.24 (d, 3H), 2.31 (quin, 2H), 3.65-3.72 (m, 2H), 4.17 (t, 2H), 4.29 (t, 2H), 4.47-4.54 (m, 1H), 6.93 (t, 1H), 7.40 (s, 1H), 7.46 (s, 1H), 8.08 (d, 1H), 8.19 (d, 1H); m/z 407 (M+H)$^+$ Methyl 3-{[5-(azetidin-1-ylcarbonyl)-3-chloropyridin-2-yl]oxy}-5-{[(1S)-2-hydroxy-1-methylethyl]oxy}benzoate

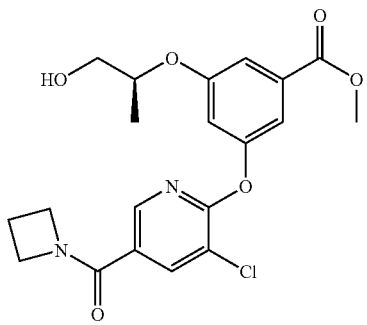

A mixture of methyl 3-hydroxy-5-[(1S)-2-hydroxy-1-methylethoxy]benzoate (2.35 g, 10.39 mmol), 5-(azetidin-1-ylcarbonyl)-2,3-dichloropyridine (2.41 g, 10.39 mmol) and potassium carbonate (2.87 g, 20.8 mmol) in acetonitrile (20 mL) was stirred in a microwave reactor at 160° C. for 6 hours. The solvent was removed in vacuo and the residue partitioned between ethyl acetate (50 mL) and water (50 mL). The organic layer was washed with brine (50 mL), dried (MgSO$_4$), and the solvent removed in vacuo. The crude oil was chromatographed on silica, eluting with 30-100% ethyl acetate in isohexane, to give the desired compound as a yellow oil (5.3 g).
$^1$H NMR δ (CDCl$_3$): 1.24 (d, 3H), 1.94 (t, 1H), 2.32 (quin, 2H), 3.65-3.72 (m, 2H), 3.83 (s, 3H), 4.16 (t, 2H), 4.28 (t, 2H), 4.47-4.54 (m, 1H), 6.90 (t, 1H), 7.37-7.38 (m, 1H), 7.43-7.45 (m, 1H), 8.08 (d, 1H), 8.18 (d, 1H); m/z 421 (M+H)$^+$ The preparations of methyl 3-hydroxy-5-[(1S)-2-hydroxy-1-methylethoxy]benzoate and 5-(azetidin-1-ylcarbonyl)-2,3-dichloropyridine were described earlier.

EXAMPLE 55

3-{[5-(Azetidin-1-ylcarbonyl)pyridin-2-yl]oxy}-5-{[(1S)-2-hydroxy-1-methylethyl]oxy}-N-(3-methyl-1,2,4-thiadiazol-5-yl)benzamide

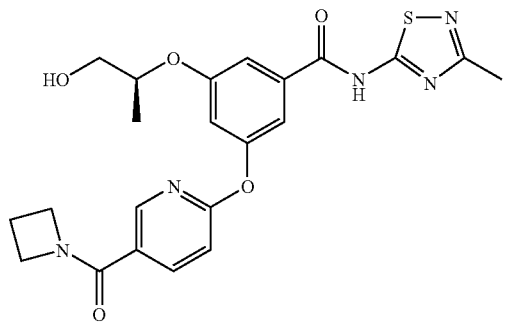

A mixture of 3-hydroxy-5-{[(1S)-2-hydroxy-1-methylethyl]oxy}-N-(3-methyl-1,2,4-thiadiazol-5-yl)benzamide (237 mg, 0.77 mmol), 5-(azetidin-1-ylcarbonyl)-2-chloropyridine (151 mg, 0.77 mmol) and potassium carbonate (213 mg, 1.54 mmol) in acetonitrile (5 mL) was stirred in a microwave reactor at 140° C. for 5 hours and at 160° C. for 10 hours. The mixture was reduced in vacuo and ethyl acetate (50 mL) added. The mixture was washed with water (50 mL), brine (50 mL), dried (MgSO₄), and reduced in vacuo to give a brown oil which was chromatographed on silica, eluting with 0-10% methanol in ethyl acetate, to give the desired compound as a white foam (64 mg).

¹H NMR δ (CDCl₃): 1.29 (d, 3H), 2.38 (quin, 2H), 2.49 (s, 3H), 2.72 (s, 1H), 3.75-3.77 (m, 2H), 4.20-4.41 (m, 4H), 4.51-4.59 (m, 1H), 6.95 (t, 1H), 6.99 (d, 1H), 7.35 (t, 1H), 7.37-7.38 (m, 1H), 8.05-8.08 (m, 1H), 8.40 (d, 1H), 11.08 (s, 1H); m/z 470 (M+H)⁺

The preparation of 5-(azetidin-1-ylcarbonyl)-2-chloropyridine was described earlier.

The preparation of 3-hydroxy-5-{[(1S)-2-hydroxy-1-methylethyl]oxy}-N-(3-methyl-1,2,4-thiadiazol-5-yl)benzamide is described below.

3-Hydroxy-5-{[(1S)-2-hydroxy-1-methylethyl]oxy}-N-(3-methyl-1,24-thiadiazol-5-yl)benzamide

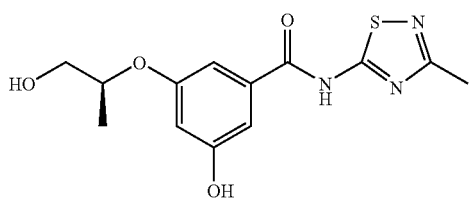

Iodotrimethylsilane (5.51 mL, 38.7 mmol) was added to 3-hydroxy-5-{[(1S)-2-methoxy-(1-methylethyl)oxy}-N-(3-methyl-1,2,4-thiadiazol-2-yl)benzamide (2.5 g, 7.73 mmol) in acetonitrile (25 mL) and the reaction stirred at RT for 48 hours. Methanol (15 mL) was added and the reaction stirred for 1 hour then a saturated solution of sodium thiosulphate (10 mL) was added and stirred for 20 mins. The volatiles were removed in vacuo and the aqueous residue extracted into ethyl acetate (2×150 mL). The organics were washed with water, brine, dried (MgSO₄), and reduced in vacuo to give a yellow solid. The solid was triturated with DCM and then with ethyl acetate to give the desired compound as a white solid (1.44 g).
¹H NMR δ (d₆-DMSO): 1.23 (d, 3H), 2.49 (s, 3H), 3.46-3.59 (m, 2H), 4.48-4.52 (m, 1H), 4.89 (t, 1H), 6.60 (s, 1H), 7.08 (s, 1H), 7.24 (s, 1H), 9.91 (s, 1H), 13.28 (s, 1H); m/z 310 (M+H)⁺

The preparation of 3-hydroxy-5-{[(1S)-2-methoxy-(1-methylethyl)oxy}-N-(3-methyl-1,2,4-thiadiazol-2-yl)benzamide was described earlier.

EXAMPLE 56

N-(1-methyl-1H-pyrazol-3-yl)-3-{[6-(pyrrolidin-1-ylcarbonyl)pyridin-3-yl]oxy}-5-[(3S)-tetrahydrofuran-3-yloxy]benzamide

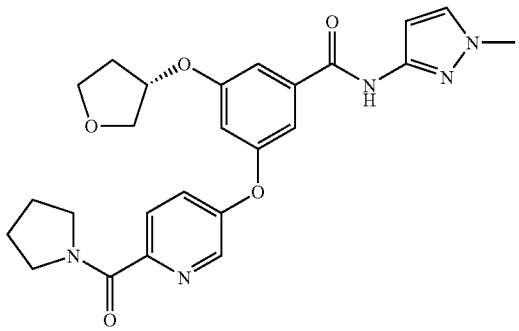

Copper (I) iodide (95 mg, 0.5 mmol), 2,2,6,6-tetramethyl-3,5-heptanedione (0.42 mL, 2.0 mmol) and cesium carbonate (489 mg, 1.5 mmol) were added to a solution of 3-hydroxy-N-(1-methyl-1H-pyrazol-3-yl)-5-[(3S)-tetrahydrofuran-3-yloxy]benzamide (152 mg, 0.5 mmol) and 5-bromo-2-(pyrrolidin-1-ylcarbonyl)pyridine (141 mg, 0.55 mmol) in NMP (5 mL) and the stirred mixture heated at 160° C. in a microwave reactor for 12 hours. The mixture was cooled to RT and pressure, the mixture partitioned between water (75 mL) and ethyl acetate (50 mL), the organic layer washed with brine, dried (MgSO₄) and evaporated to a residue which was chromatographed on silica, eluting with ethyl acetate, to give the desired material (81 mg).
¹H NMR δ (CDCl₃): 1.8-1.95 (m, 4H), 2.0-2.2 (m, 2H), 3.6 (m, 2H), 3.75 (s, 3H), 3.85 (m, 2H), 3.95 (m, 2H), 4.9 (m, 1H), 6.65 (m, 1H), 6.75 (m, 1H), 7.1 (m, 1H), 7.2 (s, 1H), 7.25 (m, 1H), 7.3 (dd, 1H), 7.8 (d, 1H), 8.25 (d, 1H), 8.8 (s, 1H); m/z 478 (M+H)⁺.

The preparation of 3-hydroxy-N-(1-methyl-1H-pyrazol-3-yl)-5-[(3S)-tetrahydrofuran-3-yloxy]benzamide was described earlier.

The preparation of 5-bromo-2-(pyrrolidin-1-ylcarbonyl)pyridine is described below.

5-Bromo-2-(pyrrolidin-1-ylcarbonyl)pyridine

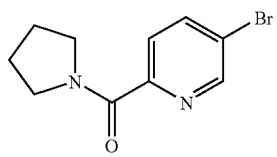

Oxalyl chloride (0.83 mL; 9.3 mmol) and DMF (1 drop) were added to a solution of 5-bromoisonicotinic acid (1.57 g; 7.75 mmol) and 4M hydrogen chloride in dioxan (1.93 mL; 7.75 mmol) in DCM (50 mL). The mixture was stirred at RT for 18 hours, the DCM removed in vacuo and the residue azeotroped with toluene (2×15 mL). The residue was and added to a solution of pyrrolidine (0.78 mL; 9.3 mmol) and triethylamine (2.6 mL; 18.6 mmol) in DCM (40 mL) and the mixture stirred at RT for 6 hours. The DCM was removed in vacuo, the residue partitioned between water (75 mL) and ethyl acetate (100 mL), the organic layer washed with brine, dried (MgSO₄) and evaporated to a residue which was chromatographed on silica, eluting with 50% ethyl acetate in iso hexane, to give the desired material (1.40 g). ¹H NMR δ (CDCl₃): 1.85 (m, 4H), 3.6 (m, 2H), 3.7 (s, 3H), 7.7 (d, 1H), 7.85 (s, 1H), 8.55 (s, 1H); m/z 257 (M+H)⁺.

EXAMPLE 57

3-{[6-(Azetidin-1-ylcarbonyl)pyridin-3-yl]oxy}-N-pyrazin-2-yl-5-[(3S)-tetrahydrofuran-3-yloxy]benzamide

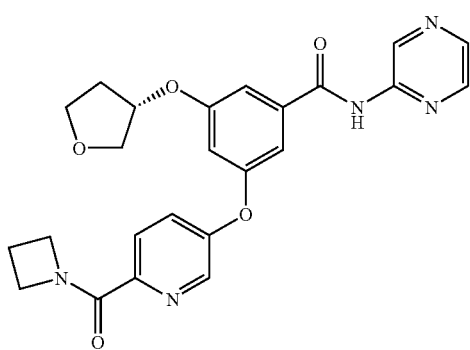

1-Chloro-N,N,2-trimethyl-1-propenylamine (0.095 mL, 0.75 mmol) was added to a solution of 3-{[6-(azetidin-1-ylcarbonyl)pyridin-3-yl]oxy}-5-[(3S)-tetrahydrofuran-3-yloxy]benzoic acid (250 mg, 0.65 mmol) in DCM (6 mL) and stirred at RT for 30-40 minutes. 2-Aminopyrazine (125 mg, 1.31 mmol) and pyridine (0.106 mL, 1.31 mmol) were added and the reaction stirred at RT for 2 hours. The solvent was removed in vacuo, water (20 mL) was added and the mixture was extracted with ethyl acetate (3×20 mL). The organic extracts were combined and washed with 2N hydrochloric acid (20 mL), a saturated solution of sodium bicarbonate (20 mL), water (20 mL), brine (20 mL), dried (MgSO₄) and evaporated in vacuo. The crude product was chromatographed on silica, eluting with a gradient of 0-10% methanol in DCM, to give the desired compound (71 mg).

¹H NMR δ (CDCl₃): 2.13-2.30 (m, 2H), 2.32-2.39 (m, 2H), 3.89-4.04 (m, 4H), 4.25 (t, 2H), 4.71 (t, 2H), 4.97-5.01 (m, 1H), 6.77 (t, 1H), 7.16 (t, 1H), 7.25 (s, 1H), 7.40 (dd, 1H), 8.14 (d, 1H), 8.28 (dd, 1H), 8.34 (d, 1H), 8.38 (s, 1H), 8.40 (d, 1H), 9.66 (d, 1H); m/z 462 (M+H)⁺, 460 (M−H)⁻

The following compounds were prepared in an analogous fashion from 3-{[6-(azetidin-1-ylcarbonyl)pyridin-3-yl]oxy}-5-[(3S)-tetrahydrofuran-3-yloxy]benzoic acid and either 1,1-dimethylethyl 3-amino-5-methyl-1H-pyrazole-1-carboxylate or 1,1-dimethylethyl 3-amino-1H-pyrazole-1-carboxylate. The material produced was dissolved in acetonitrile (3 mL) and heated at 150° C. in a microwave reactor for 10 minutes to give the desired material after chromatography.

| Example | Structure | m/z | NMR |
|---|---|---|---|
| 57a | 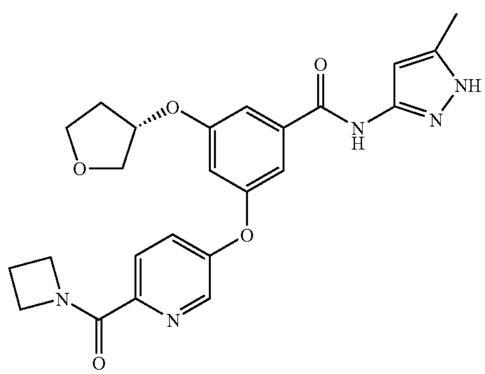 | 464 (M + H)⁺ 462 (M − H)⁻ | ¹H NMR δ (CDCl₃): 2.12-2.27 (2H, m), 2.31-2.39, (2H, m), 2.33 (3H, s), 3.87-4.01 (4H, m), 4.24 (2H, t), 4.70 (2H, t), 4.95-4.98 (1H, m), 6.57 (1H, s), 6.73 (1H, t), 7.13 (1H, t), 7.24 (1H, t), 7.35-7.38 (1H, m), 8.10 (1H, d), 8.31 (1H, d), 8.79 (1H, s) |
| 57b | 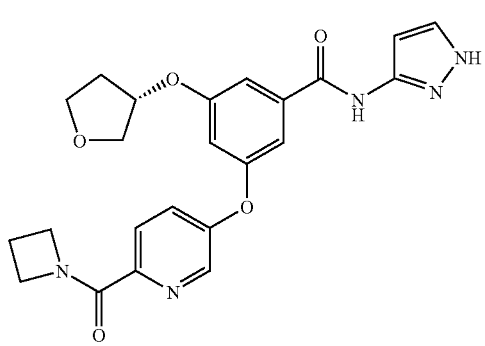 | 450 (M + H)⁺ 448 (M − H)⁻ | ¹H NMR δ (CDCl₃): 2.11-2.27 (2H, m), 2.30-2.38 (2H, m), 3.87-4.02 (4H, m), 4.22 (2H, t), 4.69 (2H, t), 4.95-4.97 (1H, m), 6.74 (1H, t), 6.77 (1H, s), 7.19 (1H, s), 7.30 (1H, s), 7.32-7.35 (1H, m), 7.51 (1H, d), 8.06 (1H, d), 8.30 (1H, d), 9.59 (1H, s) |

The preparations of 3-{[6-(azetidin-1-ylcarbonyl)pyridin-3-yl]oxy}-5-[(3S)-tetrahydrofuran-3-yloxy]benzoic acid and 1,1-dimethylethyl 3-amino-1H-pyrazole-1-carboxylate were described earlier.

The preparation of 1,1-dimethylethyl 3-amino-5-methyl-1H-pyrazole-1-carboxylate is described below.

1,1-Dimethylethyl 3-amino-5-methyl-1H-pyrazole-1-carboxylate

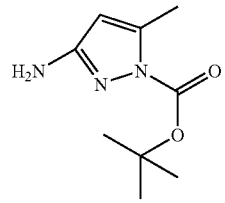

5-Methyl-1H-pyrazol-3-amine (800 mg, 8.25 mmol) was dissolved in DMF (10 mL) at 0° C. and treated with sodium hydride (336 mg, 8.25 mmol) followed by stirring for a further 30 minutes. Warmed di-tert-butyl dicarbonate (1.80 g, 8.25 mmol) was then slowly added via syringe over 5 min and the reaction was allowed to warm to RT and stirred for a further 1 hour. The reaction was taken up in saturated aqueous sodium hydrogencarbonate (50 mL) and ethyl acetate (100 mL). The organic layer was separated then dried (MgSO$_4$), filtered and evaporated. Purification by column chromatography, eluting with 50-100% ethyl acetate in isohexane, afforded the title compound as a colourless oil (380 mg).

$^1$H NMR δ (CDCl$_3$): 1.62 (s, 9H), 2.43 (s, 3H), 3.87 (br. s, 2H), 5.60 (s, 1H)

EXAMPLE 58

3-{[5-(Azetidin-1-ylcarbonyl)-3-chloropyridin-2-yl]oxy}-5-{[2-fluoro-1-(fluoromethyl)ethyl]oxy}-N-(5-methylpyrazin-2-yl)benzamide

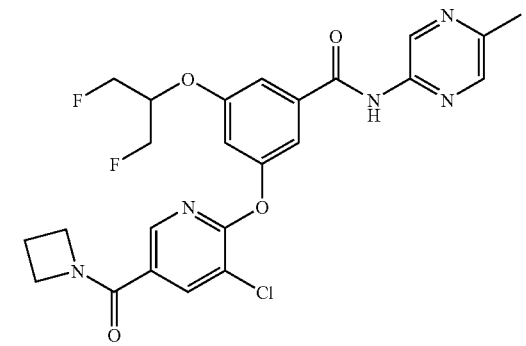

1-Chloro-N,N-2-trimethylpropenylamine (0.08 mL, 0.60 mmol) was added to a solution of 3-{[5-(azetidin-1-ylcarbonyl)-3-chloropyridin-2-yl]oxy}-5-{[2-fluoro-1-(fluoromethyl)ethyl]oxy}benzoic acid (215 mg, 0.5 mmol) in DCM (5 mL) and the reaction stirred at RT for 30-40 minutes. Pyridine (0.08 mL, 1.0 mmol) and 2-amino-5-methylpyrazine (108 mg, 1.0 mmol) were added and the reaction stirred for 16 hours before being concentrated in vacuo and water (20 mL) added. The mixture was extracted with ethyl acetate (3×20 mL), washed with 1N hydrochloric acid (20 mL), a saturated solution of sodium hydrogen carbonate (20 mL), brine (20 mL), dried (MgSO$_4$) and concentrated in vacuo. The crude product was chromatographed on silica, eluting with a gradient of 0-10% methanol in DCM, to give the desired compound as a white solid (150 mg). $^1$H NMR δ (CDCl$_3$): 2.40 (quintet, 2H), 2.56 (s, 3H), 4.22-4.31 (m, 2H), 4.32-4.40 (m, 2H), 4.62-4.82 (m, 5H), 7.06 (t, 1H), 7.38 (t, 1H), 7.47 (t, 1H), 8.15 (s, 1H), 8.17 (s, 1H), 8.25 (d, 1H), 8.46 (s, 1H), 9.55 (s, 1H); m/z 518 (M+H)$^+$, 516 (M−H)$^-$ The following compounds were prepared in an analogous fashion from the appropriate benzoic acid and either 2-amino-5-methylpyrazine, 1,1-dimethylethyl 3-amino-5-methyl-1H-pyrazole-1-carboxylate or 1,1-dimethylethyl 3-amino-1H-pyrazole-1-carboxylate. In the instances where either 1,1-dimethylethyl 3-amino-5-methyl-1H-pyrazole-1-carboxylate or 1,1-dimethylethyl 3-amino-1H-pyrazole-1-carboxylate were used, an additional step was required to obtain the desired material. This additional step required the material to be dissolved in acetonitrile (3 mL) and heated at 150° C. in a microwave reactor for 10 minutes, the desired material was then isolated after chromatography.

| Example | Structure | m/z | NMR |
|---|---|---|---|
| 58a | 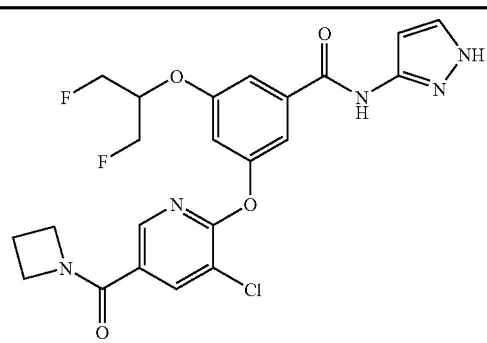 | 492 (M + H)$^+$ 490 (M − H)$^-$ | $^1$H NMR δ (CDCl$_3$): 2.39 (quin, 2H), 4.22 (t, 2H), 4.33 (t, 2H), 4.59-4.81 (m, 5H), 6.86 (s, 1H), 6.99 (s, 1H), 7.37 (s, 1H), 7.41 (s, 2H), 8.16 (d, 1H), 8.19 (d, 1H), 10.32 (s, 1H) |

-continued

| Example | Structure | m/z | NMR |
|---|---|---|---|
| 58b | 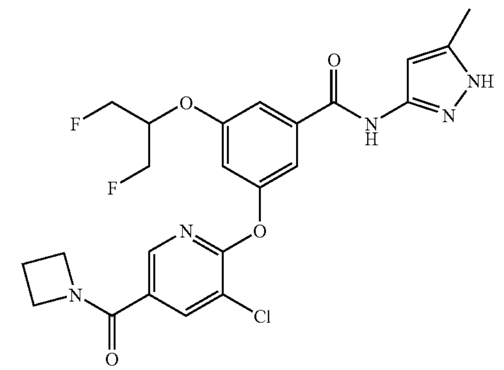 | 506 (M + H)$^+$ 504 (M − H)$^−$ | $^1$H NMR δ (CDCl$_3$): 2.24 (s, 3H), 2.38 (quin, 2H), 4.23 (t, 2H), 4.34 (t, 2H), 4.59-4.79 (m, 5H), 6.59 (s, 1H), 7.00 (t, 1H), 7.34 (s, 1H), 7.37 (s, 1H), 8.16 (d, 1H), 8.19 (d, 1H), 9.95 (s, 1H) |
| 58c | 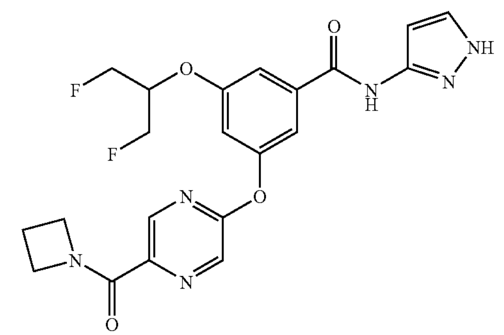 | 459 (M + H)$^+$ 457 (M − H)$^−$ | $^1$H NMR δ (d$_6$-DMSO): 2.25-2.35 (m, 2H), 4.12-4.18 (m, 2H), 4.50-4.70 (m, 7H), 6.65 (s, 1H), 6.9 (s, 1H), 7.35 (s, 1H), 7.37 (s, 1H), 7.45 (s, 1H), 8.25 (s, 1H), 8.70 (s, 1H), 10.60 (s, 1H) |
| 58d | 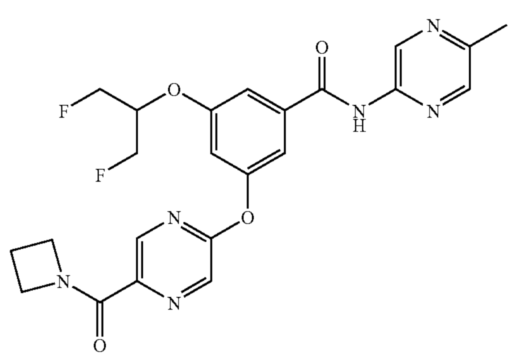 | 485 (M + H)$^+$ 483 (M − H)$^−$ | $^1$H NMR δ (CDCl$_3$): 2.34-2.42 (m, 2H), 2.58 (s, 3H), 4.26 (t, 2H), 4.69 (t, 2H), 4.63-4.81 (m, 5H), 7.05 (t, 1H), 7.37 (t, 1H), 7.45-7.46 (m, 1H), 8.14 (d, 1H), 8.34 (s, 1H), 8.37 (d, 1H), 8.86 (d, 1H), 9.53 (d, 1H) |

The preparations of 1,1-dimethylethyl 3-amino-5-methyl-1H-pyrazole-1-carboxylate or 1,1-dimethylethyl 3-amino-1H-pyrazole-1-carboxylate were described earlier.

The preparation of 3-{[5-(azetidin-1-ylcarbonyl)-3-chloropyridin-2-yl]oxy}-5-{[2-fluoro-1-(fluoromethyl)ethyl]oxy}benzoic acid is described below.

3-{[5-(Azetidin-1-ylcarbonyl)-3-chloropyridin-2-yl]oxy}-5-{[2-fluoro-1-(fluoromethyl)ethyl]oxy}benzoic acid

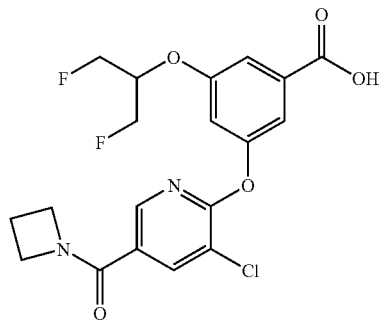

A mixture of methyl 3-{[5-(azetidin-1-ylcarbonyl)-3-chloropyridin-2-yl]oxy}-5-{[2-fluoro-1-(fluoromethyl)ethyl]oxy}benzoate (3.6 g, 8.2 mmol) in THF (50 mL) and water (50 mL) was treated with 1M sodium hydroxide solution (8.2 mL, 8.2 mmol) and allowed to stir at RT for 210 minutes. The THF was removed in vacuo, the residue filtered and extracted with ethyl acetate (30 mL). The aqueous layer was acidified with 2N hydrochloric acid, extracted with ethyl acetate (3×50 mL) and the combined organic extracts washed with water (10 mL), brine (10 mL) and concentrated in vacuo to give the desired material as a pale yellow foam (2.84 g). $^1$H NMR δ (CDCl$_3$): 2.36-2.44 (m, 2H), 4.26 (t, 2H), 4.37 (t, 2H), 4.62-4.79 (m, 5H), 7.08 (t, 1H), 7.56-7.57 (m, 1H), 7.58-7.59 (m, 1H), 8.17 (d, 1H), 8.27 (d, 1H); m/z 426 (M+H)$^+$, 424 (M−H)$^−$ 3-{[5-(Azetidin-1-ylcarbonyl)pyrazin-2-yl]oxy}-5-{[2-fluoro-1-(fluoromethyl)ethyl]oxy}benzoic acid was prepared in an analogous fashion from methyl 3-{[5-(azetidin-1-ylcarbonyl)pyrazin-2-yl]oxy}-5-{[2-fluoro-1-(fluoromethyl)ethyl]oxy}benzoate The preparation of methyl 3-{[5-(azetidin-1-ylcarbonyl)-3-chloropyridin-2-yl]oxy}-5-{[2-fluoro-1-(fluoromethyl)ethyl]oxy}benzoate is described below.

Methyl 3-{[5-(azetidin-1-ylcarbonyl)-3-chloropyridin-2-yl]oxy}-5-{[2-fluoro-1-(fluoromethyl)ethyl]oxy}benzoate

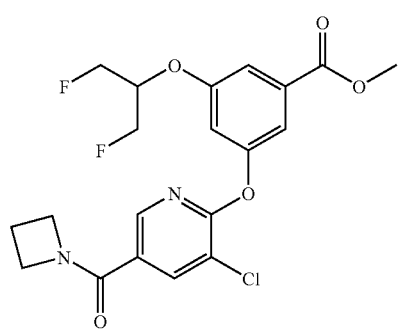

A solution of methyl 3-{[2-fluoro-1-(fluoromethyl)ethyl]oxy}-5-hydroxybenzoate (1.78 g, 7.24 mmol), potassium carbonate (2.0 g, 14.5 mmol) and 5-(azetidin-1-ylcarbonyl)-2,3-dichloropyridine (2.08 g, 8.7 mmol) in acetonitrile (15 mL) was heated in a microwave reactor at 130° C. for 1 hour. The solution was diluted with ethyl acetate (150 mL), washed with water (3×50 mL), brine (20 mL), dried (MgSO$_4$), and the solvent removed in vacuo to give the desired material as an orange oil (3.6 g). $^1$H NMR δ (CDCl$_3$): 2.35-2.44 (m, 2H), 3.91 (s, 3H), 4.24-4.27 (m, 2H), 4.34-4.37 (m, 2H), 4.62-4.81 (m, 5H), 7.04 (t, 1H), 7.51 (t, 1H), 7.55 (m, 1H), 8.15 (d, 1H), 8.25 (d, 1H); m/z 441 (M+H)$^+$ Methyl 3-{[5-(azetidin-1-ylcarbonyl)pyrazin-2-yl]oxy}-5-{[2-fluoro-1-(fluoromethyl)ethyl]oxy}benzoate was prepared in an analogous fashion from methyl 3-{[2-fluoro-1-(fluoromethyl)ethyl]oxy}-5-hydroxybenzoate

| Structure | m/z | NMR |
|---|---|---|
| 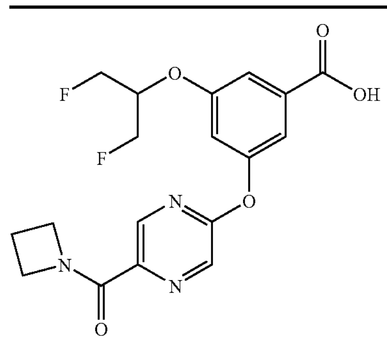 | 394 (M + H)$^+$, 392 (M − H)$^−$ | $^1$H NMR δ (d$_6$-DMSO): 2.26-2.34 (m, 2H), 4.08-4.15 (m, 2H), 4.56 (t, 2H), 4.60-5.10 (m, 5H), 7.29 (t, 1H), 7.38-7.39 (m, 1H), 7.46-7.47 (m, 1H), 8.56 (d, 1H), 8.65-8.67 (m, 1H) |

| Structure | m/z | NMR |
|---|---|---|
| (structure shown) | 408 (M + H)+ | 1H NMR δ (CDCl3): 2.34-2.43 (m, 2H), 3.91 (s, 3H), 4.26 (t, 2H), 4.59-4.79 (m, 5H), 4.65-4.71 (m, 2H), 7.03 (t, 1H), 7.49-7.50 (m, 1H), 7.54-7.55 (m, 1H), 8.33 (d, 1H), 8.84-8.86 (m, 1H) |

The preparation of methyl 3-{[2-fluoro-1-(fluoromethyl) ethyl]oxy}-5-hydroxybenzoate is described below.

Methyl 3-{[2-fluoro-1-(fluoromethyl)ethyl]oxy}-5-hydroxybenzoate

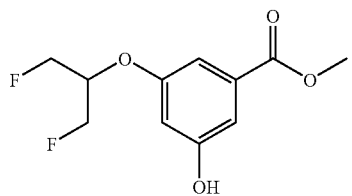

10% Palladium on charcoal (Pd/C; 50 mg) was added to a mixture of methyl 3-{[2-fluoro-1-(fluoromethyl)ethyl]oxy}-5-[(phenylmethyl)oxy]benzoate (1.2 g, 3.62 mmol) and ammonium formate (500 mg, 8.0 mmol) in ethanol (7 mL) and then heated at 140° C. for 20 minutes in a microwave reactor. The reaction was repeated on the same scale and the two reaction mixtures combined, filtered and filtrate concentrated in vacuo to give the desired material as a pale yellow oil (2.1 g). 1H NMR δ (CDCl3): 3.82 (s, 3H), 4.58-4.77 (m, 5H), 6.72 (t, 1H), 7.17-7.22 (m, 2H); m/z 245 (M–H)−

The preparation of methyl 3-{[2-fluoro-1-(fluoromethyl) ethyl]oxy}-5-[(phenylmethyl)oxy]benzoate was described earlier.

EXAMPLE 59

3-{[5-(Azetidin-1-ylcarbonyl)pyrazin-2-yl]oxy}-5-{[(1S)-2-hydroxy-1-methylethyl]oxy}-N-(5-methylpyrazin-2-yl)benzamide

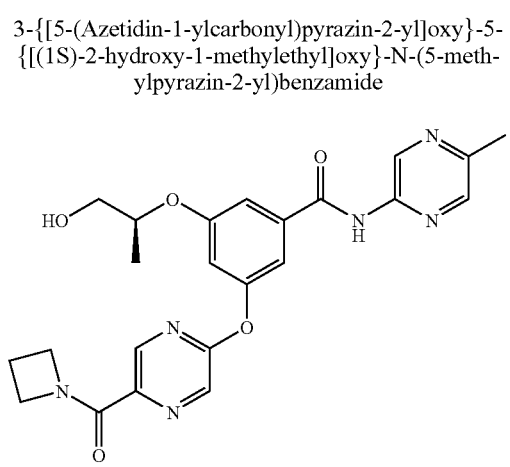

1M Hydrochloric acid (5 mL) was added to a solution of 3-{[5-(azetidin-1-ylcarbonyl)pyrazin-2-yl]oxy}-5-[((1S)-2-{[(1,1-dimethylethyl)(dimethyl)silyl]oxy}-1-methylethyl) oxy]-N-(5-methylpyrazin-2-yl)benzamide (90 mg, 0.16 mmol) in methanol (5 mL) and the mixture stirred at RT for 1 hour. The methanol was removed in vacuo, the residue adjusted to pH6 and then extracted into ethyl acetate (3×50 mL). The combined organics were washed with brine (50 mL), dried (MgSO4), and reduced in vacuo to give a yellow oil which was chromatographed on silica, eluting with 0-5% methanol in ethyl acetate, to give the desired compound as a white foam (28 mg).

1H NMR δ (CDCl3): 1.33 (d, 3H), 2.11 (s, 1H), 2.38 (quin, 2H), 2.55 (s, 3H), 3.74-3.82 (m, 2H), 4.26 (t, 2H), 4.55-4.62 (m, 1H), 4.69 (t, 2H), 6.97 (t, 1H), 7.30 (t, 1H), 7.40 (t, 1H), 8.13 (s, 1H), 8.35 (d, 1H), 8.41 (s, 1H), 8.85 (d, 1H), 9.53 (d, 1H); m/z 465 (M+H)+

The preparation of 3-{[5-(azetidin-1-ylcarbonyl)pyrazin-2-yl]oxy}-5-[((1S)-2-{[(1,1-dimethylethyl)(dimethyl)silyl] oxy}-1-methylethyl)oxy]-N-(5-methylpyrazin-2-yl)benzamide is described below.

3-{[5-(Azetidin-1-ylcarbonyl)pyrazin-2-yl]oxy}-5-[((1S)-2-{[(1,1-dimethylethyl)(dimethyl)silyl]oxy}-1-methylethyl)oxy]-N-(5-methylpyrazin-2-yl)benzamide

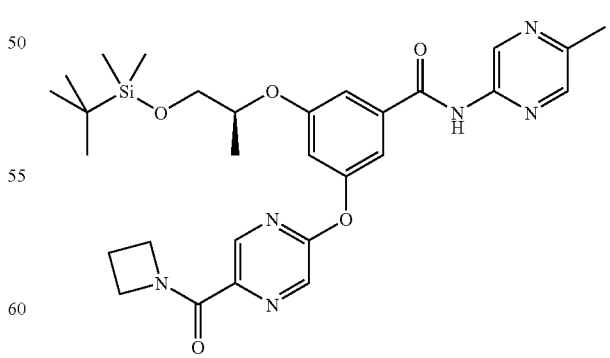

A mixture of 3-[((1S)-2-{[(1,1-dimethylethyl)(dimethyl) silyl]oxy}-1-methylethyl)oxy]-5-hydroxy-N-(5-methylpyrazin-2-yl)benzamide (0.12 g, 0.29 mmol), 2-(azetidin-1-ylcarbonyl)-5-chloropyrazine (57 mg, 0.29 mmol) and potassium carbonate (80 mg, 0.57 mmol) in acetonitrile (5 mL) was stirred in a microwave reactor at 140° C. for 1 hour. The mixture was reduced in vacuo and ethyl acetate (50 mL) added. The mixture was washed with water (50 mL), brine (50 mL), dried (MgSO$_4$), filtered and reduced in vacuo to give a brown oil which was chromatographed on silica, eluting with 50 to 100% ethyl acetate in isohexane, to give the desired compound as a colourless oil (90 mg). $^1$H NMR δ (CDCl$_3$): −0.03 (s, 3H), 0.00 (s, 3H), 0.81 (s, 9H), 1.26 (d, 3H), 2.32 (quin, 2H), 2.49 (s, 3H), 3.61-3.76 (m, 2H), 4.20 (t, 2H), 4.46 (sextet, 1H), 4.62 (t, 2H), 6.91 (t, 1H), 7.21 (t, 1H), 7.32 (t, 1H), 8.07 (s, 1H), 8.28 (d, 1H), 8.30 (s, 1H), 8.79 (d, 1H), 9.48 (d, 1H). m/z 579 (M+H)$^+$ 3-[((1S)-2-{[(1,1-Dimethylethyl)(dimethyl)silyl]oxy}-1-methylethyl)oxy]-5-hydroxy-N-(5-methylpyrazin-2-yl)benzamide

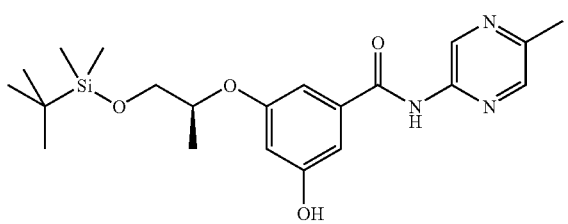

Lithium hydroxide monohydrate (0.38 g, 9.12 mol) in water (20 mL) was added to a solution of 3-{[(1,1-dimethylethyl)(dimethyl)silyl]oxy}-5-[((1S)-2-{[(1,1-dimethylethyl)(dimethyl)silyl]oxy}-1-methylethyl)oxy]-N-(5-methylpyrazin-2-yl)benzamide (1.94 g, 3.65 mol) in THF (40 mL) and stirred at RT for 20 hours. The THF was removed in vacuo and the aqueous layer was adjusted to pH7. Ethyl acetate (50 mL) and water (50 mL) were added then the aqueous layer re-extracted into ethyl acetate (50 mL) and the combined organics washed with water (50 mL), brine (50 mL), dried (MgSO$_4$), filtered and reduced in vacuo. The crude material was chromatographed on silica, eluting with 20-50% ethyl acetate in isohexane, to give the desired material as a white solid (0.8 g). $^1$H NMR δ (CDCl$_3$): 0.04 (s, 3H), 0.08 (s, 3H), 0.87 (s, 9H), 1.30 (d, 3H), 2.56 (s, 3H), 3.65-3.81 (m, 2H), 4.46-4.51 (m, 1H), 5.63 (s, 1H), 6.63 (t, 1H), 6.98 (t, 1H), 7.04 (t, 1H), 8.15 (s, 1H), 8.41 (s, 1H), 9.57 (s, 1H); m/z 418 (M+H)$^+$ 3-{[(1,1-Dimethylethyl)(dimethyl)silyl]oxy}-5-[((1S)-2-{[(1,1-dimethylethyl)(dimethyl)silyl]oxy}-1-methylethyl)oxy]-N-(5-methylpyrazin-2-yl)benzamide

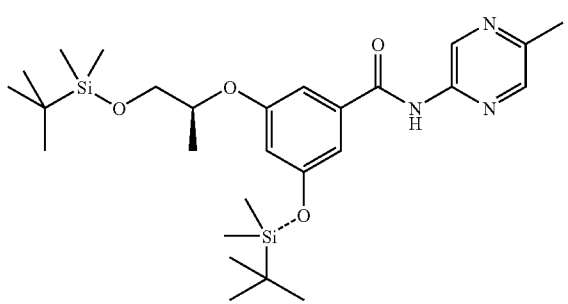

tert-Butyldimethylsilyl chloride (2.61 g, 17.31 mmol) was added to a solution of 3-hydroxy-5-{[(1S)-2-hydroxy-1-methylethyl]oxy}-N-(5-methylpyrazin-2-yl)benzamide (1.5 g, 4.95 mmol) and imidazole (2.36 g, 34.62 mmol) in DMF (15 mL) and the reaction stirred at RT for 24 hours. Water was added and the product extracted into ether (2×100 mL). The combined organics were washed with brine, dried (MgSO$_4$), filtered and reduced in vacuo to give a yellow oil which was chromatographed on silica, eluting with 0-40% ethyl acetate in isohexane, to give the desired material as a colourless oil (1.94 g).

$^1$H NMR δ (CDCl$_3$): −0.03 (s, 3H), 0.01 (s, 3H), 0.16 (s, 6H), 0.81 (s, 9H), 0.92 (s, 9H), 1.23 (d, 3H), 2.48 (s, 3H), 3.58-3.74 (m, 2H), 4.37-4.42 (m, 1H), 6.54 (t, 1H), 6.86 (t, 1H), 6.99 (t, 1H), 8.06 (s, 1H), 8.21 (s, 1H), 9.48 (d, 1H).

3-Hydroxy-5-{[(1S)-2-hydroxy-1-methylethyl]oxy}-N-(5-methylpyrazin-2-yl)benzamide

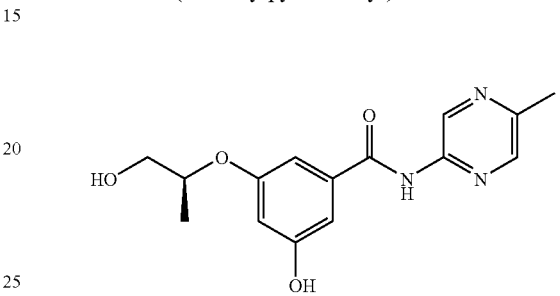

Trimethylsilyl iodide (6.06 mL, 42.75 mmol) was added to a solution of 3-hydroxy-5-{[(1S)-1-methyl-2-(methyloxy)ethyl]oxy}-N-(5-methylpyrazin-2-yl)benzamide (2.71 g, 8.55 mmol) in dry acetonitrile (150 mL) and stirred for 24 hours. Methanol (30 mL) was added to quench the reaction and stirred for 10 minutes. 10% w/v Aqueous sodium thiosulfate pentahydrate (20 mL) was added to the mixture and the organic solvents removed in vacuo. The residue was brought to pH5 with 1M hydrochloric acid and ethyl acetate (80 mL) added. A yellow solid (1.4 g) was separated by filtration. The aqueous filtrate was reextracted into ethyl acetate (2×80 mL) and the combined organic layers dried (MgSO$_4$), filtered and the solvents removed in vacuo. This residue was combined with the yellow solid obtained above and purified by column chromatography, eluting with 5% to 10% methanol in DCM, to give the title compound (1.70 g)

$^1$H NMR δ (d$_6$-DMSO): 1.21 (d, 3H), 2.50 (s, 3H), 3.40-3.60 (m, 2H), 4.45 (sex, 1H), 4.80 (t, 1H), 6.50 (s, 1H), 6.97 (s, 1H), 7.08 (s, 1H), 8.32 (s, 1H), 9.21 (s, 2H), 9.63 (s, 1H), 10.80 (brs, 1H). m/z 304 (M+H)$^+$ The preparation of 3-hydroxy-5-{[(1S)-1-methyl-2-(methyloxy)ethyl]oxy}-N-(5-methylpyrazin-2-yl)benzamide was described earlier.

EXAMPLE 59

3-{[5-(azetidin-1-ylcarbonyl)pyrazin-2-yl]oxy}-5-{[(1S)-2-hydroxy 1-methylethyl]oxy}-N-(5-methylpyrazin-2-yl)benzamide was also prepared in the following manner A mixture of 3-hydroxy-5-{[(1S)-2-hydroxy-1-methylethyl]oxy}-N-(5-methylpyrazin-2-yl)benzamide (3.03 g, 10.0 mmol), 2-(azetidin-1-ylcarbonyl)-5-chloropyrazine (2.17 g, 11.0 mmol) and potassium carbonate (4.14 g, 30.0 mmol) in acetonitrile (30.3 mL) was heated at 60° C. overnight. The solvent was removed by evaporation and the residue partitioned between ethyl acetate (15 vol) and water (10 vol). The aqueous phase was further extracted into ethyl acetate and the combined organics washed water, brine, dried (MgSO$_4$), filtered and the solvent removed in vacuo. The residue was chromatographed on silica, eluting with 0.5-6% methanol in ethyl acetate, to give the desired material as a foam (3.1 g). A sample of this material (100 mg) was dissolved in the minimum volume of acetonitrile then isohexane (5 mL) added. The mixture was stirred for 3 days, the liquid decanted and the residue triturated with diethyl ether. The crystalline material was collected by filtration. $^1$H NMR δ (d$_6$-DMSO): 1.25 (d, 3H), 2.30 (quin, 2H), 2.48 (s, 3H), 3.49-3.61 (m, 2H), 4.09 (t, 2H), 4.55-4.63 (m, 3H), 4.92 (t, 1H), 7.12 (t, 1H), 7.47 (t, 1H), 7.57 (t, 1H), 8.37 (d, 1H), 8.58 (d, 1H), 8.69 (d, 1H), 9.26 (d, 1H), 11.06 (s, 1H); m/z 465 (M+H)$^+$. Mpt (melting onset) 100.6° C.

The title compound was also crystallised by stirring a slurry of the compound in ethyl acetate (melting point 125.0° C.), toluene, nitromethane or methanol.

EXAMPLE 60

3-{[5-(Azetidin-1-ylcarbonyl)pyrazin-2-yl]oxy}-5-({(1S)-2-[(difluoromethyl)oxy]-1-methylethyl}oxy)-N-1H-pyrazol-3-ylbenzamide

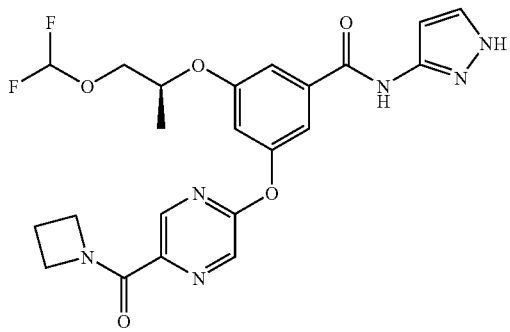

Trifluoroacetic acid (2 mL) was added to a solution of 1,1-dimethylethyl 3-({[3-{[5-(azetidin-1-ylcarbonyl)pyrazin-2-yl]oxy}-5-({(1S)-2-[(difluoromethyl)oxy]-1-methylethyl}oxy)phenyl]carbonyl}amino)-1H-pyrazole-1-carboxylate (115 mg, 0.17 mmol) in DCM (16 mL) and stirred at RT for 2 hours. The solvent was removed in vacuo, DCM (20 mL) added and the mixture washed with water (20 mL), a saturated solution of sodium bicarbonate (20 mL), brine (20 mL), dried (MgSO$_4$), filtered and reduced in vacuo to give the desired compound as a white foam (93 mg).

$^1$H NMR δ (CDCl$_3$): 1.36 (d, 3H), 2.37 (quin, 2H), 3.93-4.02 (m, 2H), 4.24 (t, 2H), 4.59-4.69 (m, 3H), 6.24 (t, 1H), 6.82 (s, 1H), 6.89 (t, 1H), 7.29-7.31 (m, 1H), 7.36-7.38 (m, 1H), 7.40 (d, 1H), 8.35 (d, 1H), 8.79 (d, 1H), 10.23 (s, 1H), 10.48 (s, 1H); m/z 489 (M+H)$^+$ The preparation of 1,1-dimethylethyl 3-({[3-{[5-(azetidin-1-ylcarbonyl)pyrazin-2-yl]oxy}-5-({(1S)-2-[(difluoromethyl)oxy]-1-methylethyl}oxy)phenyl]carbonyl}amino)-1H-pyrazole-1-carboxylate is described below.

1,1-Dimethylethyl 3-({[3-{[5-(azetidin-1-ylcarbonyl)pyrazin-2-yl]oxy}-5-({(1S)-2-[(difluoromethyl)oxy]-1-methylethyl}oxy)phenyl]carbonyl}amino)-1H-pyrazole-1-carboxylate

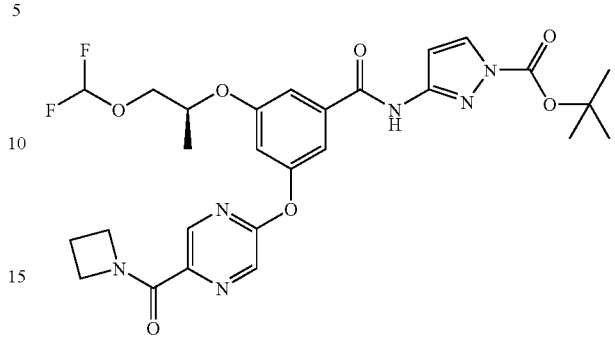

1-Chloro-N,N,2-trimethyl-1-propenylamine (0.12 mL, 0.92 mmol) was added to a solution of 3-{[5-(azetidin-1-ylcarbonyl)pyrazin-2-yl]oxy}-5-({(1S)-2-[(difluoromethyl)oxy]-1-methylethyl}oxy)benzoic acid (0.26 g, 0.61 mmol) in DCM (8 mL) and stirred for 1 hour. 1,1-Dimethylethyl 3-amino-1H-pyrazole-1-carboxylate (169 mg, 0.92 mmol) then pyridine (0.1 mL, 1.23 mmol) were added and stirred for a further 20 hours. The reaction mixture was reduced in vacuo and ethyl acetate (50 mL) and water (50 mL) were added. The aqueous layer was re-extracted into ethyl acetate (50 mL) and the combined organics washed with water (50 mL), brine (50 mL), dried (MgSO$_4$), filtered and reduced in vacuo. The crude oil was chromatographed on silica, eluting with 25-50% ethyl acetate in isohexane, to give the desired compound as a colourless oil (100 mg).

$^1$H NMR δ (CDCl$_3$): 1.38 (d, 3H), 1.62 (s, 9H), 2.38 (quin, 2H), 3.93-4.04 (m, 2H), 4.26 (t, 2H), 4.61-4.65 (m, 1H), 4.69 (t, 2H), 6.26 (t, 1H), 6.95 (t, 1H), 7.08 (d, 1H), 7.25-7.26 (m, 1H), 7.33 (t, 1H), 8.01 (d, 1H), 8.34 (d, 1H), 8.84 (s, 1H), 8.85 (d, 1H); m/z 587 (M−H)$^-$ The preparation of 1,1-dimethylethyl 3-amino-1H-pyrazole-1-carboxylate was described earlier.

The preparation of 3-{[5-(azetidin-1-ylcarbonyl)pyrazin-2-yl]oxy}-5-({(1S)-2-[(difluoromethyl)oxy]-1-methylethyl}oxy)benzoic acid is described below.

3-{[5-(Azetidin-1-ylcarbonyl)pyrazin-2-yl]oxy}-5-({(1S)-2-[(difluoromethyl)oxy]-1-methylethyl}oxy)benzoic acid

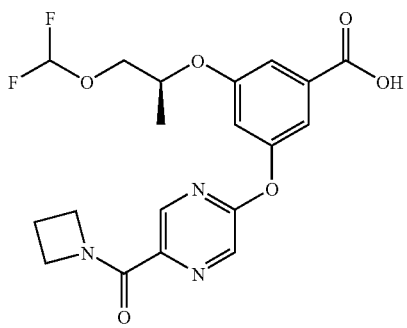

Lithium hydroxide monohydrate (48 mg, 1.13 mmol) in water (5 mL) was added to a solution of methyl 3-{[5-(azetidin-1-ylcarbonyl)pyrazin-2-yl]oxy}-5-({(1S)-2-[(difluoromethyl)oxy]-1-methylethyl}oxy)benzoate (0.33 g, 0.75 mmol) in THF (10 mL) and stirred at RT for 20 hours. The THF was removed in vacuo and the aqueous layer washed with ethyl acetate (50 mL) to remove any impurities. The aqueous layer was acidified and extracted into ethyl acetate (2×50 mL), washed with brine, dried (MgSO$_4$), filtered and the solvent removed in vacuo to give the desired compound as a white foam (0.26 g). m/z 424 (M+H)$^+$ Methyl 3-{[5-(azetidin-1-ylcarbonyl)pyrazin-2-yl]oxy}-5-({(1S)-2-[(difluoromethyl)oxy]-1-methylethyl}oxy)benzoate

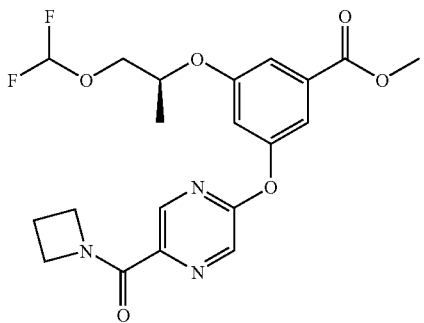

A mixture of methyl 3-({(1S)-2-[(difluoromethyl)oxy]-1-methylethyl}oxy)-5-hydroxybenzoate (0.28 g, 1.01 mmol), 2-(azetidin-1-ylcarbonyl)-5-chloropyrazine (201 mg, 1.01 mmol) and potassium carbonate (280 mg, 2.03 mmol) in acetonitrile (5 mL) was stirred in a microwave reactor at 140° C. for 5 hours. The reaction mixture was reduced in vacuo, ethyl acetate (50 mL) added and the organics washed with water (50 mL), brine (50 mL), dried (MgSO$_4$), filtered and reduced in vacuo. The crude oil was chromatographed on silica, eluting with 20 to 70% ethyl acetate in isohexane, to give the desired compound as a colourless oil (330 mg). $^1$H NMR δ (CDCl$_3$): 1.38 (d, 3H), 2.37 (quin, 2H), 3.90 (s, 3H), 3.93-4.04 (m, 2H), 4.26 (d, 2H), 4.61-4.70 (m, 3H), 6.25 (t, 1H), 6.95 (t, 1H), 7.43-7.44 (m, 1H), 7.49-7.50 (m, 1H), 8.32 (d, 1H), 8.85 (d, 1H); m/z 438 (M+H)$^+$ Methyl 3-({(1S)-2-[(difluoromethyl)oxy]-1-methylethyl}oxy)-5-hydroxybenzoate

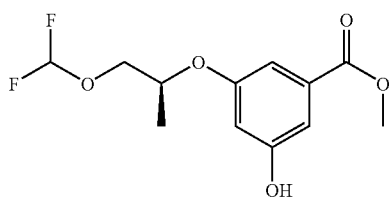

Methyl 3-({(1S)-2-[(difluoromethyl)oxy]-1-methylethyl}oxy)-5-[(phenylmethyl)oxy]benzoate (0.48 g, 1.08 mmol) was dissolved in ethanol (10 mL) and THF (10 mL) and the flask evacuated and purged with argon (3 times). 10% Palladium on carbon (140 mg) was added and the flask further evacuated and finally purged with hydrogen gas. The reaction mixture was stirred at RT for 20 hours until completion. The reaction mixture was evacuated and purged with argon (3 times) then the catalyst removed by filtration through Celite®. The filtrate was concentrated in vacuo to give the desired compound as a colourless oil (1.05 g). $^1$H NMR δ (CDCl$_3$): 1.35 (d, 3H), 3.90 (s, 3H), 3.90-4.02 (m, 2H), 4.57-4.64 (m, 1H), 5.20 (s, 1H), 6.26 (t, 1H), 6.63 (t, 1H), 7.14-7.15 (m, 1H), 7.17-7.18 (m, 1H); m/z 275 (M−H)$^-$ The preparations of methyl 3-({(1S)-2-[(difluoromethyl)oxy]-methylethyl}oxy)-5-[(phenylmethyl)oxy]benzoate and 2-(azetidin-1-ylcarbonyl)-5-chloropyrazine were described earlier.

EXAMPLE 61

3-{[15-(Azetidin-1-ylsulfonyl)-4-methyl-1,3-thiazol-2-yl]oxy}-5-{[(1S)-1-methyl-2-(methyloxy)ethyl]oxy}-N-(5-methylpyrazin-2-yl)benzamide

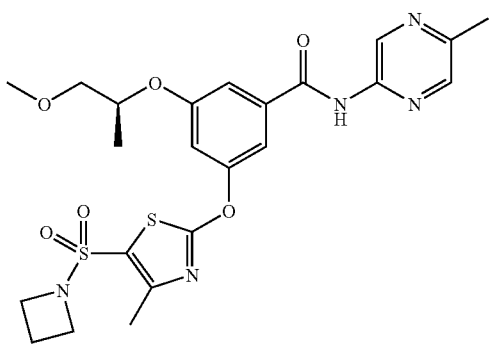

Cesium carbonate (293 mg, 0.9 mmol) was added to a solution of 3-hydroxy-5-{[(1S)-1-methyl-2-(methyloxy)ethyl]oxy}-N-(5-methylpyrazin-2-yl)benzamide (95 mg, 0.3 mmol) and 5-(azetidin-1-ylsulfonyl)-2-chloro-4-methyl-1,3-thiazole (90 mg, 0.36 mmol) in acetonitrile (5 mL) and the stirred mixture heated in a microwave reactor at 120° C. for 1 hour. The mixture was cooled to RT and pressure, the acetonitrile removed in vacuo, and the residue partitioned between water (15 mL) and ethyl acetate (30 mL). The organic layer was washed with brine, dried (MgSO$_4$) and evaporated in vacuo to a residue which was chromatographed on silica, eluting with 60% ethyl acetate in isohexane, to give the desired material as a colourless solid (79 mg).

$^1$H NMR δ (CDCl$_3$): 1.3 (d, 3H), 2.15 (m, 2H), 2.5 (s, 3H), 2.5 (s, 3H), 3.35 (s, 3H), 3.45-3.55 (m, 2H), 3.85 (t, 4H), 4.55 (m, 1H), 7.0 (d, 1H), 7.35 (d, 2H), 8.05 (s, 1H), 8.3 (s, 1H), 9.45 (s, 1H); m/z 534 (M+H)$^+$

The preparation of 3-hydroxy-5-{[(1S)-1-methyl-2-(methyloxy)ethyl]oxy}-N-(5-methylpyrazin-2-yl)benzamide was described earlier.

The preparation of 5-(azetidin-1-ylsulfonyl)-2-chloro-4-methyl-1,3-thiazole is described below.

5-(Azetidin-1-ylsulfonyl)-2-chloro-4-methyl-1,3-thiazole

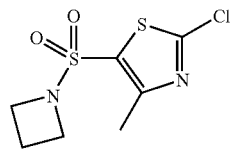

A solution of 2-chloro-4-methylthiazole-5-sulphonylchloride (462 mg; 2.0 mmol) in DCM (5 mL) was added to an ice-cold solution of azetidine hydrochloride (196 mg; 2.1 mmol) and triethylamine (1.0 mL; 7.2 mmol) in DCM (15 mL) and the mixture stirred at 0° C. for 30 minutes. The DCM was removed in vacuo to give a residue which was partitioned between water (50 mL) and ethyl acetate (75 mL). The organic layer was washed with brine, dried (MgSO$_4$) and evaporated to a residue which was chromatographed on silica, eluting with 10% ethyl acetate in isohexane, to give the desired material as a solid which was crystallised from ethyl acetate and isohexane (100 mg).

$^1$H NMR δ (CDCl$_3$): 2.2 (dt, 2H), 2.65 (s, 3H), 3.9 (t, 4H); m/z 253 (M+H)$^+$

EXAMPLE 62

3-{[6-(Azetidin-1-ylcarbonyl)pyridin-3-yl]oxy}-N-[1-(difluoromethyl)-1H-pyrazol-3-yl]-5-[(3S)-tetrahydrofuran-3-yloxy]benzamide

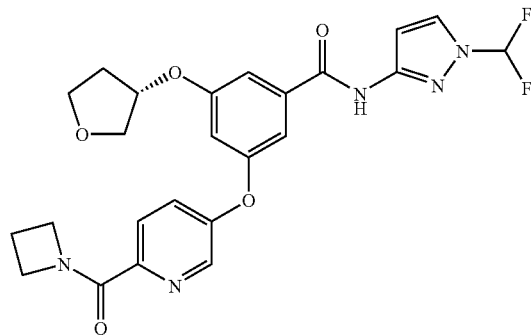

1-Chloro-N,N,2-trimethyl-1-propenylamine (0.088 mL, 0.66 mmol) was added to a solution of 3-{[6-(azetidin-1-ylcarbonyl)pyridin-3-yl]oxy}-5-[(3S)-tetrahydrofuran-3-yloxy]benzoic acid (171 mg, 0.44 mmol) in DCM (10 mL) and the reaction was stirred at RT for 30 minutes. After this time 1-(difluoromethyl)pyrazol-3-amine hydrochloride (75 mg, 0.44 mmol) and DIPEA (0.154 mL, 0.89 mmol) were added sequentially. The resulting solution was stirred at RT for 16 hours after which time the solvent was removed in vacuo and ethyl acetate (20 mL) and water (20 mL) were added. The aqueous phase was extracted with ethyl acetate (2×20 mL), washed with a saturated solution of sodium hydrogen carbonate (20 mL), and brine (20 mL). The combined organic extracts were dried (MgSO$_4$), filtered and evaporated. The residue was purified by flash column chromatography on silica, eluting with 50-100% ethyl acetate in isohexane, to give the desired product as a white solid (132 mg). $^1$H NMR δ (CDCl$_3$): 2.40-2.12 (m, 4H), 4.03-3.89 (m, 4H), 4.25 (t, 2H), 4.71 (t, 2H), 5.01-4.96 (m, 1H), 6.76 (t, 1H), 7.03 (t, 1H), 7.08 (d, 1H), 7.11 (s, 1H), 7.22 (s, 1H), 7.38 (dd, 1H), 7.75 (d, 1H), 8.13 (d, 1H), 8.33 (d, 1H), 8.50 (s, 1H); $^{19}$F NMR δ (CDCl$_3$): −93.84; m/z 500 (M+H)$^+$.

The following compounds were made in an analogous fashion.

| Example | Structure | m/z | NMR |
|---|---|---|---|
| 62a | 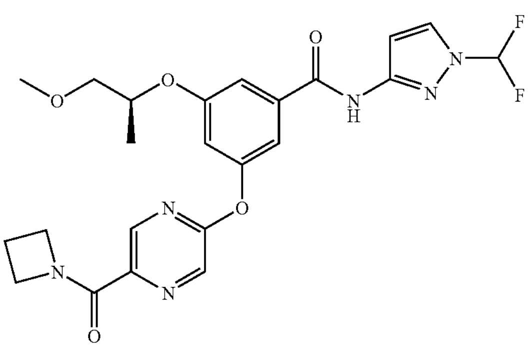 | 503 (M + H)$^+$ | $^1$H NMR δ (CDCl$_3$): 1.34 (d, 4H), 2.37 (quin, 2H), 3.40 (s, 3H), 3.51 (dd, 2H), 3.59 (dd, 2H), 4.25 (t, 2H), 4.60 (m, 1H), 4.68 (t, 2H), 6.96 (t, 1H), 7.02 (s, 1H), 7.02 (t, 1H), 7.08 (d, 1H), 7.26 (s, 1H), 7.37 (t, 1H), 7.73 (d, 1H), 8.33 (d, 1H), 8.54 (s, 1H), 8.85 (d, 1H) |
| 62b | 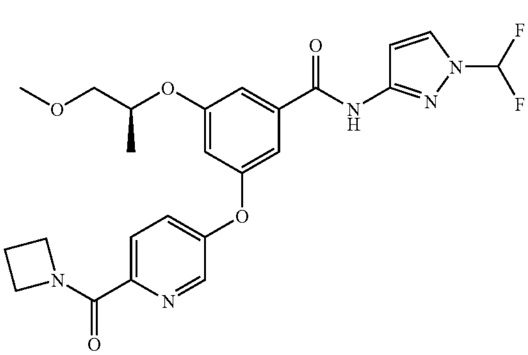 | 502 (M + H)$^+$ | $^1$H NMR δ (CDCl$_3$): 1.26 (d, 3H), 2.24-2.32 (m, 2H), 3.46-3.55 (m, 2H), 4.08 (t, 2H), 4.59 (t, 2H), 4.77 (m, 1H), 6.89 (d, 1H), 6.97 (t, 1H), 7.30 (s, 1H), 7.50 (s, 1H), 7.58 (dd, 1H), 7.71 (t, 1H), 8.00 (d, 1H), 8.15 (d, 1H), 8.42 (d, 1H), 11.22 (s, 1H) |

The preparations of 3-{[6-(azetidin-1-ylcarbonyl)pyridin-3-yl]oxy}-5-[(3S)-tetrahydrofuran-3-yloxy]benzoic acid, 3-{[5-(azetidin-1-ylcarbonyl)pyrazin-2-yl]oxy}-5-{[(1S)-1-methyl-2-(methyloxy)ethyl]oxy}benzoic acid and 3-{[6-(azetidin-1-ylcarbonyl)pyridin-3-yl]oxy}-5-{[(1S)-1-methyl-2-(methyloxy)ethyl]oxy}benzoic acid were described earlier.

The preparation of 1-(difluoromethyl)pyrazol-3-amine is described in the literature [WO2005090332, PCT Int. Appl. (2005)].

EXAMPLE 63

3-{[5-(Azetidin-1-ylcarbonyl)pyrazin-2-yl]oxy}-5-{[(1R)-1-methyl-2-(methyloxy)ethyl]oxy}-N-(5-methylpyrazin-2-yl)benzamide

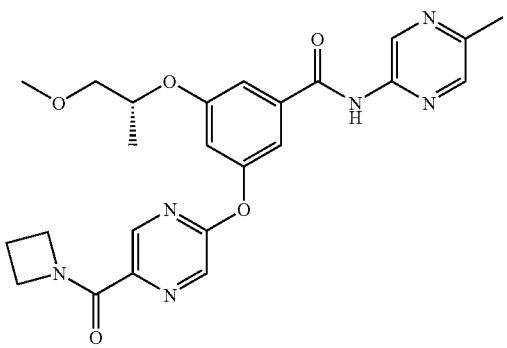

1-Chloro-N,N,2-trimethyl-1-propenylamine (0.042 mL, 0.31 mmol) was added to a solution of 3-{[5-(azetidin-1-ylcarbonyl)pyrazin-2-yl]oxy}-5-{[(1R)-1-methyl-2-(methyloxy)ethyl]oxy}benzoic acid (0.102 g, 0.0.31 mmol) in DCM (3 mL) under argon and stirred at RT for 40 minutes. 2-Amino-5-methylpyrazine (57 mg, 0.52 mmol) and pyridine (0.043 mL, 0.52 mmol) were added and the reaction stirred for a further 3 hours. The solvent was removed in vacuo and the residue taken up in ethyl acetate (30 mL), washed with water (2×10 mL), a saturated aqueous solution of sodium bicarbonate (10 mL), brine (10 mL), dried (MgSO$_4$), filtered, and evaporated in vacuo. The crude material was chromatographed on silica, eluting with a gradient of 60-100% ethyl acetate in isohexane, to give the desired compound as a white foam (86 mg).

$^1$H NMR δ (CDCl$_3$): 1.35 (d, 3H), 2.32-2.44 (m, 2H), 2.56 (s, 3H), 3.41 (s, 3H), 3.47-3.64 (m, 2H), 4.26 (t, 2H), 4.62 (q, 1H), 4.69 (t, 2H), 6.98 (s, 1H), 7.29 (s, 1H), 7.41 (s, 1H), 8.13 (s, 1H), 8.35 (s, 2H), 8.86 (s, 1H), 9.54 (s, 1H); m/z 479 (M+H)$^+$

The preparation of 3-{[5-(azetidin-1-ylcarbonyl)pyrazin-2-yl]oxy}-5-{[(1R)-1-methyl-2-(methyloxy)ethyl]oxy}benzoic acid is described below.

3-{[5-(Azetidin-1-ylcarbonyl)pyrazin-2-yl]oxy}-5-{[(1R)-1-methyl-2-(methyloxy)ethyl]oxy}benzoic acid

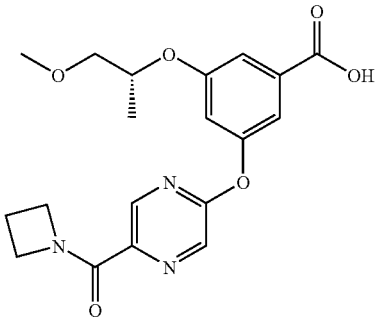

Methyl 3-{[5-(azetidin-1-ylcarbonyl)pyrazin-2-yl]oxy}-5-{[(1R)-1-methyl-2-(methyloxy)ethyl]oxy}benzoate (1.06 g, 2.6 mmol) was dissolved in THF (24 mL) and methanol (8 mL) then 1N lithium hydroxide solution (3.12 mL) added, followed by the dropwise addition of water (10 mL). The resultant solution was stirred for 3 hours at RT, a further portion of 1N lithium hydroxide solution (1.3 mL), the reaction stirred a further 2 hours, then further 1N lithium hydroxide solution (0.6 mL) added and stirring continued for another hour. The organics were removed by evaporation under reduced pressure, the aqueous solution was washed with diethyl ether (10 mL) then acidified with 2N hydrochloric acid and extracted with ethyl acetate (3×20 mL). The combined organics were washed with water (10 mL), brine (10 mL) and evaporated to dryness under reduced pressure to give the desired compound as a white solid (887 mg).

$^1$H NMR δ (CDCl$_3$): 1.34 (d, 3H), 2.38 (quin, 2H), 3.41 (s, 3H), 3.47-3.64 (m, 2H), 4.27 (t, 2H), 4.55-4.65 (m, 1H), 4.69 (t, 2H), 6.99 (s, 1H), 7.45 (s, 1H), 7.55 (s, 1H), 8.33 (s, 1H), 8.84 (s, 1H); m/z 388 (M+H)$^+$ Methyl 3-{[5-(azetidin-1-ylcarbonyl)pyrazin-2-yl]oxy}-5-{[(1R)-1-methyl-2-(methyloxy)ethyl]oxy}benzoate

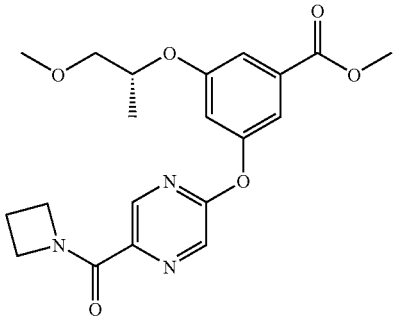

A mixture of methyl 3-hydroxy-5-{[(1R)-1-methyl-2-(methyloxy)ethyl]oxy}benzoate (727 mg, 3 mmol), 2-(azetidin-1-ylcarbonyl)-5-chloropyrazine (712 mg, 3.6 mmol) and potassium carbonate (828 mg, 6 mmol) in DMA (10 mL) was stirred at 120° C. for 2 hours. The solution was diluted with ethyl acetate (150 mL) washed with water (3×50 mL), brine (20 mL), dried (MgSO$_4$), filtered and the solvent removed in vacuo. The residue was purified by chromatography on silica, eluting with 50% ethyl acetate in isohexane, to give the desired material as a colourless oil (1.07 g). $^1$H NMR δ (CDCl$_3$): 1.27 (d, 3H), 2.4 (quintet, 2H), 3.4 (s, 3H), 3.5-3.6 (m, 2H), 3.9 (s, 3H), 4.25 (t, 2H), 4.53 (q, 1H), 4.7 (t, 2H), 6.95 (s, 1H), 7.4 (s, 1H), 7.5 (s, 1H), 8.3 (s, 1H), 8.85 (s, 1H); m/z 402 (M+H)$^+$ The preparation of 2-(azetidin-1-ylcarbonyl)-5-chloropyrazine was described earlier.

Methyl 3-hydroxy-5-{[(1R)-1-methyl-2-(methyloxy)ethyl]oxy}benzoate

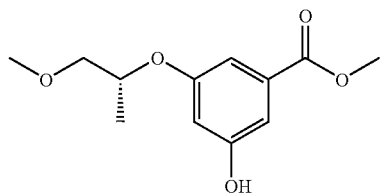

A solution of methyl 3-{[(1R)-1-methyl-2-(methyloxy)ethyl]oxy}-5-[(phenylmethyl)oxy]benzoate in THF (5 mL) and ethanol (5 mL), containing 10% palladium on carbon, was stirred under an atmosphere of hydrogen for 16 hours. The palladium on carbon was removed by filtration and the filtrate evaporated under reduced pressure to give the desired material as a clear gum (723 mg).
$^1$H NMR δ (CDCl$_3$): 1.31 (d, 3H), 3.42 (s, 3H), 3.48-3.64 (m, 2H), 3.88 (s, 3H), 4.54-4.63 (m, 1H), 5.75 (s, 1H), 6.64 (s, 1H), 7.11 (s, 1H), 7.17 (s, 1H); m/z 241 (M+H)$^+$ Methyl 3-{[(1R)-1-methyl-2-(methyloxy)ethyl]oxy}-5-[(phenylmethyl)oxy]benzoate

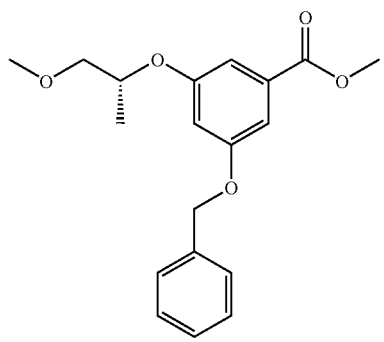

DIAD (4.6 g, 0.029 mol) was added dropwise to a solution of methyl 3-hydroxy-5-{[phenylmethyl]oxy}benzoate (6 g, 0.023 mol), (S)-(+)-1-methoxy-2-propanol (2.59 g, 0.029 mol) and triphenylphosphine (7.53 g, 0.029 mol) in THF (100 mL), under argon, at 0° C. The reaction was stirred at 0° C. for 1 hour and at RT for 20 hours. The volatiles were removed in vacuo and isohexane/ethyl acetate 2:1 added followed by stirring for 1 hour. A white solid was removed by filtration and the filtrate was evaporated to a residue which was chromatographed on silica, eluting with a gradient of 0-20% ethyl acetate in isohexane, to give the desired compound (5.11 g).
$^1$H NMR δ (CDCl$_3$): 1.31 (d, 3H), 3.40 (s, 3H), 3.45-3.60 (m, 2H), 3.88 (s, 3H), 4.57 (sex, 1H), 5.07 (s, 2H), 6.76 (m, 1H), 7.25 (m, 2H), 7.40 (m, 5H). m/z 331 (M+H)$^+$.

The preparation of methyl 3-hydroxy-5-{[phenylmethyl]oxy}benzoate was described earlier.

EXAMPLE 64

3-{[6-(Azetidin-1-ylcarbonyl)pyridin-3-yl]oxy}-5-{[(1R)-1-methyl-2-(methyloxy)ethyl]oxy}-N-(5-methylpyrazin-2-yl)benzamide

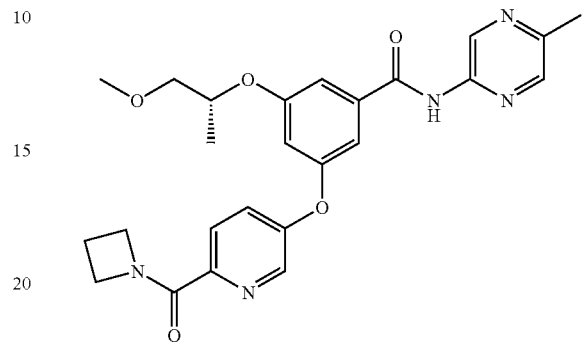

A mixture of 3-{[6-(azetidin-1-ylcarbonyl)pyridin-3-yl]oxy}-5-hydroxy-N-(5-methylpyrazin-2-yl)benzamide (101 mg, 0.25 mmol), S-(+)-methoxy-2-propanol (0.049 mL, 0.50 mmol) and triphenyl phosphine (131 mg, 0.50 mmol) in dry THF (10 mL) was treated dropwise with DIAD (0.099 mL, 0.50 mmol) at 0° C. under an argon atmosphere. The mixture was allowed to warm to RT and stirred overnight. The THF was removed by evaporation under reduced pressure and the residue purified twice by chromatography on silica, eluting with 0-7% methanol in DCM. The desired fractions were combined and purified by elution through an SCX column, eluted with 5% methanol in DCM then 50% 7N ammonia (in methanol) in DCM. The desired fractions were purified by elution though an NH$_2$ column, eluting with 5% methanol in DCM, to give the desired compound (35 mg) with a purity estimated to be 85%. $^1$H NMR δ (CDCl$_3$): 1.26 (d, 3H), 2.28 (quin, 2H), 2.49 (s, 3H), 3.33 (s, 3H), 3.41-3.54 (m, 2H), 4.18 (t, 2H), 4.50-4.58 (m, 1H), 4.64 (t, 2H), 6.77 (s, 1H), 7.08 (s, 1H), 7.25 (s, 1H), 7.31 (d, 1H), 8.04 (d, 1H), 8.07 (s, 1H), 8.26 (d, 1H), 8.30 (s, 1H), 9.46 (s, 1H); m/z 478 (M+H)$^+$ The preparation of 3-{[6-(azetidin-1-ylcarbonyl)pyridin-3-yl]oxy}-5-hydroxy-N-(5-methylpyrazin-2-yl)benzamide is described below.

3-{[6-(Azetidin-1-ylcarbonyl)pyridin-3-yl]oxy}-5-hydroxy-N-(5-methylpyrazin-2-yl)benzamide

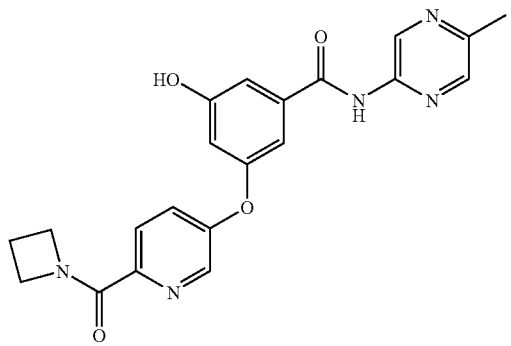

3-{[6-(Azetidin-1-ylcarbonyl)pyridin-3-yl]oxy}-N-(5-methylpyrazin-2-yl)-5-[(phenylmethyl)oxy]benzamide (3.9 g, 7.9 mmol) was dissolved in ethyl acetate (200 mL) and ethanol (200 mL) then 10% palladium on charcoal added. The reaction was stirred under an atmosphere of hydrogen for 16 hours. Methanol (150 mL) was added to aid solubilisation of the material and the suspension filtered, the residue taken up in DMF, filtered and the combined filtrates evaporated to dryness to give the desired material (3.17 g). $^1$H NMR δ (d$_6$-DMSO): 2.33 (quin, 2H), 2.53 (s, 3H), 4.13 (t, 2H), 4.64 (t, 2H), 6.81 (s, 1H), 7.31 (s, 1H), 7.34 (s, 1H), 7.62 (d, 1H), 8.05 (d, 1H), 8.40 (s, 1H), 8.47 (s, 1H), 9.26 (s, 1H), 10.35 (s, 1H), 11.02 (s, 1H); m/z 406 (M+H)$^+$ 3-[{6-(Azetidin-1-ylcarbonyl)pyridin-3-yl]oxy}-N-(5-methylpyrazin-2-yl)-5-[(phenylmethyl)oxy]benzamide

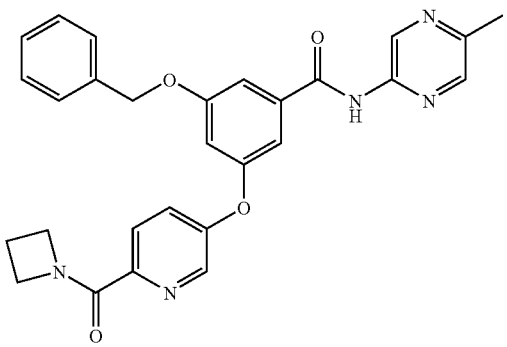

1-Chloro-N,N,2-trimethyl-1-propenylamine (2.67 mL, 20 mmol) was added to a solution of 3-{[6-(azetidin-1-ylcarbonyl)pyridin-3-yl]oxy}-5-[(phenylmethyl)oxy]benzoic acid (6.18 g, 15.3 mmol) in DCM (100 mL) and the reaction stirred at RT for 50 mins. 2-Amino-5-methylpyrazine (3.34 g, 30.6 mmol) and pyridine (2.5 mL, 30.6 mmol) were added and the reaction stirred overnight. The solvent was removed in vacuo, and the residue taken up in ethyl acetate (350 mL). The organic phase was washed with water (2×100 mL), brine (100 mL), dried (MgSO$_4$), filtered, and evaporated in vacuo. The residue was chromatographed on silica, eluting with a gradient of 50-75% ethyl acetate in isohexane, to give the desired material (4.01 g). $^1$H NMR δ (CDCl$_3$): 2.28 (quin, 2H), 2.49 (s, 3H), 4.18 (t, 2H), 4.63 (t, 2H), 5.05 (s, 2H), 6.78 (s, 1H), 7.10 (s, 1H), 7.25-7.37 (m, 7H), 8.04 (d, 1H), 8.07 (s, 1H), 8.25 (s, 2H), 9.46 (s, 1H); m/z 496 (M+H)$^+$ 3-{[6-(Azetidin-1-ylcarbonyl)pyridin-3-yl]oxy}-5-[(phenylmethyl)oxy]benzoic acid

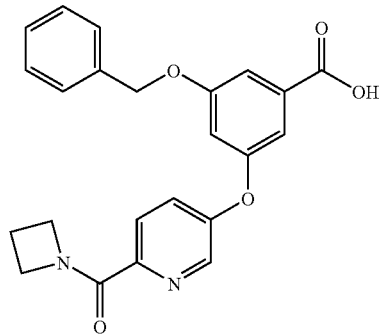

A mixture of methyl 3-hydroxy-5-{[phenylmethyl]oxy}benzoate (5.16 g, 20 mmol), 2-(azetidin-1-ylcarbonyl)-5-bromopyridine (5.3 g, 22 mmol), cesium carbonate (19.56 g, 60 mmol) and bromotris(triphenylphosphine)copper (3.73 g, 4 mmol) in DMA (100 mL) was stirred at 160° C. for 6 hours in a microwave reactor. The DMA was evaporated under reduced pressure and the residue was dissolved in water (200 mL) and washed with ethyl acetate (3×50 mL). The aqueous layer was acidified with 2N hydrochloric acid and extracted with ethyl acetate (3×100 mL), the combined organics were washed with water (2×20 mL), brine (20 mL), dried (MgSO$_4$), filtered and the solvent removed in vacuo to give the desired material (6.18 g). $^1$H NMR δ (CDCl$_3$): 2.29 (s, 2H), 4.20 (s, 2H), 4.64 (s, 2H), 5.04 (s, 2H), 6.83 (s, 1H), 7.22-7.44 (m, 7H), 7.49 (s, 1H), 7.79-8.63 (m, 2H); m/z 405 (M+H)$^+$ The preparations of methyl 3-hydroxy-5-{[phenylmethyl]oxy}benzoate and 2-(azetidin-1-ylcarbonyl)-5-bromopyridine were described earlier.

Biological Tests:

The biological effects of the compounds of formula (I) may be tested in the following way:

(1) Enzymatic Activity

Enzymatic activity of recombinant human pancreatic GLK may be measured by incubating GLK, ATP and glucose. The rate of product formation may be determined by coupling the assay to a G-6-P dehydrogenase, NADP/NADPH system and measuring the linear increase with time of optical density at 340 nm (Matschinsky et al 1993). Activation of GLK by compounds can be assessed using this assay in the presence or absence of GLKRP as described in Brocklehurst et al (Diabetes 2004, 53, 535-541).

Production of Recombinant GLK and GLKRP:

Human GLK and GLKRP cDNA was obtained by PCR from human pancreatic and hepatic mRNA respectively, using established techniques described in Sambrook J, Fritsch E F & Maniatis T, 1989. PCR primers were designed according to the GLK and GLKRP cDNA sequences shown in Tanizawa et al 1991 and Bonthron, D. T. et al 1994 (later corrected in Warner, J. P. 1995).

Cloning in Bluescript II Vectors

GLK and GLKRP cDNA was cloned in E. coli using pBluescript II, (Short et al 1998) a recombinant cloning vector system similar to that employed by Yanisch-Perron C et al (1985), comprising a colEI-based replicon bearing a polylinker DNA fragment containing multiple unique restriction sites, flanked by bacteriophage T3 and T7 promoter sequences; a filamentous phage origin of replication and an ampicillin drug resistance marker gene.

Transformations

E. Coli transformations were generally carried out by electroporation. 400 mL cultures of strains DH5a or BL21(DE3) were grown in L-broth to an OD 600 of 0.5 and harvested by centrifugation at 2,000 g. The cells were washed twice in ice-cold deionised water, resuspended in 1 mL 10% glycerol and stored in aliquots at −70° C. Ligation mixes were desalted using Millipore V Series™ membranes (0.0025 mm) pore size). 40 mL of cells were incubated with 1 mL of ligation mix or plasmid DNA on ice for 10 minutes in 0.2 cm electroporation cuvettes, and then pulsed using a Gene Pulser™ apparatus (BioRad) at 0.5 kVcm$^{-1}$, 250 mF. Transformants were selected on L-agar supplemented with tetracyline at 10 mg/mL or ampicillin at 100 mg/mL.

Expression

GLK was expressed from the vector pTB375NBSE in *E. coli* BL21 cells, producing a recombinant protein containing a 6-His tag immediately adjacent to the N-terminal methionine. Alternatively, another suitable vector is pET21 (+)DNA, Novagen, Cat number 697703. The 6-His tag was used to allow purification of the recombinant protein on a column packed with nickel-nitrilotriacetic acid agarose purchased from Qiagen (cat no 30250).

GLKRP was expressed from the vector pFLAG CTC (IBI Kodak) in *E. coli* BL21 cells, producing a recombinant protein containing a C-terminal FLAG tag. The protein was purified initially by DEAE Sepharose ion exchange followed by utilisation of the FLAG tag for final purification on an M2 anti-FLAG immunoaffinity column purchased from Sigma-Aldrich (cat no. A1205).

(2) Oral Glucose Tolerance Test (OGTT)

Oral glucose tolerance tests were done on conscious Zucker obese fa/fa rats (age 12-13 weeks or older) fed a high fat diet (45% kcal fat) for at least two weeks prior to experimentation. The animals were fasted for 2 hours before use for experiments. A test compound or a vehicle was given orally 120 minutes before oral administration of a glucose solution at a dose of 2 g/kg body weight. Blood glucose levels were measured using a Accucheck glucometer from tail bled samples taken at different time points before and after administration of glucose (time course of 60 minutes). A time curve of the blood glucose levels was generated and the area-under-the-curve (AUC) for 120 minutes was calculated (the time of glucose administration being time zero). Percent reduction in glucose excursion was determined using the AUC in the vehicle-control group as zero percent reduction.

Compounds of the invention generally have an activating activity for glucokinase with an $EC_{50}$ of less than about 1 µM and generally less than about 500 nM. For example, Example 3 has an $EC_{50}$ of 31 nm.

Example 3 exhibits 54% OGTT activity at 10 mg/kg.

REFERENCES

1 Printz, R. L., Magnuson, M. A. and Granner, D. K. (1993) Annual Review of Nutrition 13, 463-96
2 DeFronzo, R. A. (1988) Diabetes 37, 667-87
3 Froguel, P., Zouali, H., Vionnet, N., Velho, G., Vaxillaire, M., Sun, F., Lesage, S., Stoffel, M., Takeda, J. and Passa, P. (1993) New England Journal of Medicine 328, 697-702
4 Bell, G. I., Pilkis, S. J., Weber, I. T. and Polonsky, K. S. (1996) Annual Review of Physiology 58, 171-86
5 Velho, G., Petersen, K. F., Perseghin, G., Hwang, J. H., Rothman, D. L., Pueyo, M. E., Cline, G. W., Froguel, P. and Shulman, G. I. (1996) Journal of Clinical Investigation 98, 1755-61
6 Christesen, H. B., Jacobsen, B. B., Odili, S., Buettger, C., Cuesta-Munoz, A., Hansen, T., Brusgaard, K., Massa, O., Magnuson, M. A., Shiota, C., Matschinsky, F. M. and Barbetti, F. (2002) Diabetes 51, 1240-6
6a Gloyn, A. L., Noordam, K., Willemsen, M. A. A. P., Ellard, S., Lam, W. W. K., Campbell, I. W., Midgley, P., Shiota, C., Buettger, C., Magnuson, M. A., Matschinsky, F. M., and Hattersley, A. T.; Diabetes 52: 2433-2440
7 Glaser, B., Kesavan, P., Heyman, M., Davis, E., Cuesta, A., Buchs, A., Stanley, C. A., Thornton, P. S., Permutt, M. A., Matschinsky, F. M. and Herold, K. C. (1998) New England Journal of Medicine 338, 226-30
8 Caro, J. F., Triester, S., Patel, V. K., Tapscott, E. B., Frazier, N. L. and Dohm, G. L. (1995) Hormone & Metabolic Research 27, 19-22
9 Desai, U. J., Slosberg, E. D., Boettcher, B. R., Caplan, S. L., Fanelli, B., Stephan, Z., Gunther, V. J., Kaleko, M. and Connelly, S. (2001) Diabetes 50, 2287-95
10 Shiota, M., Postic, C., Fujimoto, Y., Jetton, T. L., Dixon, K., Pan, D., Grimsby, J., Grippo, J. F., Magnuson, M. A. and Cherrington, A. D. (2001) Diabetes 50, 622-9
11 Ferre, T., Pujol, A., Riu, E., Bosch, F. and Valera, A. (1996) Proceedings of the National Academy of Sciences of the United States of America 93, 7225-30
12 Seoane, J., Barbera, A., Telemaque-Potts, S., Newgard, C. B. and Guinovart, J. J. (1999) Journal of Biological Chemistry 274, 31833-8
13 Moore, M. C., Davis, S, N., Mann, S. L. and Cherrington, A. D. (2001) Diabetes Care 24, 1882-7
14 Alvarez, E., Roncero, I., Chowen, J. A., Vazquez, P. and Blazquez, E. (2002) Journal of Neurochemistry 80, 45-53
15 Lynch, R. M., Tompkins, L. S., Brooks, H. L., Dunn-Meynell, A. A. and Levin, B. E. (2000) Diabetes 49, 693-700
16 Roncero, I., Alvarez, E., Vazquez, P. and Blazquez, E. (2000) Journal of Neurochemistry 74, 1848-57
17 Yang, X. J., Kow, L. M., Funabashi, T. and Mobbs, C. V. (1999) Diabetes 48, 1763-1772
18 Schuit, F. C., Huypens, P., Heimberg, H. and Pipeleers, D. G. (2001) Diabetes 50, 1-11
19 Levin, B. E. (2001) International Journal of Obesity 25, supplement 5, S68-S72.
20 Alvarez, E., Roncero, I., Chowen, J. A., Thorens, B. and Blazquez, E. (1996) Journal of Neurochemistry 66, 920-7
21 Mobbs, C. V., Kow, L. M. and Yang, X. J. (2001) American Journal of Physiology—Endocrinology & Metabolism 281, E649-54
22 Levin, B. E., Dunn-Meynell, A. A. and Routh, V. H. (1999) American Journal of Physiology 276, R1223-31
23 Spanswick, D., Smith, M. A., Groppi, V. E., Logan, S. D. and Ashford, M. L. (1997) Nature 390, 521-5
24 Spanswick, D., Smith, M. A., Mirshamsi, S., Routh, V. H. and Ashford, M. L. (2000) Nature Neuroscience 3, 757-8
25 Levin, B. E. and Dunn-Meynell, A. A. (1997) Brain Research 776, 146-53
26 Levin, B. E., Govek, E. K. and Dunn-Meynell, A. A. (1998) Brain Research 808, 317-9
27 Levin, B. E., Brown, K. L. and Dunn-Meynell, A. A. (1996) Brain Research 739, 293-300
28 Rowe, I. C., Boden, P. R. and Ashford, M. L. (1996) Journal of Physiology 497, 365-77
29 Fujimoto, K., Sakata, T., Arase, K., Kurata, K., Okabe, Y. and Shiraishi, T. (1985) Life Sciences 37, 2475-82
30 Kurata, K., Fujimoto, K. and Sakata, T. (1989) Metabolism: Clinical & Experimental 38, 46-51
31 Kurata, K., Fujimoto, K., Sakata, T., Etou, H. and Fukagawa, K. (1986) Physiology & Behavior 37, 615-20
32 Jetton T. L., Liang Y., Pettepher C. C., Zimmerman E. C., Cox F. G., Horvath K., Matschinsky F. M., and Magnuson M. A., J. Biol. Chem., February 1994; 269: 3641-3654
33 Reimann F. and Gribble F. M., Diabetes 2002 51: 2757-2763
34 Cheung A. T., Dayanandan B., Lewis J. T., Korbutt G. S., Rajotte R. V., Bryer-Ash M., Boylan M. O., Wolfe M. M., Kieffer T. J., *Science*, Vol 290, Issue 5498, 1959-1962, 8 Dec. 2000

The invention claimed is:

1. The compound 3-{[5-(azetidin-1-ylcarbonyl)pyrazin-2-yl]oxy}-5-[(1-methylethyl)oxy]-N-1H-pyrazol-3-ylbenzamide or a salt thereof.

2. A pharmaceutical composition comprising the compound 3-{[5-(azetidin-1-ylcarbonyl)pyrazin-2-yl]oxy}-5-[(1-methylethyl)oxy]-N-1H-pyrazol-3-ylbenzamide or a pharmaceutically-acceptable salt thereof, together with a pharmaceutically acceptable diluent or carrier.

3. A process for the preparation of the compound 3-{[5-(azetidin-1-ylcarbonyl)pyrazin-2-yl]oxy}-5-[(1-methylethyl)oxy]-N-1H-pyrazol-3-ylbenzamide or a salt thereof comprising reacting 1,1-dimethylethyl 3-[({3-hydroxy-5-[(1-methylethyl)oxy]phenyl}carbonyl)amino]-1H-pyrazole-1-carboxylate with 2-(azetidin-1-ylcarbonyl)-5-chloropyrazine to form 3-{[5-(azetidin-1-ylcarbonyl)pyrazin-2-yl]oxy}-5-[(1-methylethyl)oxy]-N-1H-pyrazol-3-ylbenzamide and thereafter optionally forming a salt thereof.

* * * * *